(12) United States Patent
Graversen et al.

(10) Patent No.: US 9,724,426 B2
(45) Date of Patent: Aug. 8, 2017

(54) AGENTS, USES AND METHODS

(75) Inventors: Niels Jonas Heilskov Graversen, Homslet (DK); Pia Svendsen, Risskov (DK); Peter Astrup Christensen, Randers NV (DK); Maciej Bogdan Maniecki, Århus C (DK); Søren Kragh Moestrup, Århus N (DK); Holger Jon Møller, Risskov (DK); Gabriele Anton, Skanderborg (DK)

(73) Assignees: AFFINICON APS, Aarhus N. (DK); AARHUS UNIVERSITY HOSPITAL, Aarhus N. (DK)

( * ) Notice: Subject to any disclaimer, the term of this patent is extended or adjusted under 35 U.S.C. 154(b) by 812 days.

(21) Appl. No.: 13/498,504

(22) PCT Filed: Sep. 29, 2010

(86) PCT No.: PCT/GB2010/001827
§ 371 (c)(1),
(2), (4) Date: Jun. 6, 2012

(87) PCT Pub. No.: WO2011/039510
PCT Pub. Date: Apr. 7, 2011

(65) Prior Publication Data
US 2012/0258107 A1  Oct. 11, 2012

(30) Foreign Application Priority Data

Sep. 29, 2009 (GB) .................................. 0917044.0

(51) Int. Cl.
*A61K 39/395* (2006.01)
*C07K 16/28* (2006.01)
*A61K 47/48* (2006.01)
*A61K 51/10* (2006.01)
*A61K 39/00* (2006.01)

(52) U.S. Cl.
CPC .... *A61K 47/48561* (2013.01); *A61K 51/1027* (2013.01); *C07K 16/2896* (2013.01); *A61K 2039/505* (2013.01); *C07K 2317/24* (2013.01); *C07K 2317/34* (2013.01); *C07K 2317/55* (2013.01); *C07K 2317/92* (2013.01)

(58) Field of Classification Search
None
See application file for complete search history.

(56) References Cited

U.S. PATENT DOCUMENTS 5,439,665 A * 8/1995 Hansen et al. .............. 424/1.49
2002/0155995 A1 * 10/2002 Moestrup et al. ............ 514/6

FOREIGN PATENT DOCUMENTS

| WO | 03/100419 | 12/2003 |
|---|---|---|
| WO | 2004/100995 | 11/2004 |
| WO | 2006/094402 | 9/2006 |
| WO | 2008/019186 | 2/2008 |
| WO | 2011/039511 | 4/2011 |

OTHER PUBLICATIONS

Van den Heuvel et al., Regulation of CD163 on human macrophages: cross-linking of CD163 induces signaling and activation, J. Leukocyte Biol., 66, 858-866, 1999.*
Madsen, M., et al. "Molecular characterization of the haptoglobin.hemoglobin receptor CD163. Ligand binding properties of the scavenger receptor cysteine-rich domain region." J Biol Chem. Dec. 3, 2004;279(49):51561-7. Epub Sep. 24, 2004.
Wijbrandts, C.A., et al. "The clinical response to infliximab in rheumatoid arthritis is in part dependent on pretreatment tumour necrosis factor alpha expression in the synovium." Ann Rheum Dis. Aug. 2008;67(8):1139-44. Epub Nov. 29, 2007.
Zhou, Y., et al., "Development of RNAi technology for targeted therapy—A track of siRNA based agents to RNAi therapeutics" Journal of Controlled Release (2014) 193:270-281.
Baschant, U., et al., "The multiple facets of glucocorticoid action in rheumatoid arthritis" Nat. Rev. Rheumatol. (2012) 8:645-655.
Barnes, P.J., "How corticosteroids control inflammation: Quintiles Prize Lecture 2005" British Journal of Pharmacology (2006) 148:245-254.
Walker, S., et al., "Cleavage behavior of calicheamicin gamma1 and calicheamicin T" Proc. Natl. Acad. Sci. (1992) 89:4608-4612.
Zhang, C. et al., "Biochemical and structural insights of the early glycosylation steps in calicheamicin biosynthesis" Chem Biol. (2008) 15(8):842-853.
Shin, H.-J., et al., "Etoposide induced cytotoxicity mediated by ROS and ERK in human kidney proximal tubule cells" Sci. Rep. (2016) 6:34064.
Tacar, O., et al., "Doxorubicin: an update on anticancer molecular action, toxicity and novel drug delivery systems" Journal of Pharmacy and Pharmacology (2012) 65:157-170.
Gidding, C.E.M., et al., "Vincristine revisited" Critical Reviews in Oncology:Hematology (1999) 29:267-287.
Lee, A.U., et al., "Mechanism of azathioprine-induced injury to hepatocytes: roles of glutathione depletion and mitochondrial injury" Journal of Hepatology (2001) 35:756-764.
Goodsell, D.S., "The Molecular Perspective: Methotrexate" The Oncologist (1999) 4:340-341.
Wang, D., et al., "Cellular Processing of Platinum Anticancer Drugs" Nat Rev. Drug Disc. (2005) 4:307-320.
Wessels, J.A.M., et al., "Recent insights in the pharmacological actions of methotrexate in the treatment of rheumatoid arthritis" Rheumatology (2008)47:249-255.
Beutler, E., "Enzyme Replacement in Gaucher Disease" PLoS Medicine (2004) 1(2):e21.

* cited by examiner

*Primary Examiner* — Elly-Gerald Stoica
(74) *Attorney, Agent, or Firm* — Robert C. Netter, Jr.; Dann, Dorfman, Herrell & Skillman

(57) ABSTRACT

The present invention relates to agents comprising a binding moiety with binding specificity for SRCR domain 1 of the CD163 receptor, for use in medicine. The invention also relates to methods, uses, kits and compositions comprising such agents.

32 Claims, 68 Drawing Sheets

Figure 2A:
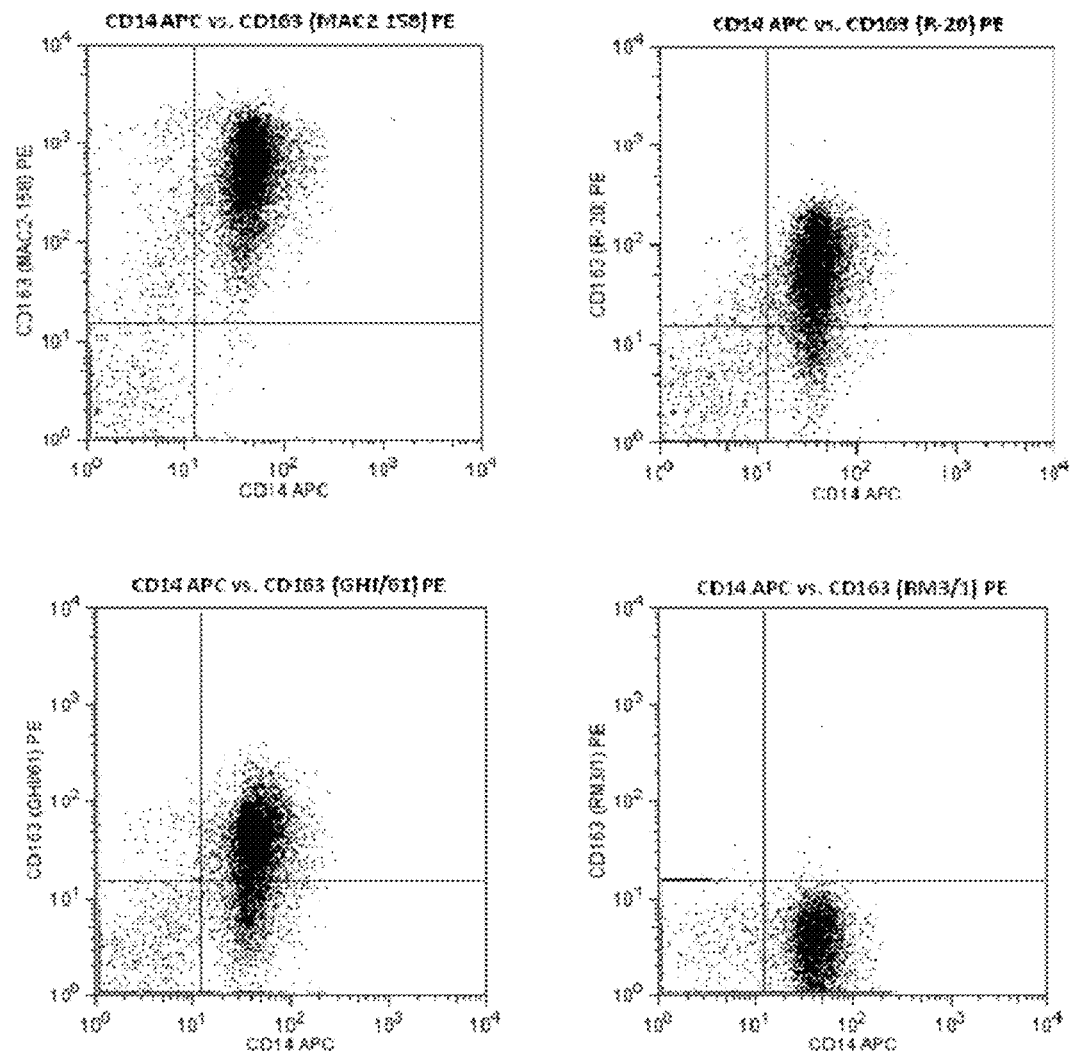

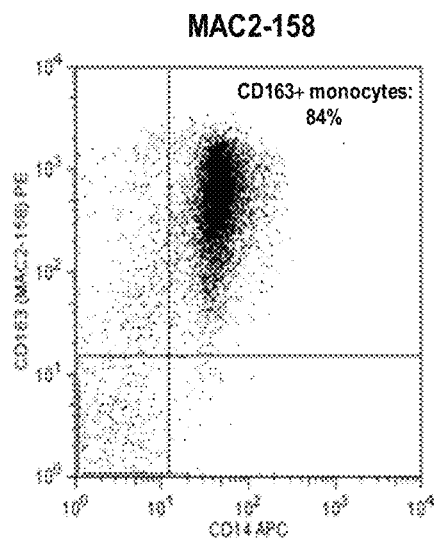
FIG. 1A MAC2-158
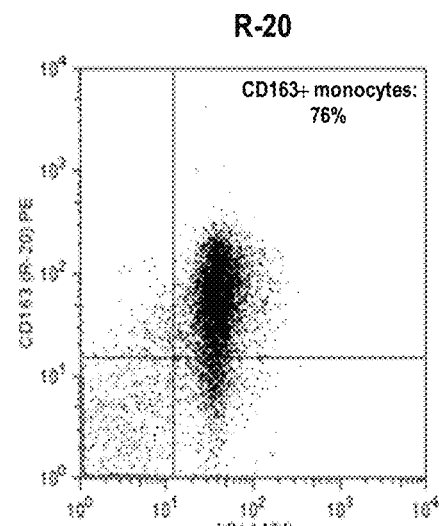
FIG. 1B R-20
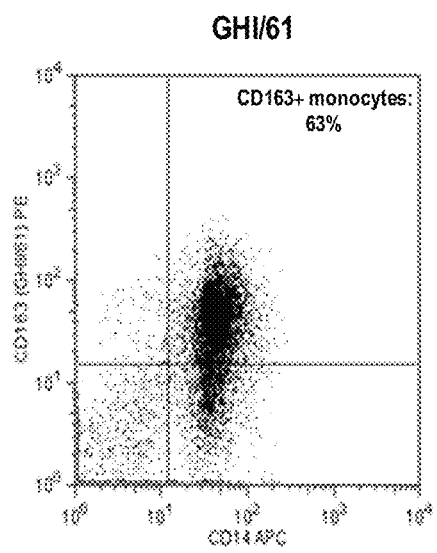
FIG. 1C GHI/61
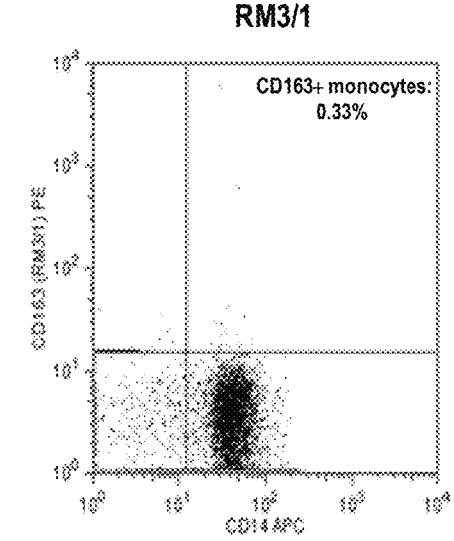
FIG. 1D RM3/1

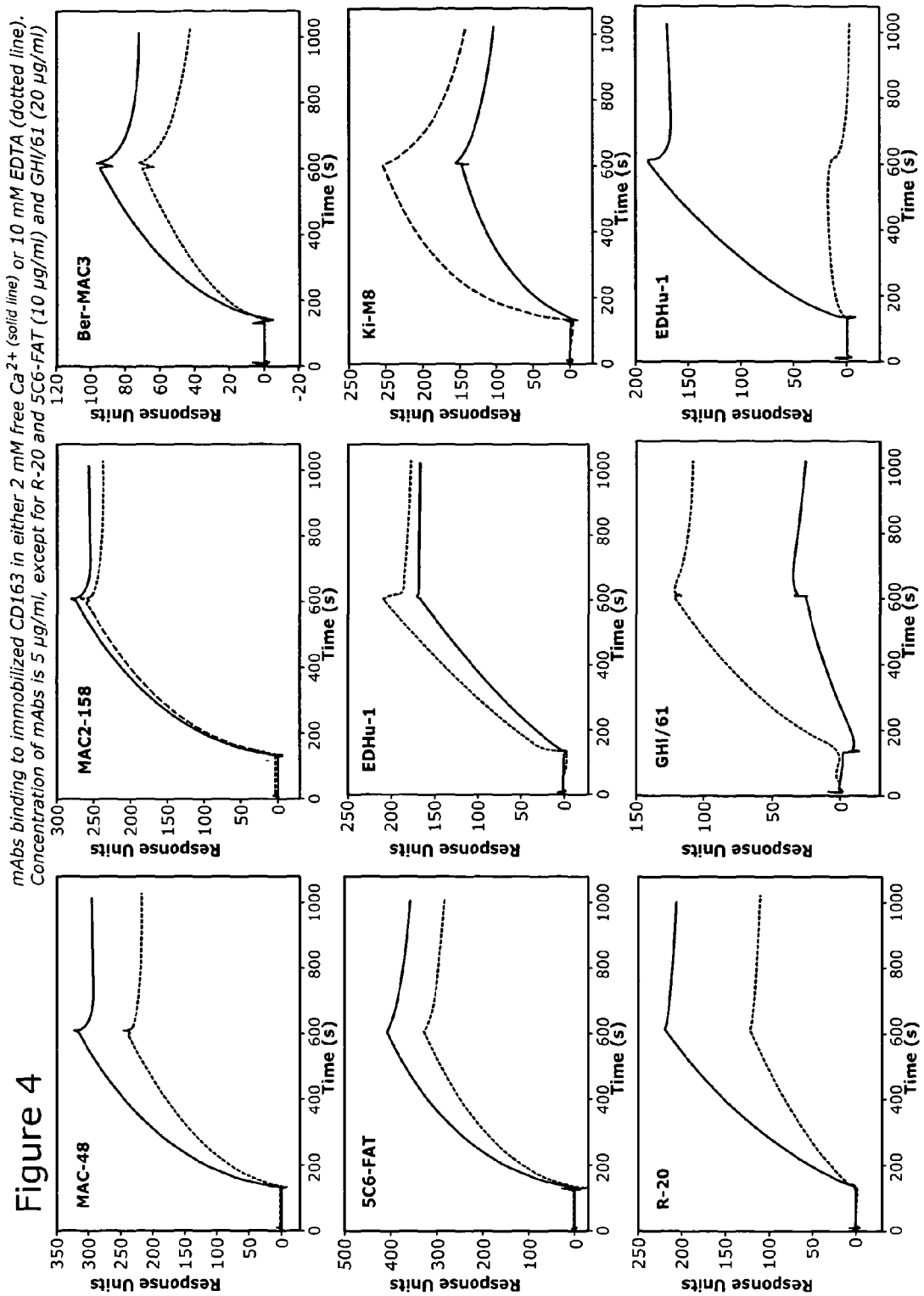

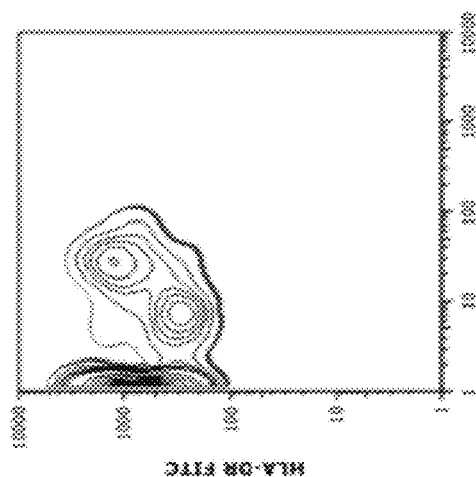
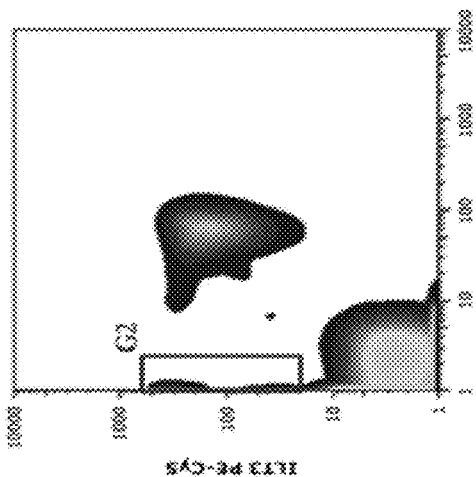
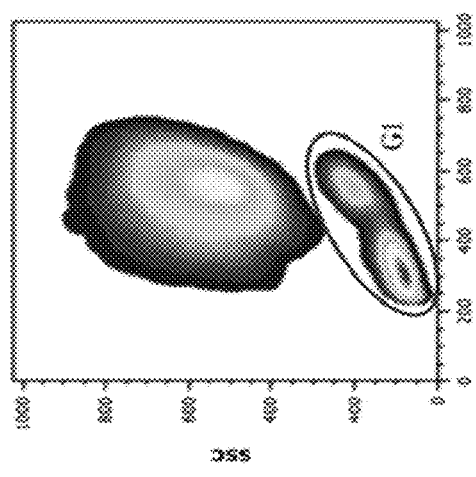
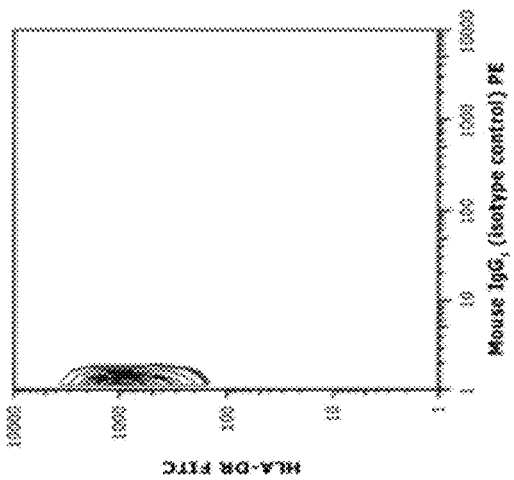
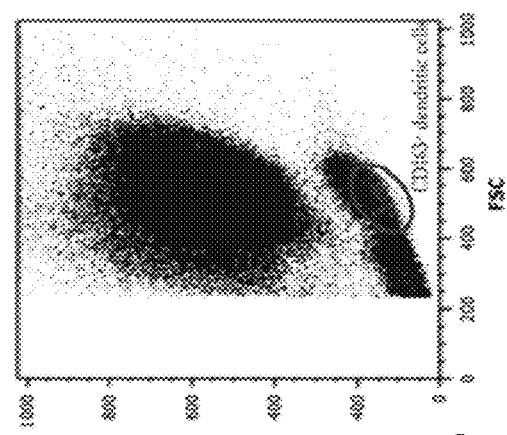

FIG. 14D

FIG. 14E

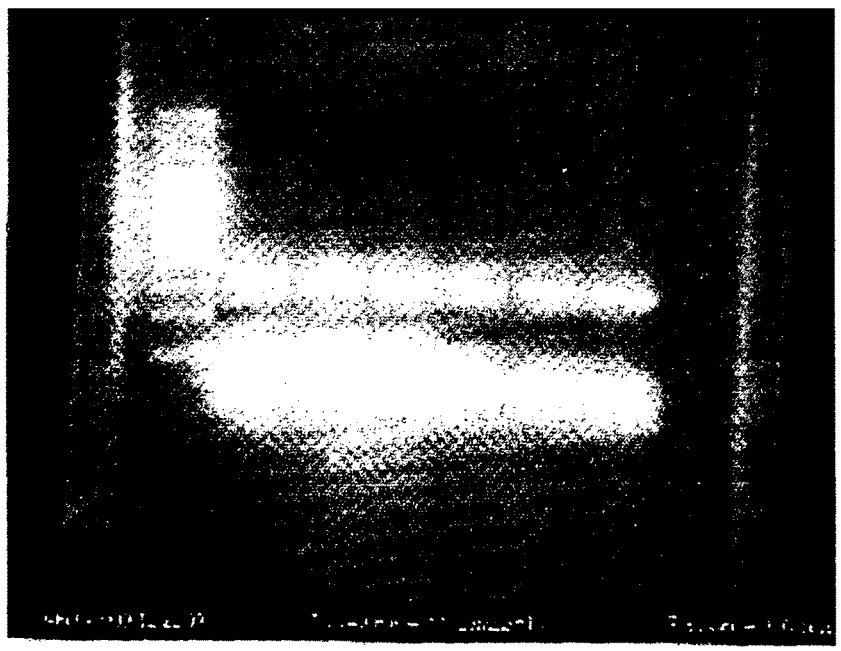
Fig. 15

Figure 16

VH

```
Template dbj|BAG64279.1|  -VQLQE S GP G LVKPSETLSLITCAVSGYSITSGYYWGWIRQPPGKGLEWIGSIYHSGSTYYNPSLKSRVTLSVDTSKNQFSLKMSSVTAADTAVYYCARERNYMDVWGEGTTVTVSS
Germline IGHV4-b*01        VQLQE S GP G LVKPSETLSLTCAVSGYSISSGYYWGWIRQPPGKGLEWIGSIYHSGSTYYNPSLKSRVTISVDTSKNQFSLKLSSVTAADTAVYYCAR
KN2                       QVQLQE S GP G LVKPSETLSLITCAVSGYSITSGYSITSDYAWNWIRQFPGNKLEWMGYITYSGSTYYNPSLKSRVTISVDTSKNQFSLKLSSVTAADTATYYCVSGTYYFDYWGQGTTLTVSS
KN1IN5                    QVQLQE S GP G LVKPSETLNLTCTVSGYSITSGYSITSDYAWNWIRQFPGNKLEWMGYITYSGITNYNPSLKSRVTISVDTSKNQFSLKLSSVTAADTATYYCVSGTYYFDYWGQGTTLTVSS
KN1IN5 VR1                QVQLQE S GP G LVKPSETLNLTCTVSGYSITSGYSITSDYAWNWIRQFPGNKLEWMGYITYSGITNYNPSLKSRVTISEDTSKNQFSLKLSSVTAADTATYYCVSGTYYFDYWGQGTTLTVSS
KN1IN5 QD2                DVQLQE S GP G LVKPSETLNLTCTVSGYSITSGYSITSDYAWNWIRQFPGNKLEWMGYITYSGITNYNPSLKSRVTISVDTSKNQFSLKLSSVTAADTATYYCVSGTYYFDYWGQGTTLTVSS
```

VL

```
Template emb|CAD43020.1|  DIVMTQ S PS S LSASVGDRVTITCRASQSISSYLNWYQQKRPGKAPKLLIYAASSLQSGVPSRFSGSGSGTDFTLTISSLQPEDFATYYCQQSYSTPRTFGGGTKVEIKRA
Germline IGKV1D-39*01      DIQMTQ S PS S LSASVGDRVTITCRASQSISSYLNWYQQKRPGKAPKLLIYAASSLQSGVPSRFSGSGSGTDFTLTISSLQPEDFATYYCQQSYSTP
NRY                       DIVMTQ S PS S LSASVGDRVTITCRASQSVSSDVAWFQQKPGKSPKPLIYYASNRYSGVPSRFSGSGSGTDFTLTISSLQAEDFAVYFCGQDYSSPRTFGGGTKLEIKRA
NRY d3                    DIVMTQ S PS S LSASVGDRVTITCRASQSVSSDVAWFQQKPGKSPKLLIYYASNRYSGVPSRFSGSGSGTDFTLTISSLQAEDFAVYFCGQDYSSPRTFGGGTKLEIKRA
```

| Combination | % human (out of 657 residues) |
|---|---|
| KN2/NRY | 93,6 |
| KN1IN5/NRY | 93,1 |
| KN1IN5/d3 | 93,5 |
| VR1/NRY | 93 |
| VR1/d3 | 93,3 |
| QD2/NRY | 93 |
| QD2/d3 | 93,3 |

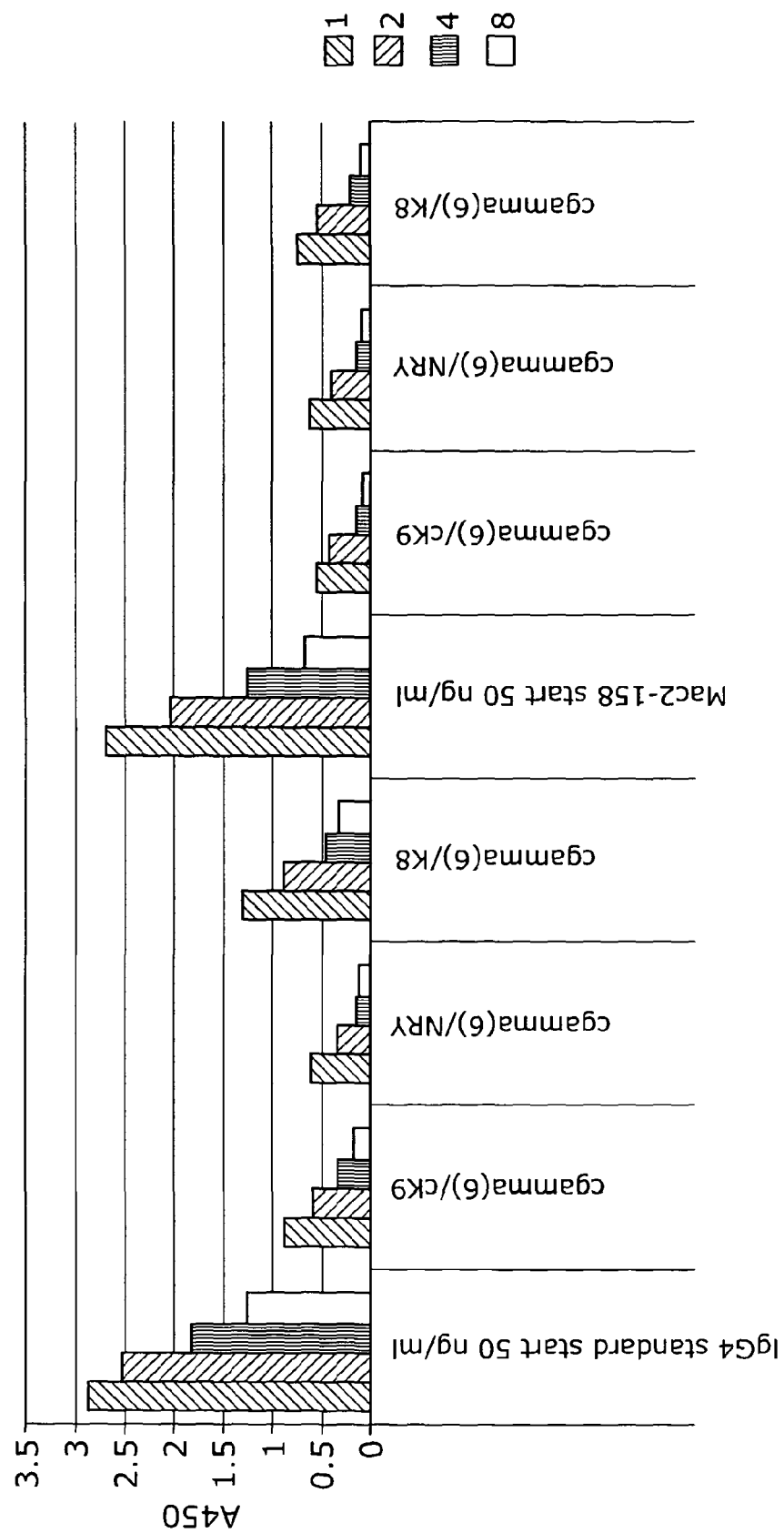

| Conjugate | total corticosteroid concentration | protein concentration | Ratio | free corticosteroid | free corticosteroid-HS |
|---|---|---|---|---|---|
| | mg/l | mg/ml | M/M | % | % |
| ED2-dexamethasone, | 11.11 | 1.08 | 3.71 | 0.18 | 1.77 |
| ED2-prednisolone-NHS | 32.70 | 1.65 | 5.70 | 2.69 | 0.7 |
| ED2-fluocinolone-acetonide-NHS | 30.24 | 2.13 | 6.80 | 2.81 | 0.7 |
| | | | | | |
| KN2NRY-dexamethasone-NHS | 13.94 | 0.89 | 5.85 | 0.48 | 1.65 |

FIG. 28D

| Conjugate | total corticosteroid concentration | protein concentration | Ratio | free dexamethasone | free MVCP-dexamethasone (estimated) |
|---|---|---|---|---|---|
| | mg/l | mg/ml | M/M | % | % |
| ED2-MVCP-dexamethasone | 37.13 | 1.73 | 8.17 | 0.33 | 1.00 |
| | | | | | |
| 3E10B10-MVCP-dexamethasone | 91.50 | 2.91 | 12.00 | 0.19 | 1.20 |
| | | | | | |
| 3E10B10-MVCP-dexamethasone, 50% DTT | 50.13 | 2.46 | 7.41 | 0.05 | 4.98 |
| | | | | | |
| KN2NRY-MVCP-dexamethasone | 126.45 | 3.60 | 13.12 | 2.21 | 4.84 |

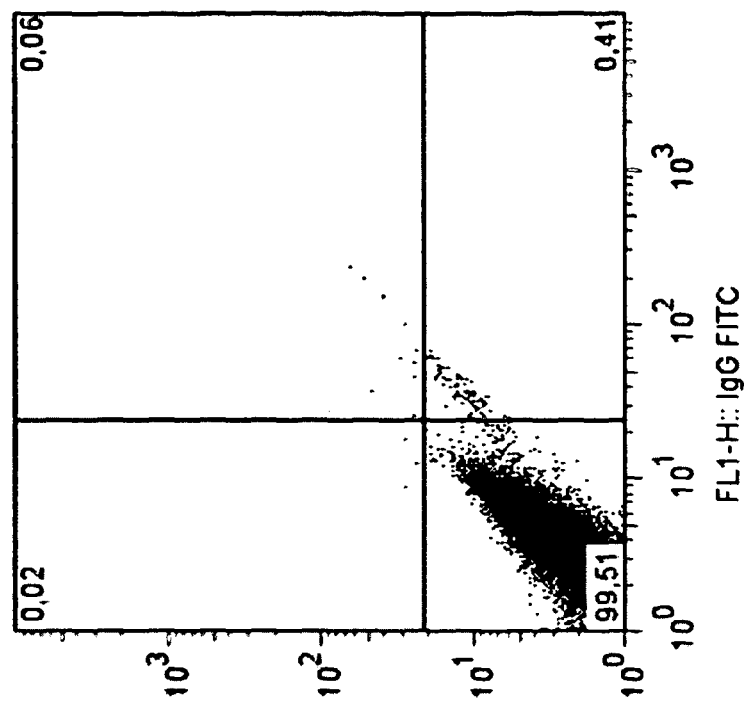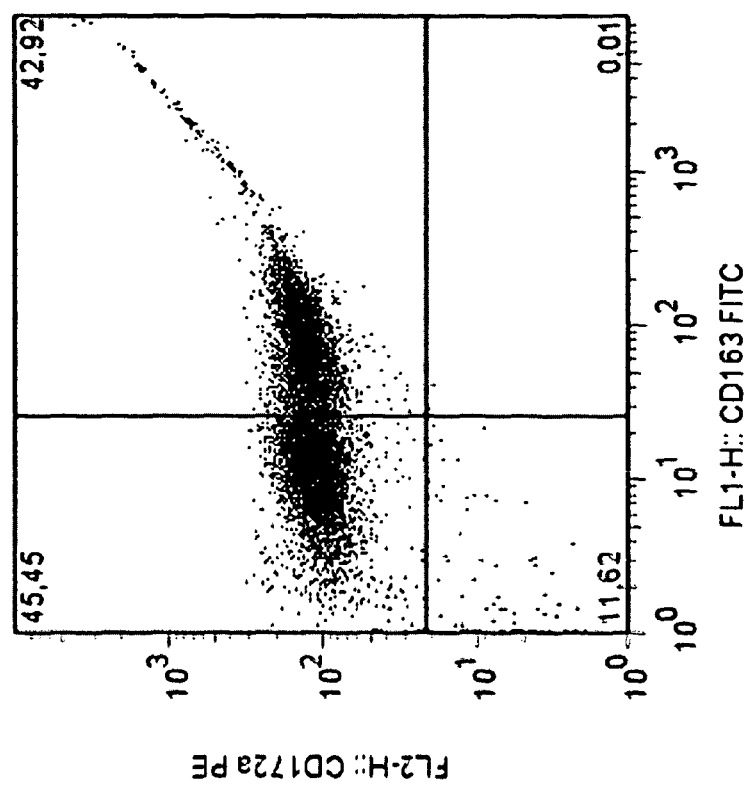
Figure 35

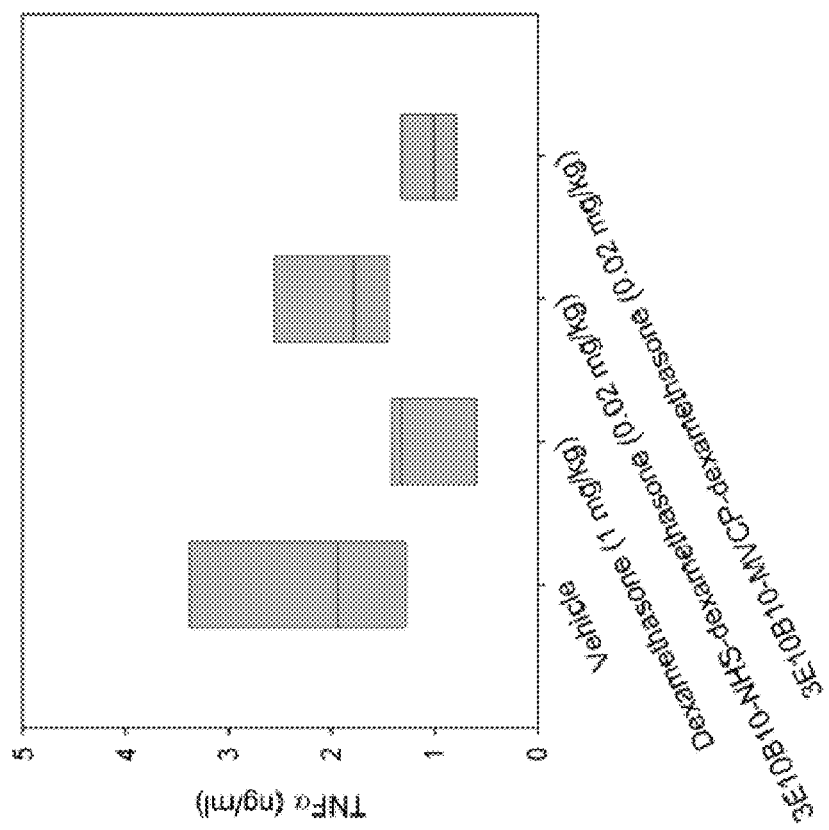
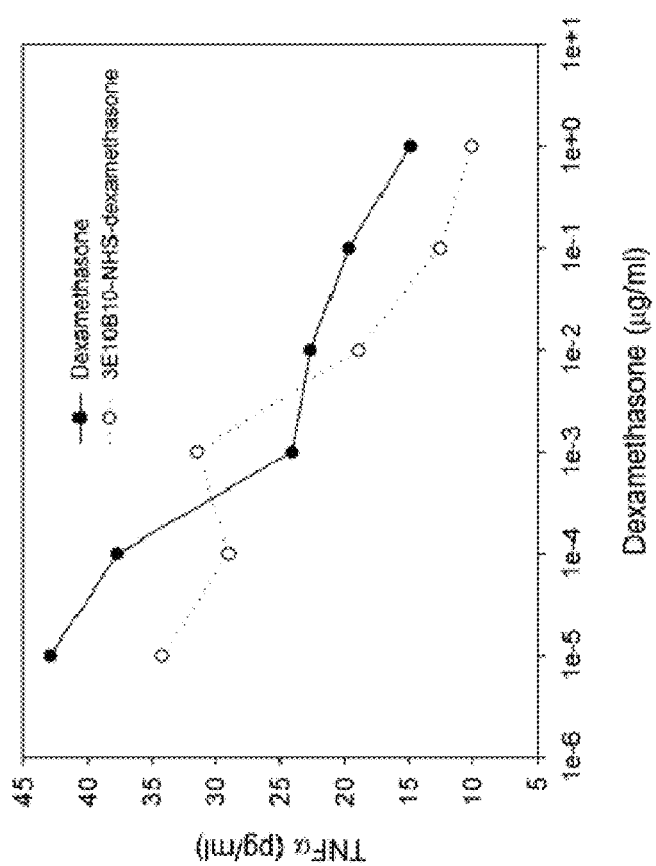
FIG. 42B
FIG. 42A

CD163 domæne 1 species differences

```
Human  LVDGENKCSGRVEVKVQEEWGTVCNNGWSMEAVSVICNQLGCPTAIKAPGWANSSAGSGRIWMDHVSCRGNESALWDCKHDGWGKHSNCTHQQDAGVTCS
Rhesus LVDGENKCSGRVEVKVQEEWGTVCNNGWSMEAVSVICNQLGCPTAIKATGWANSSAGSGRIWMDHVSCRGNESALWDCKHDGWGKHSNCTHQQDAGVTCS
Chimp  LVDGENKCSGRVEVKVQEEWGTVCNNGWSMEAVSVICNQLGCPTAIKATGWANSSAGSGRIWMDHVSCRGNESALWDCKHDGWGKHSNCTHQQDAGVTCS
Pig    LTGGENKCSGRVEVKVQEEWGTVCNNGWDMDVVSVVCRQLGCPTAIKATGWANFSAGSGRIWMDHVSCRGNESALWDCKHDGWGKH-NCTHQQDAGVTCS
Dog    LTDGEDNCSGRVEVKVQEEWGTVCNNGWGMDEVSVICRQLGCPTAIKAAGWANSRAGSGRIWMDHVSCRGNESALWDCKHDGWGKH-NCSHQQDAGVTCS
Rat    LAGGENNCSGRVELKIHEKWGTVCGNGWSMNEVSVVCQQLGCPTLIKAPGWANASAGSGDIWMDKVSCTGNESALWDCKHEGWGKH-NCTHEQDAGVTCA
Murine LAGGENNCSGRVELKIH KWGTVCSNGWSMNEVSVVCQQLGCPTSIKALGWANSSAGSGYIWMDKVSCTGNESALWDCKHDGWGKH-NCTHEKDAGVTCS
```

Sequence in red is the potentially most interesting with regard to mutating

Human CD163, dom 1-9 alignement,

```
dom1 LRLVDGEN--KCSGRVEVKVQEEWGTVCNNGWSMEAVSVICNQLGCPTAIKAPGWANSSAGSGRIWMDHVSCRGNESALWDCKHDGWGKHSNCTHQQDAGVTCS
dom2 MRLTRGGN--MCSGRIEIKFQGRWGTVCDDNFNIDHASVICRQLECGSAVSFSGSSNFGEGSGPIWFDDLICNGNESALWNCKHQGWGKHN-CDHAEDAGVICS
dom3 LRLVDGVT--ECSGRLEVRFQGEWGTICDDGWDSYDAAVACKQLGCPTAVTAIGRVNASKGFGHIWLDSVSCQGHEPAVWQCKHHEWGKHY-CNHNEDAGVTCS
dom4 LRLRGGGS--RCAGTVEVEIQRLLGKVCDRGWGLKEADVVCRQLGCGSALKTSYQVYSKIQATNTWLFLSSCNGNETSLWDCKNWQWGGLT-CDHYEEAKITCS
dom5  RLVGGDI--PCSGRVEVKHGDTWGSICDSDFSLEAASVLCRELQCGTVVSILGGAHFGEGNGQIWAEEFQCEGHESHLSLCPVAPRPEGT-CSHSRDVGVVCS
dom6 IRLVNGKT--PCEGRVELKTLGAWGSLCNSHWDIEDAHVLCQQLKCGVALSTPGGARFGKGNGQIWRHMFHCTGTEQHMGDCPVTALGASL-CPSEQVASVICS
dom7 LRLVNGGG--RCAGRVEIYHEGSWGTICDDSWDLSDAHVVCRQLGCGEAINATGSAHFGEGTGPIWLDEMKCNGKESRIWQCHSHGWGQQN-CRHKEDAGVICS
dom8 LRLTSEASREACAGRLEVFYNGAWGTVGKSSMSETTVGVVCRQLGCADKGKINPASLDKAMSIPMWVDNVQCPKGPDTLWQCPSSPWEKRL-ASPSEETWITC
dom9 IRLQEGPT--SCSGRVEIWHGGSWGTVCDDSWDLDDAQVVCQQLGCGPALKAFKEAEFGQGTGPIWLNEVKCKGNESSLWDCPARRWGHSE-CGHKEDAAVNCT
```

MOST IDENTICAL ALIGNED:

```
dom1 LRLVDGENKCSGRVEVKVQEEWGTVCNNGWSMEAVSVICNQLGCPTAIKAPGWANSSAGSGRIWMDHVSCRGNESALWDCKHDGWGKHSNCTHQQDAGVTCS
dom3 LRLVDGVTECSGRLEVRFQGEWGTICDDGWDSYDAAVACKQLGCPTAVTAIGRVNASKGFGHIWLDSVSCQGHEPAVWQCKHHEWGKHY-CNHNEDAGVTCS
dom2 MRLTRGGNMCSGRIEIKFQGRWGTVCDDNFNIDHASVICRQLECGSAVSFSGSSNFGEGSGPIWFDDLICNGNESALWNCKHQGWGKHN-CDHAEDAGVICS
```

ONLY THE 2 MOST IDENTICAL

```
dom1 LRLVDGENKCSGRVEVKVQEEWGTVCNNGWSMEAVSVICNQLGCPTAIKAPGWANSSAGSGRIWMDHVSCRGNESALWDCKHDGWGKHSNCTHQQDAGVTCS
dom3 LRLVDGVTECSGRLEVRFQGEWGTICDDGWDSYDAAVACKQLGCPTAVTAIGRVNASKGFGHIWLDSVSCQGHEPAVWQCKHHEWGKHY-CNHNEDAGVTCS
```

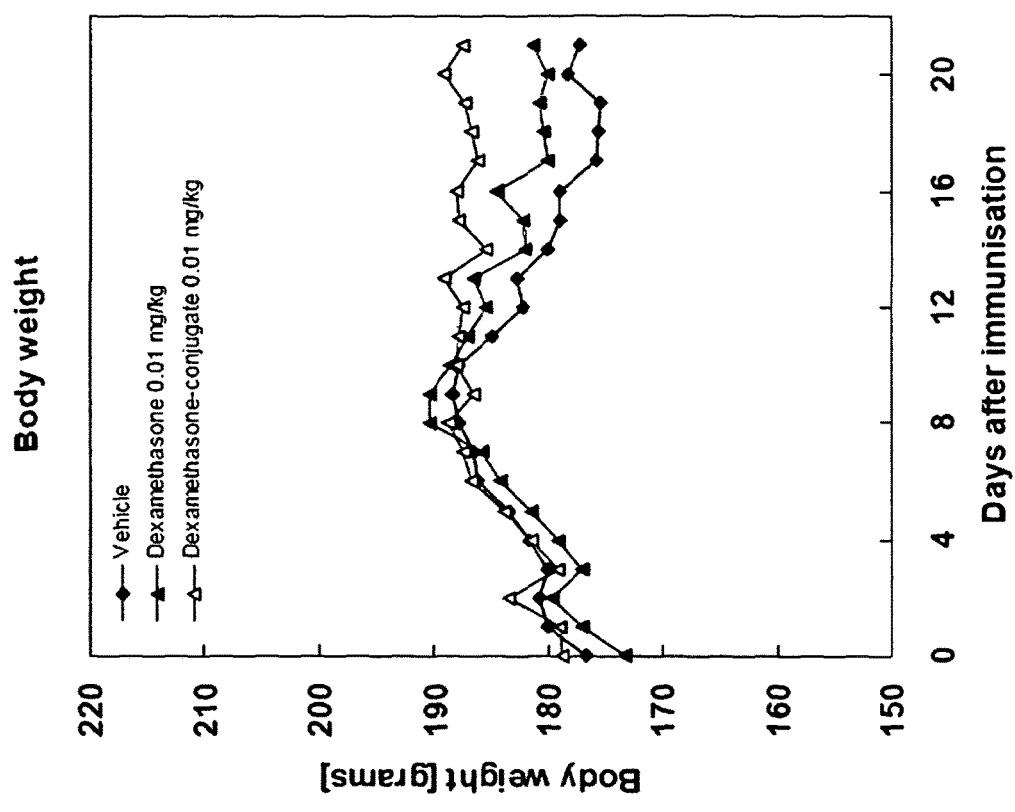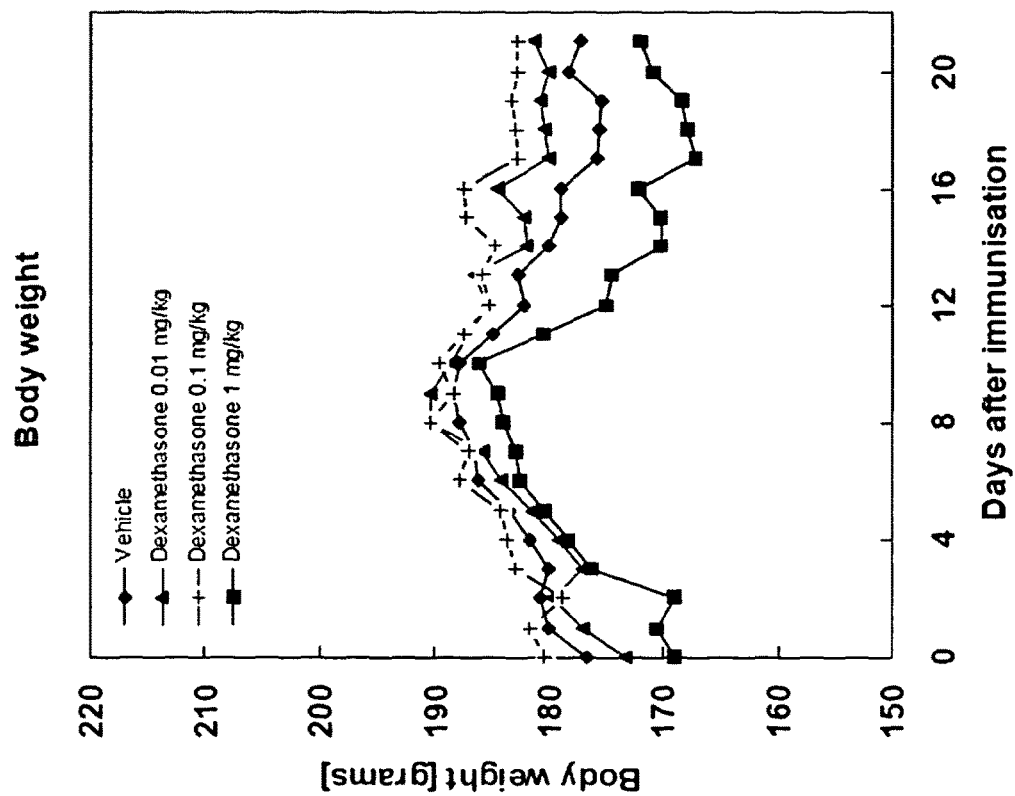
Figure 47

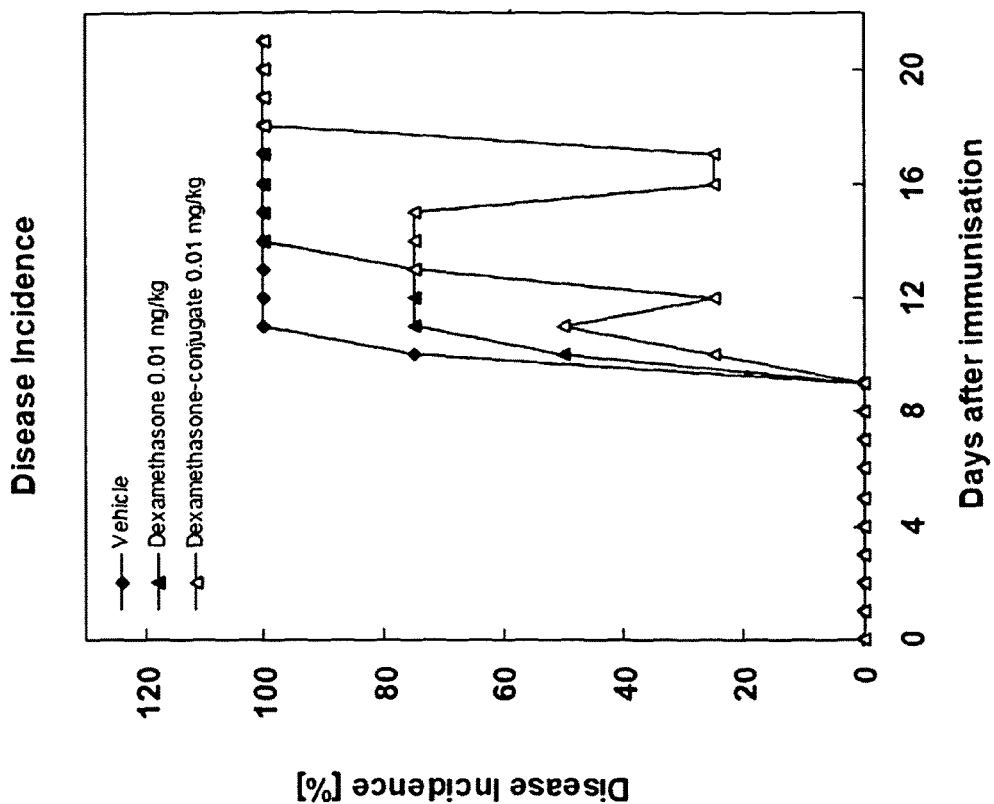
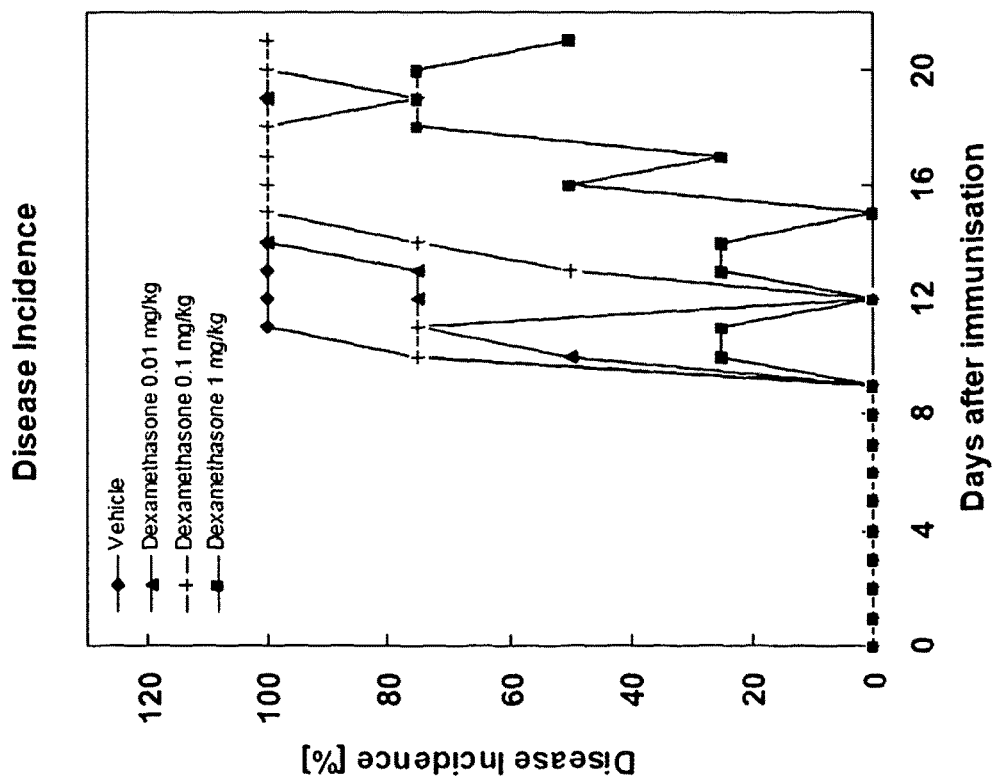
Figure 49

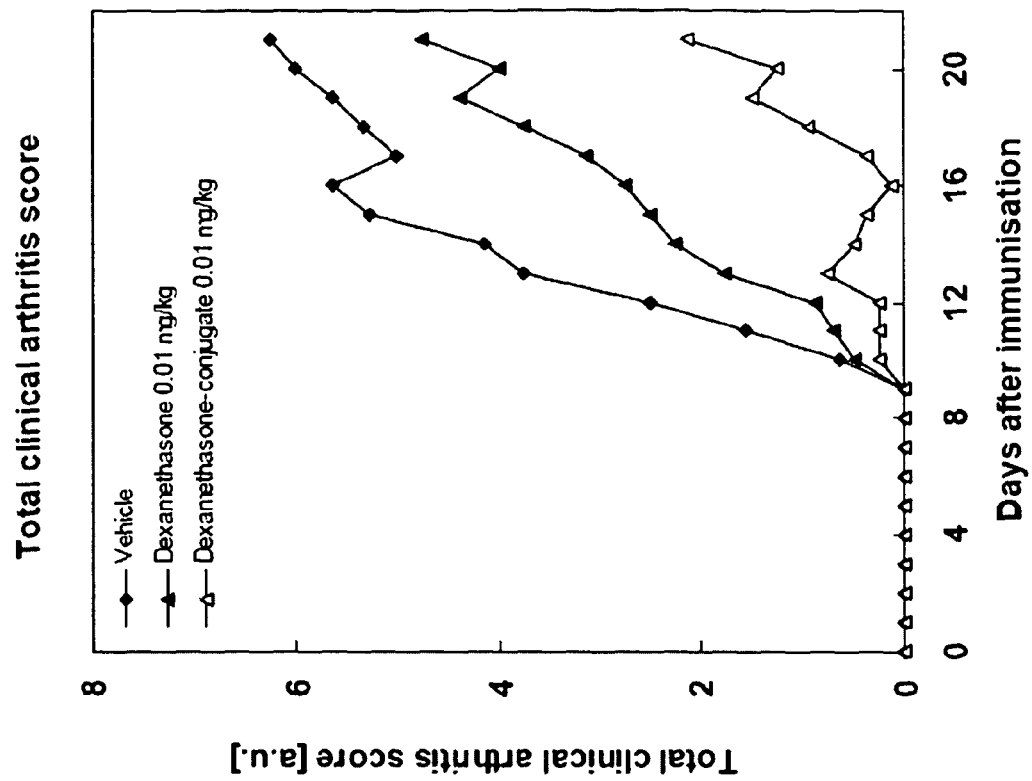
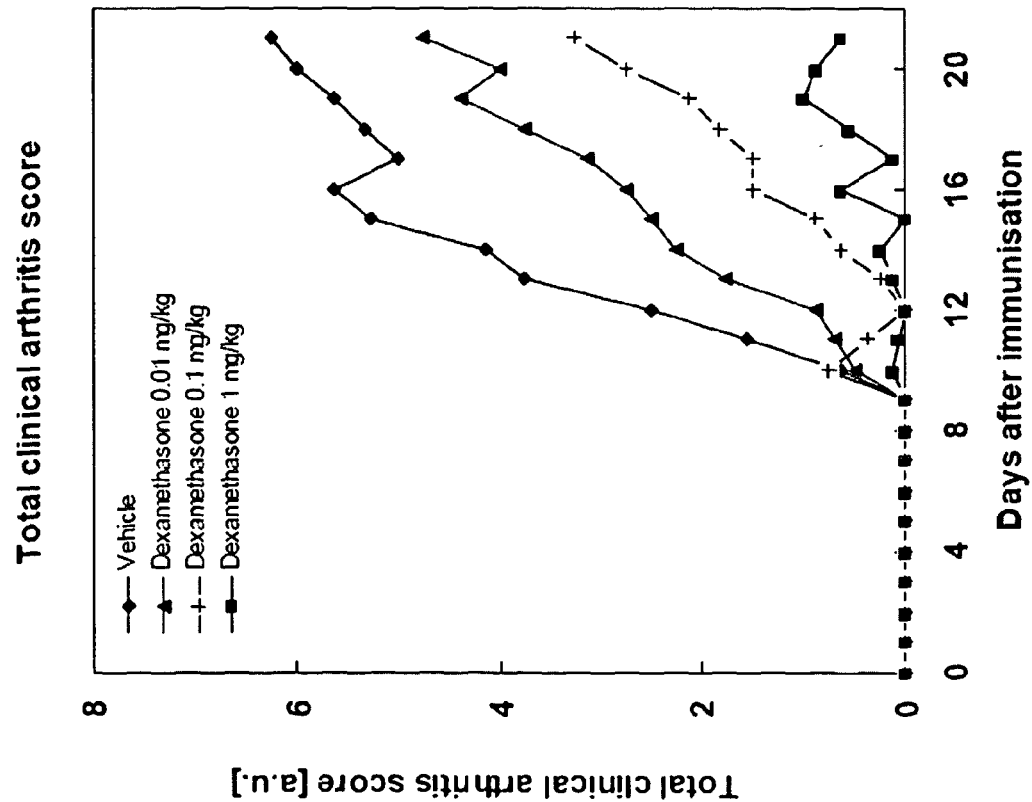
Figure 50

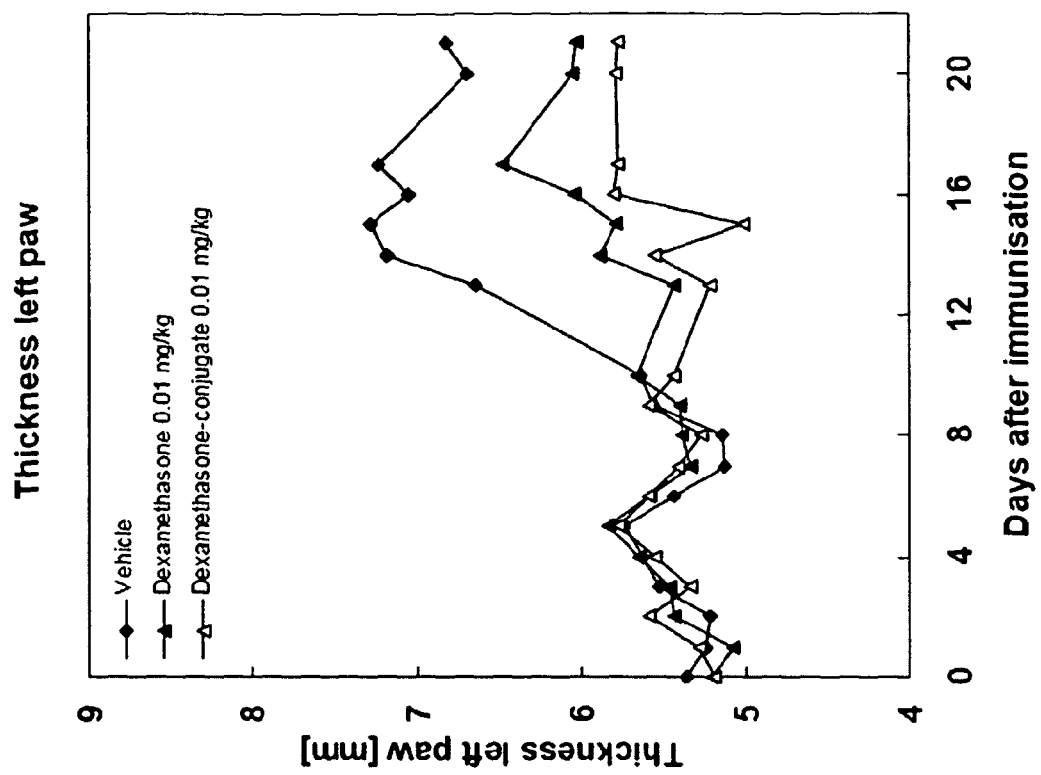
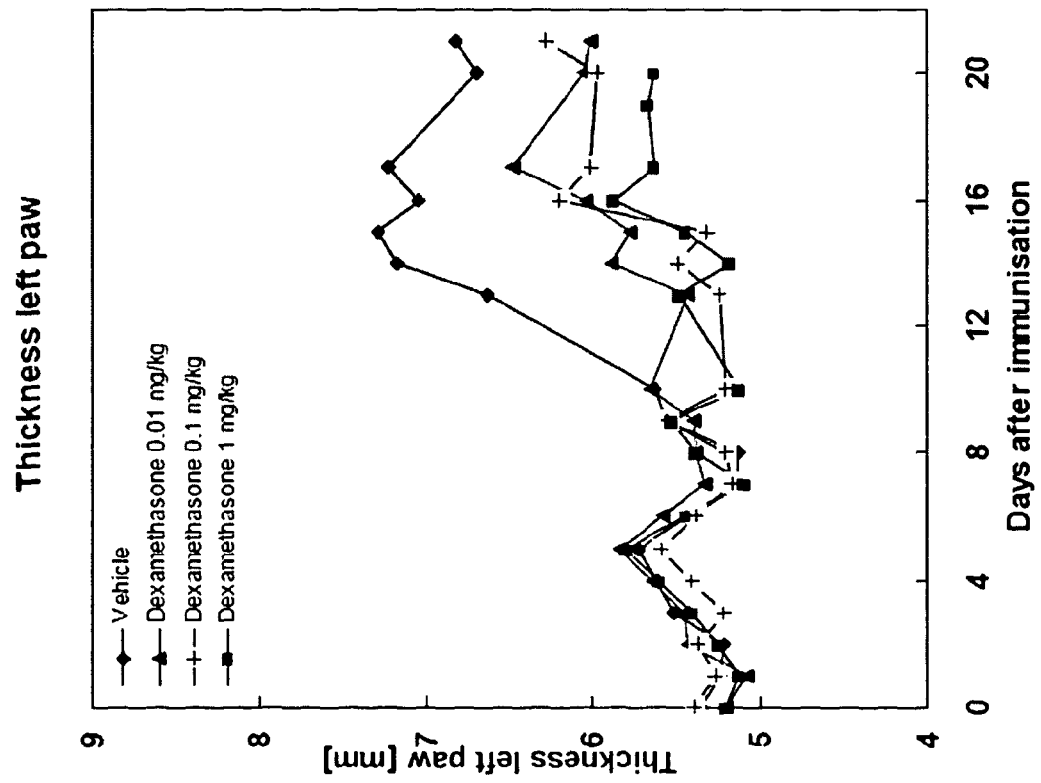
Figure 52

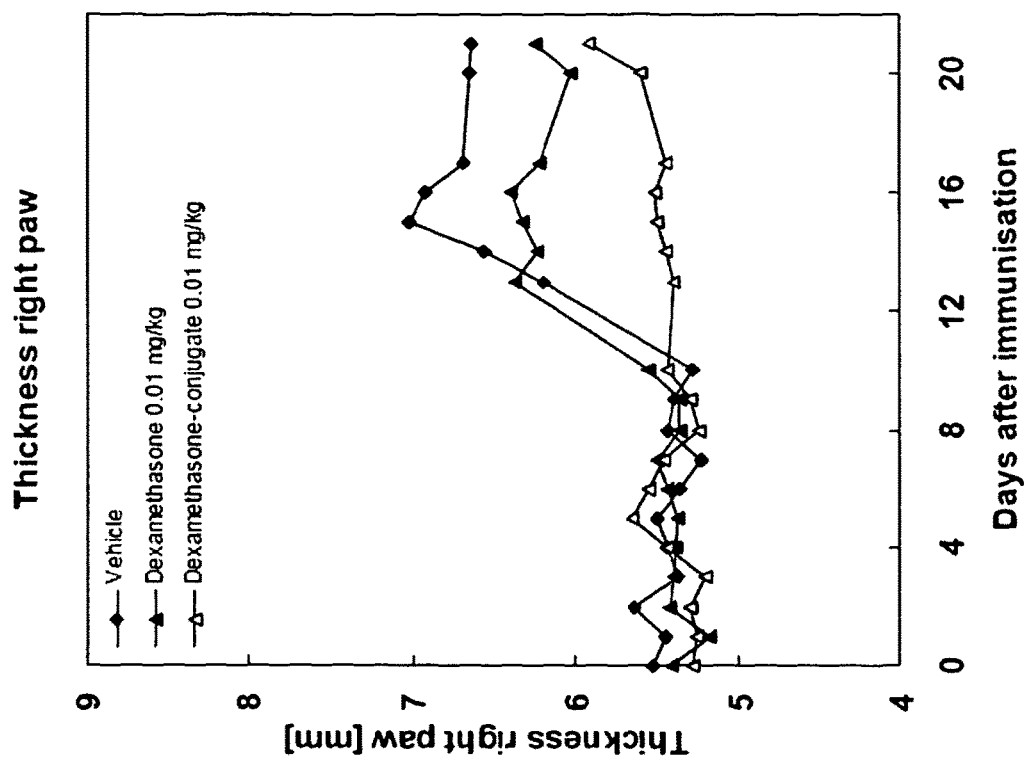
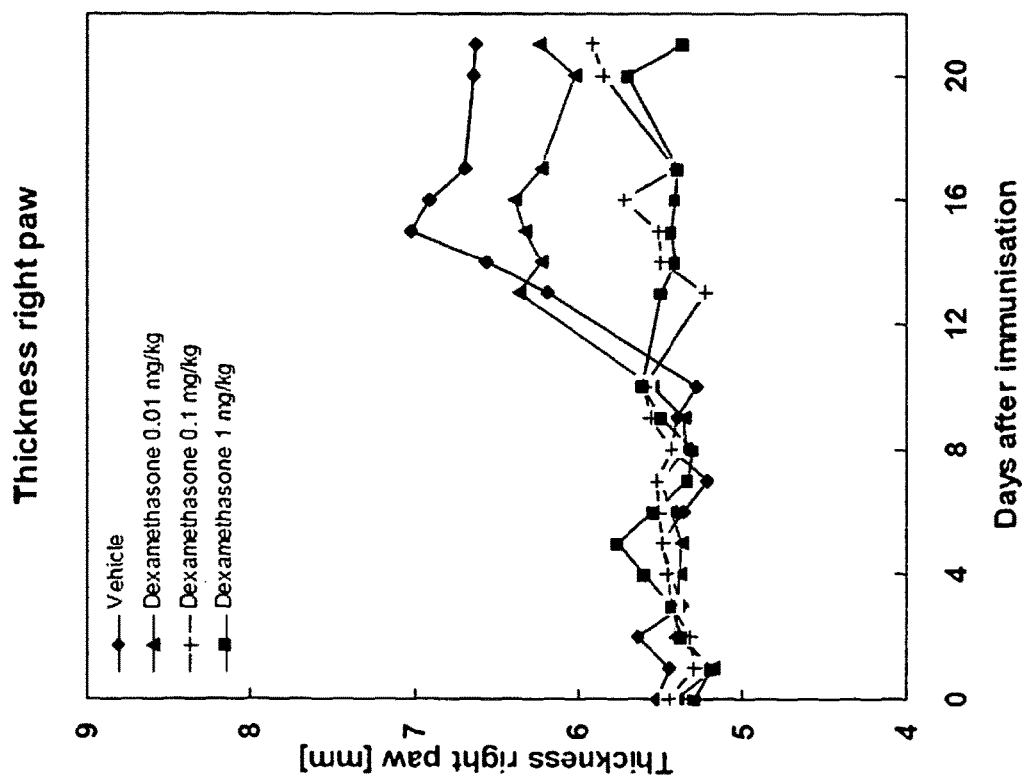
Figure 54

Figure 56:
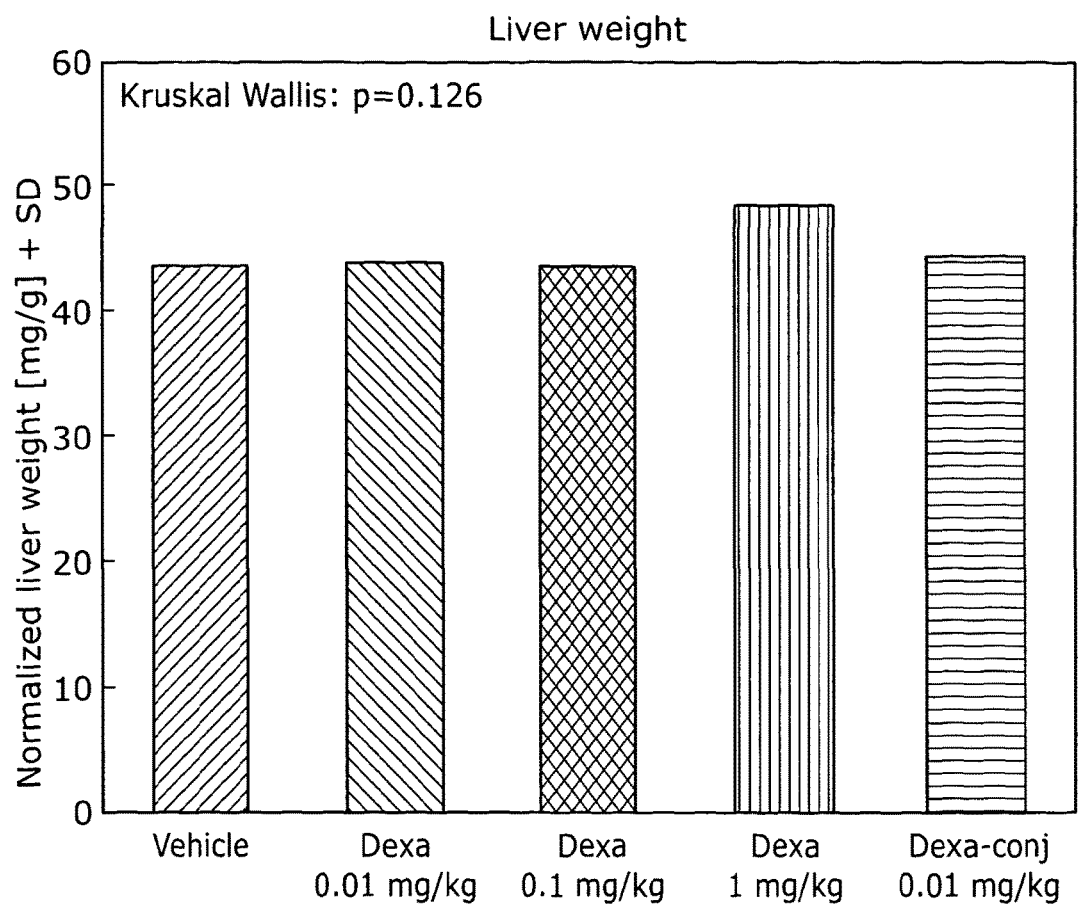

Figure 56
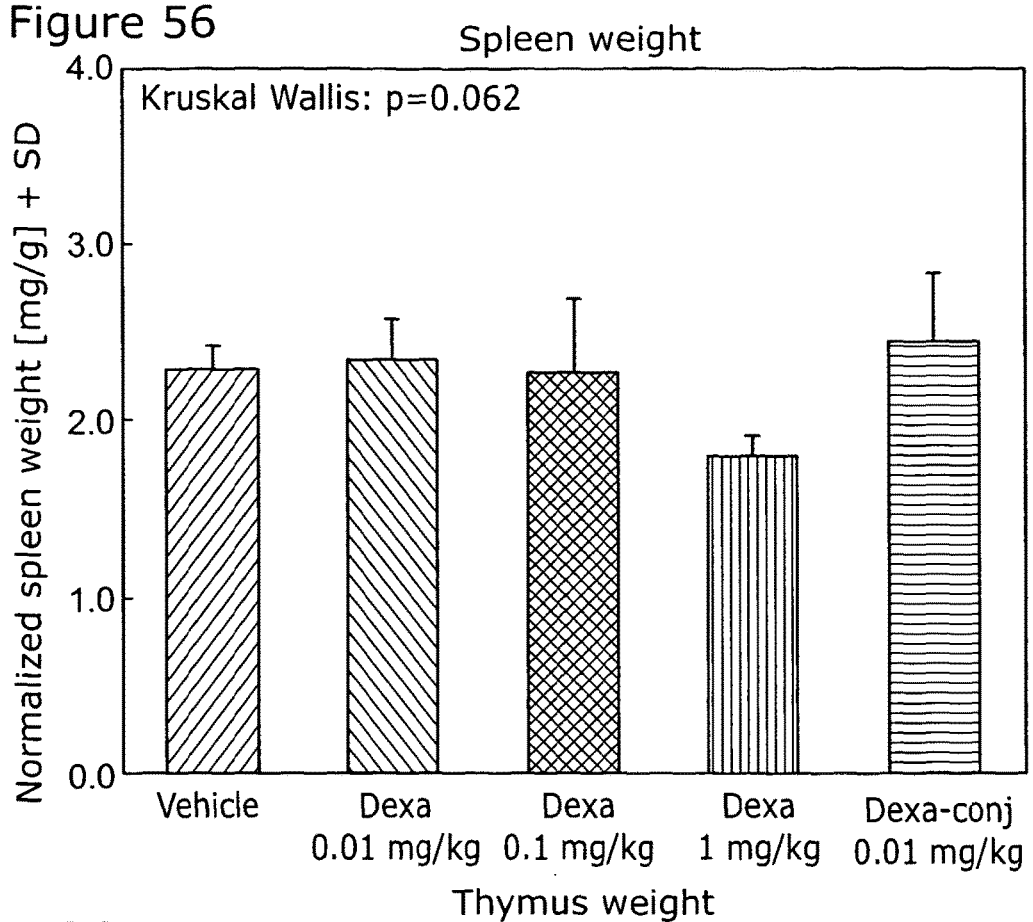
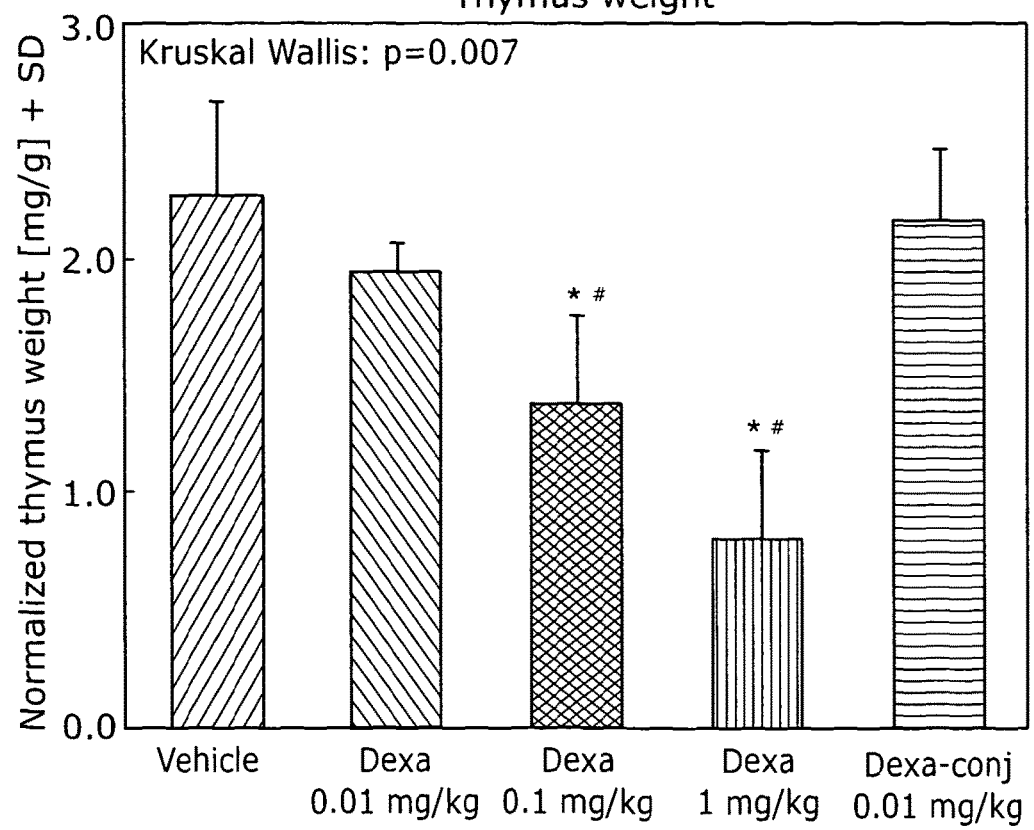

AGENTS, USES AND METHODS

The present application is §371 application of PCT/GB2010/001827, filed Sep. 29, 2010, which claims priority to GB Application No. 0917044.0, filed Sep. 29, 2009. The entire disclosure of each of the foregoing applications is incorporated by reference herein.

The present invention relates to agents comprising a binding moiety with binding specificity for SRCR domain 1 of the CD163 receptor, for use in medicine. The invention also relates to methods, uses, kits and compositions comprising such agents.

CD163 is a membrane receptor molecule expressed on macrophages, which functions as an endocytic receptor for haemoglobin-haptoglobin-complexes. By this physiologically very important function, CD163 each day takes up more than 1 g of haemoglobin, and the protein therefore is probably the most highly expressed receptor on macrophages.

Macrophages are part of the innate immune defence and play a central role in many infectious, autoimmune, and malignant diseases.

In autoimmune/inflammatory disease such as Rheumatoid Arthritis, macrophages are the main source of inflammatory molecules such as TNF-alpha, known to be of crucial importance in disease progression. In many infectious diseases such as TB and HIV, macrophages harbour the infectious agent. A few malignant diseases have their origin in cells of the monocytic/macrophage lineage such as histiocytic sarcoma.

Direct targeting of drugs to macrophages (for example, to down-regulate production of inflammatory cytokines, to kill intracellular organisms, or to kill malignant cells) may therefore have significant impact on certain diseases without influencing other cells in the body. The targeting may therefore increase the therapeutic index of the drug.

In a first aspect, the invention provides an agent comprising a binding moiety with binding specificity for SRCR domain 1 of the CD163 receptor, for use in medicine.

The high expression and the almost exclusive expression on macrophages makes CD163 an ideal target when directing drugs specifically to macrophages. The endocytic properties of CD163 furthermore ensures that drugs linking to the receptor will be taken up by the cell and carried inside the cell to the lysosomes.

CD163 is a scavenging receptor consisting of nine extracellular scavenger receptor cysteine-rich (SRCR) type B domains. It mediates the clearance of the haptoglobin-hemoglobin (Hp-Hb) complexes formed when hemoglobin is librated to the circulation during intravascular hemolysis is involved in regulation of inflammatory processes. CD163 is considered to be expressed exclusively on the surface of the monocytic lineage. It is expressed by resident monocytes in the circulation and upregulated during maturation to macrophages. It is highly expressed on tissue-resident macrophages, as well as on alternatively activated macrophages (M2), and TIE2+ macrophages, and has been shown to be expressed by a $CD34^+$ subpopulation of hematopoietic stem/progenitor cells and proposed to be expressed on a subset of myeloid dendritic cells.

By "SRCR domain 1", we mean domain number 1 of the nine extracellular scavenger receptor cysteine-rich (SRCR) type B domains of CD 163, according to the well known molecular characterisation of that molecule.

By "an agent" we include any purified or isolated natural or chemically-synthesised entity comprising one or more molecule. Preferably, the term includes one more polypeptide and/or one or more small chemical molecule, wherein said polypeptide and/or small chemical molecule may or may not be modified by the ionic and/or hydrophobic and/or covalent addition of chemical groups.

By "binding moiety" we include a region or regions of the agent of the invention capable of reversibly and/or irreversibly associating with a region or regions of another molecule or molecules by covalent and/or ionic interaction.

Alternatively, the agent may be produced as a fusion compound by recombinant DNA techniques whereby a length of DNA comprises respective regions encoding the two moieties of the agent of the invention either adjacent one another or separated by a region encoding a linker peptide which does not destroy the desired properties of the agent. Conceivably, the two portions of the agent may overlap wholly or partly.

By "binding specificity" for SRCR domain 1 of the CD163 receptor, we mean a binding moiety which is capable of binding to SRCR domain 1 of the CD163 receptor. It is preferred that the binding moiety is capable of binding to SRCR domain 1 of the CD163 receptor in vivo, i.e. under the physiological conditions in which a CD163 receptor exists inside the body. Such binding specificity may be determined by methods well known in the art, such as e.g. ELISA, immunohistochemistry, immunoprecipitation, Western blots and flow cytometry using transfected cells expressing SRCR domain 1 of the CD163 receptor (see the accompanying Examples).

In another embodiment, the binding moiety is capable of binding to SRCR domain 1 of the CD163 receptor selectively. By "capable of binding selectively" we include such antibody-derived binding moieties which bind at least 10-fold more strongly to SRCR domain 1 of the CD163 receptor than to another protein; for example at least 50-fold more strongly or at least 100-fold more strongly. The binding moiety may be capable of binding selectively to SRCR domain 1 of the CD163 receptor under physiological conditions, e.g. in vivo. Suitable methods for measuring relative binding strengths include immunoassays, for example where the binding moiety is an antibody (see Harlow & Lane, "Antibodies: A Laboratory", Cold Spring Harbor Laboratory Press, New York, which is incorporated herein by reference). Alternatively, binding may be assessed using competitive assays or using Biacore® analysis (Biacore International AB, Sweden).

In a further embodiment, the antibody or antigen-binding fragment, or variant, fusion or derivative thereof, binds exclusively to an SRCR domain 1 of the CD163 receptor.

Preferably, the invention provides an agent wherein the binding moiety with specificity for SRCR domain 1 of the CD163 receptor is selected from the group comprising or consisting of:
- (a) an antibody or an antigen-binding fragment thereof, or a variant, fusion or derivative of said antibody or an antigen-binding fragment, or a fusion of a said variant or derivative thereof, which retains the binding specificity for SRCR domain 1 of the CD163 receptor;
- (b) antibody mimics (for example, based on non-antibody scaffolds);
- (c) RNA aptamers;
- (d) small molecules; and
- (e) CovX-bodies.

CovX-Bodies are created by covalently joining a pharmacophore via a linker to the binding site of a specially-designed antibody, effectively reprogramming the antibody (Tryder et al., 2007, *Bioorg. Med. Chem. Lett.*, 17:501-6). The result is a new class of chemical entities that is formed where each component contributes desirable traits to the intact CovX-Body—in particular, the entity has the biologic actions of the peptide and the extended half-life of the antibody.

Preferably, the CD163 receptor is a human protein, but it may be from any mammal such as a domesticated mammal (preferably of agricultural or commercial significance including a horse, pig, cow, sheep, dog and cat). By "mammalian protein" we include any protein found in, derived from, and/or isolated from, one or more cells of a mammal; for example, the term "human protein" includes a protein found in, derived from, and/or isolated from one or more cells of a human.

Preferably, the CD163 receptor is selected from the group of proteins defined by database accession nos. CAB45233; AAY99762; AAH51281; EAW8862; EAW8863; EAW8864; EAW8865; EAW8866; NP_004235; NP_98161; Swiss-Prot. Q86VB7.1. In a preferred embodiment the CD163 receptor is a human CD163 receptor.

Database Accession no. AAH51281, NP 004325 and Swiss-Prot. Q86VB7.1:

```
>sp|Q86VB7|C163A_HUMAN Scavenger receptor cysteine-
rich type 1
protein M130 OS = Homo sapiens GN = CD163 PE = 1 SV = 1
                                                   [SEQ ID NO: 28]
MSKLRMVLLEDSGSADFRRHFVNLSPFTITVVLLLSACFVTSSLGGTDKELRLVDGENKC

SGRVEVKVQEEWGTVCNNGWSMEAVSVICNQLGCPTAIKAPGWANSSAGSGRIWMDHVSC

RGNESALWDCKHDGWGKHSNCTHQQDAGVTCSDGSNLEMRLTRGGNMCSGRIEIKFQGRW

GTVCDDNFNIDHASVICRQLECGSAVSFSGSSNFGEGSGPIWFDDLICNGNESALWNCKH

QGWGKHNCDHAEDAGVICSKGADLSLRLVDGVTECSGRLEVRFQGEWGTICDDGWDSYDA

AVACKQLGCPTAVTAIGRVNASKGFGHIWLDSVSCQGHEPAVWQCKHHEWGKHYCNHNED

AGVTCSDGSDLELRLRGGGSRCAGTVEVEIQRLLGKVCDRGWGLKEADVVCRQLGCGSAL

KTSYQVYSKIQATNTWLFLSSCNGNETSLWDCKNWQWGGLTCDHYEEAKITCSAHREPRL

VGGDIPCSGRVEVKHGDTWGSICDSDFSLEAASVLCRELQCGTVVSILGGAHFGEGNGQI

WAEEFQCEGHESHLSLCPVAPRPEGTCSHSRDVGVVCSRYTEIRLVNGKTPCEGRVELKT

LGAWGSLCNSHWDIEDAHVLCQQLKCGVALSTPGGARFGKGNGQIWRHMFHCTGTEQHMG

DCPVTALGASLCPSEQVASVICSGNQSQTLSSCNSSSLGPTRPTIPEESAVACIESGQLR

LVNGGGRCAGRVEIYHEGSWGTICDDSWDLSDAHVVCRQLGCGEAINATGSAHFGEGTGP

IWLDEMKCNGKESRIWQCHSHGWGQQNCRHKEDAGVICSEFMSLRLTSEASREACAGRLE

VFYNGAWGTVGKSSMSETTVGVVCRQLGCADKGKINPASLDKAMSIPMWVDNVQCPKGPD

TLWQCPSSPWEKRLASPSEETWITCDNKIRLQEGPTSCSGRVEIWHGGSWGTVCDDSWDL

DDAQVVCQQLGCGPALKAFKEAEFGQGTGPIWLNEVKCKGNESSLWDCPARRWGHSECGH

KEDAAVNCTDISVQKTPQKATTGRSSRQSSFIAVGILGVVLLAIFVALFFLTKKRRQRQR

LAVSSRGENLVHQIQYREMNSCLNADDLDLMNSSENSHESADFSAAELISVSKFLPISGM

EKEAILSHTEKENGNL
```

Database Accession no. AAY99762; CAB45233, NP 98161 and Swiss-Prot. Q86VB7.2:

```
>sp|Q86VB7-3|C163A_HUMAN Isoform Short tail variant of Scaven-
ger
receptor cysteine-rich type 1 protein M130 OS = Homo sapiens
GN = CD163
                                                   [SEQ ID NO: 29]
MSKLRMVLLEDSGSADFRRHFVNLSPFTITVVLLLSACFVTSSLGGTDKELRLVDGENKC

SGRVEVKVQEEWGTVCNNGWSMEAVSVICNQLGCPTAIKAPGWANSSAGSGRIWMDHVSC

RGNESALWDCKHDGWGKHSNCTHQQDAGVTCSDGSNLEMRLTRGGNMCSGRIEIKFQGRW

GTVCDDNFNIDHASVICRQLECGSAVSFSGSSNFGEGSGPIWFDDLICNGNESALWNCKH

QGWGKHNCDHAEDAGVICSKGADLSLRLVDGVTECSGRLEVRFQGEWGTICDDGWDSYDA

AVACKQLGCPTAVTAIGRVNASKGFGHIWLDSVSCQGHEPAVWQCKHHEWGKHYCNHNED

AGVTCSDGSDLELRLRGGGSRCAGTVEVEIQRLLGKVCDRGWGLKEADVVCRQLGCGSAL
```

-continued

KTSYQVYSKIQATNTWLFLSSCNGNETSLWDCKNWQWGGLTCDHYEEAKITCSAHREPRL

VGGDIPCSGRVEVKHGDTWGSICDSDFSLEAASVLCRELQCGTVVSILGGAHFGEGNGQI

WAEEFQCEGHESHLSLCPVAPRPEGTCSHSRDVGVVCSRYTEIRLVNGKTPCEGRVELKT

LGAWGSLCNSHWDIEDAHVLCQQLKCGVALSTPGGARFGKGNGQIWRHMFHCTGTEQHMG

DCPVTALGASLCPSEQVASVICSGNQSQTLSSCNSSSLGPTRPTIPEESAVACIESGQLR

LVNGGGRCAGRVEIYHEGSWGTICDDSWDLSDAHVVCRQLGCGEAINATGSAHFGEGTGP

IWLDEMKCNGKESRIWQCHSHGWGQQNCRHKEDAGVICSEFMSLRLTSEASREACAGRLE

VFYNGAWGTVGKSSMSETTVGVVCRQLGCADKGKINPASLDKAMSIPMWVDNVQCPKGPD

TLWQCPSSPWEKRLASPSEETWITCDNKIRLQEGPTSCSGRVEIWHGGSWGTVCDDSWDL

DDAQVVCQQLGCGPALKAFKEAEFGQGTGPIWLNEVKCKGNESSLWDCPARRWGHSECGH

KEDAAVNCTDISVQKTPQKATTGRSSRQSSFIAVGILGVVLLAIFVALFFLTKKRRQRQR

LAVSSRGENLVHQIQYREMNSCLNADDLDLMNSSGGHSEPH

Database Accession no. Swiss-Prot. Q86VB7.3

>sp|Q86VB7-2|C163A_HUMAN Isoform Long tail variant 2 of Scavenger receptor cysteine-rich type 1 protein M130 OS = Homo sapiens GN = CD163

[SEQ ID NO: 30]

MSKLRMVLLEDSGSADFRRHFVNLSPFTITVVLLLSACFVTSSLGGTDKELRLVDGENKC

SGRVEVKVQEEWGTVCNNGWSMEAVSVICNQLGCPTAIKAPGWANSSAGSGRIWMDHVSC

RGNESALWDCKHDGWGKHSNCTHQQDAGVTCSDGSNLEMRLTRGGNMCSGRIEIKFQGRW

GTVCDDNFNIDHASVICRQLECGSAVSFSGSSNFGEGSGPIWFDDLICNGNESALWNCKH

QGWGKHNCDHAEDAGVICSKGADLSLRLVDGVTECSGRLEVRFQGEWGTICDDGWDSYDA

AVACKQLGCPTAVTAIGRVNASKGFGHIWLDSVSCQGHEPAVWQCKHHEWGKHYCNHNED

AGVTCSDGSDLELRLRGGGSRCAGTVEVEIQRLLGKVCDRGWGLKEADVVCRQLGCGSAL

KTSYQVYSKIQATNTWLFLSSCNGNETSLWDCKNWQWGGLTCDHYEEAKITCSAHREPRL

VGGDIPCSGRVEVKHGDTWGSICDSDFSLEAASVLCRELQCGTVVSILGGAHFGEGNGQI

WAEEFQCEGHESHLSLCPVAPRPEGTCSHSRDVGVVCSRYTEIRLVNGKTPCEGRVELKT

LGAWGSLCNSHWDIEDAHVLCQQLKCGVALSTPGGARFGKGNGQIWRHMFHCTGTEQHMG

DCPVTALGASLCPSEQVASVICSGNQSQTLSSCNSSSLGPTRPTIPEESAVACIESGQLR

LVNGGGRCAGRVEIYHEGSWGTICDDSWDLSDAHVVCRQLGCGEAINATGSAHFGEGTGP

IWLDEMKCNGKESRIWQCHSHGWGQQNCRHKEDAGVICSEFMSLRLTSEASREACAGRLE

VFYNGAWGTVGKSSMSETTVGVVCRQLGCADKGKINPASLDKAMSIPMWVDNVQCPKGPD

TLWQCPSSPWEKRLASPSEETWITCDNKIRLQEGPTSCSGRVEIWHGGSWGTVCDDSWDL

DDAQVVCQQLGCGPALKAFKEAEFGQGTGPIWLNEVKCKGNESSLWDCPARRWGHSECGH

KEDAAVNCTDISVQKTPQKATTGRSSRQSSFIAVGILGVVLLAIFVALFFLTKKRRQRQR

LAVSSRGENLVHQIQYREMNSCLNADDLDLMNSSGLWVLGGSIAQGFRSVAAVEAQTFYF

DKQLKKSKNVIGSLDAYNGQE

Database Accession no. Swiss-Prot.Q86VB7.3

```
>sp|Q86VB7-4|C163A_HUMAN Isoform 4 of Scavenger receptor
cysteine-rich type 1 protein M130 OS = Homo sapiens GN = CD163
                                              [SEQ ID NO: 31]
MSKLRMVLLEDSGSADFRRHFVNLSPFTITVVLLLSACFVTSSLGGTDKELRLVDGENKC

SGRVEVKVQEEWGTVCNNGWSMEAVSVICNQLGCPTAIKAPGWANSSAGSGRIWMDHVSC

RGNESALWDCKHDGWGKHSNCTHQQDAGVTCSDGSNLEMRLTRGGNMCSGRIEIKFQGRW

GTVCDDNFNIDHASVICRQLECGSAVSFSGSSNFGEGSGPIWFDDLICNGNESALWNCKH

QGWGKHNCDHAEDAGVICSKGADLSLRLVDGVTECSGRLEVREQGEWGTICDDGWDSYDA

AVACKQLGCPTAVTAIGRVNASKGFGHIWLDSVSCQGHEPAVWQCKHHEWGKHYCNHNED

AGVTCSDGSDLELRLRGGGSRCAGTVEVEIQRLLGKVCDRGWGLKEADVVCRQLGCGSAL

KTSYQVYSKIQATNTWLFLSSCNGNETSLWDCKNWQWGGLTCDHYEEAKITCSAHREPRL

VGGDIPCSGRVEVKHGDTWGSICDSDFSLEAASVLCRELQCGTVVSILGGAHFGEGNGQI

WAEEFQCEGHESHLSLCPVAPRPEGTCSHSRDVGVVCSSKTQKTSLIGSYTVKGTGLGSH

SCLFLKPCLLPGYTEIRLVNGKTPCEGRVELKTLGAWGSLCNSHWDIEDAHVLCQQLKCG

VALSTPGGARFGKGNGQIWRHMFHCTGTEQHMGDCPVTALGASLCPSEQVASVICSGNQS

QTLSSCNSSSLGPTRPTIPEESAVACIESGQLRLVNGGGRCAGRVEIYHEGSWGTICDDS

WDLSDAHVVCRQLGCGEAINATGSAHFGEGTGPIWLDEMKCNGKESRIWQCHSHGWGQQN

CRHKEDAGVICSEFMSLRLTSEASREACAGRLEVFYNGAWGTVGKSSMSETTVGVVCRQL

GCADKGKINPASLDKAMSIPMWVDNVQCPKGPDTLWQCPSSPWEKRLASPSEETWITCDN

KIRLQEGPTSCSGRVEIWHGGSWGTVCDDSWDLDDAQVVCQQLGCGPALKAFKEAEFGQG

TGPIWLNEVKCKGNESSLWDCPARRWGHSECGHKEDAAVNCTDISVQKTPQKATTGRSSR

QSSFIAVGILGVVLLAIFVALFFLTKKRRQRQRLAVSSRGENLVHQIQYREMNSCLNADD

LDLMNSSGGHSEPH
```

It is preferred that the SRCR domain 1 of the CD163 receptor comprises or consists of any one of SEQ ID NO:1 to SEQ ID NO:8.

Human [*Homo sapiens*] CD163 domain 1
[SEQ ID NO: 1]
LVDGENKCSGRVEVKVQEEWGTVCNNGWSMEAVSVICNQLGCPTAIKAPG
WANSSAGSGRIWMDHVSCRGNESALWDCKHDGWGKHSNCTHQQDAGVTCS Rhesus [*Macaca mulatta*] CD163 domain 1
[SEQ ID NO: 2]
LVDGENKCSGRVEVKVQEEWGTVCNNGWSMEAVSVICNQLGCPTAIKATG
WANSSAGSGRIWMDHVSCRGNESALWDCKHDGWGKHSNCTHQQDAGVTCS Chimpanzee [*Pan troglodytes*] CD163 domain 1
[SEQ ID NO: 3]
LVDGENKCSGRVEVKVQEEWGTVCNNGWSMEAVSVICNQLGCPTAIKATG
WANSSAGSGRIWMDHVSCRGNESALWDCKHDGWGKHSNCTHQQDAGVTCS Pig [*Sus scrofa*] CD163 domain 1
[SEQ ID NO: 4]
LTGGENKCSGRVEVKVQEEWGTVCNNGWDMDVVSVVCRQLGCPTAIKATG
WANFSAGSGRIWMDHVSCRGNESALWDCKHDGWGKHNCTHQQDAGVTCS Dog [*Canis lupus familiaris*] CD163 domain 1
[SEQ ID NO: 5]
LTDGEDNCSGRVEVKVQEEWGTVCNNGWGMDEVSVICRQLGCPTAIKAAG
WANSRAGSGRIWMDHVSCRGNESALWDCKHDGWGKHNCSHQQDAGVTCS Rat [*Rattus norvegicus*] CD163 domain 1
[SEQ ID NO: 6]
LAGGENNCSGRVELKIHEKWGTVCGNGWSMNEVSVVCQQLGCPTLIKAPG
WANASAGSGDIWMDKVSCTGNESALWDCKHEGWGKHNCTHEQDAGVTCA Murine [*Mus musculus*] CD163 domain 1
[SEQ ID NO: 7]
LAGGENNCSGRVELKIHKWGTVCSNGWSMNEVSVVCQQLGCPTSIKALGW
ANSSAGSGYIWMDKVSCTGNESALWDCKHDGWGKHNCTHEKDAGVTCS Bovine [*Bos primigenius taurus*] CD163 domain 1
[SEQ ID NO: 8]
LVAGQTKCSGRVEVKVQEEWGTVCNTGWDLAAVSVVCKQLGCPSVIKATG
WTNSSAGTGRIWMDHVSCRGNESALWDCKHEGWGKHNCTHQQDVGVTCS The term 'amino acid' as used herein includes the standard twenty genetically-encoded amino acids and their corresponding stereo-isomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be components of polypeptide sequences defined herein, as long as the desired functional property is retained by the polypeptide sequence. For the polypeptide sequences shown herein, each encoded amino acid residue, where appropriate, is represented by a single letter designation, corresponding to the trivial name of the conventional amino acid.

In one embodiment, the polypeptides of the invention comprise or consist of L-amino acids.

Preferably, the binding moiety is capable of binding to the following consensus sequence (wherein X represents any amino acid):

K-X$_1$-VKVQEE-X$_2$-R    [SEQ ID NO: 26]

wherein:
X$_1$ represents Xaa$_{5-8}$ (wherein Xaa represents any amino acid(s)); and;
X$_2$ is absent or represents Xaa$_{38-42}$ (wherein Xaa represents any amino acid(s)).

More preferably, the binding moiety is capable of binding to the sequence:

KCSGRVEVKVQEEWGTVCNNGWSMEAVSVICNQLGCPTAIKAPGWAN    [SEQ ID NO: 27]
SSAGSGR

Even more preferably, the binding moiety is capable of binding to the consensus sequence of SEQ ID NO:26 and/or the sequence of SEQ ID NO:27 when that sequence is present in SRCR domain 1 of the CD163 receptor (for example, SRCR domain 1 of the human CD163 receptor). Those sequences are thought to be involved in the binding of Mac2-48 and Mac2-158 to SRCR domain 1 of the CD163 receptor.

Conveniently, the CD163 receptor is localised on the surface of a cell, preferably a malignant cell, immune modulatory cell, inflamed cell or infected cell expressing the CD163 receptor.

By "localised on the surface of a cell" we include the meaning that the CD163 receptor is associated with the cell such that one or more region of the CD163 receptor is present on outer face of the cell surface. For example, the CD163 receptor may be inserted into the cell plasma membrane (i.e. orientated as a transmembrane protein) with one or more region presented on the extracellular surface. Alternatively, the entire CD163 receptor may be outside the cell with covalent and/or ionic interactions localising it to a specific region or regions of the cell surface.

The term "malignant cell" will be understood by those skilled in the art of cell biology, and includes a cell which is capable of, or exhibits, uncontrolled cellular division and/or proliferation and/or the ability to metastasize and/or invade tissues in a body. Such cells may comprise cancerous tumours and are frequently resistant to many anti-proliferative therapies.

The term "immune modulatory cell" will be understood by those skilled in the art of cell biology, and includes a cell which is capable of modifying or regulating an immune response. Such cells include helper T cells, γδ T cells, B lymphocytes (B cells), mast cells and dendritic cells.

The term "infected cell" will be understood by those skilled in the art of cell biology, and includes any cell that has been invaded by or is otherwise associated with an infectious or pathogenic microorganism. Such microorganisms include intracellular pathogens such as *Mycobacterium tuberculosis* and human immunodeficiency virus (HIV).

The term "inflamed cell" will be understood by those skilled in the art of cell biology, and includes any cell in which an inflammatory response has been induced.

In a preferred embodiment, the cell is a monocyte and/or monocyte-derived cell, which can advantageously be selected from the group consisting of: monocytes; macrophages; monocyte-derived dendritic cells; activated macrophage subtypes (e.g. M1, M2).

It is well known that monocytes are mononuclear phagocytic cells that act within the immune system—that is, they are white cells having a single nucleus, and which are capable of ingesting foreign material. Monocytes migrate from blood into tissues of the body and differentiate into cells such as macrophages. Thus, by "monocyte-derived cell", we include those cell types that have differentiated from monocytes.

Most preferably, the cell is a macrophage, for example, a Kupffer cell.

It will be well known by those skilled in the art of immunology that macrophages are phagocytic cells derived from monocytes, and which play a role in the destruction of certain bacteria, protozoa and tumour cells, release substances that stimulate other immune cells and are involved in antigen presentation.

In a particularly preferred embodiment of the invention, the agent is internalised into the cell when bound to the CD163 receptor.

By "internalised into the cell" we include the molecular, biochemical and cellular events associated with the process of translocating a molecule from the extracellular surface of a cell to the intracellular surface of a cell. The processes responsible for intracellular internalisation of molecules is well-known to those skilled in the field of molecular and cellular biology and can involve the internalisation of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule).

Preferably, the binding moiety exhibits greater binding affinity for SRCR domain 1 of the CD163 receptor in the presence of calcium than in the absence of calcium. Methods useful for determining the binding affinity of a binding moiety for SRCR domain 1 of the CD163 receptor are described herein and can be found in the accompanying Examples.

In a preferred embodiment, the invention provides an agent wherein the binding moiety comprises an antibody or an antigen-binding fragment thereof, or a variant, fusion or derivative of said antibody or an antigen-binding fragment, or a fusion of a said variant or derivative thereof, which retains the binding specificity for SRCR domain 1 of the CD163 receptor.

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

For example, the antibody or antigen-binding fragment, or variant, fusion or derivative thereof, may comprise, consist or consist essentially of an intact antibody. By "consist essentially of" we mean that the antibody or antigen-binding fragment, variant, fusion or derivative thereof consists of a portion of an intact antibody sufficient to retain binding specificity for SRCR domain 1 of the CD163 receptor.

The term 'antibody' also includes all classes of antibodies, including IgG, IgA, IgM, IgD and IgE. Thus, the antibody may be an IgG molecule, such as an IgG1, IgG2, IgG3, or IgG4 molecule.

Preferably, the antibody is an IgG antibody, for example, an IgG2 or IgG4 antibody. In one preferred embodiment, the antibody is an IgG4 antibody in which the Serine amino acid at position 241 has been substituted with a Proline residue (i.e. S241P)—such a substitution is known to stabilise the disulphide bridges in IgG4 molecule, resulting in a more stable antibody (Angal et al., 1993, *Mol. Immunol.*, 30:105-8).

In a preferred embodiment, the antibody, antigen-binding fragment, variant, fusion or derivative thereof is in an isolated and/or purified form.

In one embodiment, the antibody is a non-naturally occurring antibody. Of course, where the antibody is a naturally occurring antibody, it is provided in an isolated form (i.e. distinct from that in which it is found in nature).

It will be appreciated by persons skilled in the art that the binding specificity of an antibody or antigen binding fragment thereof is conferred by the presence of Complementarity Determining Regions (CDRs) within the variable regions of the constituent heavy and light chains.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent-parented antibody (Morrison at al (1984) *Proc. Natl. Acad. Sci. USA* 81, 6851-6855).

Antigenic specificity is conferred by variable domains and is independent of the constant domains, as known from experiments involving the bacterial expression of antibody fragments, all containing one or more variable domains. These molecules include Fab-like molecules (Better at al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward at al (1989) *Nature* 341, 544). A general review of the techniques involved in the synthesis of antibody fragments which retain their specific binding sites is to be found in Winter & Milstein (1991) *Nature* 349, 293-299.

Thus, by "antigen-binding fragment" we mean a functional fragment of an antibody that is capable of binding to SRCR domain 1 of the CD163 receptor.

Exemplary antigen-binding fragments of the invention may be selected from the group consisting of Fv fragments (e.g. single chain Fv and disulphide-bonded Fv), and Fab-like fragments (e.g. Fab fragments, Fab' fragments and F(ab)$_2$ fragments).

In a preferred embodiment, the antigen-binding fragment is an scFv.

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli* or yeast, thus allowing the facile production of large amounts of the said fragments.

Also included within the scope of the invention are modified versions of antibodies and an antigen-binding fragments thereof, e.g. modified by the covalent attachment of polyethylene glycol or other suitable polymer.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

The antibody or antigen-binding fragment or derivative thereof may be produced by recombinant means.

Preferably, the antibody is a monoclonal antibody.

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982), which are incorporated herein by reference.

Antibody fragments can also be obtained using methods well known in the art (see, for example, Harlow & Lane, 1988, "*Antibodies: A Laboratory Manual*", Cold Spring Harbor Laboratory, New York, which is incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods. Alternatively, antibody fragments can be obtained by cell-free in vitro expression, as is known in the art.

As defined herein, the binding moiety may be a variant, fusion or derivative thereof of an antibody or antigen-binding fragment, provided such variants, fusions and derivatives retain binding specificity for SRCR domain 1 of the CD163 receptor.

Variants may be made using the methods of protein engineering and site-directed mutagenesis well known in the art using the recombinant polynucleotides (see example, see *Molecular Cloning: a Laboratory Manual,* 3rd edition, Sambrook & Russell, 2001, Cold Spring Harbor Laboratory Press, which is incorporated herein by reference).

In other preferred embodiments, the antibody variant may be a single-domain antibody, such as a nanobody. Such antibodies are known to exist in camelids (*Curr. Opin. Pharmacol.,* 8, (2008), 600-608) and sharks (e.g. IgNAR; *Curr. Opin. Pharmacol.,* 8, (2008), 600-608). Other preferred antibody variants include isolated heavy-chain variable ($V_H$) regions or isolated light-chain ($V_L$) regions, for example from human antibodies (*Curr. Opin. Pharmacol.,* 8, (2008), 600-608), and iMabs (WO 03/050283).

By 'fusion' we include an antibody or antigen-binding fragment (as defined herein) fused to any other polypeptide. For example, the antibody or antigen-binding fragment may be fused to a polypeptide such as glutathione-S-transferase (GST) or protein A in order to facilitate its purification. Examples of such fusions are well known to those skilled in the art. Similarly, the said antibody or antigen-binding fragment may be fused to an oligo-histidine tag such as His6 or to an epitope recognised by a further antibody (such as the well-known Myc tag epitope).

The fusion may comprise a further portion which confers a desirable feature on the antibody or antigen-binding fragment of the invention; for example, the portion may be useful in detecting or isolating the antibody or antigen-binding fragment, or promoting cellular uptake of the antibody or antigen-binding fragment. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art, or may be a lipophilic molecule or polypeptide domain that is capable of promoting cellular uptake, as known to those skilled in the art.

Methods for conjugating additional moieties to an antibody (or a fusion, variant or derivative thereof) are well known in the art. Exemplary methods are described in Bioconjugate Techniques, 2nd Edition (2008); Hermanson (Academic Press, Inc.) and in Veronese et al., (1999; Farmaco 54(8): 497-516); Stayton et al., (2005; Orthod Craniofac Res 8(3): 219-225); Schrama et al., (2006; Nat Rev Drug Discov 5(2): 147-159); Doronina et al. (2003; Nat Biotechnol 21(7): 778-784); Carter at al., (2008; Cancer J 14(3): 154-169); Torchilin (2006; Annu Rev Biomed Eng 8: 343-375); Rihova (1998; Adv Drug Deliv Rev 29(3): 273-289); Goyal at al. (2005; Acta Pharm 55(1): 1-25); Chari (1998; Adv Drug Deliv Rev 31(1-2): 89-104); Garnett (2001; Adv Drug Deliv Rev 53(2): 171-216); Allen (2002; Nat Rev Cancer 2(10): 750-763).

By 'variants' of the antibody or antigen-binding fragment of the invention we include insertions, deletions and substitutions, either conservative or non-conservative. In particular we include variants of the sequence of the antibody or antigen-binding fragment where such variations do not substantially alter the activity of the antibody or antigen-binding fragment. In particular, we include variants of the antibody or antigen-binding fragment where such changes do not substantially alter the binding specificity for SRCR domain 1 of the CD163 receptor.

The polypeptide variant may have an amino acid sequence which has at least 70% identity with one or more of the amino acid sequences of the antibody or antigen-binding fragment of the invention as defined herein—for example, at least 75%, at least 80%, at least 90%, at least 95%, at least 96%, at least 97%, at least 98%, or at least 99% identity with one or more of the amino acid sequences of the antibody or antigen-binding fragment of the invention as defined herein.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, Nucl. Acid Res. 22:4673-4680, which is incorporated herein by reference).

The parameters used may be as follows:
Fast pair-wise alignment parameters: K-tuple(word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

The antibody or antigen-binding fragment, variant, fusion or derivative of the invention may comprise one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, the present invention includes peptidomimetic compounds which are capable of binding SRCR domain 1 of the CD163 receptor. The term 'peptidomimetic' refers to a compound that mimics the conformation and desirable features of a particular peptide as a therapeutic agent.

For example, the antibody, antigen-binding fragment, variant, fusion or derivative thereof of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al., (1997) J. Immunol. 159, 3230-3237, which is incorporated herein by reference. This approach involves making pseudo-peptides containing changes involving the backbone, and not the orientation of side chains. Retro-inverse peptides, which contain NH—CO bonds instead of CO—NH peptide bonds, are much more resistant to proteolysis. Alternatively, the antibody, antigen-binding fragment, variant, fusion or derivative thereof of the invention may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will be appreciated that the antibody, antigen-binding fragment, variant, fusion or derivative thereof of the invention may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

A common theme among many of the synthetic strategies has been the introduction of some cyclic moiety into a peptide-based framework. The cyclic moiety restricts the conformational space of the peptide structure and this frequently results in an increased specificity of the peptide for a particular biological receptor. An added advantage of this strategy is that the introduction of a cyclic moiety into a peptide may also result in the peptide having a diminished sensitivity to cellular peptidases.

Thus, exemplary antibody, antigen-binding fragment, variant, fusion or derivative thereof of the invention may comprise terminal cysteine amino acids. Such polypeptides may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminus cysteines may circumvent problems of specificity and half-life sometime observed with linear peptides, by decreasing proteolysis and also increasing the rigidity of the structure, which may yield higher specificity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, peptides can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872, which is incorporated herein by reference. Other examples of cyclisation methods are discussed and disclosed in U.S. Pat. No. 6,008,058, which is incorporated herein by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), which is incorporated herein by reference, has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification because of the stable structures formed by cyclisation and in view of the biological activities observed for cyclic peptides.

By "retains the binding specificity" we mean that the antibody or antigen-binding fragment, or variant, fusion or derivative thereof, is capable of competing for binding to the SRCR domain 1 of the CD163 receptor with one or more of the exemplary antibodies of the invention (namely, Mac2-158, Mac2-48, 5C6-FAT and/or BerMac3; as described in the accompanying Examples).

For example, the antibody or antigen-binding fragment, or variant, fusion or derivative thereof, may bind to the same epitope on SRCR domain 1 of the CD163 receptor with one or more of the exemplary antibodies of the invention (namely, Mac2-158, Mac2-48, 5C6-FAT and/or BerMac3; as described in the accompanying Examples).

Advantageously, the invention provides an agent wherein the antibody or antigen-binding fragment thereof is human or humanised.

It will be appreciated by persons skilled in the art that, for human therapy or diagnostics, humanised antibodies may be used. Humanised forms of non-human (e.g. murine) antibodies are genetically engineered chimaeric antibodies or antibody fragments having minimal-portions derived from non-human antibodies. Humanised antibodies include antibodies in which complementary determining regions of a human antibody (recipient antibody) are replaced by residues from a complementary determining region of a non human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported Complementarity Determining Region (CDR) or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596, which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567, which are incorporated herein by reference) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95, Soderlind at al., 2000, *Nat Biotechnol* 18:852-6 and WO 98/32845 which are incorporated herein by reference).

Once suitable antibodies are obtained, they may be tested for activity, such as binding specificity or a biological activity of the antibody, for example by ELISA, immunohistochemistry, flow cytometry, immunoprecipitation, Western blots, etc. The biological activity may be tested in different assays with readouts for that particular feature.

In a preferred embodiment, the antibody comprises a framework region sequence consisting of SEQ ID NO:9 or SEQ ID NO:10.

SEQ ID NO:9 corresponds to the human framework region sequence IGHV4-b01:

```
                                                [SEQ ID NO: 9]
VQLQESGPGLVKPSETLSLTCAVSGYSISSGYYWGWIRQPPGKGLEWIGS

IYHSGSTYYNPSLKSRVTISVDTSKNQFSLKLSSVTAADTAVYYCAR
```

SEQ ID NO:10 corresponds to the human framework region sequence IGKV1D-39*01:

```
                                                [SEQ ID NO: 10]
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTP
```

Methods for generating humanised antibodies are well known to those in the art. An approach for generating humanised Mac2-158 and Mac2-48 is described in the accompanying Examples.

In one embodiment, the antibody, antigen-binding fragment, variant, fusion or derivative thereof comprises a heavy-chain variable ($V_H$) region comprising one or more CDR sequences selected from the group consisting of:

```
                                                SEQ ID NO: 11
                GYSITSDY

SEQ ID NO: 12
                YSG

SEQ ID NO: 13
                CVSGTYYFDYWG
```

SEQ ID NOs: 11, 12 and 13 represent the three CDR sequences from the heavy-chain variable ($V_H$) region sequence of the exemplary antibodies, Mac2-48 and Mac2-158 (as described in the accompanying Examples).

In one embodiment, the antibody, antigen-binding fragment, variant, fusion or derivative thereof comprises a light-chain variable ($V_L$) region comprising one or more CDR sequences selected from the group consisting of:

```
                                                SEQ ID NO: 14
                ASQSVSSDV

SEQ ID NO: 15
                YAS

SEQ ID NO: 16
                QDYTSPRT
```

SEQ ID NOs: 14, 15 and 16 represent three CDR sequences from the light-chain variable ($V_L$) region sequence of the exemplary antibody, Mac2-158 (as described in the accompanying Examples).

In an alternative embodiment, the antibody, antigen-binding fragment, variant, fusion or derivative thereof comprises a light chain variable region comprising one or more CDR sequences selected from the group consisting of:

```
                                                SEQ ID NO: 17
                ASQSVSHDV

SEQ ID NO: 18
                YTS

SEQ ID NO: 19
                QDYSSPRT
```

SEQ ID NOs: 17, 18 and 19 represent three CDR sequences from the light-chain variable ($V_L$) region sequence of the exemplary antibody, Mac2-48 (as described in the accompanying Examples).

In one embodiment, the antibody, antigen-binding fragment, variant, fusion or derivative thereof comprises a heavy chain variable ($V_H$) region comprising or consisting of the amino acid sequence of SEQ ID NO:20:

```
                                                [SEQ ID NO: 20]
DVQLQESGPGLVKPSQSLSLTCTVTGYSITSDYAWNWIRQFPGNKLEWMG

YITYSGITNYNPSLKSQISITRDTSKNQFFLQLNSVTTEDTATYYCVSGT

YYFDYWGQGTTLTVSS
```

Preferably, the antibody, antigen-binding fragment, variant, fusion or derivative thereof comprises a light-chain variable ($V_L$) region comprising or consisting of the amino acid sequence of SEQ ID NO:21:

```
                                                [SEQ ID NO: 21]
SVVMTQTPKSLLISIGDRVTITCKASQSVSSDVAWFQQKPGQSPKPLIYY

ASNRYTGVPDRFTGSGYGTDFTFTISSVQAEDLAVYFCGQDYTSPRTFGG

GTKLEIKRA
```

SEQ ID NOs: 20 and 21 represent the variable heavy-chain ($V_H$) and variable light-chain ($V_L$) sequences of the exemplary antibody, Mac2-158 (as described in the accompanying Examples).

In one embodiment, the antibody, antigen-binding fragment, variant, fusion or derivative thereof comprises a heavy-chain variable ($V_H$) region comprising or consisting of the amino acid sequence of SEQ ID NO:22:

[SEQ ID NO: 22]
DVQLQESGPGLVKPSQSLSLTCTVTGYSITSDYAWNWIRQFPGNKLEWMG

FISYSGITSYNPSLKSRISITRDTSKNQFFLQLNSVTTEDSATYYCVSGT

YYFDYWGQGTTLTVSS

Preferably, the antibody, antigen-binding fragment, variant, fusion or derivative thereof comprises a light-chain variable ($V_L$) region comprising or consisting of the amino acid sequence of SEQ ID NO:23:

[SEQ ID NO: 23]
SIVMTQTPKFLLVSAGDRVTITCKASQSVSHDVSWFQQKPGQSPKLLIYY

TSNRYTGVPDRFTGSGYGTDFTFTISTVQAEDLAIYFCQQDYSSPRTFGG

GTKLEIKRA

SEQ ID NOs: 22 and 23 represent the heavy-chain variable ($V_H$) region and light-chain variable ($V_L$) region sequences of the exemplary antibody, Mac2-48 (as described in the accompanying Examples).

In one embodiment, the antibody, antigen-binding fragment, variant, fusion or derivative thereof comprises a heavy-chain variable ($V_H$) region comprising or consisting of the amino acid sequence of SEQ ID NO:24:

[SEQ ID NO: 24]
QVQLQESGPGLVKPSETLSLTCTVSGYSITSDYAWNWIRQFPGNKLEWMG

YITYSGSTYYNPSLKSRVTISVDTSKNQFSLKLSSVTAADTATYYCVSGT

YYFDYWGQGTTLTVSS

Preferably, the antibody, antigen-binding fragment, variant, fusion or derivative thereof comprises a light-chain variable ($V_L$) region comprising or consisting of the amino acid sequence of SEQ ID NO:25:

[SEQ ID NO: 25]
DIVMTQSPSSLSASVGDRVTITCRASQSVSSDVAWFQQKPGKSPKPLIYY

ASNRYSGVPSRFSGSGSGTDFTLTISSLQAEDFAVYFCGQDYTSPRTFGG

GTKLEIKR

SEQ ID NOs: 24 and 25 represent the heavy-chain variable ($V_H$) region and light-chain variable ($V_L$) region sequences of a preferred humanised antibody of the invention.

The invention contemplates binding moieties having variations in the sequence of the heavy-chain variable ($V_H$) region and light-chain variable ($V_L$) region, provided that those variant binding moieties retain binding specificity for SRCR domain 1 of CD163. For example, binding moieties having the variations listed below would be expected to retain binding specificity for SRCR domain 1 of the CD163 receptor For example, one or more of the following variations could be made to the numbered residues of the heavy-chain variable ($V_H$) region sequence (for example, SEQ ID NOs: 20, 22 or 24, as defined herein):
  Residue 24; variant residues include: V, A, S, T;
  Residue 26; variant residues include: G;
  Residue 27; variant residues include: S, F, Y, D;
  Residue 29; variant residues include: I, F, L;
  Residue 34; variant residues include: W, M, V, I, A, Y;
  Residue 53; variant residues include: N;
  Residue 54: variant residues include: R;
  Residue 55; variant residues include: G, D, Y;
  Residue 71; variant residues include: V, R, K, I, E;
  Residue 94; variant residues include: S, R, G, N, K.

Alternatively, or in addition, one or more of the following variations could be made to the numbered residues of the light-chain variable ($V_L$) region sequence (for example, SEQ ID NOs: 21, 23 or 25, as defined herein):

Residue 2; variant residues include: I, V;
Residue 25; variant residues include: A;
Residue 29; variant residues include: V, I;
Residue 33; variant residues include: V, I, L;
Residue 46; variant residues include: P, L;
Residue 48; variant residues include: I, V;
Residue 64; variant residues include: G;
Residue 71; variant residues include: F, Y;
Residue 90; variant residues include: Q, N, H;
Residue 95; variant residues include: P;
Residue 97; variant residues include: T, S.

In a particularly preferred embodiment, the antibody, antigen-binding fragment, variant, fusion or derivative thereof comprises a heavy-chain variable ($V_H$) region comprising or consisting of SEQ ID NO: 20 or SEQ ID NO: 22 or SEQ ID NO: 24 and a light-chain variable ($V_L$) region comprising or consisting of SEQ ID NO: 21 or SEQ ID NO: 23 or SEQ ID NO: 25.

In a more preferred embodiment, the antibody, antigen-binding fragment, variant, fusion or derivative thereof comprises:

a heavy-chain variable ($V_H$) region comprising or consisting of SEQ ID NO: 20 and a light-chain variable ($V_L$) region comprising or consisting of SEQ ID NO: 21; or a heavy-chain variable ($V_H$) region comprising or consisting of SEQ ID NO: 22 and a light-chain variable ($V_L$) region comprising or consisting of SEQ ID NO: 23; or a heavy-chain variable ($V_H$) region comprising or consisting of SEQ ID NO: 24 and a light-chain variable ($V_L$) region comprising or consisting of SEQ ID NO: 25.

In an even more preferred embodiment, the antibody, antigen-binding fragment, variant, fusion or derivative thereof comprises:

a heavy-chain variable ($V_H$) region comprising or consisting of SEQ ID NO: 20 and a light-chain variable ($V_L$) region comprising or consisting of SEQ ID NO: 21; or a heavy-chain variable ($V_H$) region comprising or consisting of SEQ ID NO: 22 and a light-chain variable ($V_L$) region comprising or consisting of SEQ ID NO: 23.

SEQ ID NOs: 20 and 21 represent the variable heavy-chain ($V_H$) and variable light-chain ($V_L$) sequences of the exemplary antibody, Mac2-158 (as described in the accompanying Examples). Mac2-158 can be obtained from IQ Products, the Netherlands, (catalogue number CD163-158U. http://www.iqproducts.nl/catalog/index.php?pr=782).

SEQ ID NOs: 22 and 23 represent the heavy-chain variable ($V_H$) region and light-chain variable ($V_L$) region sequences of the exemplary antibody, Mac2-48 (as described in the accompanying Examples). Mac2-48 can be obtained from IQ Products, the Netherlands, catalogue number CD163-48U. http://www.iqproducts.nl/catalog/index.php?pr=783).

The exemplary antibody 5C6-FAT, as described in the accompanying Examples, can be obtained from Acris, Germany (catalogue number BM-4041; http://www.acris-antibodies.com/BM4041.htm) and Bachem, Switzerland (catalogue numberT-1061; http://shop.bachem.com/ep6sf/prodT1061.html).

The exemplary antibody Ber-Mac3, as described in the accompanying Examples, can be obtained from MBL, MA, USA, catalogue number K-0147. http://www.mblintl.com/mbli/account/search_results.asp?search=K0147-3).

In a preferred embodiment, the invention provides an agent wherein the antibody, antigen-binding fragment, variant, fusion or derivative thereof is capable of competing for binding to SRCR domain 1 of the CD163 receptor with an antibody molecule as defined herein, or a variant, fusion or derivative of said antibody or antigen-binding fragment, or a fusion of a said variant or derivative thereof, which retains the binding specificity for SRCR domain 1 of the CD163 receptor.

By "capable of competing" for binding to SRCR domain 1 of the CD163 receptor with an antibody molecule as defined herein (or a variant, fusion or derivative of said antibody or antigen-binding fragment, or a fusion of a said variant or derivative thereof, which retains the binding specificity for SRCR domain 1 of the CD163 receptor) we mean that the tested antibody, antigen-binding fragment, variant, fusion or derivative thereof is capable of inhibiting or otherwise interfering, at least in part, with the binding of an antibody molecule as defined herein (or a variant, fusion or derivative of said antibody or antigen-binding fragment, or a fusion of a said variant or derivative thereof).

For example, the antibody or antigen-binding fragment, variant, fusion or derivative thereof, or fusion of a said variant or derivative thereof, may be capable of inhibiting the binding of an antibody molecule defined herein (for example, Mac2-158, Mac2-48, 5C6-FAT or BerMac3) by at least 10%, for example at least 20%, 30%, 40%, 50%, 60%, 70%, 80%, 90%, 35% or even by 100%.

Competitive binding may be determined by methods well known to those skilled in the art, such as ELISA (as described herein) and/or SPR (as described in the accompanying Examples).

In a "Sandwich ELISA", a suitable amount of, e.g. a polyclonal antibody, such as 10 µg/ml of a polyclonal rabbit antibody, directed against the cytoplasmic tail of CD163 receptor is used as a capture antibody when coated in a 96-well plate, such as e.g. Maxisorp Nunc™. Coating is done according to standard procedures known in the art. Wells may be blocked for 1 h with 3% BSA in TBS-T at e.g. room temperature. Cell extract from HEK-cells stably transfected with an expression vector expressing the CD163 receptor, or from cells in which CD163 is expressed, is then diluted in assay buffer (e.g. TBS-T supplemented with 0.1% BSA, 1 mM MgCl2 and 10 µM $CaCl_2$). Suitable amount of diluted cell extract, such as e.g. 50 µl is then added per well and incubated to allow binding to the coated antibody, e.g. for 1 h at room temperature. Plates are then washed three times with TBS-T. Primary antibody (for example, Mac2-48, Mac2-158, 5C6FAT, BerMac3 or a control antibody) conjugated with biotin is then added in a suitable amount, such as e.g. at 2 µg/ml in assay buffer. Plates are then incubated for a sufficient time to allow binding of Mac2-48, Mac2-158, 5C6FAT or BerMac3 and control antibody where possible, e.g. for 1 h at room temperature followed by three washes in TBS-T. In case where biotinylated primary antibodies are used, Streptavidin-HRP antibody (DAKO) may be used and diluted accordingly in assay buffer (1:5000), added to the wells. Plates are then incubated enough for the streptavidin-biotin complex to form, e.g. for 1 h at room temperature.

Following washing, e.g. three times with TBS-T and the plates are developed with peroxidase substrate (e.g. OPD SigmaFast, Sigma). The absorbance of the colorimetric change is determined at suitable wavelength, in this case 490 nm.

If primary antibodies are not conjugated, the same ELISA can instead be incubated with a secondary antibody against the human IgG4 directly conjugated with HRP, e.g. mouse anti-human IgG4-HRP, from e.g. Serotec, or, if not conjugated, followed by a HRP-conjugated anti-mouse antibody from e.g. DAKO. Plates are then washed and developed as outlined above.

Further methods include reversing the sandwich ELISA outlined above, and instead use the CD163 antibody (e.g. Mac2-48, Mac2-158, 5C6FAT, BerMac3) as a capture antibody, as will appreciated by those in the art.

The above ELISA assays can be used to evaluate epitope-modifying or blocking antibodies. Additional methods suitable for identifying competing antibodies are disclosed in *Antibodies: A Laboratory Manual*, Harlow & Lane, which is incorporated herein by reference (for example, see pages 567 to 569, 574 to 576, 583 and 590 to 612, 1988, CSHL, NY, ISBN 0-87969-314-2).

In a preferred embodiment, the invention provides an agent wherein the antibody, antigen-binding fragment, variant, fusion or derivative thereof is capable of binding to the same epitope as an antibody molecule as defined herein.

In an alternative embodiment, the invention provides an agent wherein the antibody, antigen-binding fragment, variant, fusion or derivative thereof is capable of binding to an epitope distinct from that to which an antibody molecule as defined herein.

By "epitope" it is herein intended to mean a site of a molecule to which an antibody binds, i.e. a molecular region of an antigen. An epitope may be a linear epitope, which is determined by e.g. the amino acid sequence, i.e. the primary structure, or a three-dimensional epitope, defined by the secondary structure, e.g. folding of a peptide chain into beta sheet or alpha helical, or by the tertiary structure, e.g. way which helices or sheets are folded or arranged to give a three-dimensional structure, of an antigen.

As discussed above, important residues involved in the binding of Mac2-48 and Mac2-158 to SRCR domain 1 of the CD163 receptor are defined in the sequences of SEQ ID NO:26 and 27.

The antibody or antigen-binding fragment, or variant, fusion or derivative thereof, which retains the binding specificity of an antibody defined herein (such as the Mac2-48, Mac2-158, 5C6FAT and BerMac3 antibodies) may also retain one or more of the same biological properties as that antibody (for example, bioavailability and stability).

Clearly, any binding moiety with specificity for SRCR domain 1 of CD163 may be used in the agent of the invention.

In an alternative aspect, the invention provides an agent according wherein the binding moiety is an antibody mimic (such as a non-antibody scaffold).

It will be appreciated that antibody mimics (for example, non-antibody scaffold structures that have a high degree of stability yet allow variability to be introduced at certain positions) may be used to create molecular libraries from which binding moieties can be derived. Those skilled in the arts of biochemistry will be familiar with many such molecules. Such molecules may be used as a binding moiety in the agent of the present invention.

Exemplary antibody mimics are discussed in Skerra et al. (2007, *Curr. Opin. Biotech.*, 18: 295-304) and include:

affibodies (also called Trinectins; Nygren, 2008, FEBS J, 275, 2668-2676); CTLDs (also called Tetranectins; *Innovations Pharmac. Technol.* (2006), 27-30); adnectins (also called monobodies; *Meth. Mol. Biol.,* 352 (2007), 95-109); anticalins (*Drug Discovery Today* (2005), 10, 23-33); DARPins (ankyrins; *Nat. Biotechnol.* (2004), 22, 575-582); avimers (*Nat. Biotechnol.* (2005), 23, 1556-1561); microbodies (*FEBS J,* (2007), 274, 86-95); peptide aptamers (*Expert. Opin. Biol. Ther.* (2005), 5, 783-797); Kunitz domains (*J. Pharmacol. Exp. Ther.* (2006) 318, 803-809); affilins (*Trends. Biotechnol.* (2005), 23, 514-522).

Accordingly, it is preferred that the antibody mimic is selected from the group comprising or consisting of affibodies, tetranectins (CTLDs), adnectins (monobodies), anticalins, DARPins (ankyrins), avimers, iMabs, microbodies, peptide aptamers, Kunitz domains and affllins.

In a further aspect, the invention provides an agent wherein the binding moiety is an RNA aptamer.

RNA aptamers represent a unique emerging class of therapeutic agents (Que-Gewirth et al, Gene Ther. 74:283 (2007); Ireson et al, Mol. Cancer. Ther. 5:2957 (2006)). They are relatively short (12-30 nucleotide) single-stranded RNA oligonucleotides that assume a stable three-dimensional shape to tightly and specifically bind selected protein targets to elicit a biological response. In contrast to antisense oligonucleotides, RNA aptamers can effectively target extracellular targets. Like antibodies, aptamers possess binding affinities in the low nanomolar to picomolar range. In addition, aptamers are heat stable, non-immunogenic, and possess minimal inter-batch variability. Chemical modifications, such as amino or fluoro substitutions at the 2' position of pyrimidines, may reduce degradation by nucleases. The biodistribution and clearance of aptamers can also be altered by chemical addition of moieties such as polyethylene glycol and cholesterol.

Aptamers may be developed by iterative selection methods such as SELEX (systematic evolution of ligands by exponential enrichment) to specifically recognize and tightly bind their targets by means of well-defined complementary three-dimensional structures. Further, SELEX (and other such methods) allows selection from libraries to generate high-affinity oligonucleotide ligands to purified biochemical targets. Recently, the aptamer pegaptanib was approved for the treatment of age-related macular degeneration (Wong et al, Lancet 370:204 (2007)). With regard to the field of oncology, the DNA aptamer GBI-10, derived from a human glioblastoma cell line, was recently demonstrated to bind tenascin-C (Daniels et al, Proc. Natl. Acad. ScL USA 100:15416 (2003)). Similarly, RNA aptamers have been demonstrated to target the Ku DNA repair proteins with resulting sensitization of breast cancer cells to etoposide (Zhang et al, Int. J. Mol. Med. 74:153 (2004)).

In a further aspect, the invention provides an agent wherein the binding moiety is a small molecule.

By "small molecule" we mean a low molecular weight organic compound of 900 Daltons or less. Although large biopolymers such as nucleic acids, proteins, and polysaccharides (such as starch or cellulose) are not included as "small molecules", their constituent monomers (ribo- or deoxyribonucleotides, amino acids, and monosaccharides, respectively) and oligomers (i.e. short polymers such as dinucleotides, peptides such as the antioxidant glutathione, and disaccharides such as sucrose) are included.

The production of small molecules is described in Mayes & Whitcombe, 2005, *Adv. Drug Deliv. Rev.* 57:1742-78 and Root-Bernstein & Dillon, 2008, *Curr. Pharma. Des.* 14:55-62.

It is preferred that, where the binding moiety is an antibody mimic, RNA aptamer or small molecule, the agent of the invention is in an isolated and/or purified form.

Preferably, the agent of the invention further comprises a detectable moiety.

By a "detectable moiety" we include the meaning that the moiety is one which, when located at the target site following administration of an agent of the invention to a patient, may be detected, typically non-invasively from outside the body and the site of the target located. The detectable moiety may be a single atom or molecule which is either directly or indirectly involved in the production of a detectable species. Thus, the agents of this embodiment of the invention are useful in imaging and diagnosis.

Suitable detectable moieties are well known in medicinal chemistry and the linking of these moieties to polypeptides and proteins is well known in the art. Examples of detectable moieties include, but are not limited to, the following: radioisotopes (e.g. $^{3}$H, $^{14}$C, $^{35}$S, $^{123}$I, $^{125}$I, $^{131}$I, $^{99}$Tc, $^{111}$In, $^{90}$Y, $^{188}$Re), radionuclides (e.g. $^{11}$C, $^{18}$F, $^{64}$Cu), fluorescent labels (e.g. FITC, rhodamine, lanthanide phosphors, carbocyanine), enzymatic labels (e.g. horseradish peroxidase, β-galactosidase, luciferase, alkaline phosphatase), chemiluminescent, biotinyl groups and predetermined polypeptide epitopes recognised by a secondary reporter (e.g. leucine zipper pair sequences, binding sites for secondary antibodies, metal binding domains, epitope tags). In some embodiments, labels are attached by spacer arms of various lengths to reduce potential steric hindrance.

Preferably, the detectable moiety comprises a radioactive atom, such as a radioactive atom selected from the group consisting of: technetium-99; technitium-99m; iodine-123; iodine-124; iodine-131; indium-111; fluorine-18; fluorine-19; carbon-11; carbon-13; copper-64; nitrogen-13; nitrogen-15; oxygen-15; oxygen-17; arsenic-72; gadolinium; manganese; iron; deuterium; tritium; yttrium-86; zirconium-89.

The radio- or other labels may be incorporated into the agents of the invention in known ways. For example, if the binding moiety is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al (1978) *Biochem. Biophys. Res. Comm.* 80, 49-57, which is incorporated herein by reference) can be used to incorporate $^{123}$I. Reference ("Monoclonal Antibodies in Immunoscintigraphy", J-F Chatal, CRC Press, 1989, which is incorporated herein by reference) describes other methods in detail.

In one embodiment, the invention provides an agent further comprising a cytotoxic moiety.

By a "cytotoxic moiety" we include the meaning that the moiety is one which is capable of inducing cell death in vivo or in vitro, for example when administered to a patient. The cytotoxic moiety may be a single atom or molecule which is either directly or indirectly involved in inducing cell death. Thus, the agents of this embodiment of the invention are useful in therapy (for example, where it is desired to remove or destroy one or more cell in an individual).

Suitable cytotoxic moieties are well known in medicinal chemistry and the linking of these moieties to polypeptides and proteins is well known in the art. For example, when each moiety of the agent of the invention is a polypeptide, the two portions may be linked together by any of the conventional ways of cross-linking polypeptides, such as those generally described in O'Sullivan et al (1979) *Anal. Biochem.* 100, 100-108. For example, the binding moiety may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Examples of cytotoxic moieties include, but are not limited to, the following: radioisotopes (e.g. $^{123}$I, $^{125}$I, $^{131}$I, $^{111}$In, $^{90}$Y), alkylating agents (e.g. cisplatin), antimetabolites (e.g. methotrexate), antimitotics (e.g. vincristine), topoisomerase inhibitors (e.g. etoposide), and toxins (e.g. calicheamicin). In some embodiments, cytotoxic moieties are attached by spacer arms of various lengths to reduce potential steric hindrance.

In one embodiment, the cytotoxic moiety comprises a radioactive atom, such as a radioactive atom selected from the group consisting of: iodine-123; iodine-125; iodine-131; indium-111; bromine-77; copper-67; arsenic-77; astatine-211; actinium-225; bismuth-212; bismuth-213; lutetium-177; holmium-166; phosphorous-33; platinum-193; platinum-195; rhenium-186; rhenium-188; strontium-89; yttrium-90.

In another embodiment, the cytotoxic moiety comprises a drug selected from the group consisting of: an alkylating agent (such as cisplatin, carboplatin); an antimetabolite (such as azathioprine, methotrexate); an antimitotic drug (such as vincristine); a topoisomerase inhibitor (such as doxorubicine, etoposide); a toxin (such as calicheamicin).

Preferably, the invention provides an agent further comprising a drug to be delivered to a cell having a CD163 receptor localised on its surface. Conveniently, the cell is as defined herein.

In a preferred embodiment, the invention provides an agent wherein the drug comprises a immunosuppressive drug, such as an anti-inflammatory drug. Such drugs are known to those in the arts of medicine and pharmacology.

Advantageously, the immunosuppressive drug may be selected from the group comprising or consisting of: a glucocorticoid; methotrexate; cyclophosphamide; 6-mercaptopurin; cyclosporine; tacrolimus; mycophenolate mofetil; sirulimus; everolimus; an siRNA molecule capable of inhibiting synthesis of proinflammatory cytokines (such as TNF); a non-steroidal anti-inflammatory drug (NSAIDs, such as aspirin, ibuprofen); a steroid (such as vitamin D); a disease-modifying anti-rheumatic drug (DMARDs, such as penicillamin, sulfasalazin, cyclosporine).

Exemplary glucocorticoids may be selected from the group comprising or consisting of: cortisone and derivatives thereof (such as hydrocortisone); prednisone and derivatives thereof (such as prednisolone, methylprednisolone, methylprednisolone-acetate, methylprednisolone-succinate); dexamethasone and derivatives thereof; triamcinolone and derivatives thereof (such as triamcinolonehexacetonuid, triamcinolonacetonamid); paramethasone; betamethasone; fluhydrocortisone; fluocinolone.

It is preferred that the agent of the invention has efficacy in the treatment of an inflammatory and/or an autoimmune condition or disorder.

By 'treatment' we include both therapeutic and prophylactic treatment of a subject/patient. The term 'prophylactic' is used to encompass the use of an agent, medicament or pharmaceutical formulation described herein which either prevents or reduces the likelihood of an inflammatory and/or an autoimmune condition or disorder in a patient or subject.

It is appreciated that for the prevention or treatment of a condition or disorder, the appropriate dosage of an agent will depend on the type of condition or disorder to be treated, the severity and of course of the condition or disorder, whether the agent is administered for prophylactic or therapeutic purposes, the course of previous therapy and the patient's clinical history and response to the agent. According to a further embodiment of the invention, the effectiveness of an agent of the invention in alleviating the symptoms, preventing or treating a condition or disorder may be improved by serial administering or administration in combination with another agent that is effective for the same condition or disorder, such as conventional therapeutic agents known for the intended therapeutic indication.

In one embodiment the condition or disorder may be selected from the group consisting of: arthritic diseases (such as rheumatoid arthritis, spondylitis, osteoarthritis); chronic inflammatory bowel disease (IBD, such as Crohn's disease, ulcerative colitis); peridontitis; psoriasis; asthma; systemic lupus erythematosus; multiple sclerosis; autoimmune chronic inflammatory diseases; connective tissue diesase; autoimmune liver disease (such as biliary cirrhosis); sepsis; hemophagocytic syndrome; liver disease; liver failure; hepatitis; atherosclerosis; diabetes; obesity; non-alcoholic fatty liver disease; non-alcoholic steatohepatitis (NASH); alcoholic steatohepatitis (ASH); acute alcoholic hepatitis; joint inflammation; inflammation-induced cartilage destruction; liver cirrhosis; organ transplantation; Idiopathic Thrombocytopenic Purpura (ITP); sarcoidosis; uveitis; HLA-B27 positive uveitis; acute uveitis; macrophage activation syndrome; giant cell arthritis.

In a preferred embodiment the agent has efficacy in the treatment of a proliferative condition or disorder. Such conditions or disorders may be selected, for example, from the group consisting of: myeloid leukaemia (such as AML types M4 and M5); cancer of monocytic or macrophage cell origin (such as histolytic sarcoma); cancer cells expressing CD163; solid tumours (such as breast cancer, bladder cancer, melanoma); tumour-associated macrophages.

In a preferred embodiment, the invention provides an agent comprising an immunostimulatory drug, preferably an immunostimulatory drug capable of stimulating one or more anti-tumour activity of a macrophage.

Preferably, the immunostimulatory drug is selected from the group consisting of: a cytokine such as gamma-interleukin-2; a toll-like-receptor agonist; an siRNA molecule; a bacterial polysaccharide.

In an alternative embodiment, the invention provides an agent wherein the drug is a recombinant protein comprising a biological activity. For example, one advantageous protein includes Glucocerebrosidase (or a protein with the enzymatic activity of Glucocerebrosidase), which is used to treat conditions affecting macrophages. Thus, in that embodiment, the agent of the invention will have efficacy in the treatment of an inherited condition or disorder affecting macrophages (such as Gaucher disease).

In an alternative embodiment, the invention provides an agent wherein the drug is an antimicrobial drug, preferably an antimicrobial drug selected from the group comprising or consisting of: an antibiotic; an anti-tuberculosis antibiotic (such as isoniazide, ethambutol); an anti-retroviral drug, for example an inhibitor of reverse transcription (such as zidovudin) or a protease inhibitor (such as indinavir); drugs with effect on leishmaniasis (such as Meglumine antimoniate).

In that embodiment, the agent of the invention will advantageously have efficacy in the treatment of a condition or disorder caused by an micro-organism, for example, a condition or disorder selected from the group comprising or consisting of: tuberculosis, AIDS; HIV infection; Leishmaniasis.

In a preferred embodiment, the agent comprises a gene to be delivered to a cell having a CD163 receptor localised on its surface.

It will be appreciated that such gene delivery can be used to treat disorders and conditions associated with macrophage dysfunction or with incorrect macrophage activity.

For example, macrophage dysfunction is associated with lipid storage diseases. Lipid storage diseases are a group of inherited metabolic disorders in which harmful amounts of fatty materials accumulate in cells (macrophages) and tissues. Individuals with such disorders either do not produce enough of one of the enzymes needed to metabolize lipids, or produce enzymes that do not function correctly. Over time, this excessive storage of fats can cause permanent cellular and tissue damage, particularly in the liver, spleen, bone marrow, and nervous system.

Gaucher disease is the most common of the lipid storage diseases. Treating these patients with enzyme replacement treatment given intravenously is known to decrease symptoms, but this treatment is expensive and need to be continued throughout life. Enzyme replacement therapy has also been developed for Fabry disease.

In a preferred embodiment, the disorder or condition associated with macrophage dysfunction is selected from the group consisting of: Gaucher disease; Tay-Sachs disease; Niemann-Pick disease; Fabry disease; Metachromatic leukodystrophy; Krabbé disease.

Preferably, the gene to be delivered is selected from the group consisting of: a gene encoding a Glucocerebrosidase; a gene encoding a Hexosaminidase (which comprises two subunits); a gene encoding a Sphingomyelinase; a gene encoding an Alphagalactosidase; a gene encoding an Arylsulfatase; a gene encoding a Galactosylceramidase. Alternatively, the gene to be delivered is selected from the group consisting of: a gene encoding a protein having Glucocerebrosidase activity; a gene encoding a protein having Hexosaminidase activity; a gene encoding a protein having Sphingomyelinase activity; a gene encoding a protein having Alphagalactosidase activity; a gene encoding a protein having Arylsulfatase activity; a gene encoding a protein having Galactosylceramidase activity.

In one embodiment, the agent of the invention comprises a gene encoding a Glucocerebrosidase and the disorder and/or condition associated with macrophage dysfunction or with incorrect macrophage activity is Gaucher disease.

In one embodiment, the agent of the invention comprises a gene encoding a Hexosaminidase and the disorder and/or condition associated with macrophage dysfunction or with incorrect macrophage activity is Tay-Sachs disease.

In one embodiment, the agent of the invention comprises a gene encoding a Sphingomyelinase and the disorder and/or condition associated with macrophage dysfunction or with incorrect macrophage activity is Niemann-Pick disease.

In one embodiment, the agent of the invention comprises a gene encoding an Alpha galactosidase and the disorder and/or condition associated with macrophage dysfunction or with incorrect macrophage activity is Fabry disease.

In one embodiment, the agent of the invention comprises a gene encoding an Arylsulfatase and the disorder and/or condition associated with macrophage dysfunction or with incorrect macrophage activity is Metachromatic leukodystrophy.

In one embodiment, the agent of the invention comprises a gene encoding a Galactosylceramidase and the disorder and/or condition associated with macrophage dysfunction or with incorrect macrophage activity is Krabbé disease.

In a further aspect, the invention provides a pharmaceutical composition comprising an effective amount of an agent as defined herein and a pharmaceutically-acceptable diluent, carrier or excipient.

As used herein, 'pharmaceutical composition' means a therapeutically effective formulation according to the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce or prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent.

In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

The agents, medicaments and pharmaceutical compositions of the invention may be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period. Preferably, delivery is performed intra-muscularly (i.m.) and/or sub-cutaneously (s.c.) and/or intravenously (i.v.).

The agents, medicaments and pharmaceutical compositions of the invention can be administered by a surgically implanted device that releases the drug directly to the required site. For example, Vitrasert releases ganciclovir directly into the eye to treat CMV retinitis. The direct application of this toxic agent to the site of disease achieves effective therapy without the drug's significant systemic side-effects.

Electroporation therapy (EPT) systems can also be employed for the administration of the agents, medicaments and pharmaceutical compositions of the invention. A device which delivers a pulsed electric field to cells increases the permeability of the cell membranes to the drug, resulting in a significant enhancement of intracellular drug delivery.

The agents, medicaments and pharmaceutical compositions of the invention can also be delivered by electro-incorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of delivery of the agents, medicaments and pharmaceutical compositions of the invention is the ReGel injectable system that is thermo-sensitive. Below body temperature, ReGel is an injectable liquid while at body temperature it immediately forms a gel reservoir that slowly erodes and dissolves into known, safe, biodegradable polymers. The active substance is delivered over time as the biopolymers dissolve.

The agents, medicaments and pharmaceutical compositions of the invention can also be delivered orally. The process employs a natural process for oral uptake of vitamin $B_{12}$ and/or vitamin D in the body to co-deliver proteins and peptides. By riding the vitamin $B_{12}$ and/or vitamin D uptake system, the agents, medicaments and pharmaceutical compositions of the invention can move through the intestinal wall. Complexes are synthesised between vitamin $B_{12}$ analogues and/or vitamin D analogues and the drug that retain both significant affinity for intrinsic factor (IF) in the vitamin $B_{12}$ portion/vitamin D portion of the complex and significant bioactivity of the active substance of the complex.

The agents, medicaments and pharmaceutical compositions of the invention can be introduced to cells by "Trojan peptides". These are a class of polypeptides called penetratins which have translocating properties and are capable of carrying hydrophilic compounds across the plasma membrane. This system allows direct targeting of oligopeptides to the cytoplasm and nucleus, and may be non-cell type specific and highly efficient. See Derossi et al., (1998), Trends Cell Biol 8, 84-87.

Preferably, the medicaments and/or pharmaceutical compositions of the present invention is a unit dosage containing a daily dose or unit, daily sub-dose or an appropriate fraction thereof, of the active ingredient.

The agents, medicaments and pharmaceutical compositions of the invention will normally be administered orally or by any parenteral route, in the form of a pharmaceutical composition comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the agents, medicaments and pharmaceutical compositions of the invention can be administered alone but will generally be administered in admixture with a suitable pharmaceutical excipient, diluent or carrier selected with regard to the intended route of administration and standard pharmaceutical practice.

For example, the agents, medicaments and pharmaceutical compositions of the invention can be administered orally, buccally or sublingually in the form of tablets, capsules, ovules, elixirs, solutions or suspensions, which may contain flavouring or colouring agents, for immediate-, delayed- or controlled-release applications. The agents, medicaments and pharmaceutical compositions of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the agents, medicaments and pharmaceutical compositions of the invention may be combined with various sweetening or flavouring agents, colouring matter or dyes, with emulsifying and/or suspending agents and with diluents such as water, ethanol, propylene glycol and glycerin, and combinations thereof.

The agents, medicaments and pharmaceutical compositions of the invention can be administered parenterally, for example, intravenously, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Medicaments and pharmaceutical compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The medicaments and pharmaceutical compositions may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the agents, medicaments and pharmaceutical compositions of the invention will usually be from 0.002 to 0.4 mg/kg and/or 0.1 mg/kg to 20 mg/kg administered in single or divided doses.

Thus, for example, the tablets or capsules of the medicaments and pharmaceutical compositions of the invention may contain from 5 mg to 1400 mg (for example, from 7 mg to 1400 mg, or 5 mg to 1000 mg) and may preferably contain 5 mg to 200 mg of active agent for administration singly or two or more at a time, as appropriate.

In one embodiment, the agents, medicaments and pharmaceutical compositions of the invention are administered at a dosage ranging from 0.02 mg/kg to 2 mg/kg and at a frequency ranging from twice per week to once per month.

The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The agents, medicaments and pharmaceutical compositions of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active agent, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of an agent of the invention and a suitable powder base such as lactose or starch.

Aerosol or dry powder formulations are preferably arranged so that each metered dose or "puff" contains 5 mg to 1400 mg (for example, from 7 mg to 1400 mg, or 5 mg to 1000 mg) and preferably contain 5 mg to 200 mg of an agent of the invention for delivery to the patient. It will be appreciated that the overall daily dose with an aerosol will vary from patient to patient, and may be administered in a single dose or, more usually, in divided doses throughout the day.

Alternatively, the agents, medicaments and pharmaceutical compositions of the invention can be administered in the form of a suppository or pessary, or they may be applied topically in the form of a lotion, solution, cream, gel, ointment or dusting powder. The agents, medicaments and pharmaceutical compositions of the invention may also be transdermally administered, for example, by the use of a skin patch. They may also be administered by the ocular route, particularly for treating diseases of the eye.

For ophthalmic use, the agents, medicaments and pharmaceutical compositions of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agents, medicaments and pharmaceutical compositions of the invention can be formulated as a suitable ointment containing the active agent suspended or dissolved in, for example, a mixture with one or more of the following: mineral oil, liquid petrolatum, white petrolatum, propylene glycol, polyoxyethylene polyoxypropylene agent, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or parenteral administration of the agents, medicaments and pharmaceutical compositions of the invention is the preferred route, being the most convenient.

For veterinary use, the agents, medicaments and pharmaceutical compositions of the invention are administered as a suitably acceptable formulation in accordance with normal veterinary practice and the veterinary surgeon will determine the dosing regimen and route of administration which will be most appropriate for a particular animal.

The agents of the invention may be formulated at various concentrations, depending on the efficacy/toxicity of the compound being used, for example as described in the accompanying Examples. For in vitro applications, formulations may comprise a lower concentration of a compound of the invention.

Thus, the present invention provides a pharmaceutical formulation comprising an amount of an antibody or antigen-binding fragment, or variant, fusion or derivative thereof, of the invention effective to treat various conditions (as described above and further below).

Preferably, the pharmaceutical composition is adapted for delivery by a route selected from the group comprising: intravenous; intramuscular; subcutaneous; intra-articular; pulmonary; intranasal; intraocular; intrathecal.

The present invention also includes pharmaceutical compositions comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the agents according to the present invention.

The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

The agents and/or polypeptide binding moieties of the invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilisation) when re-hydrated.

In a further aspect, the invention provides a kit comprising an agent or a pharmaceutical composition as defined herein.

Thus, there may be provided a kit for use in the therapeutic treatment of the conditions defined herein.

Alternatively, the kit may comprise a detectable antibody or antigen-binding fragment or derivative thereof according to the invention, suitable for use in diagnosis. Such a diagnostic kit may comprise, in an amount sufficient for at least one assay, the diagnostic agent as a separately packaged reagent. Instructions for use of the packaged reagent are also typically included. Such instructions typically include a tangible expression describing reagent concentrations and/or at least one assay method parameter such as the relative amounts of reagent and sample to be mixed, maintenance time periods for reagent/sample admixtures, temperature, buffer conditions and the like.

In a further aspect, the invention provides an agent for use in medicine.

Methods of manufacturing a medicament using an active agent, such as the agent of the invention, are well known to persons skilled in the art of medicine and pharmacy.

In a further aspect, the invention provides the use of an agent of the invention for treating an inflammatory and/or an autoimmune condition or disorder, or a proliferative condition or disorder, or an inherited condition or disorder, or a condition or disorder caused by an micro-organism, all of which are defined herein.

In a further aspect, the invention provides the use of an agent in the manufacture of a medicament for treating an inflammatory and/or an autoimmune condition or disorder, or a proliferative condition or disorder, or an inherited condition or disorder, or a condition or disorder caused by an micro-organism, all of which are defined herein.

In a still further aspect, the invention provides a method for reducing and/or alleviating an inflammatory and/or an autoimmune condition or disorder, or a proliferative condition or disorder, or an inherited condition or disorder, or a condition or disorder caused by a micro-organism, all of which are described herein, the method comprising the step of administering an effective amount of an agent or pharmaceutical composition of the invention to an individual in need thereof.

Preferably, the invention provides the use of an agent as defined herein in a method for detecting a cell expressing SRCR domain 1 of the CD163 receptor.

In such a method, it is preferred that the CD163 receptor is localised on the surface of the cell, for example, wherein the cell is a malignant cell expressing CD163, or is a monocyte and/or monocyte-derived cell (such as those selected from the group consisting or comprising of monocytes, macrophages, monocyte-derived dendritic cells, activated macrophage subtypes (e.g. M1, M2). Preferably, the invention provides a method in which the cell is a macrophage.

As used herein, the singular forms "a", "and", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

The listing or discussion in this specification of an apparently prior-published document should not necessarily be taken as an acknowledgement that the document is part of the state of the art or is common general knowledge.

Preferred, non-limiting examples which embody certain aspects of the invention will now be described, with reference to the following figures:

FIGS. 1A-1D—Peripheral blood monocyte CD163 distribution in freshly drawn samples using different anti-CD163 clones. After gating monocytes in a forward scatter [FSC] versus side scatter [SSC], the gated cells were re-plotted with CD14 APC versus CD163 PE clone (FIG. 1A) MAC2-158, SRCR domain-1, (FIG. 1B) R-20, SRCR domain-4, (FIG. 1C) GHI/61, SRCR domain-7, and (FIG. 1D) RM3/1, SRCR domain-9.

Figure 2B:
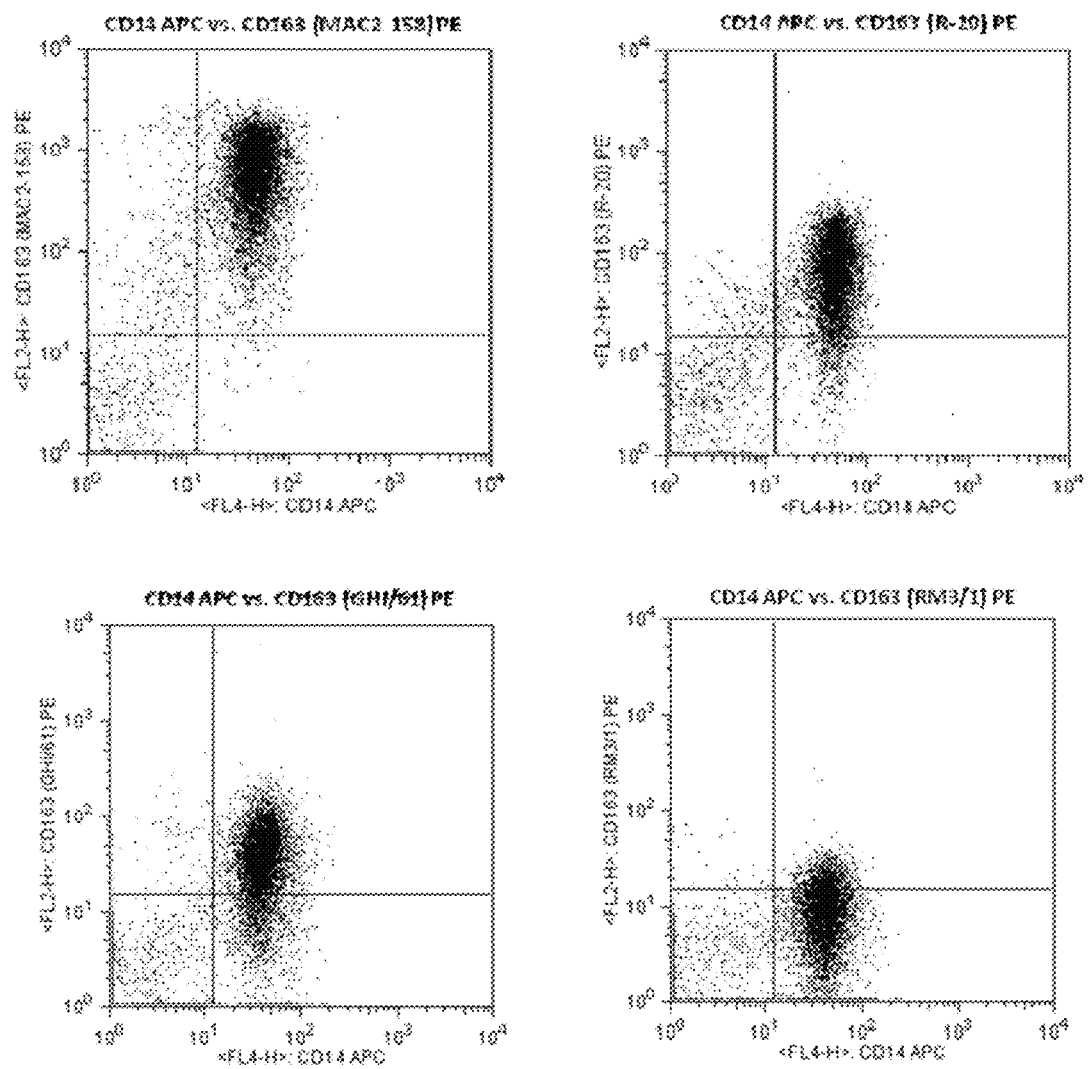
Figure 2C:
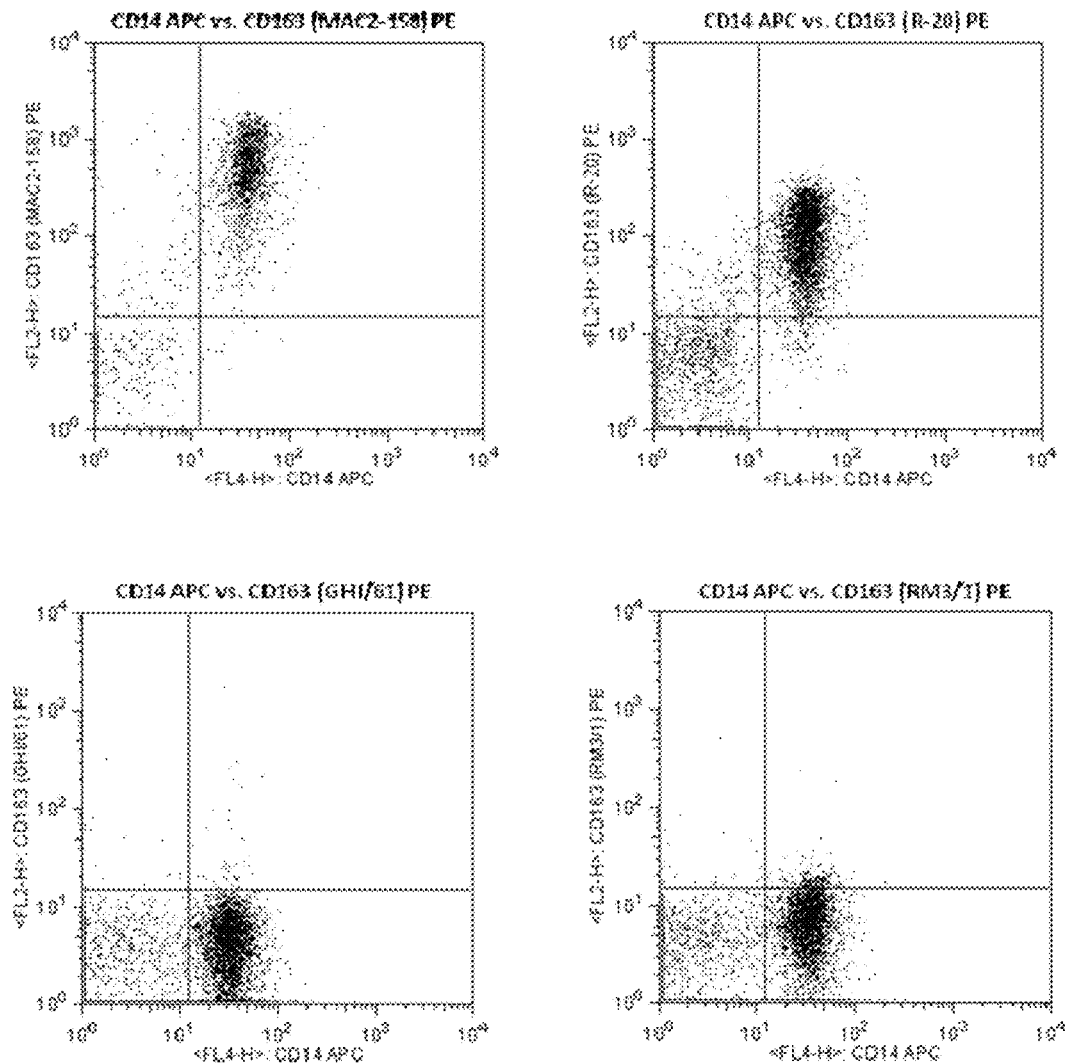

FIGS. 2A-2C—Monocytic cellular CD163 expression in blood samples under influence of various anticoagulants using different anti-CD163 clones. The influence of different extracellular calcium concentrations on monocyte surface CD163 expression determination was investigated in freshly drawn whole blood stabilized with three commonly used anticoagulants, (FIG. 2A) EDTA, (FIG. 2B) citrate, and (FIG. 2C) heparin. After gating monocytes in a forward scatter [FSC] versus side scatter [SSC], the gated cells were re-plotted with CD14 APC versus CD163 PE clone (left panels) MAC2-158, SRCR domain-1, (second panels) R-20, SRCR domain-4, (third panels) GHI/61, SRCR domain-7, and (right panels) RM3/1, SRCR domain-9.

Figure 3A:
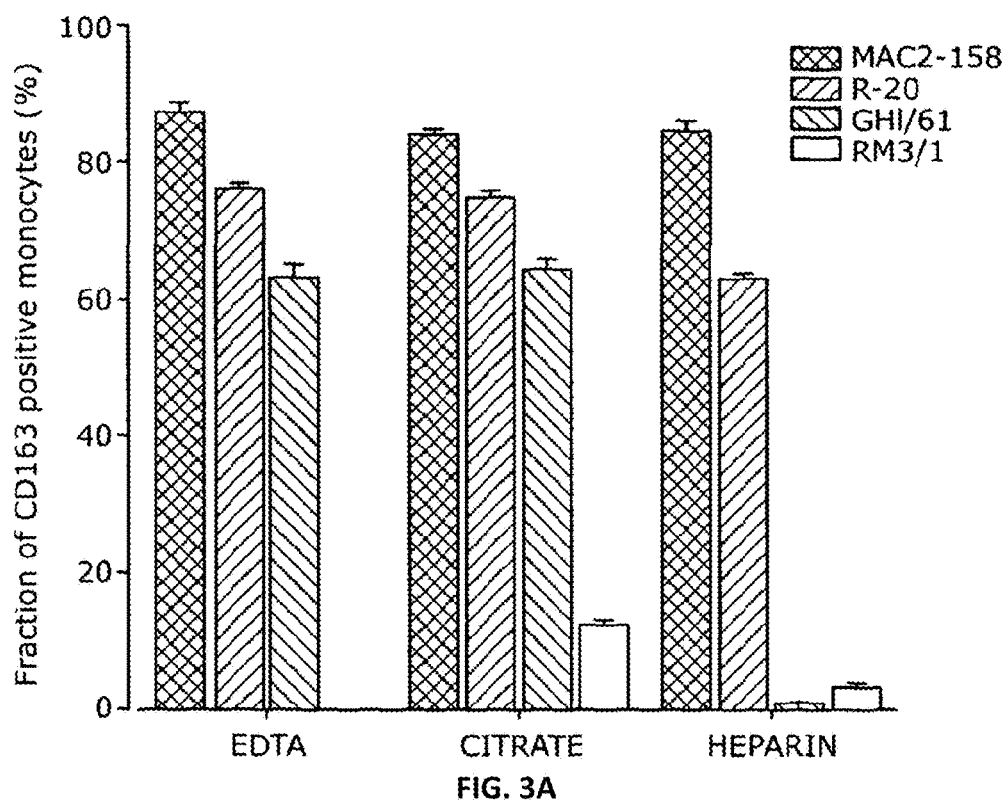
Figure 3B:
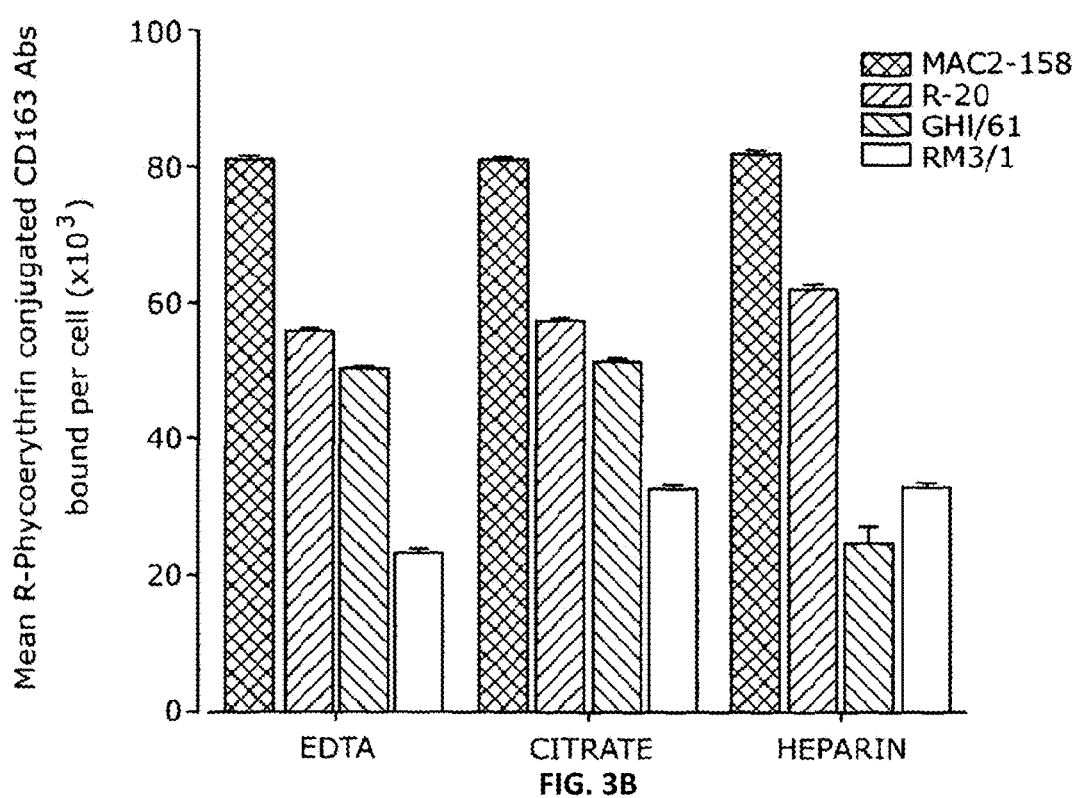

FIGS. 3A-3B—Schematic representation of the monocytic cellular CD163 expression in samples anti-coagulated with EDTA, citrate, and heparin using different CD163 mAbs. After gating monocytes in a forward scatter [FSC] versus side scatter [SSC], the gated cells were re-plotted with CD14 APC versus CD163 PE clone. Subsequently, (FIG. 3A) the fraction of CD163 positive monocytes and (FIG. 3B) the mean R-Phycoerythrin conjugated CD163 Abs bound per cell was estimated. Quantibrite PE beads were used to convert the FL2 linear fluorescence staining of cell population into the number of CD163 R-Phycoerythrin molecules bound per cell reflecting the receptor density. Results are expressed as mean±standard error (SE) of triplicate samples. The presented data are representative of several independently performed experiments.

FIG. 4—mAbs binding to immobilized CD163 in either 2 mM free $Ca^{2+}$ (solid line) or 10 mM EDTA (dotted line). Concentration of mAbs are 5 µg/ml, except for R-20 and 5C6-FAT (10 µg/ml) and GHI/61 (20 µg/ml)

Figure 5:
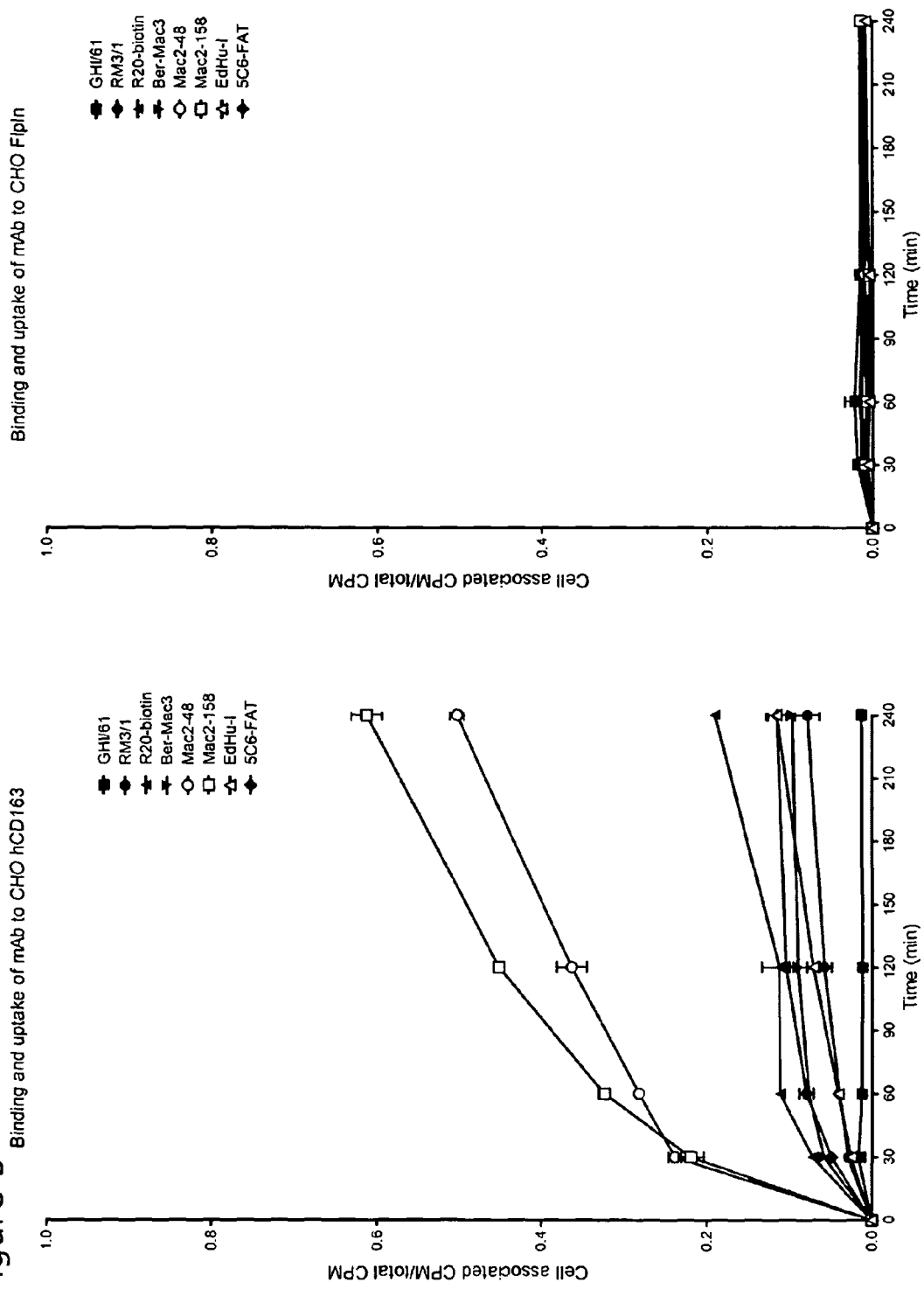

FIG. 5—Cellular binding and uptake of different $^{125}$I-labeled clones of monoclonal CD163 antibodies. To compare the endocytic ability of different clones of monoclonal CD163 antibodies, CD163 transfected Flp-In CHO cells were incubated with different $^{125}$I-labeled CD163 antibodies. The degree of cell-associated radioactivity detected in non-transfected Flp-In CHO cells was insignificant.

Figure 6:
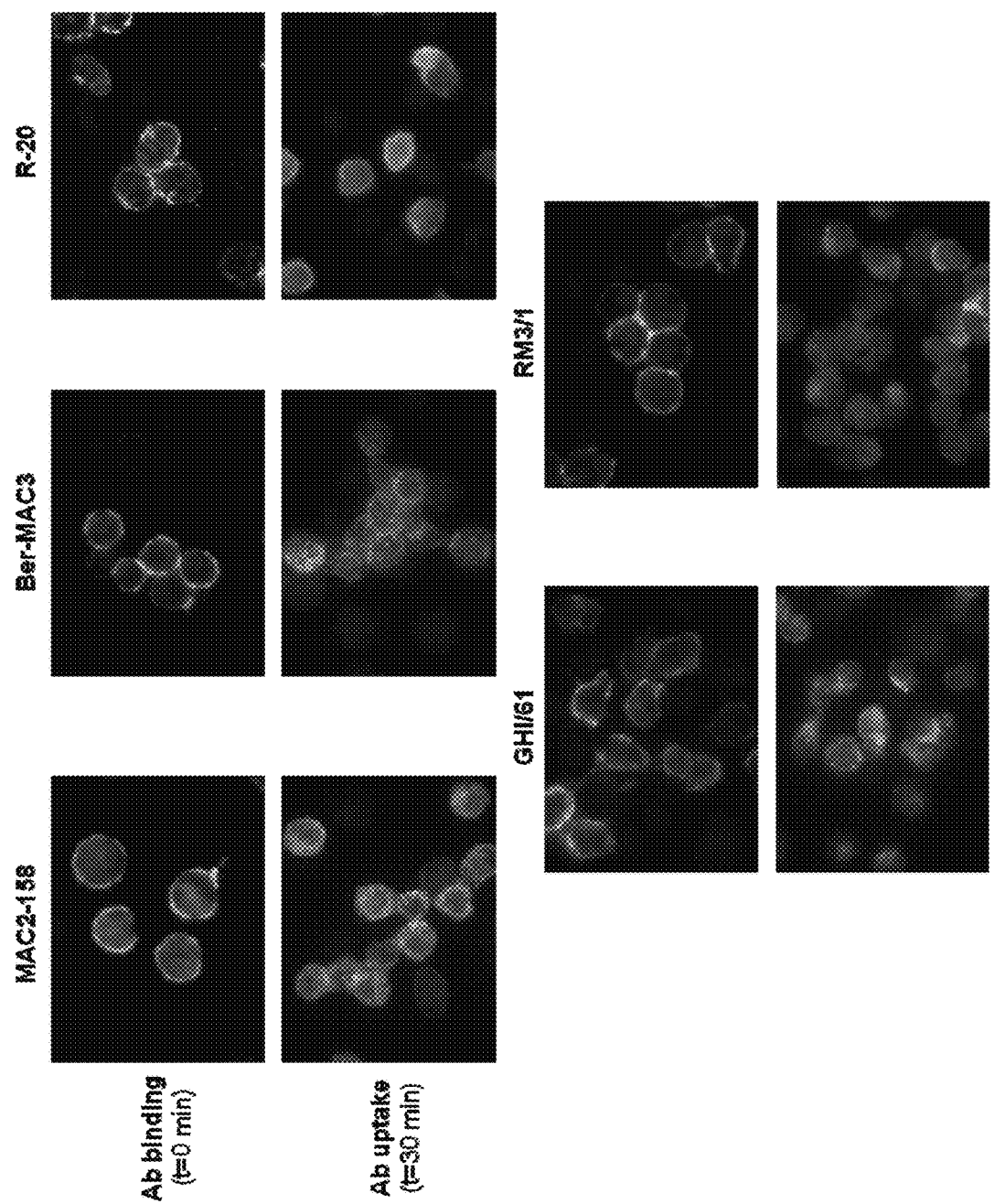

FIG. 6—CD163 antibody binding and uptake in human macrophages. Monocyte-derived macrophages incubated for 0 or 30 minutes with immunofluorescent mAbs binding CD163, detected using fluorescent laser microscopy. As can be seen MAc2-158 exhibit both best binding and uptake.

Figure 7A:
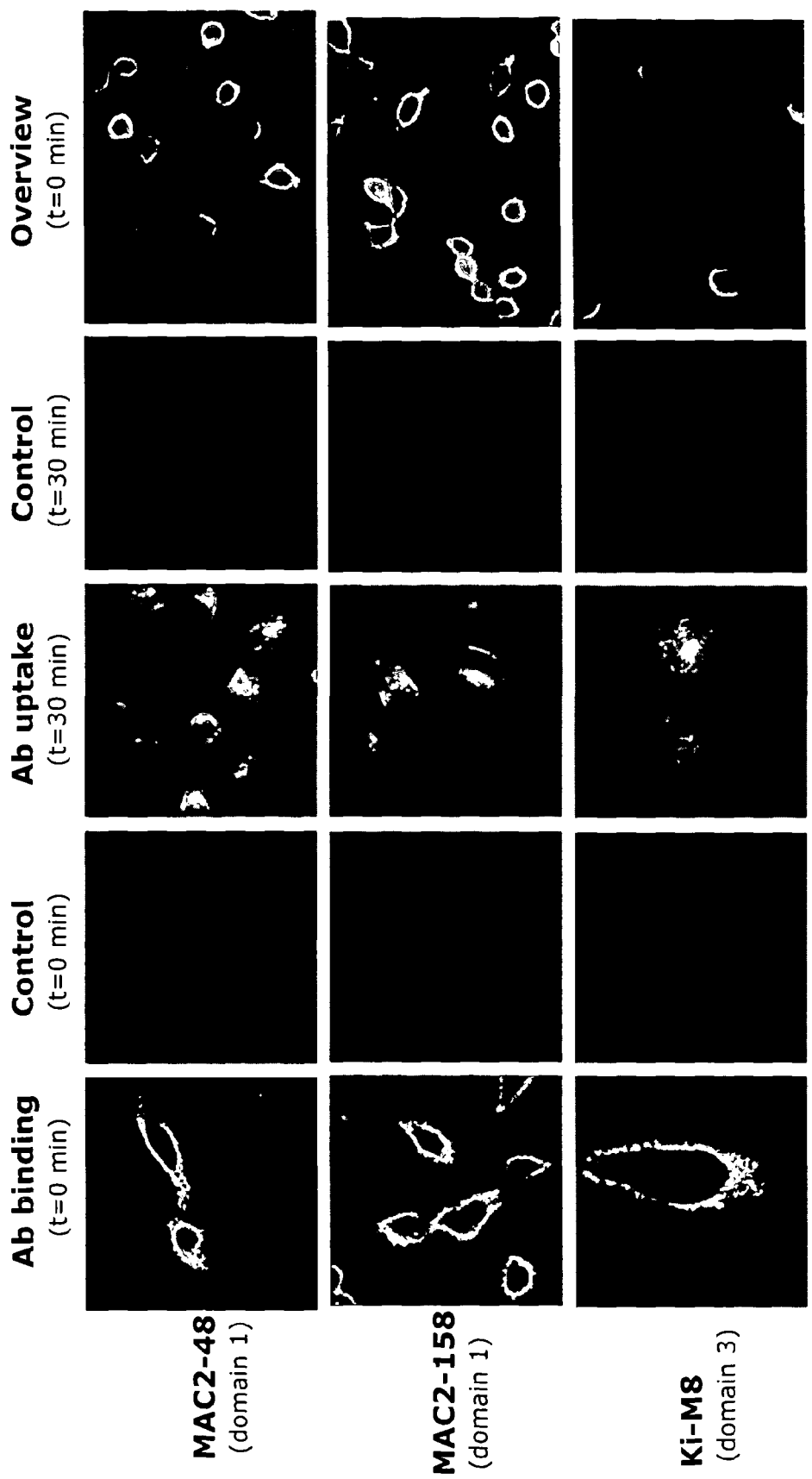
Figure 7B:
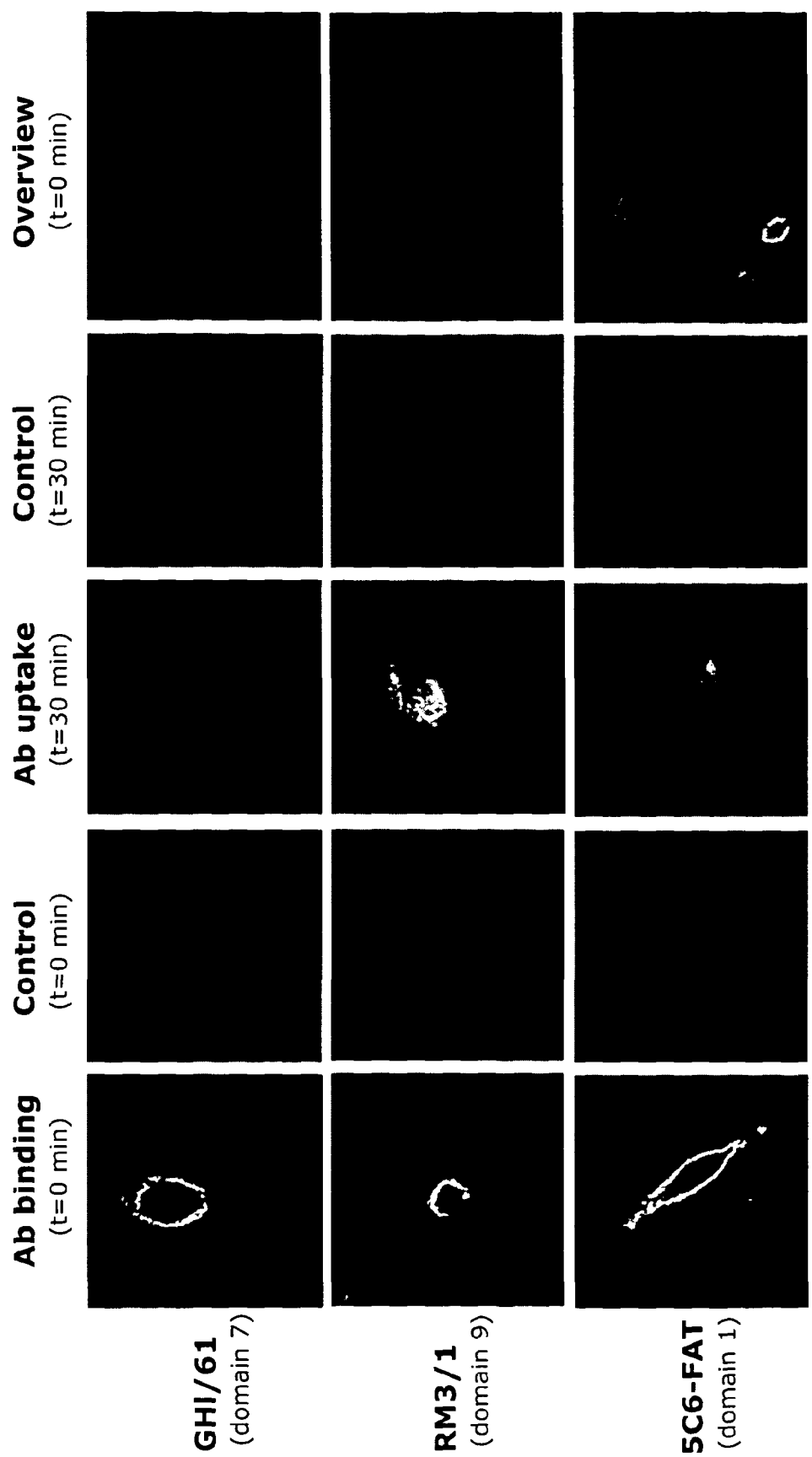

FIGS. 7A and 7B—CD163 antibody binding and uptake in CHO cells expressing CD163 and control CHO cells. Cells incubated for 0 or 30 minutes with immunofluorescent mAbs binding CD163, detected using confocal microscopy. As can be seen Mac2-48 and MAc2-158 exhibit both best binding and uptake.

Figure 8A:
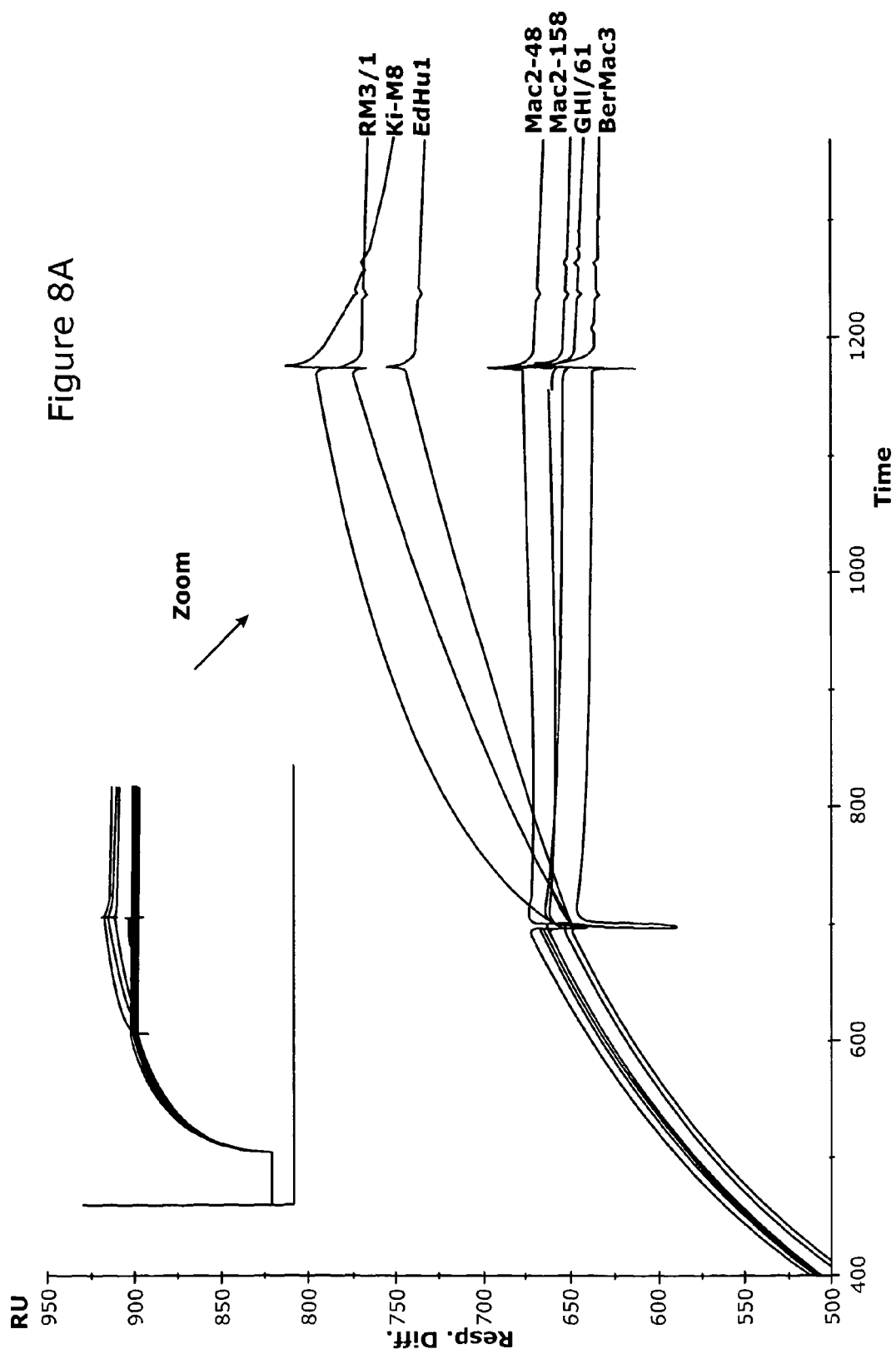
Figure 8B:
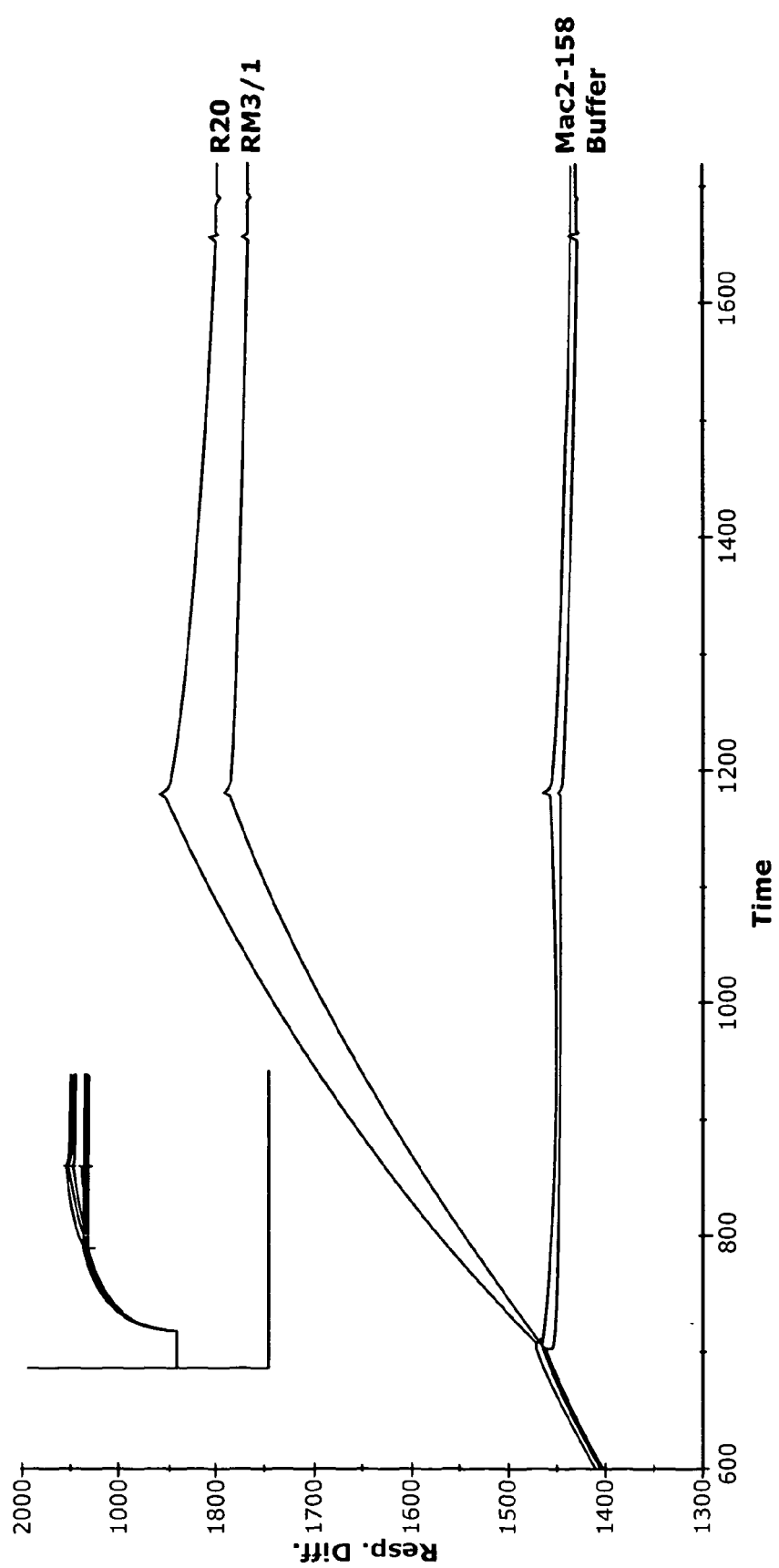

FIGS. 8A and 8B—Competition with Mac2-158. The small panel in FIG. 8A and FIG. 8B shows the entire sensorgram, whereas the zoom part shows the part of the sensorgram displaying binding of different mAbs to a Mac2-158 saturated CD163 chip. As can be seen in FIG. 8A, Mac2-158, Mac2-48, Ber-Mac3 and GHI/61 were not able to bind to a CD163-Fc saturated with Mac2-158 in a 2 mM free calcium buffer. All mAbs except GHI/61 bound to SRCR domain 1, and GHI/61 did not exhibit binding in a calcium-rich environment. The mAbs EdHU-1, Ki-M8, RM3/1 and R20 were all able to bind to the CD163-Fc regardless of the saturation and are thus not competing for binding to CD163 with Mac2-158.

Figure 9A:
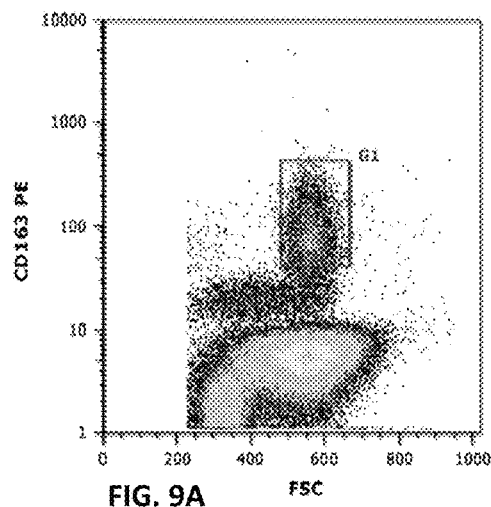
Figure 9B:
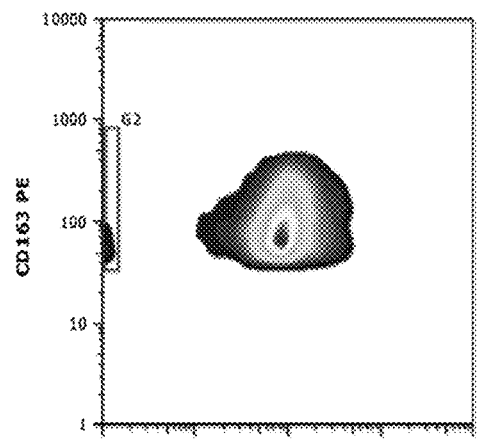
Figure 9C:
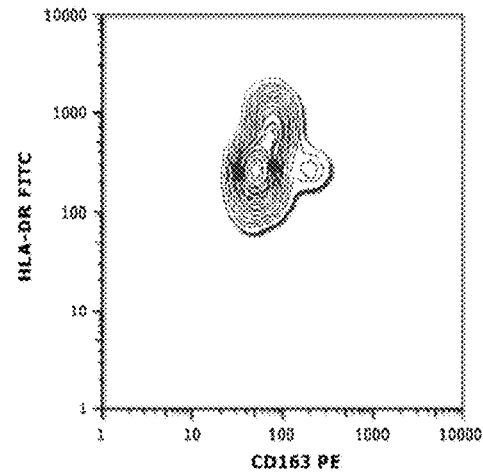

FIGS. 9A-9D—Identification of unknown tissue component expressing the macrophage scavenger receptor CD163. In a plot of forward scatter [FSC] versus CD163 PE, CD163 positive cells were gated (G1) (FIG. 9A), and the gated cells were re-plotted with CD14 APC versus CD163 PE. A gate (G2) was sat around the yet unidentified population of CD14-CD163+ cells (FIG. 9B) and re-plotted with CD163 PE versus HLA-DR FITC (FIG. 9C). Backgating analysis of CD14-HLA-DR+CD163+ cells (encircled dot plot overlay) in a FSC/SSC plot (FIG. 9D) revealed a relatively distinct cell population localized between lymphocytes and monocytes.

FIGS. 10A-10E—Flow cytometric analysis of CD163 expression on dendritic cells in peripheral blood. In a forward scatter [FSC] versus side scatter [SSC], the mononuclear cell cluster was gated (G1) (FIG. 10A), and the gated cells were re-plotted with CD14 APC versus ILT3 PE-Cy5 (FIG. 10B), and a gate was sat around CD14-ILT3+ cells (dendritic cells; G2). The gated dendritic cells were re-plotted with CD163 PE versus HLA-DR FITC depicting two subsets of CD163+ dendritic cells (FIG. 10C). Backgating analysis of CD14-ILT3+HLA-DR+CD163+ cells (encircled dot plot overlay) in a FSC/SSC plot (FIG. 10D) revealed the expected localization of dendritic cells between lymphocytes and monocytes. Isotype matched non-specific PE-conjugated IgG1 served as a negative staining control (FIG. 10E).

Figure 11A:
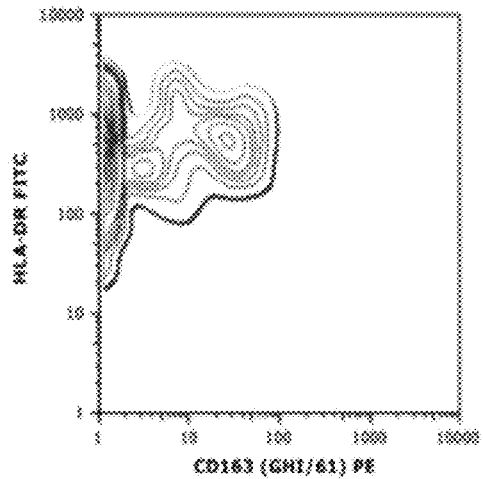
Figure 11B:
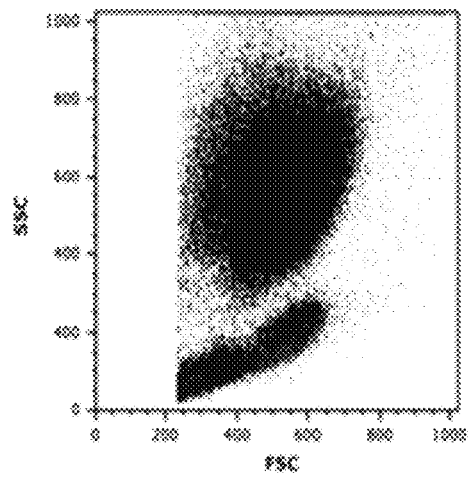
Figure 11C:
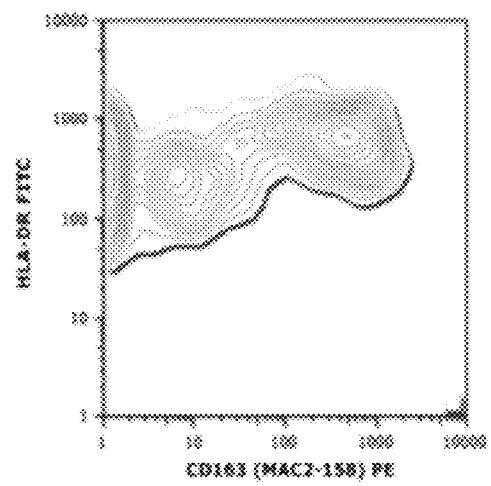
Figure 11D:
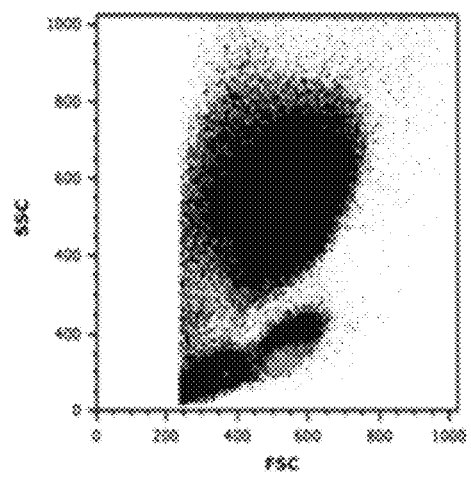

FIGS. 11A-11D—Flow cytometric analysis of peripheral blood dendritic cell CD163 expression using different CD163 mAbs. After gating of mononuclear cells and dendritic cells (CD14-ILT3+), gated cells were re-plotted with CD163 PE versus HLA-DR FITC using either GHI/61 (FIG. 11A) or MAC2-158 (FIG. 11C) clone of anti-CD163. Backgating analysis of CD14-ILT3+HLA-DR+CD163+ cells using MAC2-158 (grey dot plot overlay) in a FSC/SSC plot (FIG. 11D) showed a significantly higher fraction of CD163 expressing peripheral blood dendritic cells (32.3% [95% CI: 19.6-45.1%]) than when using GHI/61 (10.5% [95% CI: 8.0-12.5%]) (red dot plot overlay) in a FSC/SSC plot (FIG. 11B).

FIGS. 12A-12E—Phenotyping CD163 expressing peripheral blood dendritic cells. Flow cytometric analysis of CD163, HLA-DR, ILT3, CD11c, CD16, and CD91 expression on dendritic cells in peripheral blood. After gating of mononuclear cells and dendritic cells (CD14-ILT3+), gated cells were re-plotted with CD163 PE versus: (FIG. 12A) HLA-DR PerCP, (FIG. 12B) ILT3 PE-Cy5, (FIG. 12C) CD11c FITC, (FIG. 12D) CD16 FITC, and (FIG. 12E) CD91 FITC.

Figure 13A:
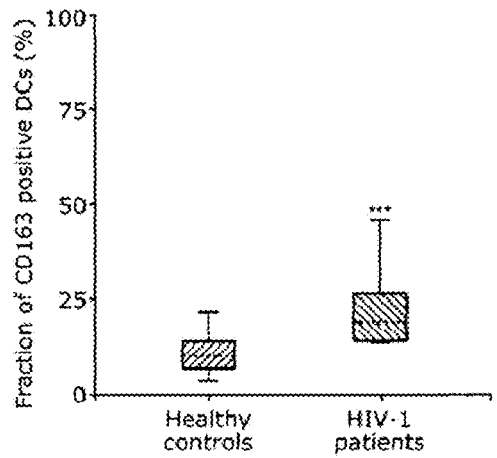
Figure 13B:
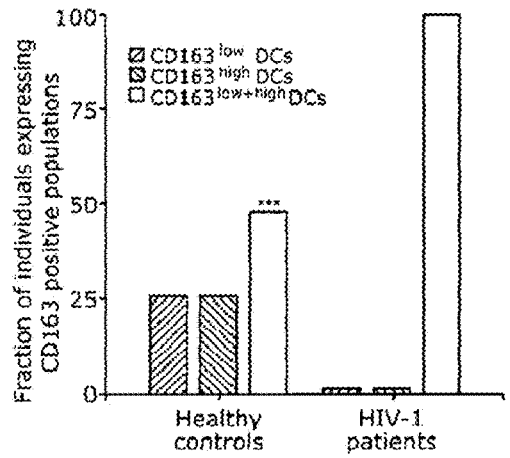
Figure 13C:
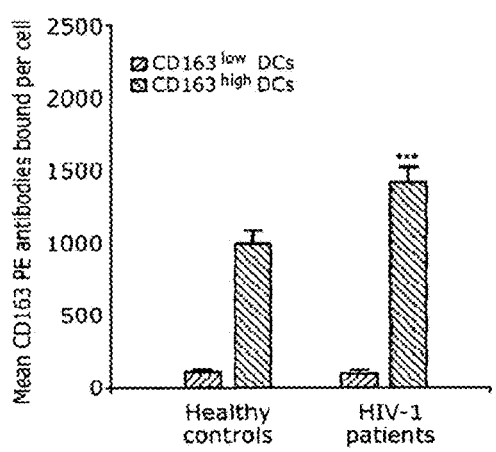

FIGS. 13A-13C—Dendritic cell CD163 expression in HIV-1 infection. Flow cytometric analysis of CD163 expression on dendritic cells in peripheral blood from HIV-1 patients compared to healthy adults. (FIG. 13A) Fraction of CD163+ dendritic cells in normal controls (n=31) and HIV-1 infected patients (n=15). Box plots indicate median, 25-75 percentiles, and range. (FIG. 13B) Level of expression of CD163 in CD163low and CD163high subsets in controls and HIV-1 infected patients. (FIG. 13C) Level of expression of CD163 in CD163low and CD163high subsets in controls and HIV-1 infected patients. Quantibrite PE beads were used to convert the FL2 linear fluorescence staining of cell population into the number of CD163 PE molecules bound per cell. Results are expressed as mean±standard error (SE). ***p<0.001.

Figure 14A:
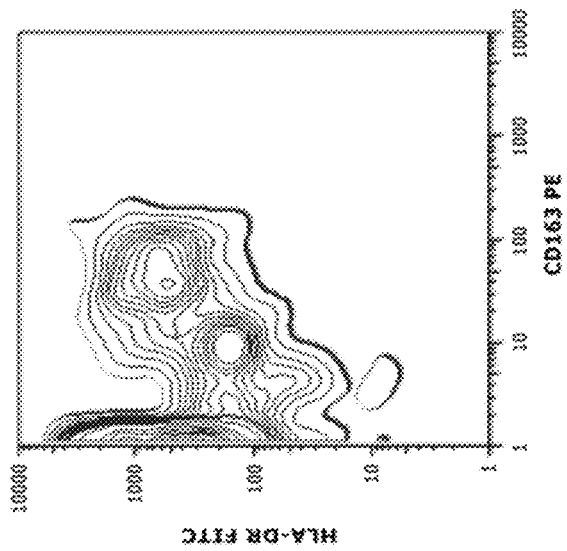
Figure 14B:
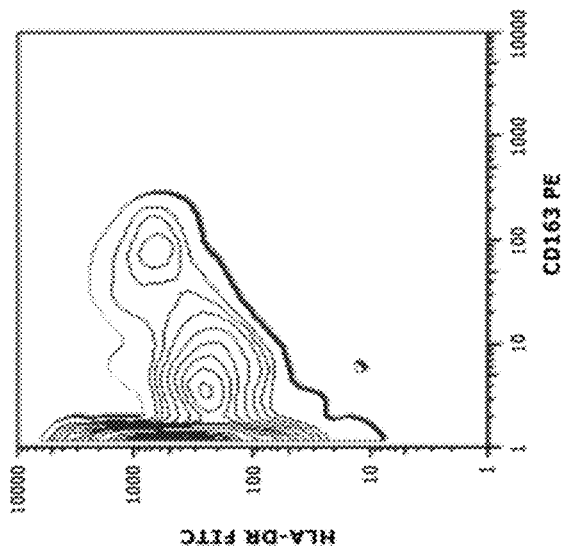
Figure 14C:
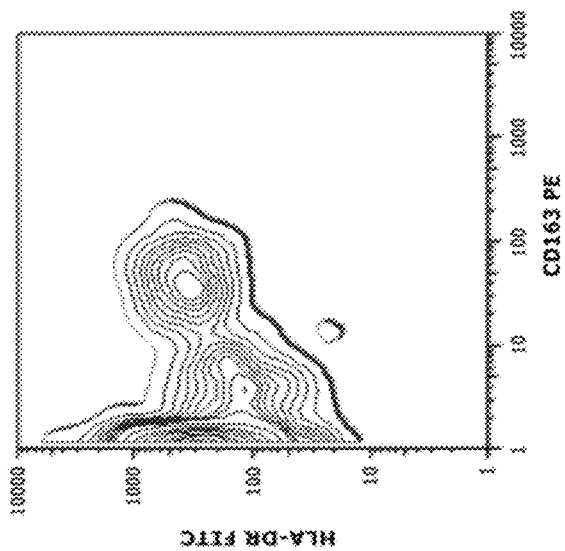

FIGS. 14A-14C—Representative plots of dendritic cell CD163 expression in HIV-1 infection. After gating of mononuclear cells and dendritic cells (CD14-ILT3+), gated cells were re-plotted with CD163 PE versus HLA-DR FITC (FIG. 14A), (FIG. 14B), and (FIG. 14C). The plots, originating from three different patients, are representative for the dendritic cell CD163 expression investigated in patients with HIV-1 infection (n=15).

Figure 14D:
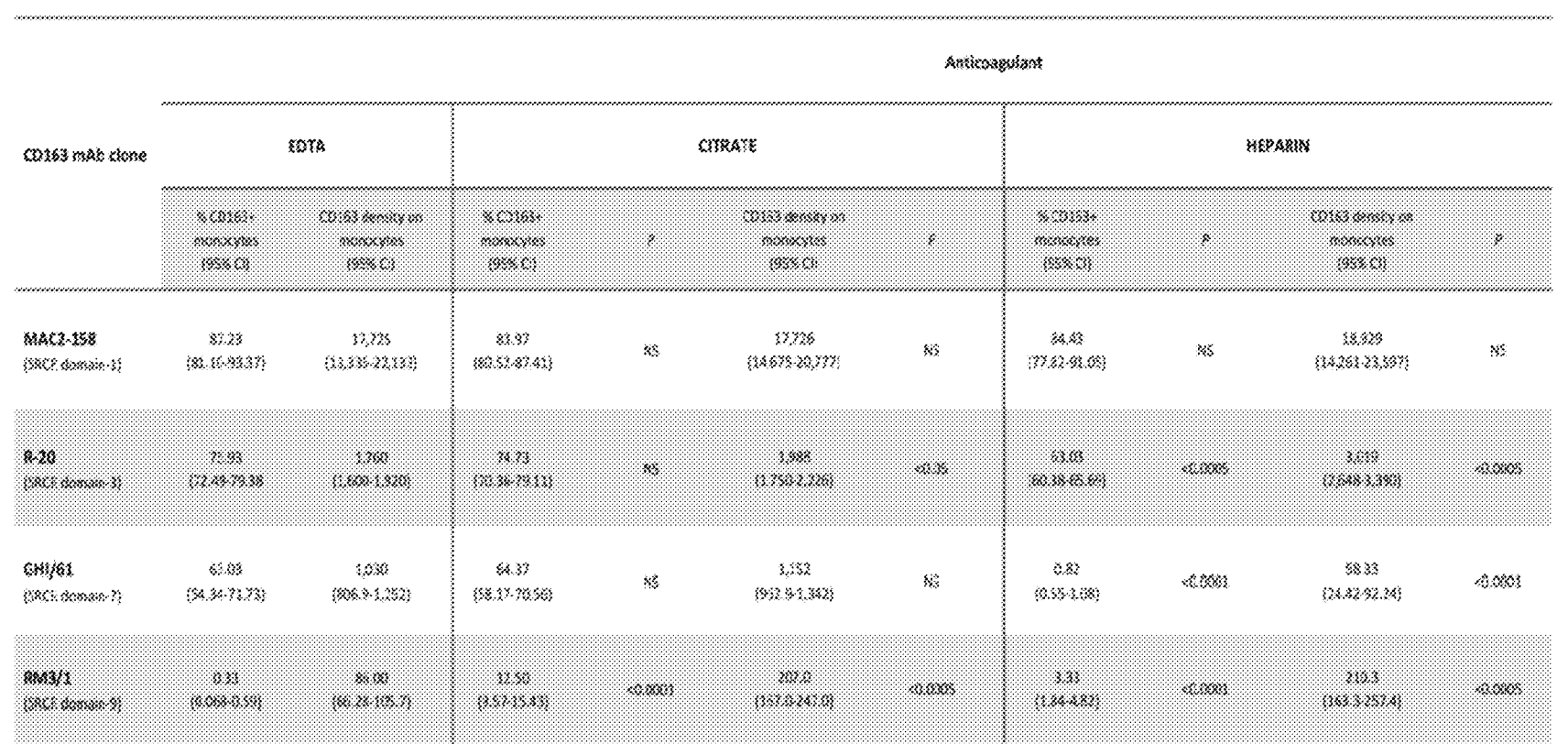

FIG. 14D—Overview of monocytic cellular CD163 expression in samples anti-coagulated with EDTA, citrate, and heparin using different CD163 mAbs. Monocytic cellular CD163 expression in heparin stabilized blood samples, which resembles physiological calcium levels, compared with samples anti-coagulated with calcium chelators; EDTA and citrate. Values are accompanied by 95% confidence intervals (95% CI) and differences between EDTA values and heparin and citrate values, respectively, are analysed for statistical significance with Student's t-test.

Figure 14E:
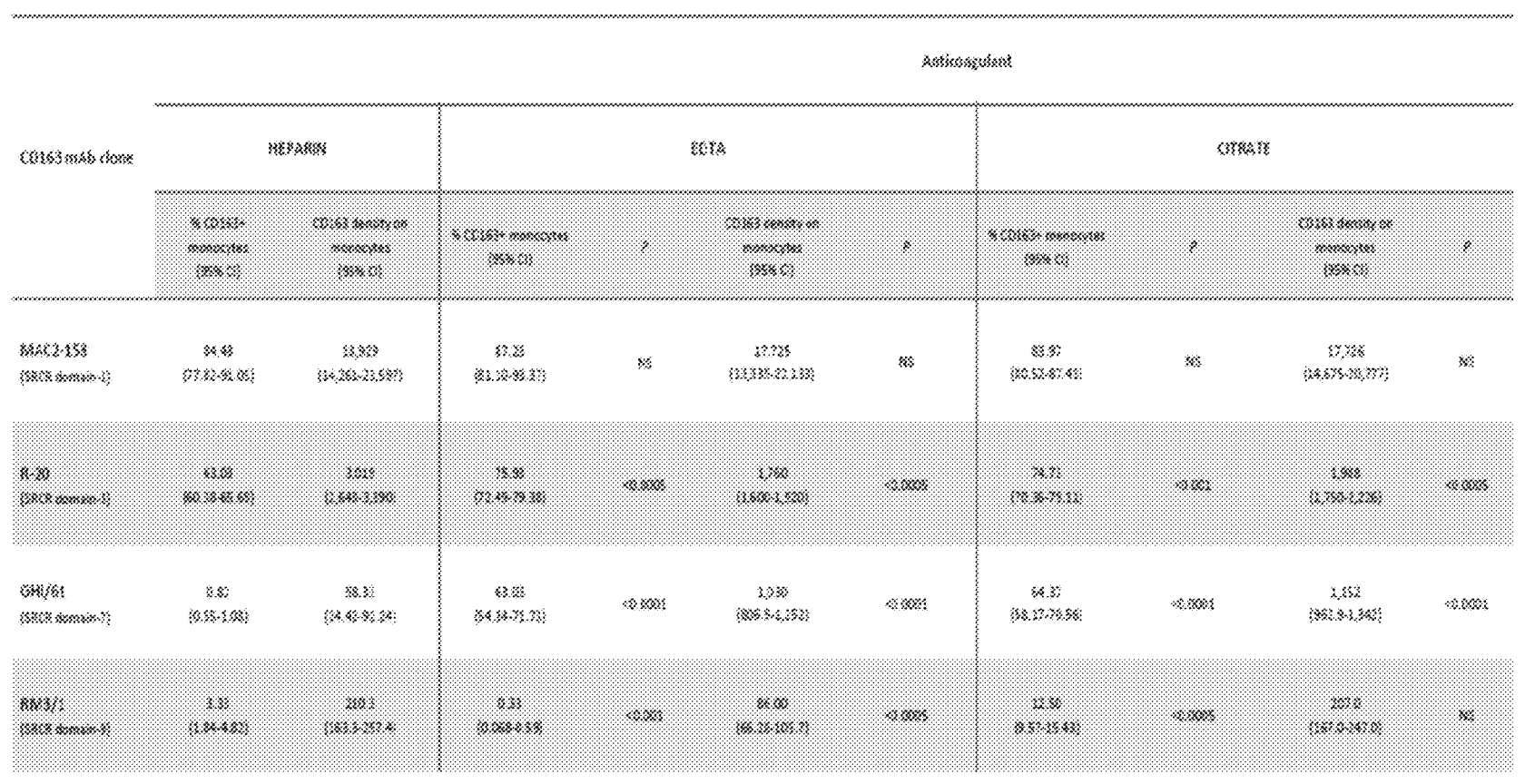

FIG. 14E—Overview of monocytic cellular CD163 expression in samples anti-coagulated with EDTA, citrate, and heparin using different CD163 mAbs. Monocytic cellular CD163 expression in heparin stabilized blood samples, which resembles physiological calcium levels, compared with samples anti-coagulated with calcium chelators; EDTA and citrate. Values are accompanied by 95% confidence intervals (95% CI) and differences between heparin values and EDTA and citrate values, respectively, are analysed for statistical significance with Student's t-test.

FIG. 15—Agarose gel of amplified fragments generated during humanisation procedure. A 1% agarose gel analysis shows that the PCRs for amplification of the variable regions worked. Left panel: Mac2-158 (100 bp Marker, heavy chain variable region, light chain variable region). Right panel: Mac2-48 (100 bp marker, 3× heavy chain variable region, 3× light chain variable region).

FIG. 16—Sequence variants tested. Template for $V_H$ and $V_L$ is the best fit overall sequence and the Germline is the best fit in germline V-sequences. The other sequences are the sequences tested in expression and ELISA.

FIG. 17—Comparison of reactivity of a heavy chain paired with either K8 light chain or NRY light chain. Apparent similar reactivities are obtained for cgamma(6)/K8 and cgamma(6)/NRY against CD163. The antibody sample cgamma(6)/K8 contained approximately twice as much antibody to obtain the same reactivity as did cgamma(6)/NRY.

Figure 18:
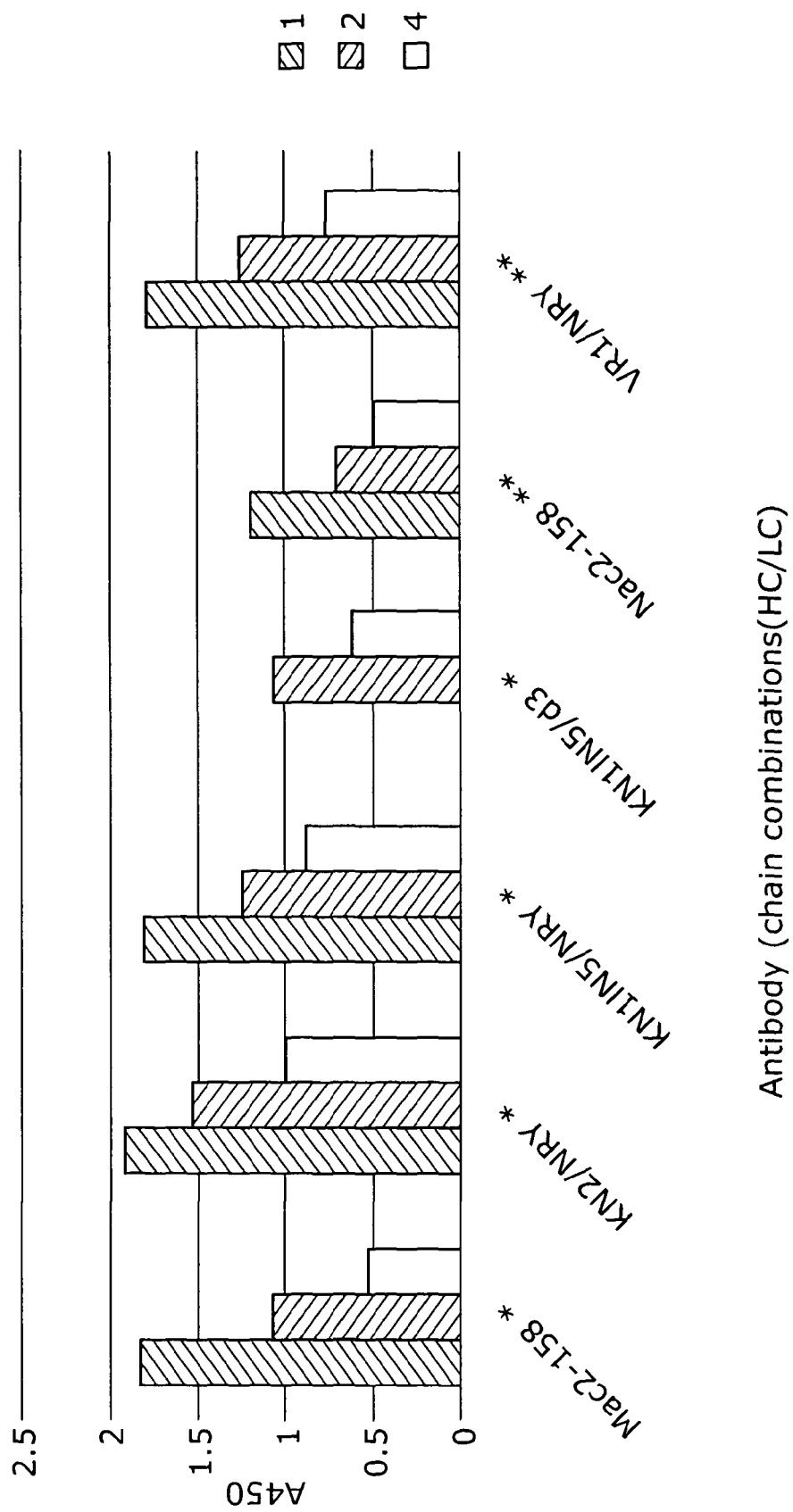

FIG. 18—Binding of humanized heavy chain variants. The humanised heavy chain variants KN2, KN1IN5, VR1, and DQ2 (all paired with the light chain NRY) had a comparable reactivity towards CD163. * or ** experiments done on the same ELISA plate.

Figure 19:
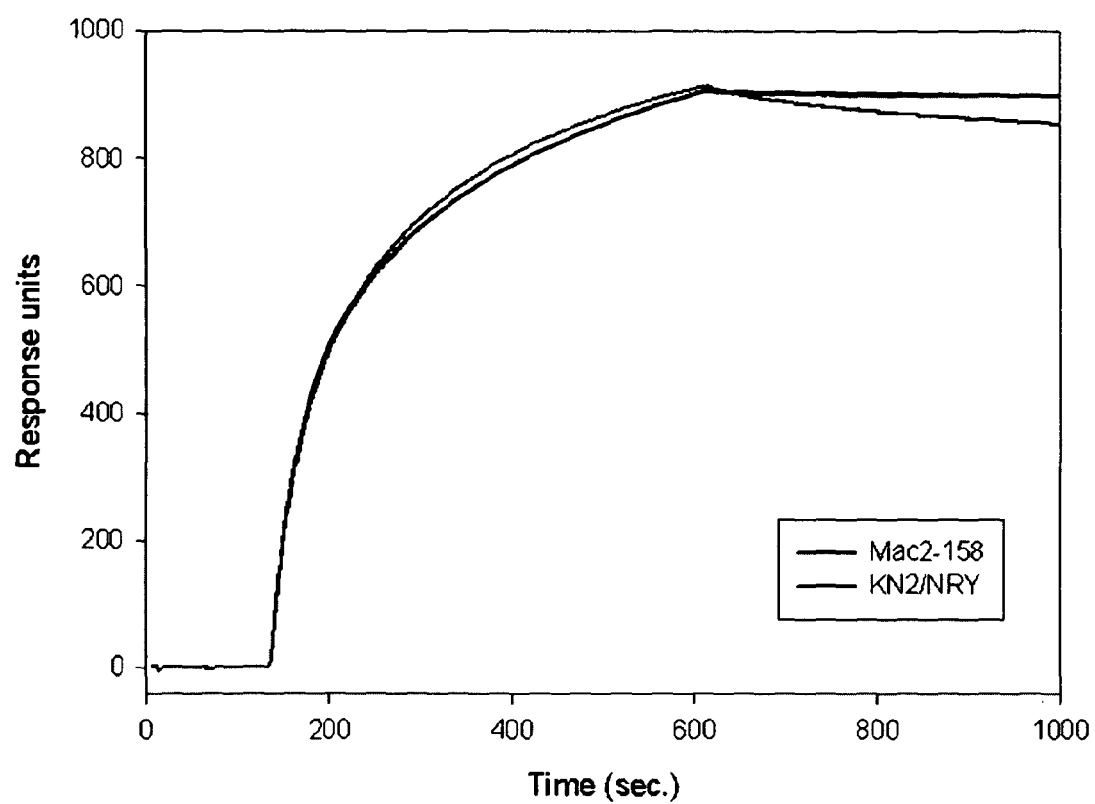

FIG. 19—Surface plasmon resonance detection of the binding of KN2/NRY and Mac2-158 to human CD163 immobilized on a Biacore chip. Virtually similar affinities for the two mAbs were displayed.

Figure 20:
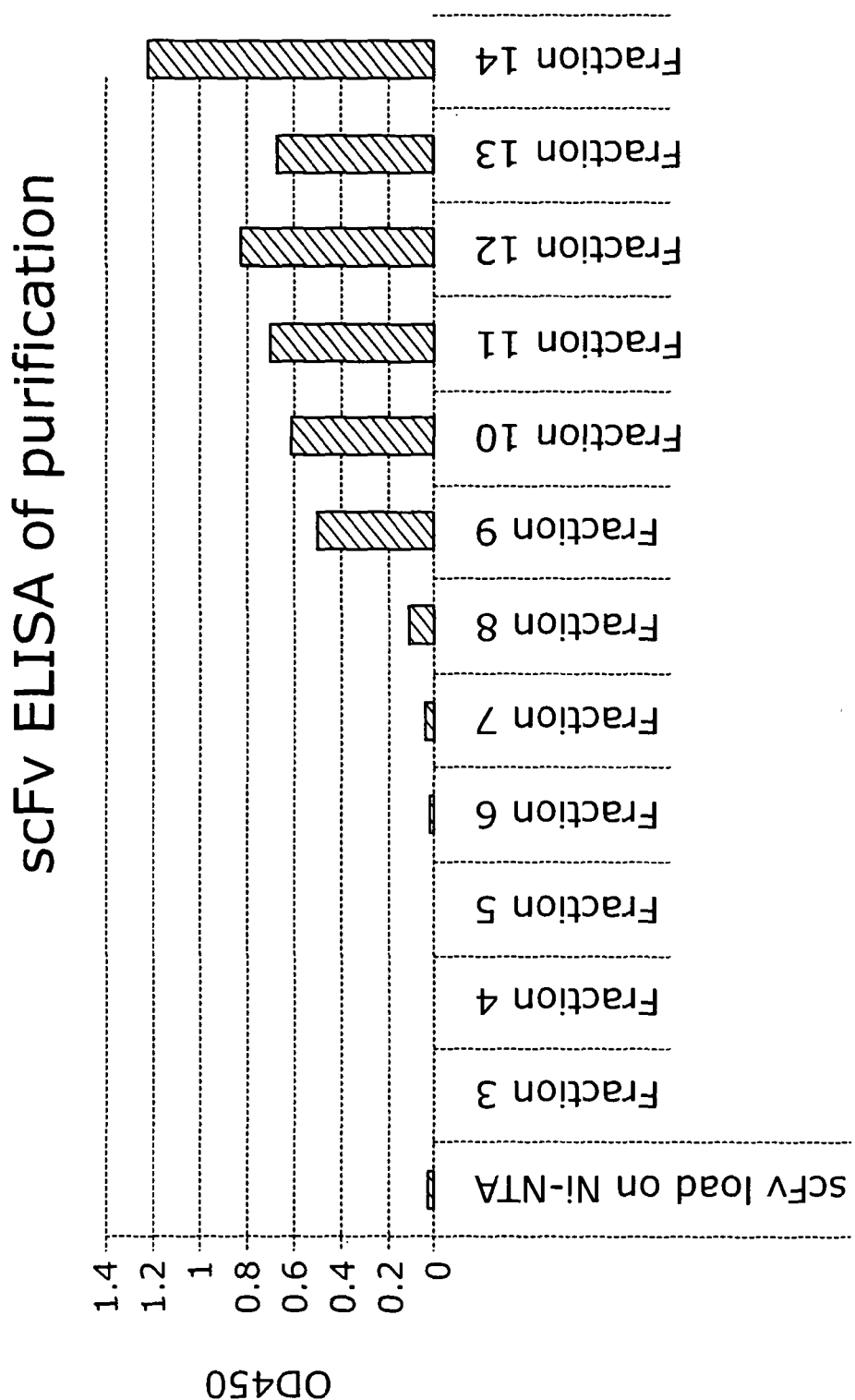

FIG. 20—ELISA of fractions from the HisTrap™ purification of expressed scFv. A sample of each fraction was diluted 1:10 in 1% BSA, PBS. The diluted samples were subsequently added to CD163 coated wells.

Figure 21:
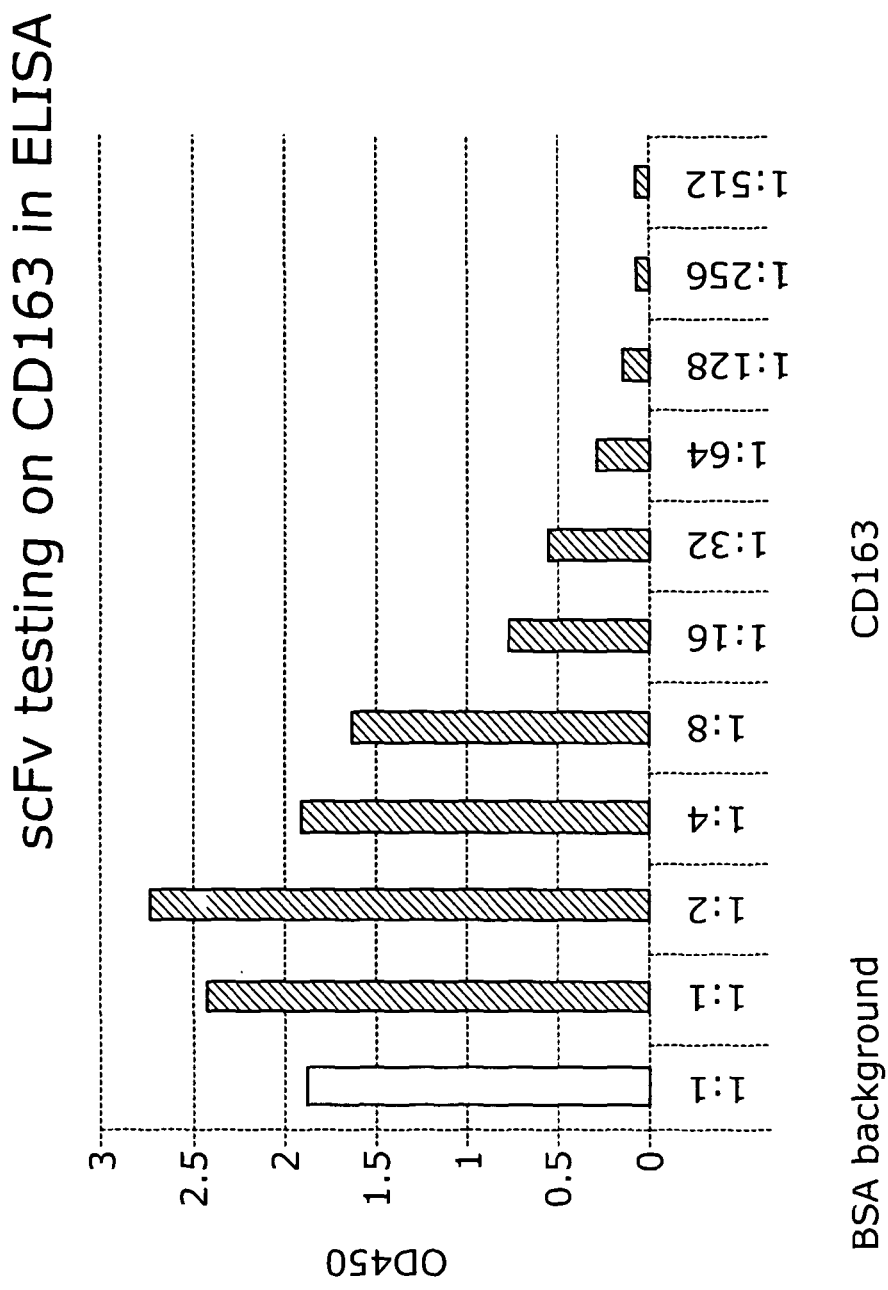

FIG. 21—ELISA of refolded scFv sample. The refolded scFv was added to the wells and 2 fold dilution series made. The refolded scFv bound to CD163 out to a 128 fold dilution in 1% BSA, PBS. The background of undiluted sample (scFv in buffer without BSA) was high (grey box to the left).

Figure 22:
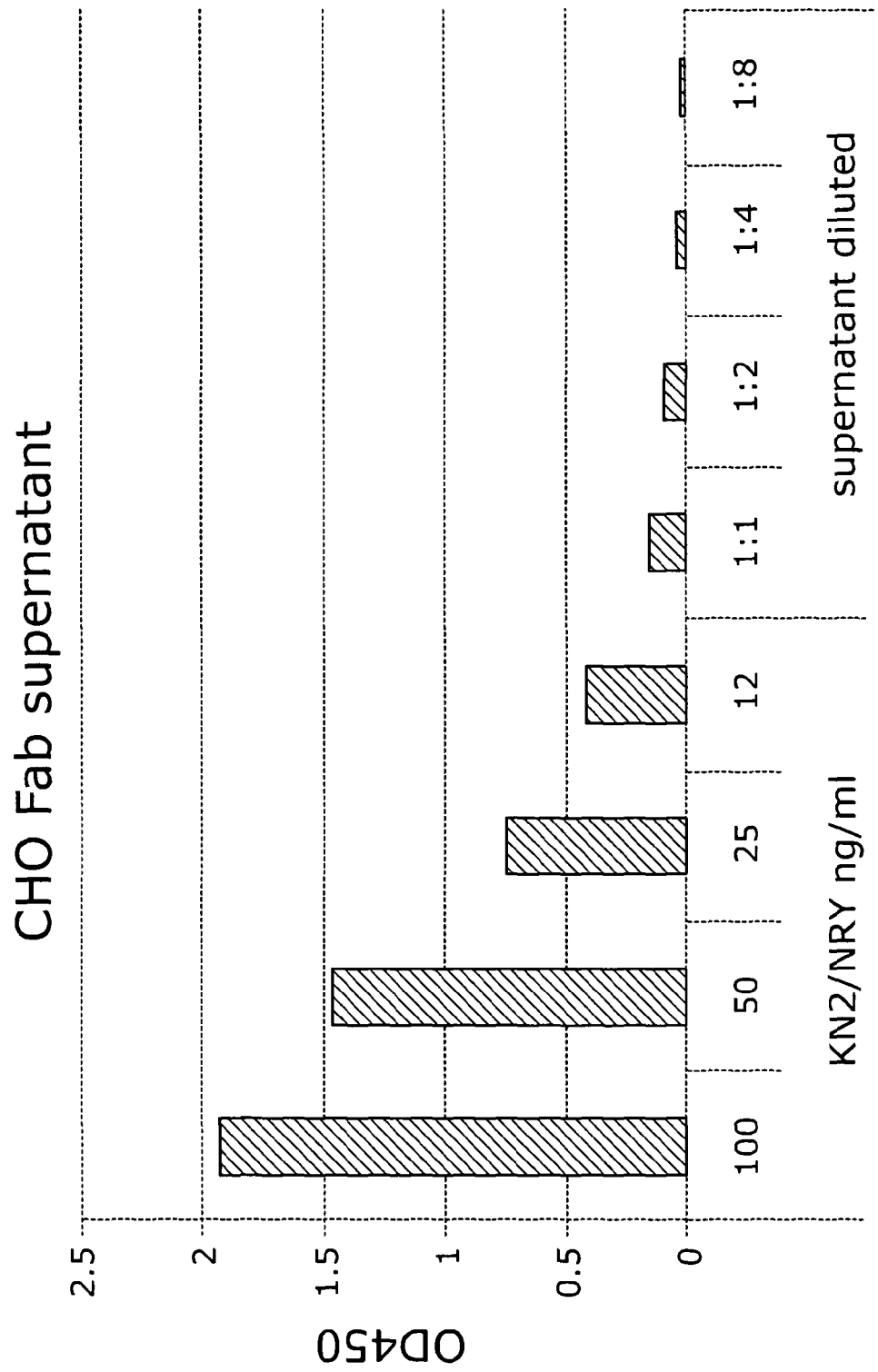

FIG. 22—Cell culture supernatant tested directly in ELISA. The ELISA signal was very low even for the undiluted supernatant.

FIG. 23—30× concentrated cell culture supernatant tested in ELISA. The ELISA signal of the 30× concentrated supernatant verified the presence of a Fab fragment. The intensity was comparable to the 100 ng/ml full length IgG4 antibody standard.

Figure 24:
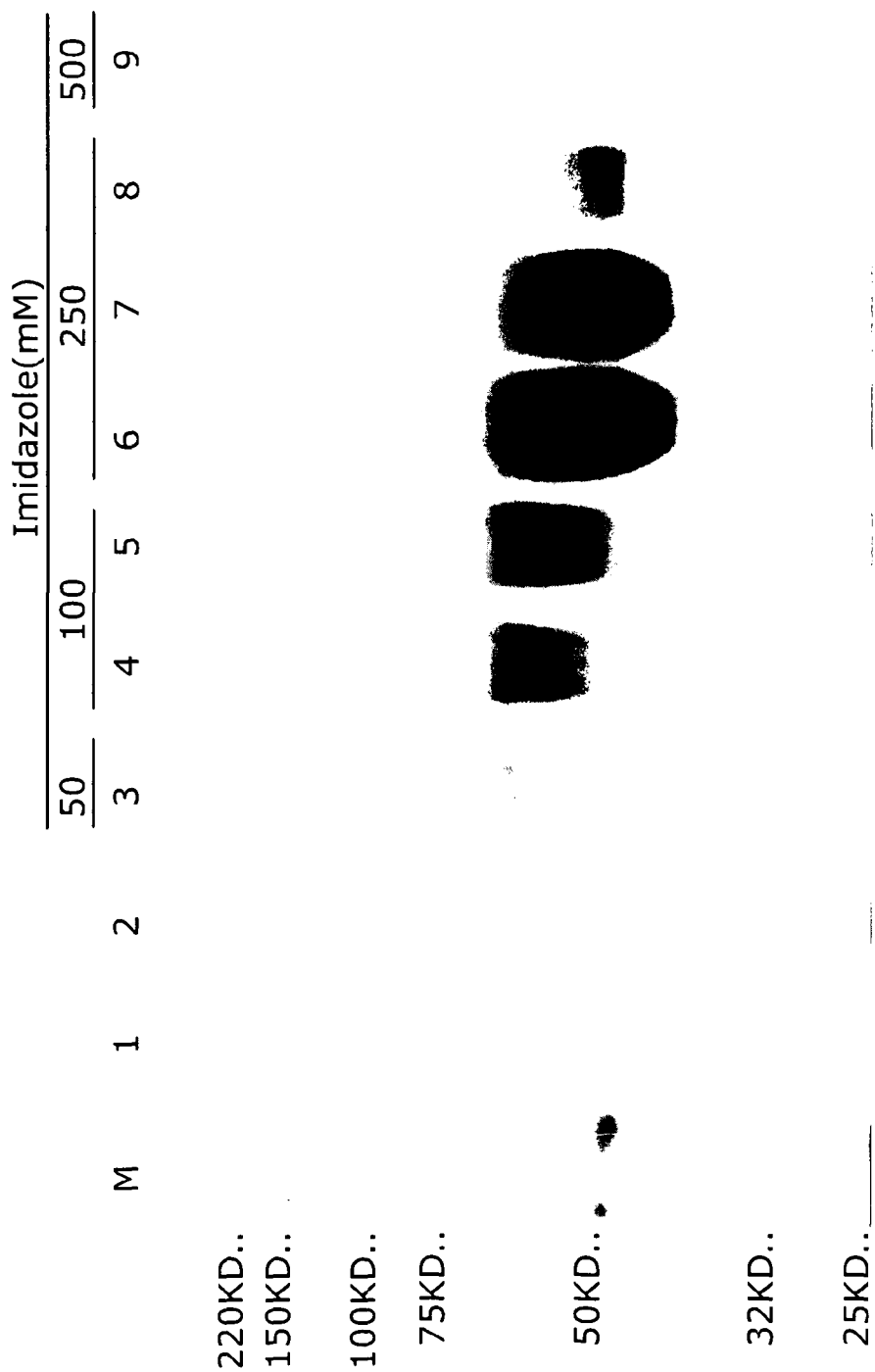

FIG. 24—SDS-PAGE analysis of 65354. Lane M: MW marker (Cat. No. MM0900, GenScript); Lane 1, crude harvest; Lane 2, Flow through; Lane 3, Eluate of 50 mM imidazole; Lane 4-5, Eluate of 100 mM imidazole; Lane 6-8, Eluate of 250 mM imidazole; Lane 9, Eluate of 500 mM imidazole. The procedure produced about 6.0 mg of mouse CD163 soluble protein domain 1-3, with a purity of over 80% in SDS-PAGE analysis.

Figure 25:

FIG. 25—1% agarose gel electrophoresis of PCR product from $V_L$ PCR on cDNA beads. Lane M 100 bp marker. Lane 2 shows a product of ~400 bp size. This band was purified by gel extraction and subsequently sequenced.

Figure 26:
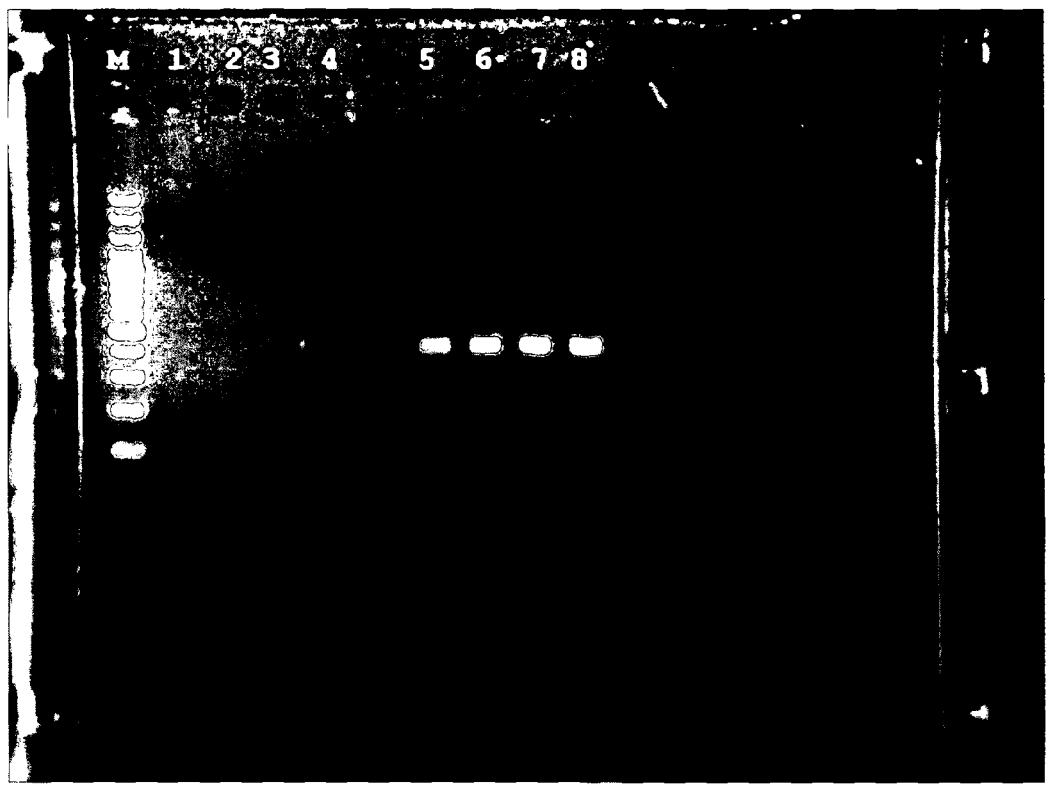

FIG. 26—1% agarose gel electrophoresis of PCR product from $V_H$ PCR on cDNA beads. Lane M 100 bp marker. Lane 7 shows a product of ~500 bp size. This band was purified by gel extraction and subsequently sequenced.

Figure 27D:
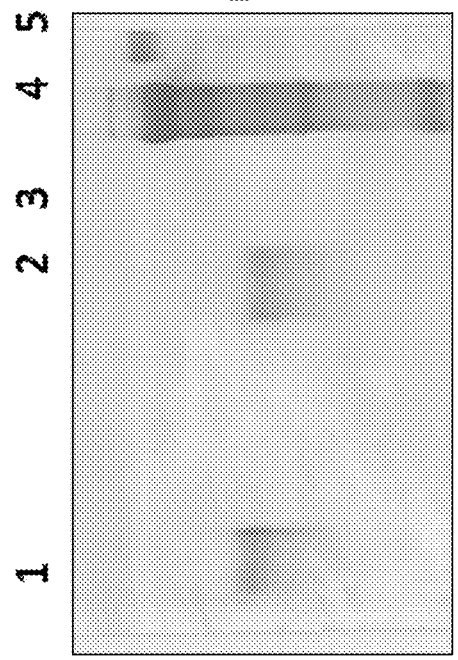
Figure 27E:
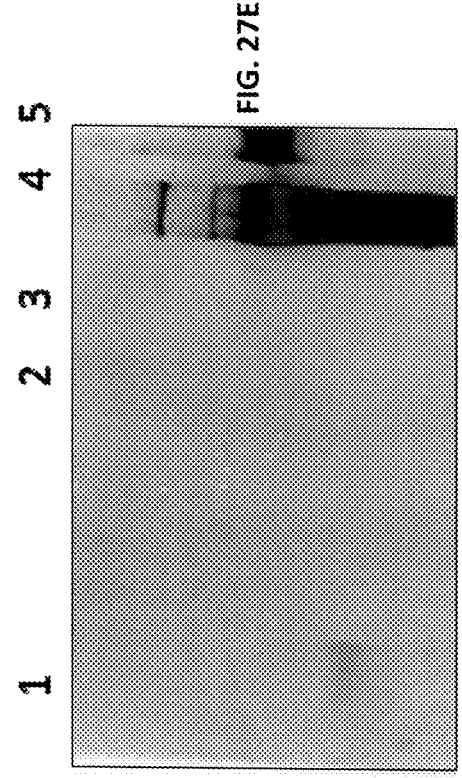
Figure 27A:
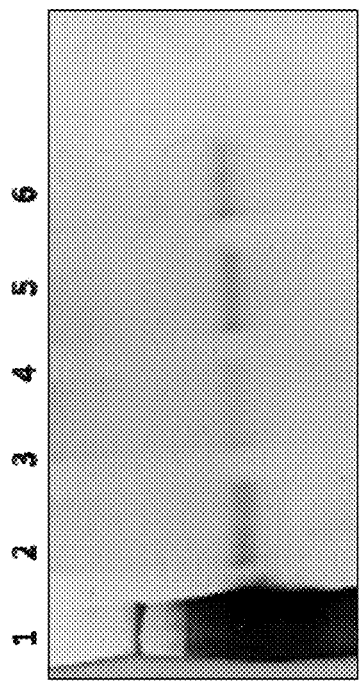
Figure 27B:
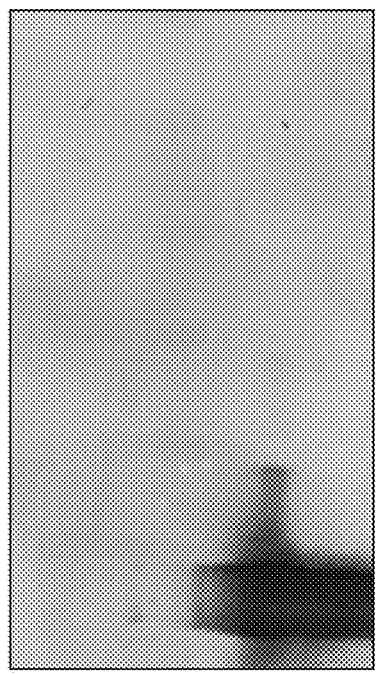

FIGS. 27A-27E—Epitope mapping of KN2/NRY and Mac2-158, knock in and out of epitope FIG. 27A: Western blot of the following samples: See-Blue plus2 prestained marker (lane 1); human CD163 wt (lane 2); human CD163 R60D (lane 3); human CD163 VKVQEE→LKIHEK (lane 4); human CD163 double mutant (lane 5); and negative transfection control (lane 6). Detection of protein expression was a done with polyclonal rabbit anti-human-CD163 and an anti-rabbit antibody conjugated with horse radish peroxidase as secondary antibody FIG. 27B: Western blot of the following samples: SeeBlue plus2 prestained marker (lane 1); human CD163 wt (lane 2); human CD163 R60D (lane 3); human CD163 VKVQEE→LKIHEK (lane 4); human CD163 double mutant (lane 5); and negative transfection control (lane 6). mac2-158 was used for detection of the epitope, with an anti-mouse antibody conjugated with horse radish peroxidase as secondary antibody.

Figure 27C:
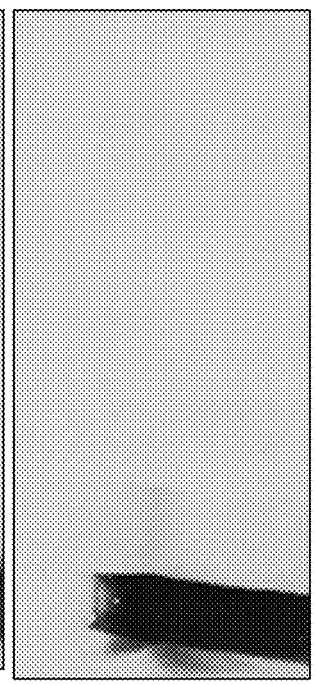

FIG. 27C: Western blot of the following samples: SeeBlue plus2 prestained marker (lane 1); human CD163 wt (lane 2); human CD163 R60D (lane 3); human CD163 VKVQEE→LKIHEK (lane 4); human CD163 double mutant (lane 5); and negative transfection control (lane 6). KN2/NRY-HRP was used for detection of the epitope.

FIG. 27D: Western blot of the following samples: (lane 1) Mouse CD163 1-5 LKIHDK→VKVQEE, Y60R mutant, (lane 2) mouse CD163 1-5 wt, (lane 3) negative transfection control, (lane 4) SeeBlue plus2 pre-stained marker, (lane 5) positive blotting control (mouse CD163, recombinant with V5 tag). The primary antibody used was Anti-V5. Detection of bound primary antibody was done with an anti-mouse antibody conjugated with horse radish peroxidase as secondary antibody.

FIG. 27E: Western blot of the following samples: (lane 1) Mouse CD163 1-5 LKIHDK→VKVQEE, Y60R mutant, (lane 2) mouse CD163 1-5 wt, (lane 3) negative transfection control, (lane 4) SeeBlue plus2 pre-stained marker, (5) positive blotting control (human CD163). The primary antibody used was Mac2-158. Detection of bound primary antibody was done with an anti-mouse antibody conjugated with horse radish peroxidase as secondary antibody.

Figure 28A:
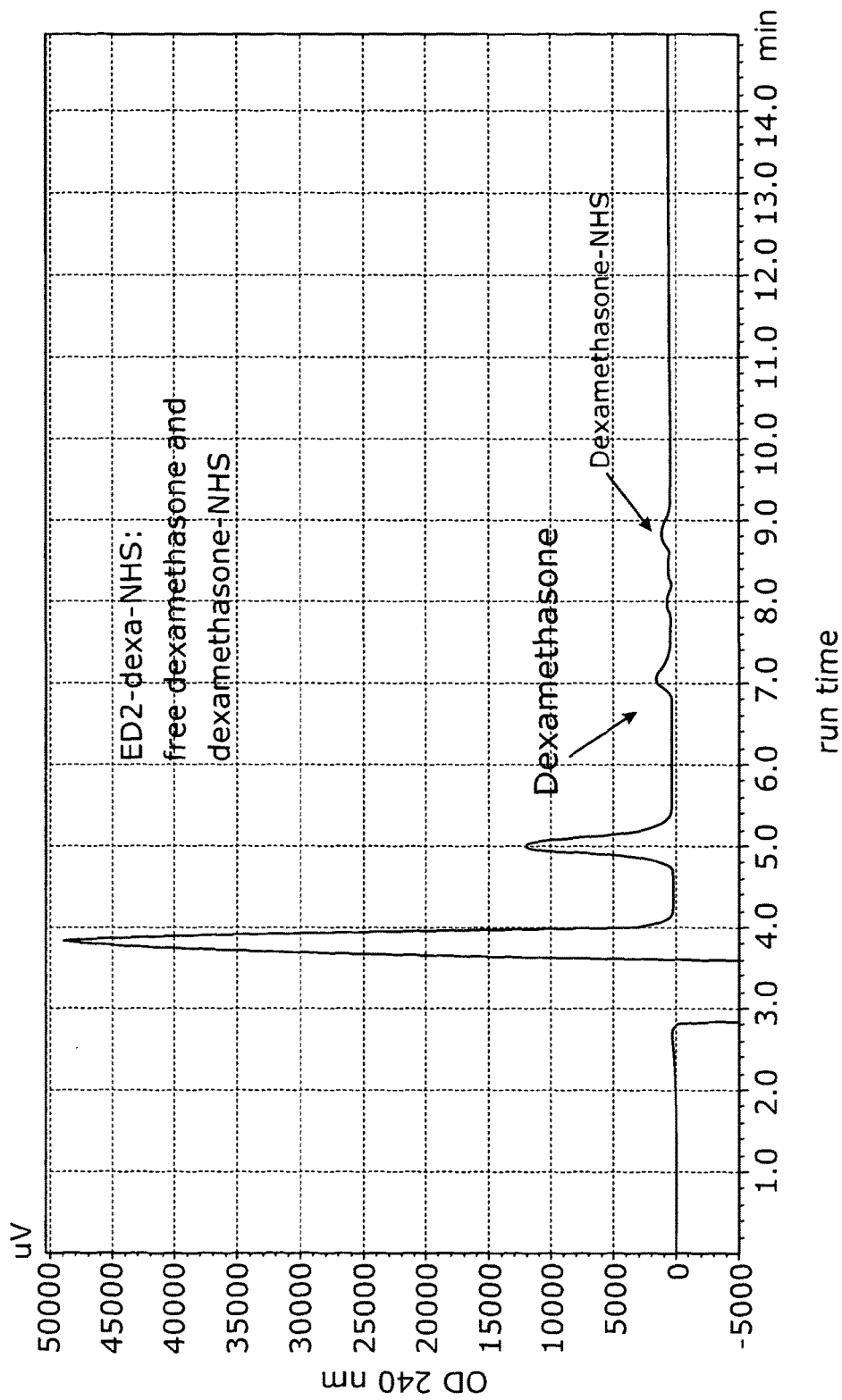
Figure 28B:
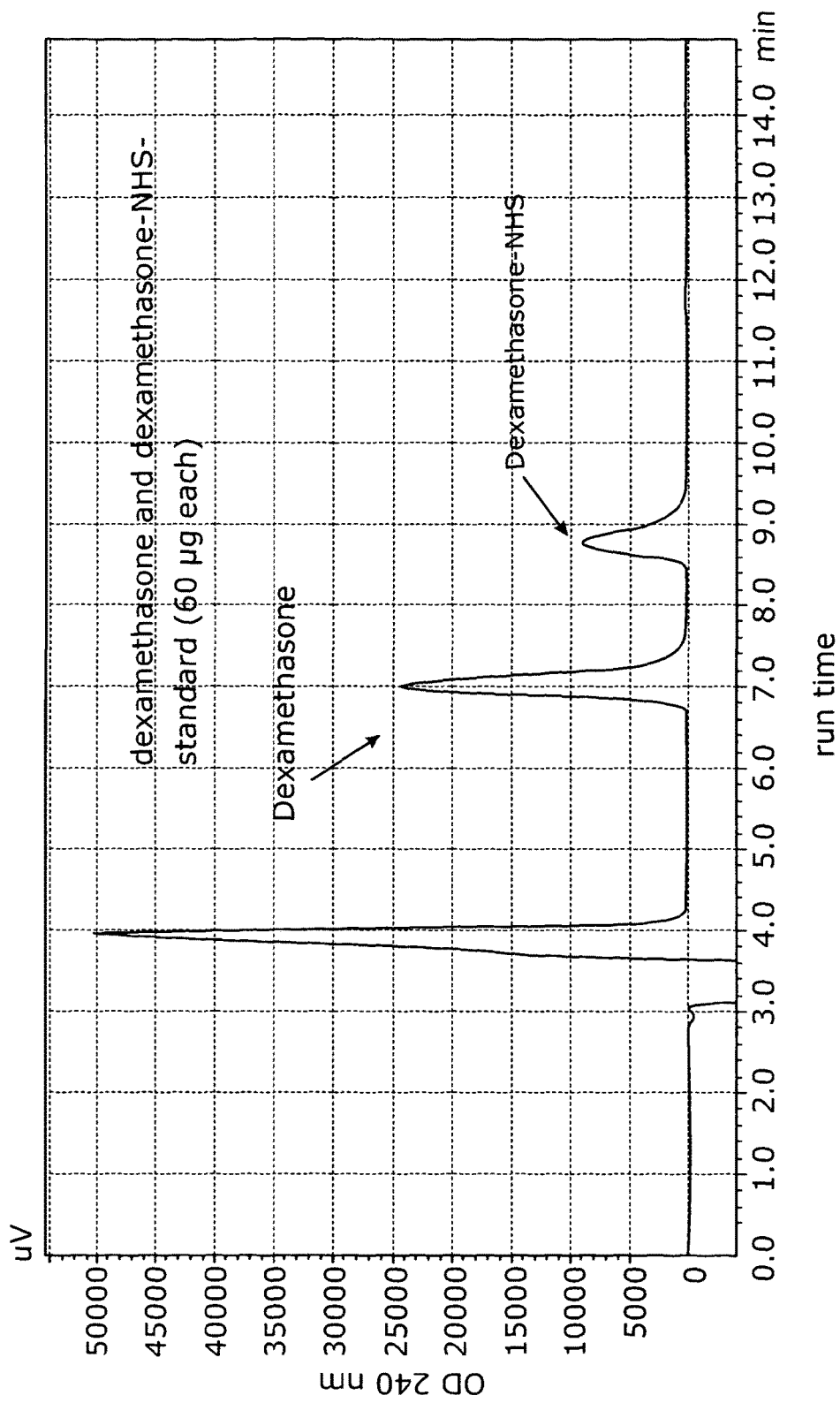
Figure 28C:
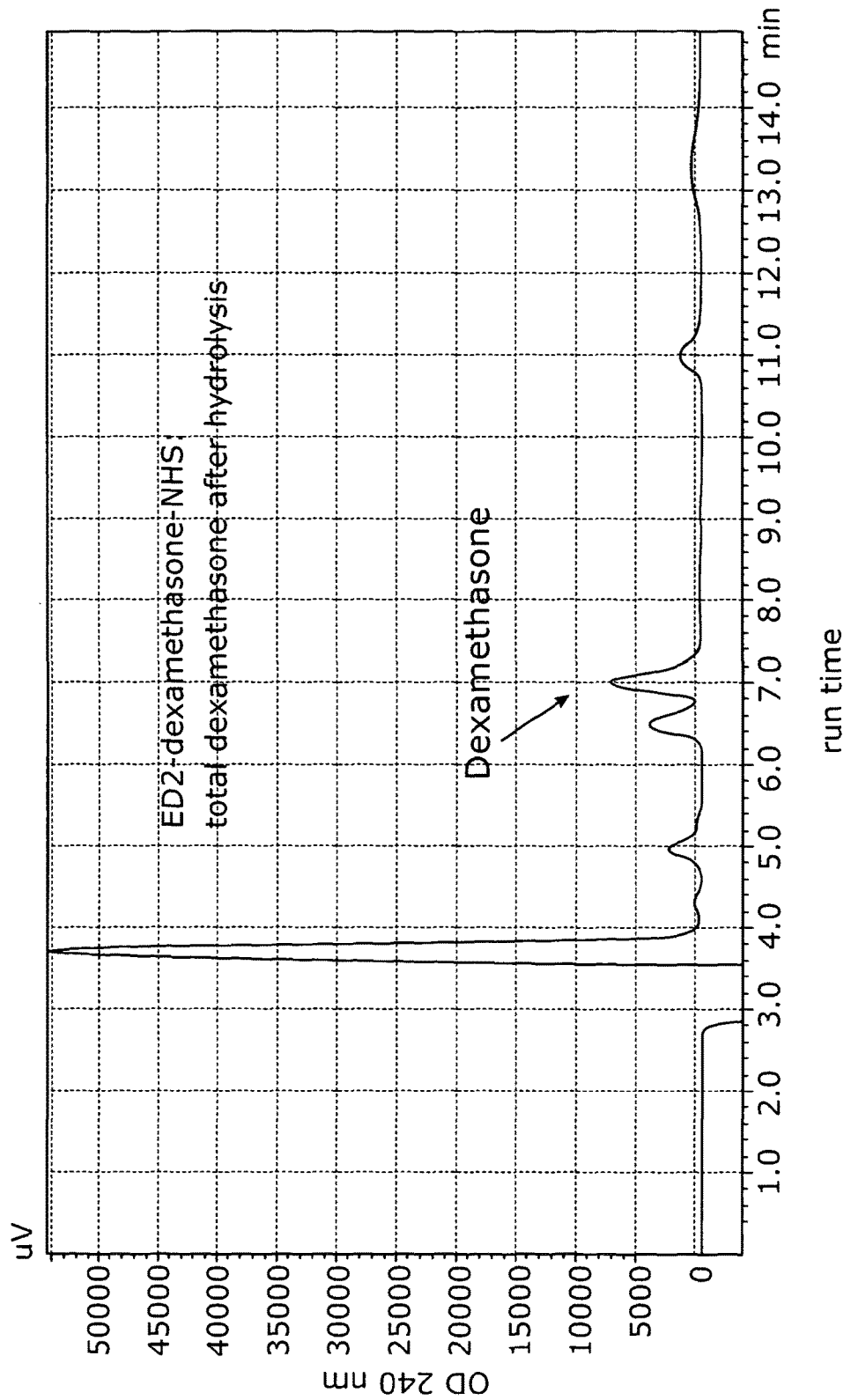

FIGS. 28A-28C—Chromatograms of dexamethasone and dexamethasone-NHS standard (FIG. 28A) and determina-tion of free dexamethasone/dexamethasone-NHS (FIG. 28B) and total dexamethasone (FIG. 28C) in an ED2-dexamethasone conjugate sample. Dexamethasone-NHS is converted to dexamethasdone-hemisuccinate on the column, so there is no discrimination between dexamethasone-NHS and dexamethasone-hemisuccinate.

FIG. 28D: Conjugation parameters of different antibody-corticosteroid-NHS-conjugates.

FIG. 28E: Conjugation parameters of different antibody-MVCP-dexamethasone conjugations.

FIGS. 29A-29F—

Figure 29C:
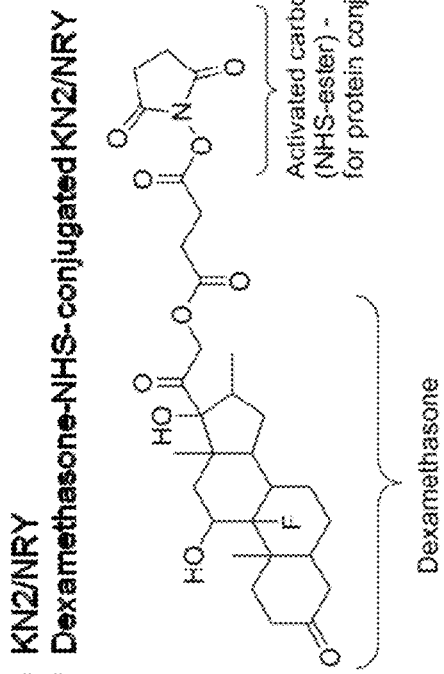
Figure 29B:
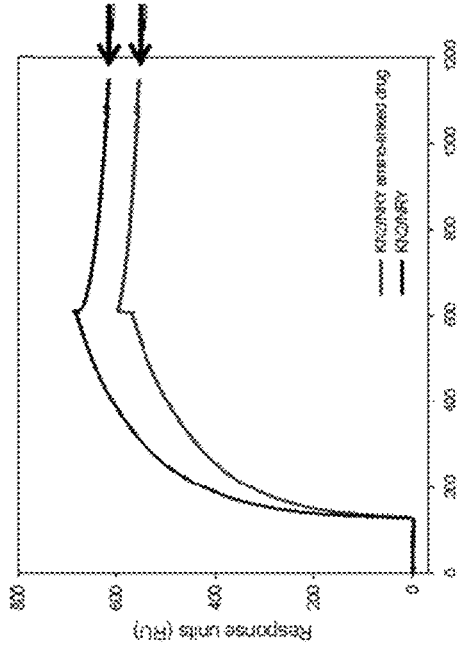
Figure 29A:

FIG. 29A: SDS-PAGE of KN2/NRY and KN2/NRY-NHS-dexamethasone conjugate. Lane 1: Mw marker; lane 2: KN2/NRY; and lane 3: KN2/NRY-NHS-dexamethasone.

FIG. 29B: Sensorgram showing CD163 binding of KN2/NRY and KN2/NRY-NHS-dexamethasone conjugate, conjugated to primary amines using NHS-dexamethasone.

FIG. 29C: Schematic structure of the dexamethasone-NHS molecule used for conjugation to produce KN2/NRY-NHS-dexamethasone.

Figures 29D, 29E, 29F:
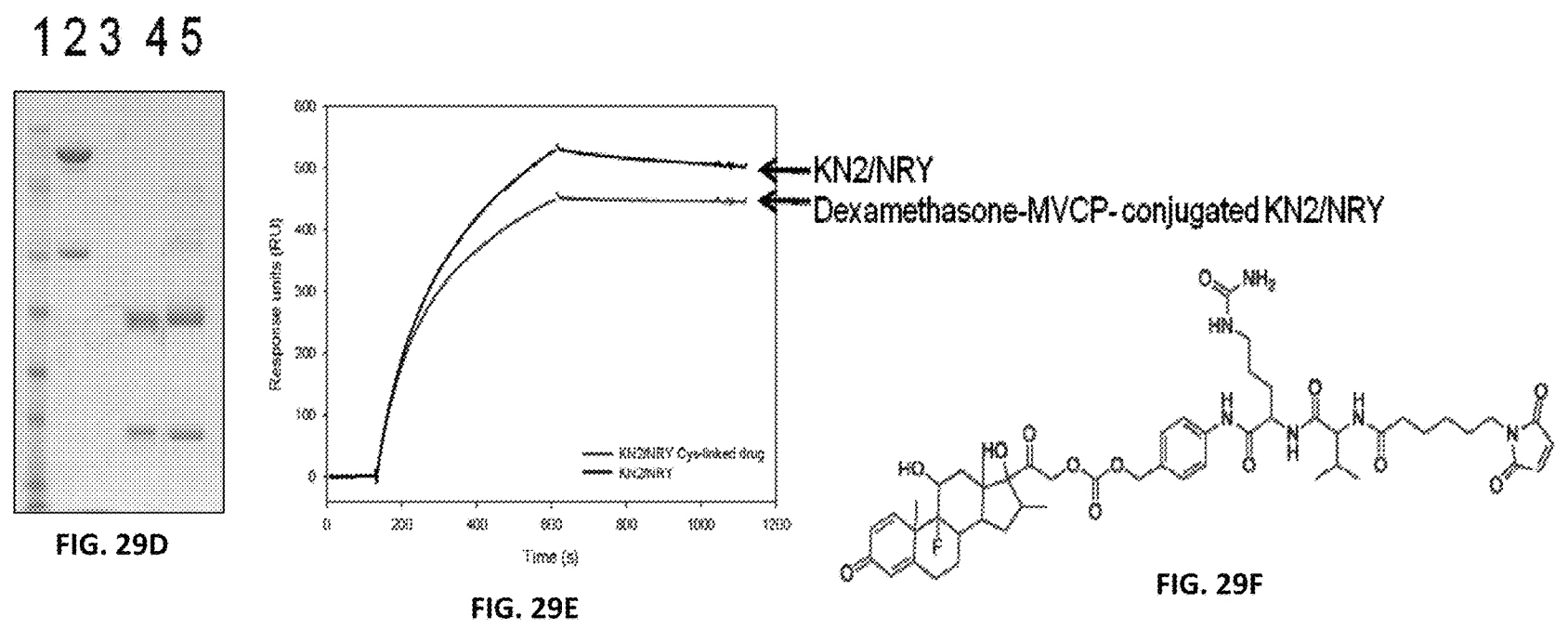

FIG. 29D: Left SDS-PAGE of KN2/NRY and KN2/NRY-MVCP-dexamethasone conjugate. Lane 1: Mw marker; lane 2: KN2/NRY; and lane 4: reduced KN2/NRY; lane 5: KN2/NRY-MVCP (non-reduced).

FIG. 29E: Sensorgram showing CD163 binding of KN2/NRY and KN2/NRY dexamethasone conjugate, conjugated to free SH groups of limited reduced KN2/NRY. Both A and B shows only very limited decrease in affinity upon conjugation and no increase in aggregation upon conjugation.

FIG. 29F: Schematic structure of the dexamethasone-MVCP molecule used for conjugation to produce KN2/NRY-MVCP-dexamethasone.

Figure 30A:
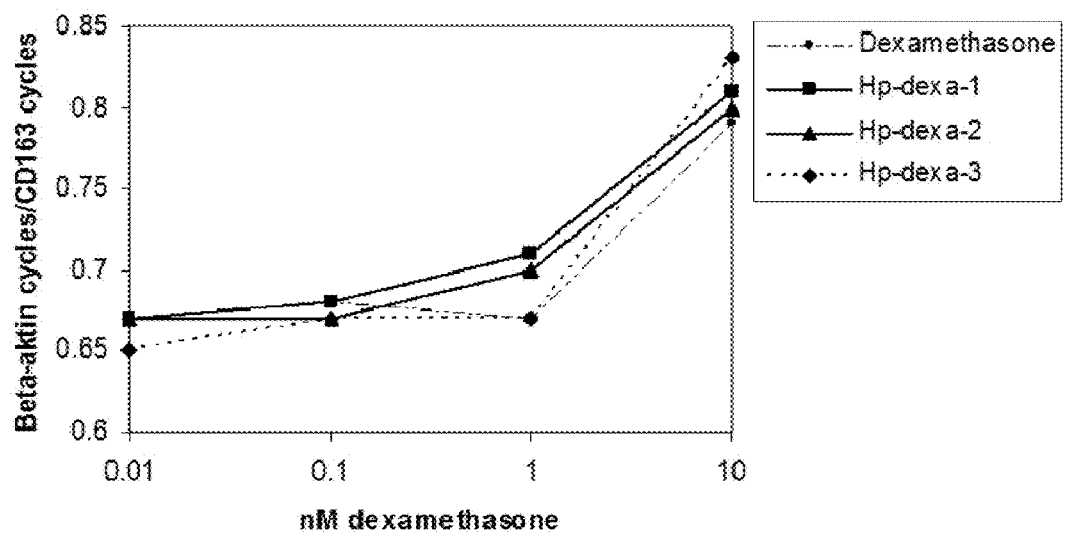
Figure 30B:
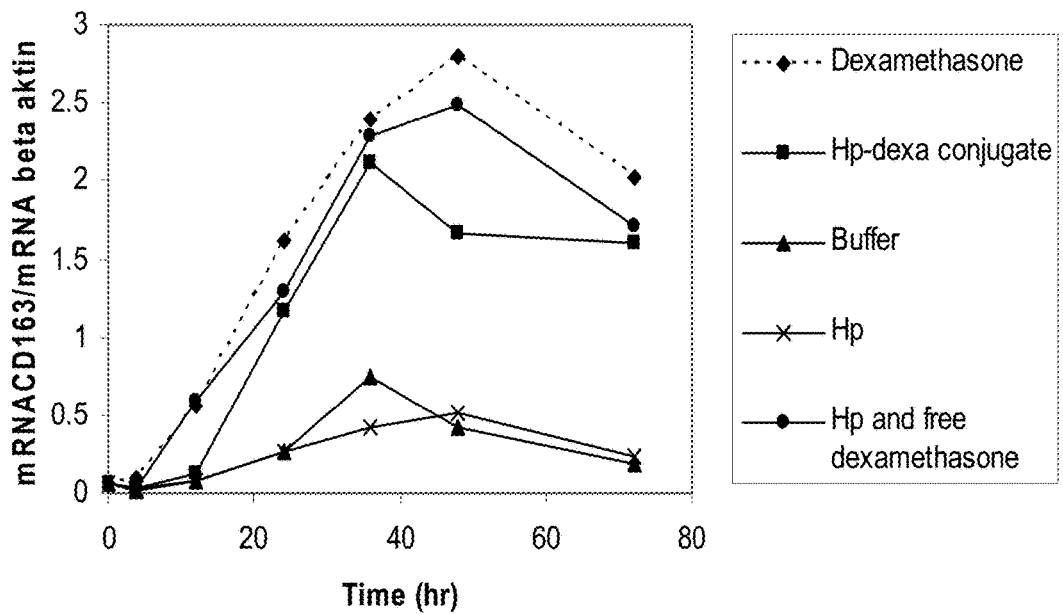

FIGS. 30A-30B—Effect of Haptoglobin dexamethasone conjugates on human monocytes

FIG. 30A: Data showing the effect on human mononuclear cells isolated from buffy coats (outdated plasma) of haptoglobin coupled with dexamethasone and afterwards complexed with hemoglobin to induce CD163 binding of the conjugate. The effect measured is the induction of CD163 mRNA synthesis by dexamethasone. The number after Hp-dexa refers to different batches of Hp-dexa.

FIG. 30B: Time study showing the effect of 10 nM dexamethasone on CD163 expression in human mononuclear cells isolated from buffy coats (outdated plasma).

Figure 31A:
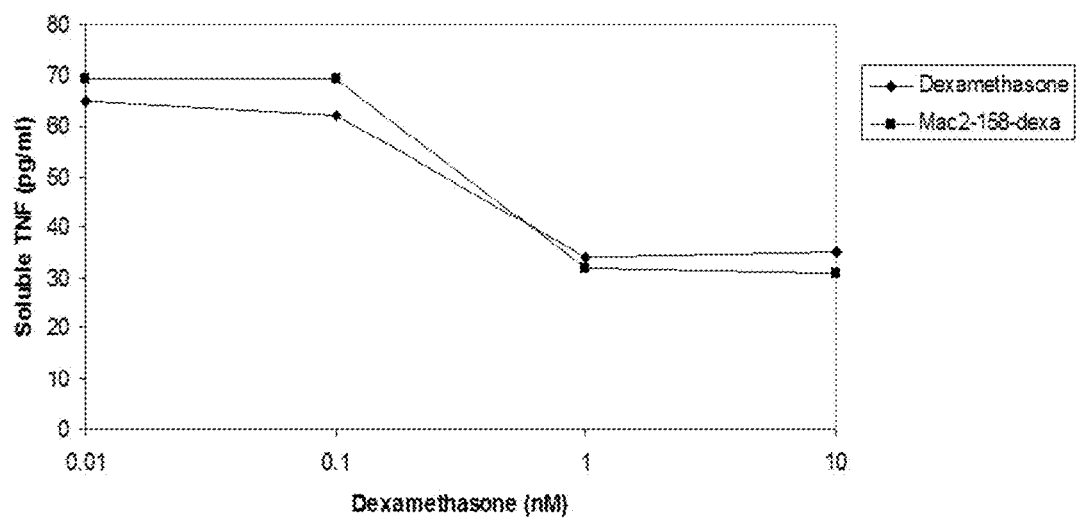
Figure 31B:
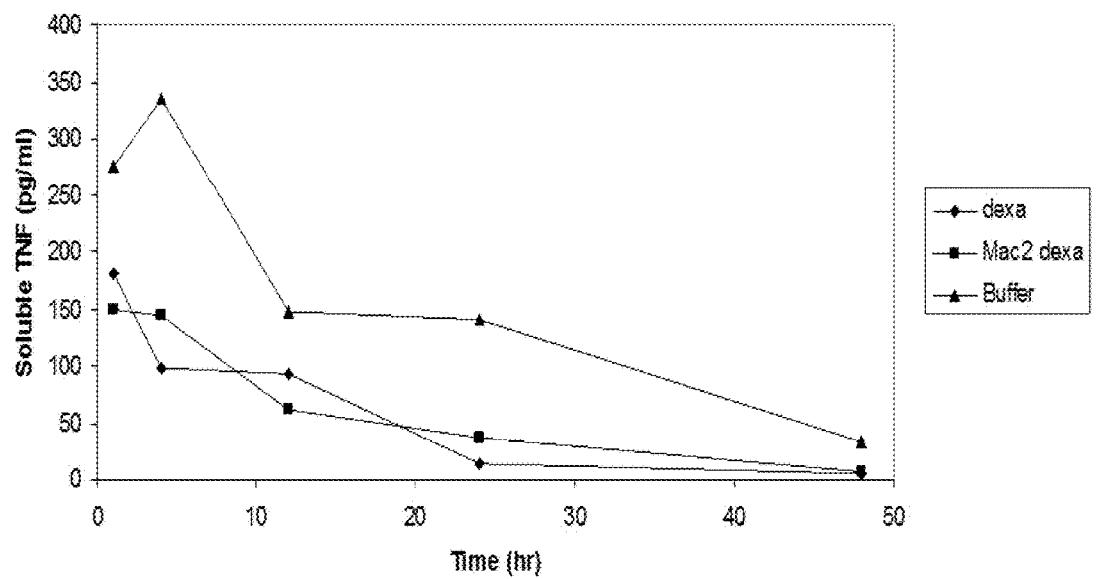

FIGS. 31A-31C—Mac2-158 dexamethasone conjugate effect on human macrophages.

FIG. 31A: Data showing the effect on human in vitro matured macrophages cells isolated from buffy coats (outdated plasma) of Mac2-158 coupled with dexamethasone. The effect measured is the inhibition of LPS induction of TNF production.

FIG. 31B: Time study showing the effect of 10 nM dexamethasone in the same set-up FIG. 32A-32D—Binding of KN2/NRY to human monocytes.

Figure 32A:
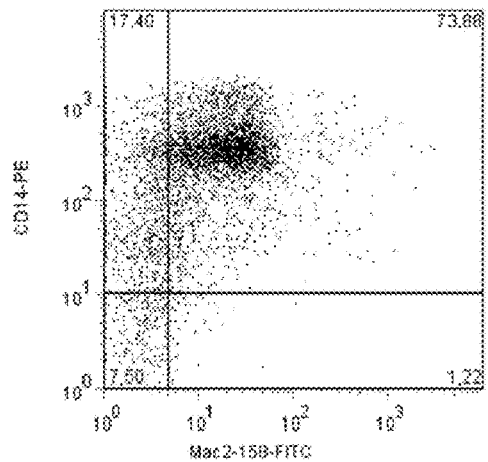
Figure 32B:
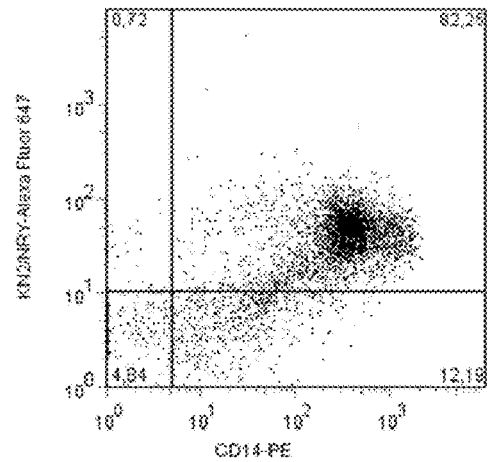
Figure 32C:
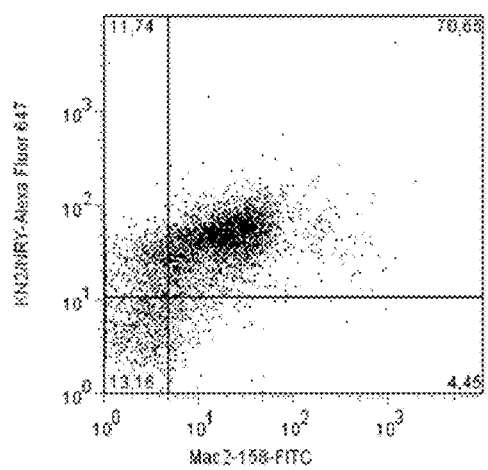
Figure 32D:
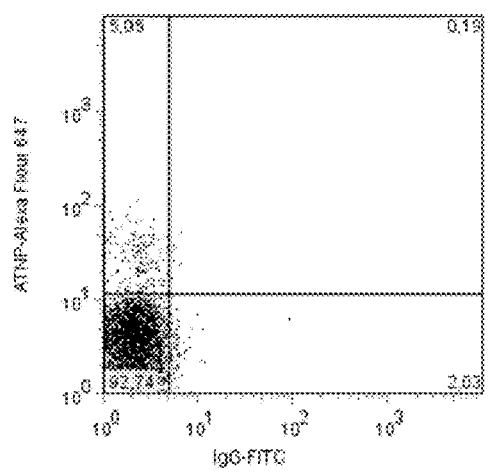

FIG. 32A-32C) Human mononuclear cells isolated from buffy coats were stained with Mac2-158-FITC, anti-CD14-PE and KN2/NRY-Alexa Fluor647 and analyzed by flow cytometry FIG. 32D). A negative control staining with IgG-FITC and an irrelevant antibody conjugated with AlexaFluor647 (ATNP-Alexa Fluor647) was included.

Figure 33:
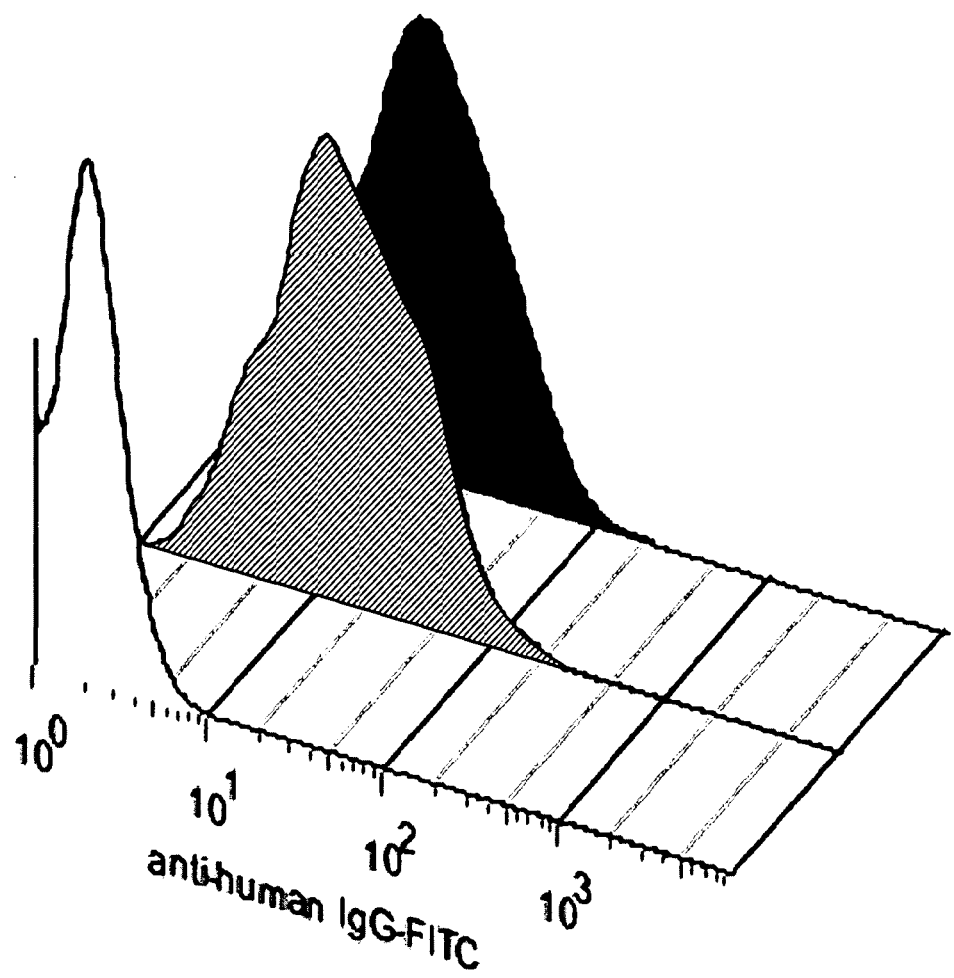

FIG. 33—Binding of KN2/NRY-dexamethasone to CD163 expressing CHO cells. CHO cells expressing human CD163 were incubated with KN2/NRY (grey histogram) or KN2/NRY-dexamethasone conjugate (black histogram), washed and stained with anti-human IgG-before flow cytometric analysis. White histogram represents negative control staining with anti-human IgG-FITC.

Figure 34:
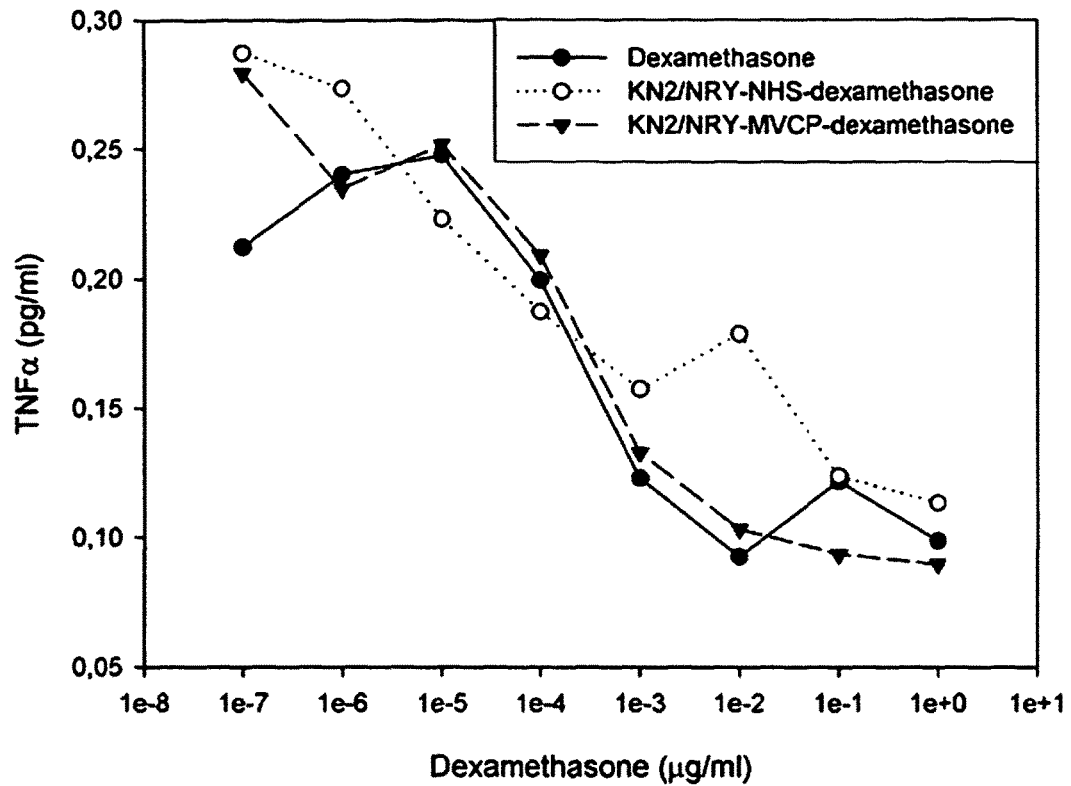

FIG. 34—KN2/NRY-dexamethasone suppression of LPS mediated TNFα in vitro. Human mononuclear cells were cultured and incubated with serial dilutions of KN2/NRY—NHS-dexamethasone, KN2/NRY-MVCP-dexamethasone or free dexamethasone for 15 minutes, washed and incubated overnight. Cell supernatants were analyzed for TNFα after 4 hours of LPS stimulation.

FIG. 35—Binding of ED2 to rat macrophages. Peritoneal macrophages were stained with anti-rat CD172a-PE (ED9) and anti-rat CD163-FITC (ED2) and analyzed by flow cytometry (left dotplot). The percentage of CD163-FITC positive macrophages are indicated in the upper right quadrant. A negative control staining with IgG-FITC was included (right dotplot).

Figure 36:
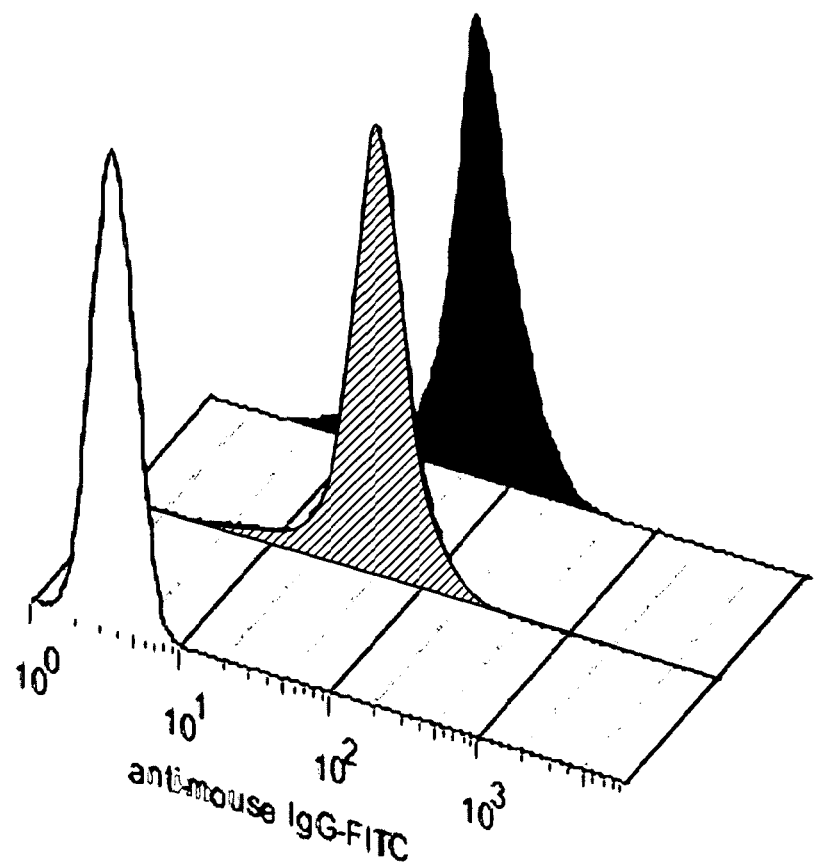

FIG. 36—Binding of ED2-dexamthasone to CD163 expressing CHO cells. CHO cells expressing rat CD163 were incubated with ED2 (grey histogram) or ED2-NHS-dexamethasone conjugate (black histogram), washed and stained with anti-mouse IgG-before flow cytometric analysis. White histogram represents negative control staining with anti-mouse IgG-FITC.

Figure 37:
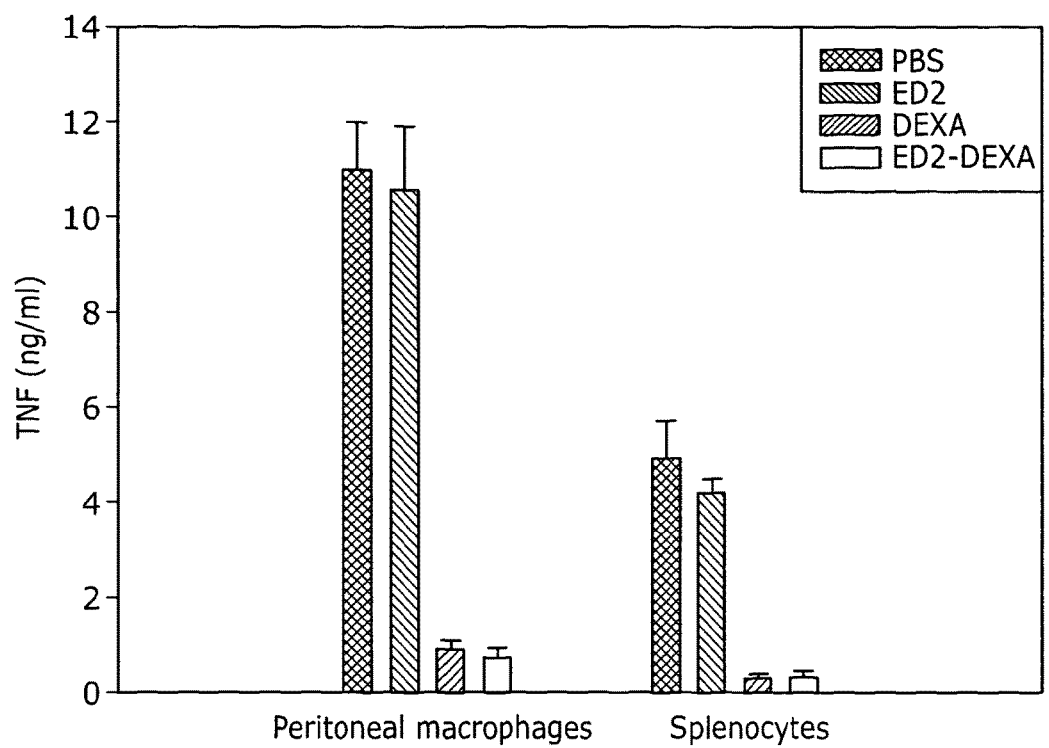

FIG. 37—ED2-dexamethasone suppression of LPS mediated TNFα stimulation in vitro. Peritoneal rat macrophages and spleen cell suspensions were incubated with 1 µg/ml ED2-NHS-dexamethasone, dexamethasone, ED2 or PBS for 3 hours before LPS stimulation for 20 hours. The concentration of TNFα in cell culture supernatants (triplicates) was determined by the BD™ Cytometric Bead Array (CBA) Flex Set assay.

Figure 38A:
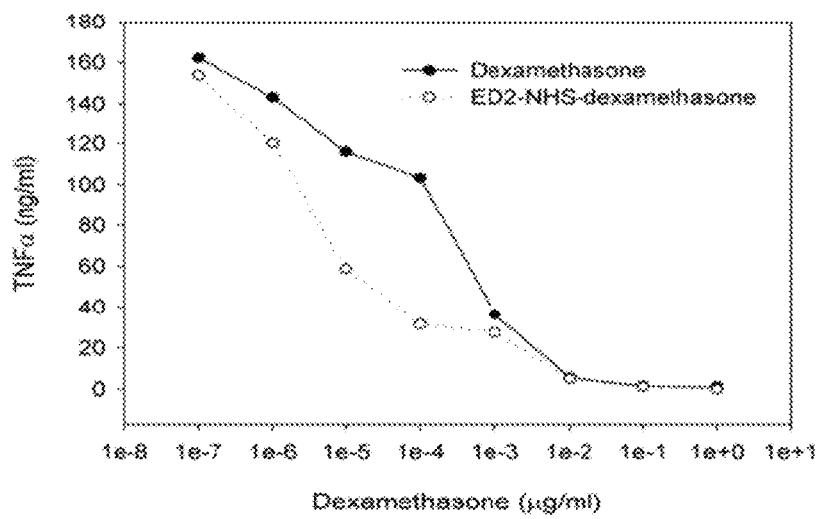
Figure 38B:
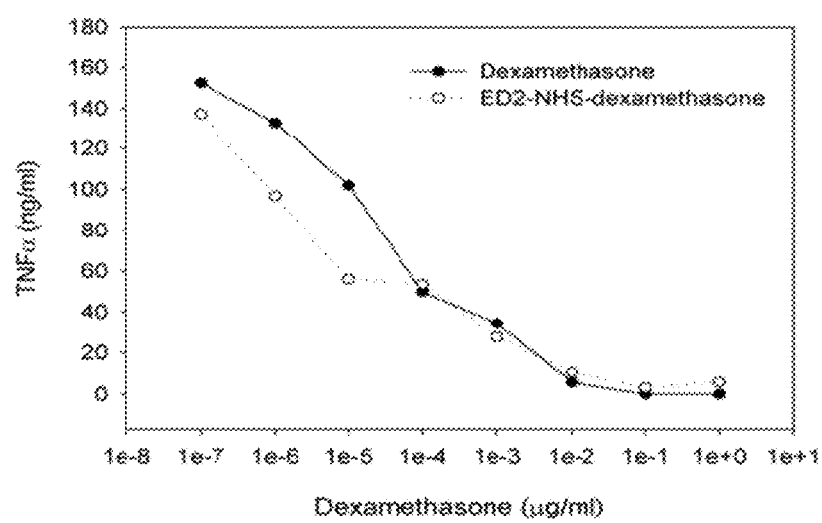
Figure 38C:
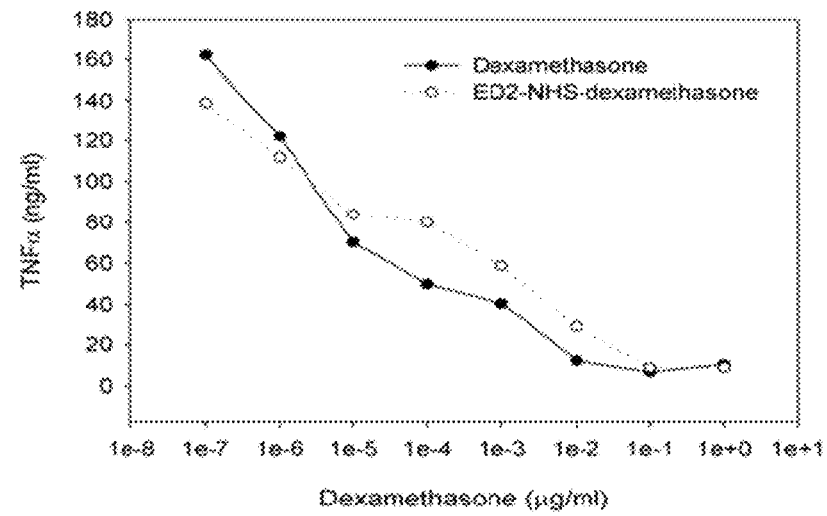

FIGS. 38A-38C—Titration of LPS mediated TNFα induction of splenocytes. Rat spleen cells were cultured and incubated with serial dilutions of ED2-NHS-dexamethasone conjugate or free dexamethasone for (FIG. 38A) 15 minutes, (FIG. 38B) 30 minutes or (FIG. 38C) 60 minutes, washed and incubated overnight. Cell supernatants were analyzed for TNFα after 4 hours of LPS stimulation.

Figure 39A:
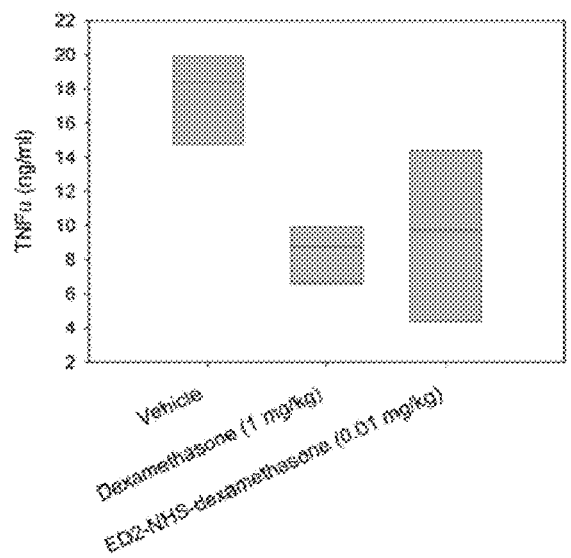
Figure 39B:
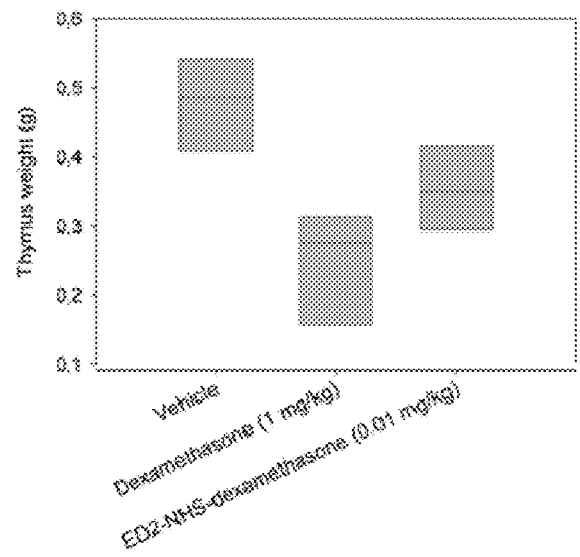
Figure 39C:
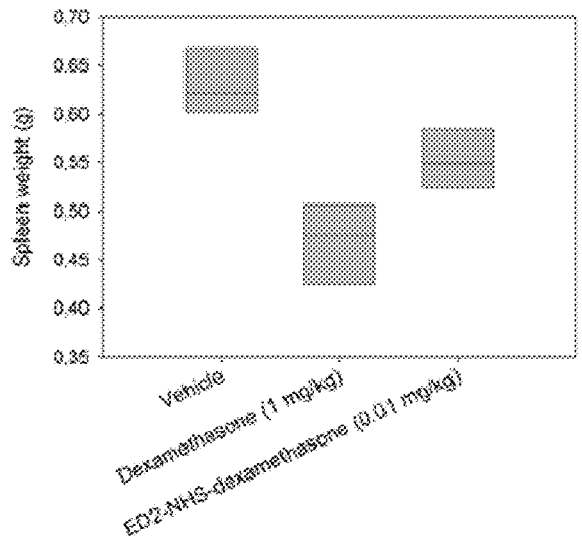

FIG. 39A-39C—ED2-dexamethasone suppression of LPS mediated TNFα stimulation in vivo. Female Lewis rats were injected intravenously with ED2-NHS-dexamethasone (n=4), free dexamethasone (in the form of dexamethason-21-acetate to increase solubility, effect of dexamethasone and dexamethasone-21-acetate at similar concentrations are identical (result not shown)) (n=4) or vehicle (n=4) 20 hours before i.v. injection of LPS.

FIG. 39A) The concentration of TNFα in serum samples were determined 2 hours post LPS injection. The serum samples were analyzed in triplicates in sandwich ELISA assay.

FIG. 39B) Thymus weight 2 days post LPS injection.

FIG. 39C) Spleen weight 2 days post LPS injection.

FIGS. 40A-40D—ED2-dexamethasone suppression of LPS mediated TNFα stimulation in vivo, comparison of amino linked and Cys linked conjugation. (FIG. 40A) Rat spleen cells were cultured and incubated with serial dilutions of ED2-NHS-dexamethasone conjugate or free dexamethasone for 15 minutes, washed and incubated overnight. Cell supernatants were analyzed for TNFα after 4 hours of LPS stimulation, Female Lewis rats were injected intravenously with ED2-NHS-dexamethasone (n=5), ED2-MVCP-dexamethasone (n=5), free dexamethasone (in the form of dexamethason-21-acetate to increase solubility) (n=5) or vehicle (n=5) 20 hours before intravenous (i.v.) injection of LPS. (FIG. 40B) The concentration of TNFα in serum samples were determined 2 hours post LPS injection. The serum samples were analyzed in triplicates in sandwich ELISA assay. (FIG. 40C) Thymus weight 2 days post LPS injection. (FIG. 40D) Spleen weight 2 days post LPS injection. Statistically significant differences between groups are indicated, with p value.

Figures 41A, 41B:
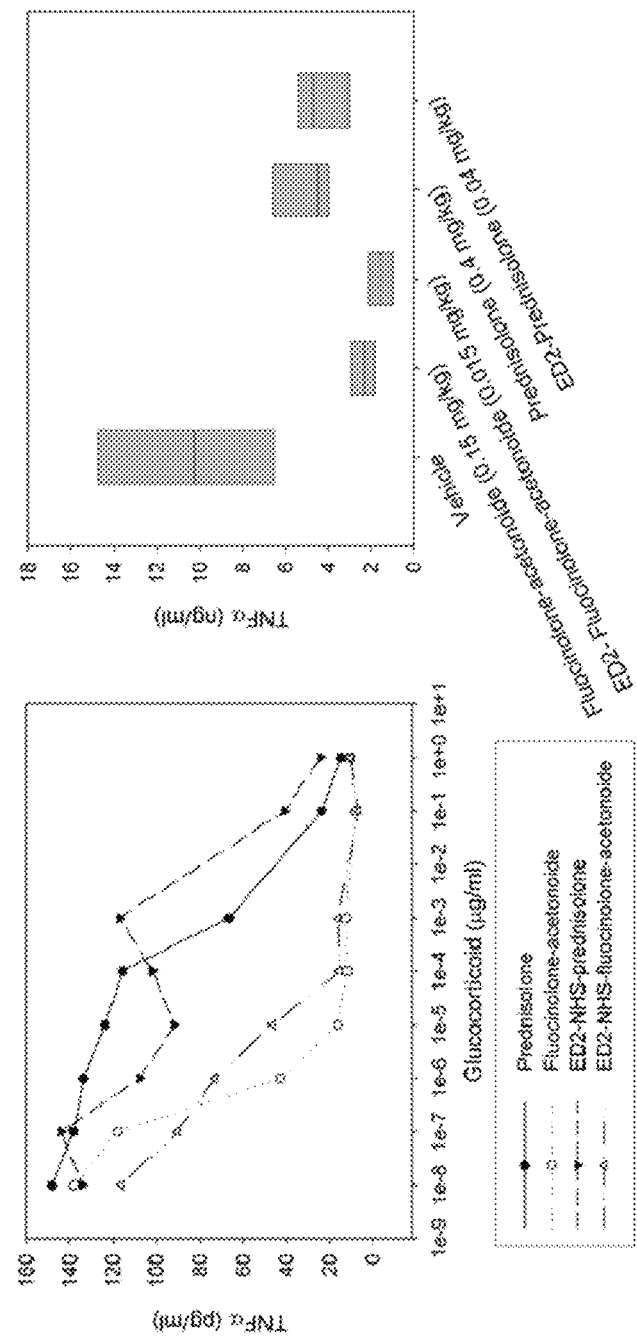

FIGS. 41A-41B—Effect of fluocinolone acetonoid and prednisolone coupled ED2 on LPS mediated TNFα production in vivo. Female Lewis rats were injected intravenously with ED2-fluocinolone acetonoid (n=4), ED2-prednisolone (n=4), free fluocinolone acetonoid (n=4), free prednisolone (n=4) or vehicle (n=4) 20 hours before intravenous (i.v.) injection of LPS. The concentration of TNFα in serum samples were determined 2 hours post LPS injection. The serum samples were analyzed in triplicates in sandwich ELISA assay.

FIGS. 42A-42B—Effect of different 3E10810-dexamethasone conjugates in vitro and in vivo. (FIG. 42A) Mouse spleen cells were cultured and incubated with serial dilutions of 3E10B10-dexamethasone conjugate or free dexamethasone for 15 minutes, washed and incubated overnight. Cell supernatants were analyzed for TNFα after 4 hours of LPS stimulation. (FIG. 42B) Female Balbc/A mice were injected intravenously with 3E10B10—NHS-dexamethasone (n=5), 3E10B10-MVCP-dexamethasone (n=5), free dexamethasone (in the form of dexamethason-21-acetate to increase solubility) (n=5) or vehicle (n=5) 20 hours before intravenous (i.v.) injection of LPS. The concentration of TNFα in serum samples were determined 2 hours post LPS injection. The serum samples were analyzed in triplicates in sandwich ELISA assay.

Figure 43B:
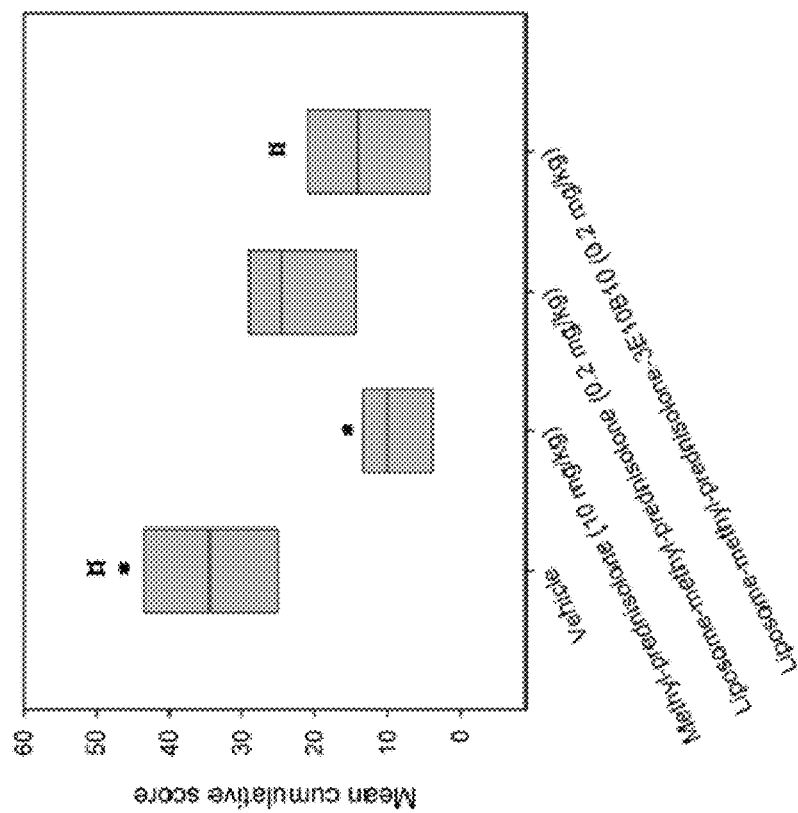
Figure 43A:
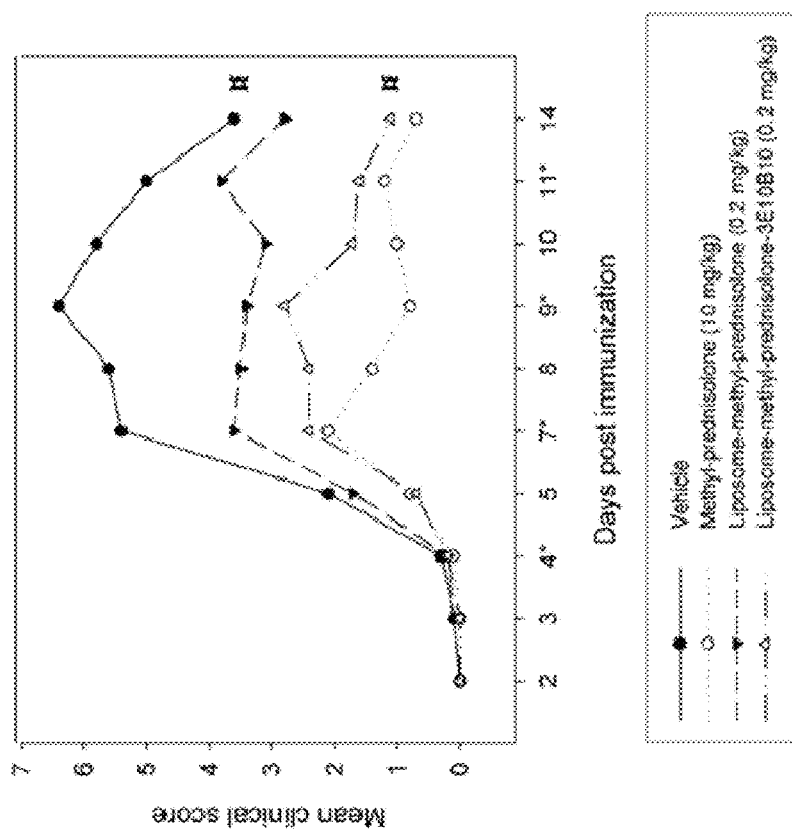

FIGS. 43A-43B—Effect of treatment of collagen antibody induced arthritis in mice. Rats were scored 6 times per week for signs of arthritis in each individual paw. (FIG. 43A) Total arthritis score was defined as the sum of score of all paws on each day. This figure shows the mean total clinical arthritis score versus time for all treatment groups. Each point represents the group mean (n=5). (FIG. 43B) The cumulative arthritis score was defined as the sum of the total clinical arthritis scores obtained from day 0 till day 14. * indicates p<0.05 for the methyl-prednisolone group versus vehicle group and # indicates p<0.05 for the methyl-prednisolone-3E10B10 group versus vehicle group.

Figure 44:
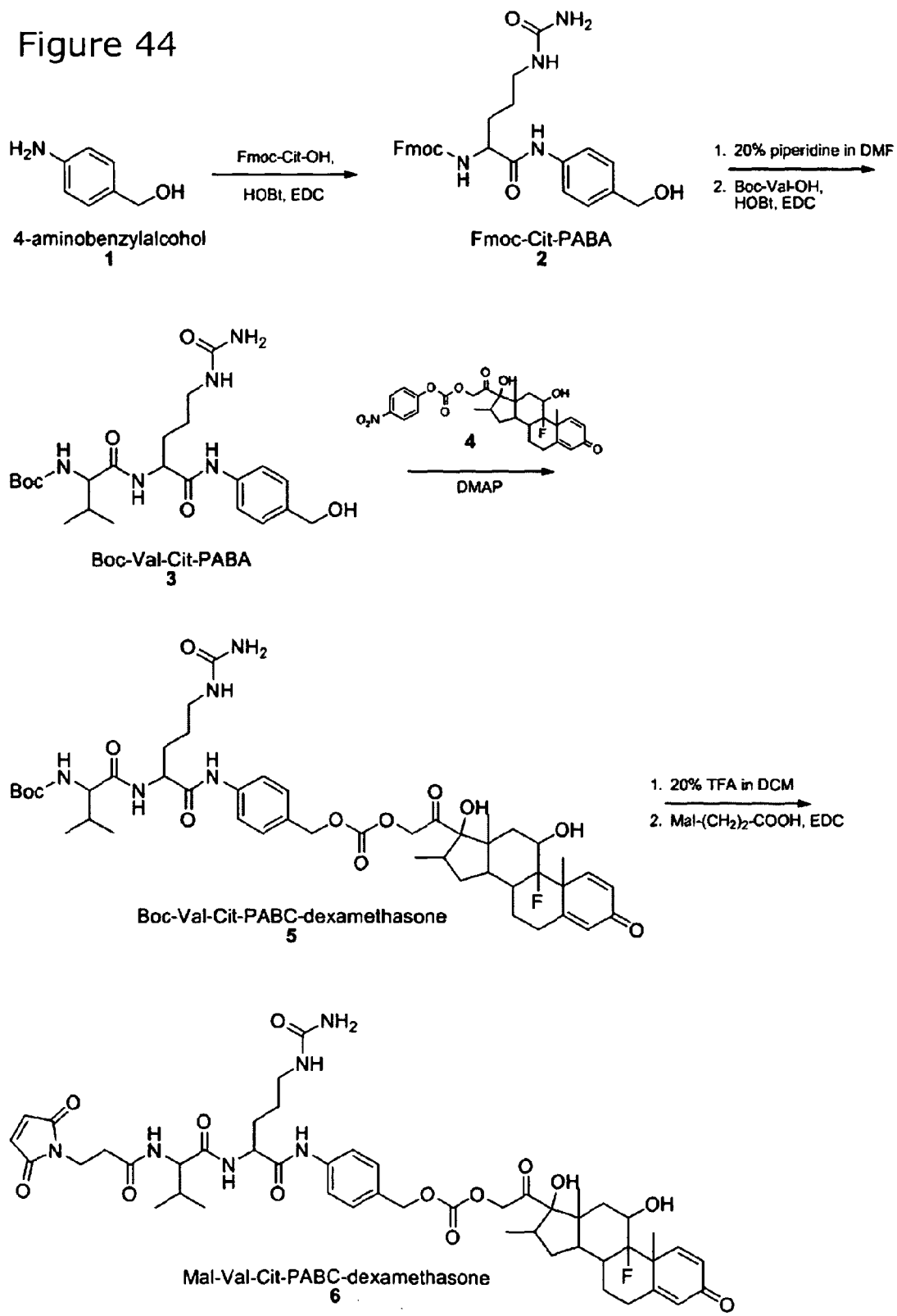

FIG. 44—Overview of synthesis route for Dexamethasone-MVCP

Figure 45:
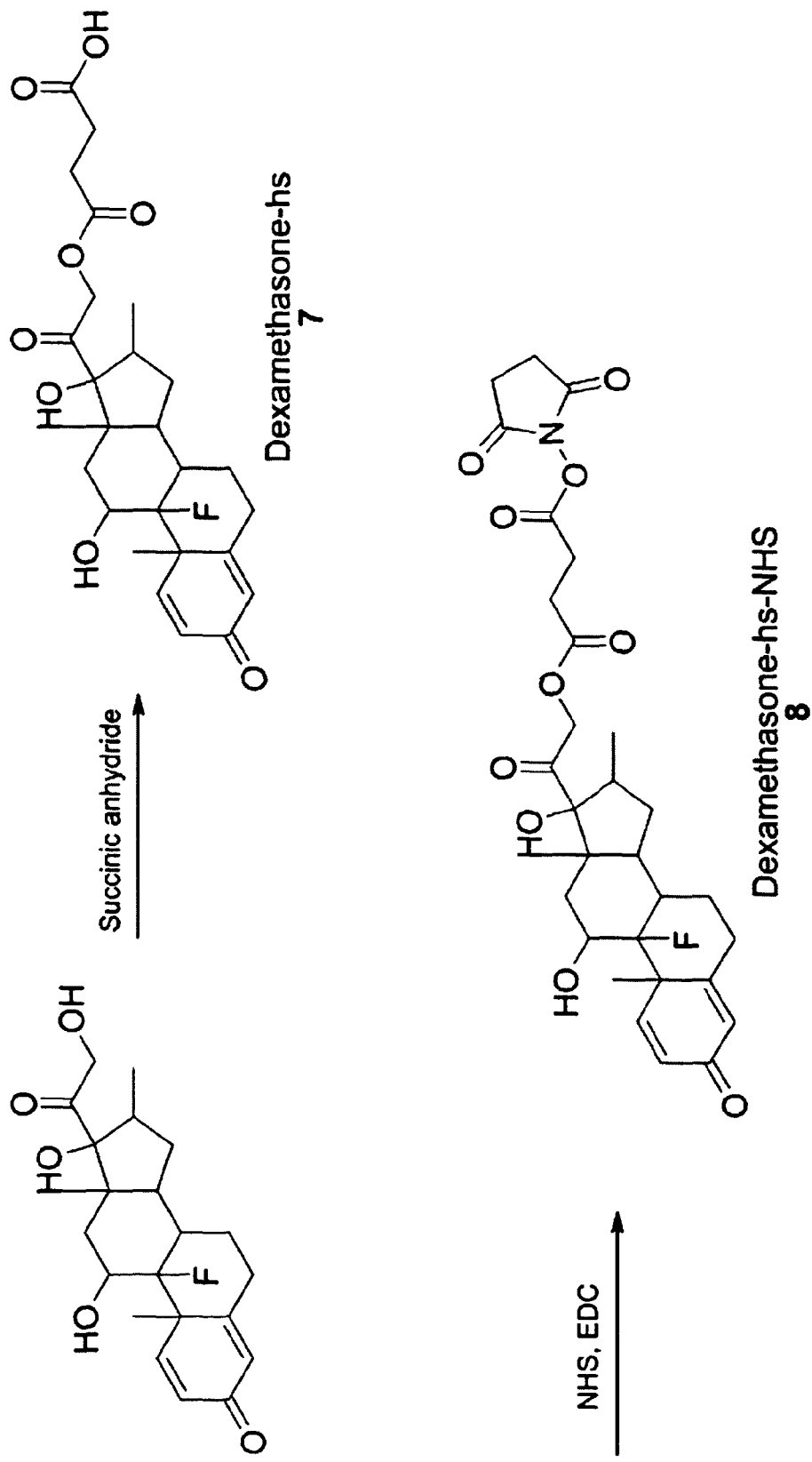

FIG. 45—Overview of synthesis route for Dexamethasone-NHS

FIG. 46—Comparison of CD163 sequences.

FIG. 47—Effect of treatment on body weight.

Individual rats were weighed six times per week and for each treatment group the mean weight was calculated. Each point represents the group mean (n=4). Note: The same vehicle and 0.01 mg/kg dexamethasone groups are presented in both panels.

Figure 48:
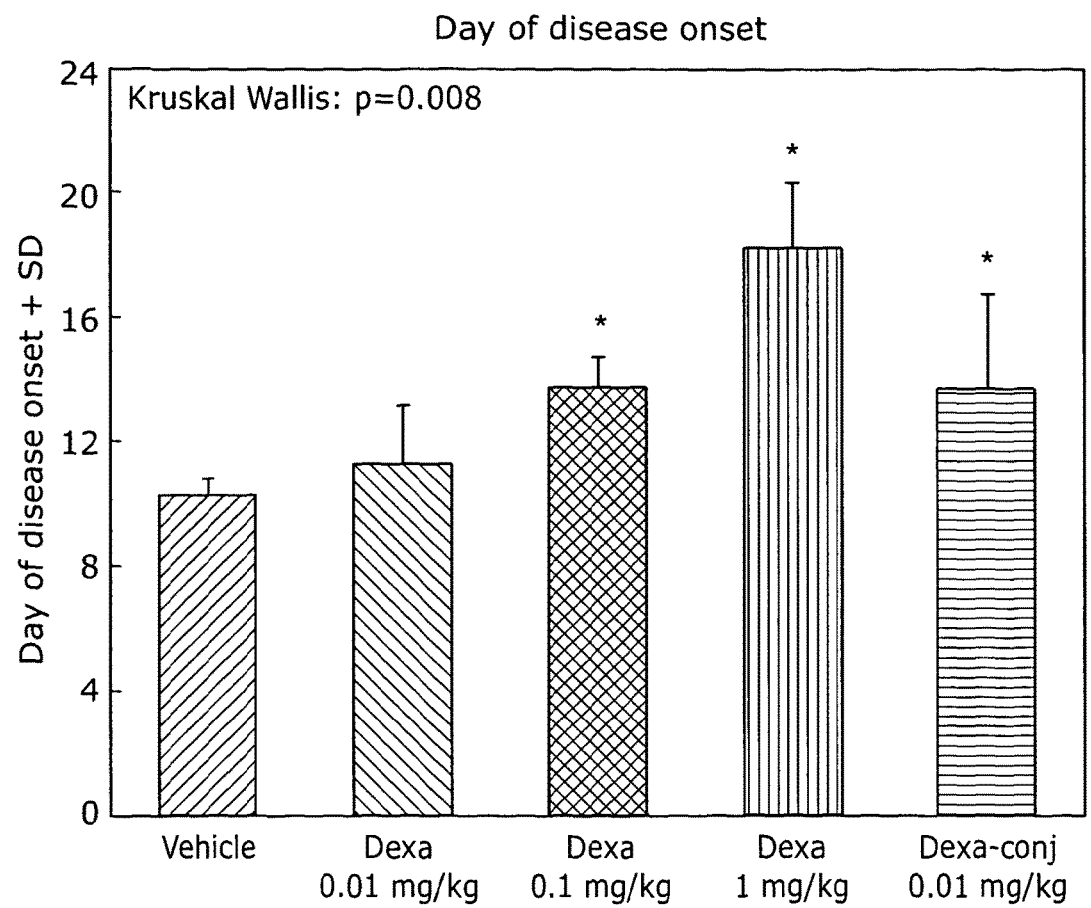

FIG. 48—Effect of treatment on day of disease onset.

Day of onset is defined as the first day of three consecutive days on which a clinical score of >0 was observed. If rats did not develop disease during the experimental period, the day of onset was arbitrarily set to day 21. Each bar represents group mean±SD. * indicates p<0.05 versus vehicle group. Dexa=dexamethasone, Dexa-conj=dexamethasone-conjugate.

FIG. 49—Effect of treatment on disease incidence. Disease was defined as a clinical score>0 on each day. This figure shows the incidence of disease versus time for all treatment groups.

FIG. 50—Effect of treatment on total clinical arthritis score. Rats were scored 6 times per week for signs of arthritis in each individual paw. Total arthritis score was defined as the sum of score of all paws on each day. This figure shows the mean total clinical arthritis score versus time for all treatment groups. Each point represents the group mean (n=4). Note: The same vehicle and 0.01 mg/kg dexamethasone groups are presented in both panels.

Figure 51:
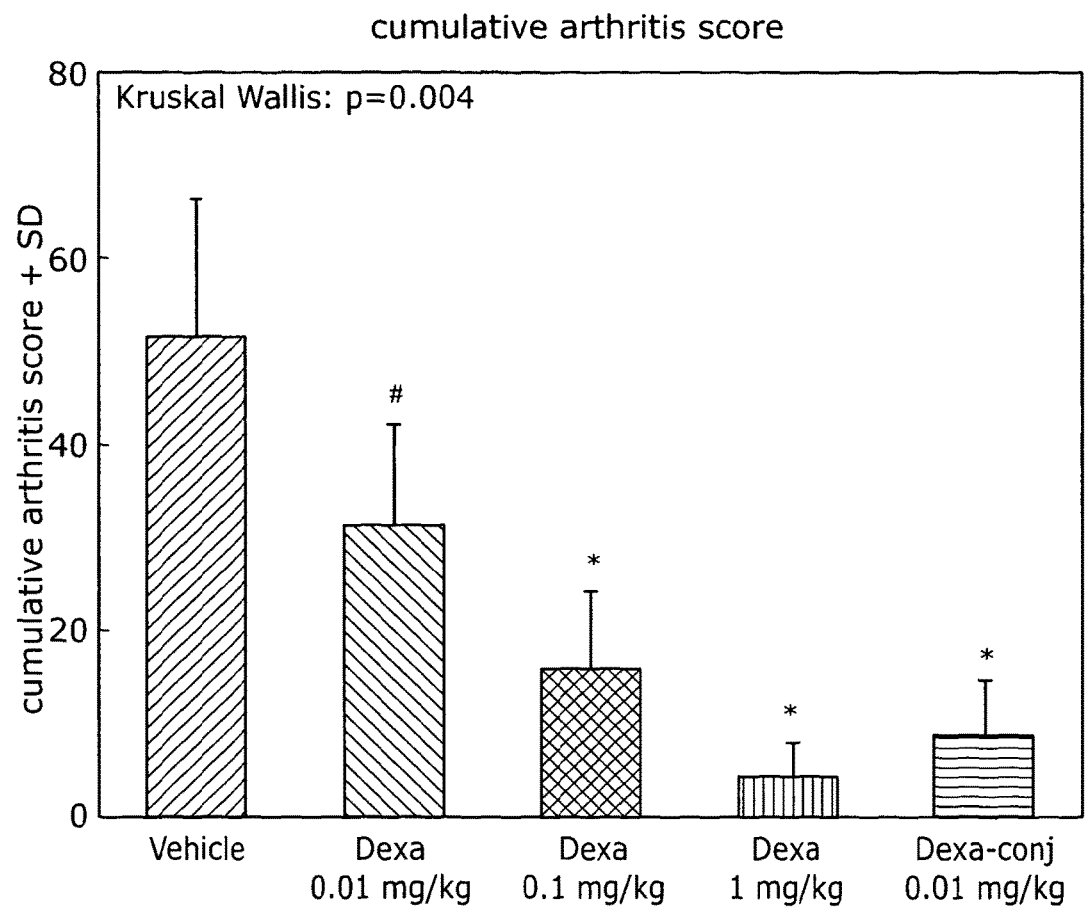

FIG. 51—Effect of treatment on cumulative arthritis score. This figure shows cumulative arthritis score which is defined as the sum of the total clinical arthritis scores obtained from day 0 till day 21. Each bar represents group means±SD. * indicates p<0.05 versus vehicle group and # indicates p<0.05 for the dexamethasone groups versus 0.01 mg/kg dexamethasone-conjugate. Dexa=dexamethasone, Dexa-conj=dexamethasone-conjugate.

FIG. 52—Effect of treatment on left hind paw thickness. Thickness of the hind paws was measured employing a laser scan micrometer. The paw thickness was measured 5 times per week. Each point represents the group mean (n=4). Note: The same vehicle and 0.01 mg/kg dexamethasone groups are presented in both panels.

Figure 53:
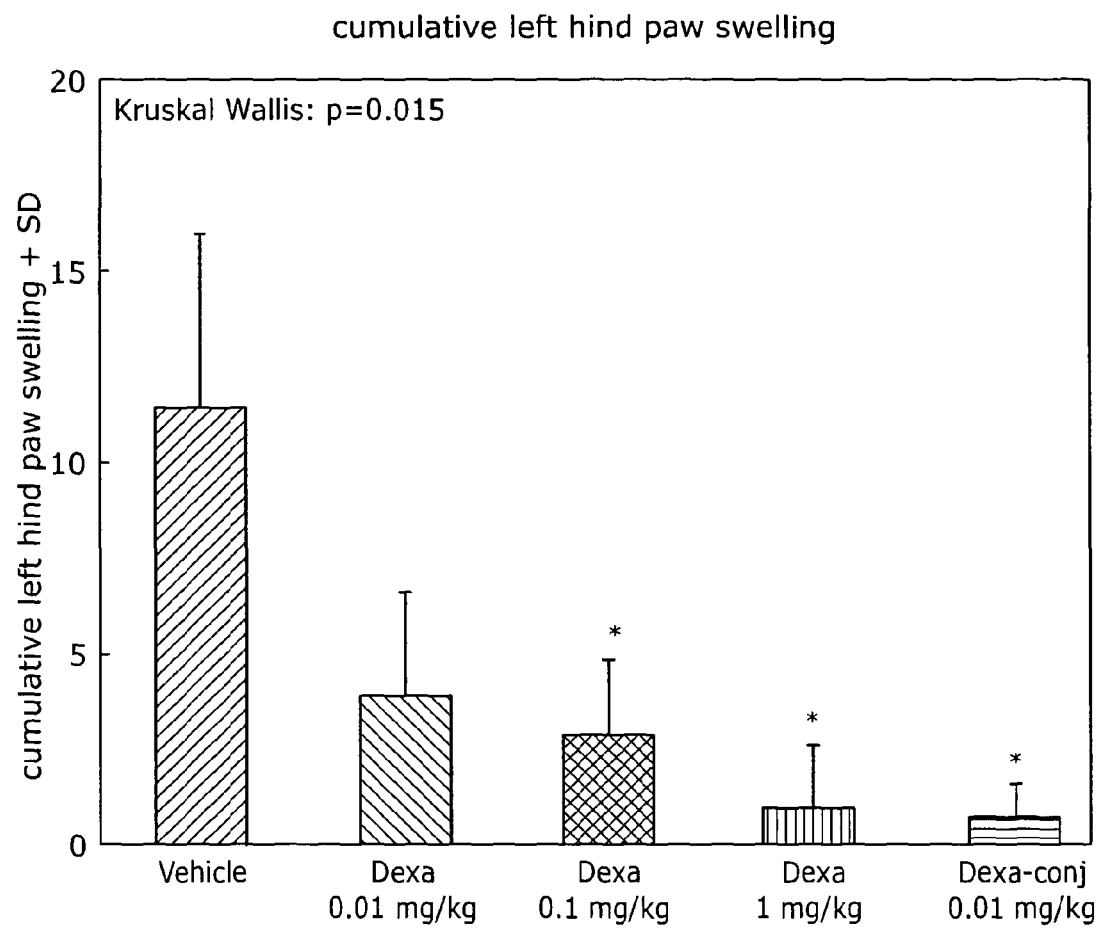

FIG. 53—Effect of treatment on cumulative left hind paw swelling. This figure shows cumulative paw swelling which is defined as the sum of the delta thickness values from day 10 till 21 (delta thickness is paw thickness minus baseline value, which is the mean value of day 0 till 9). Each bar represents group means±SD. * indicates p<0.05 versus vehicle group. Dexa=dexamethasone, Dexa-conj=dexamethasone-conjugate.

FIG. 54—Effect of treatment on right hind paw thickness. Thickness of the hind paws was measured employing a laser scan micrometer. The paw thickness was measured 5 times per week. Each point represents the group mean (n=4). Note: The same vehicle and 0.01 mg/kg dexamethasone groups are presented in both panels.

Figure 55:
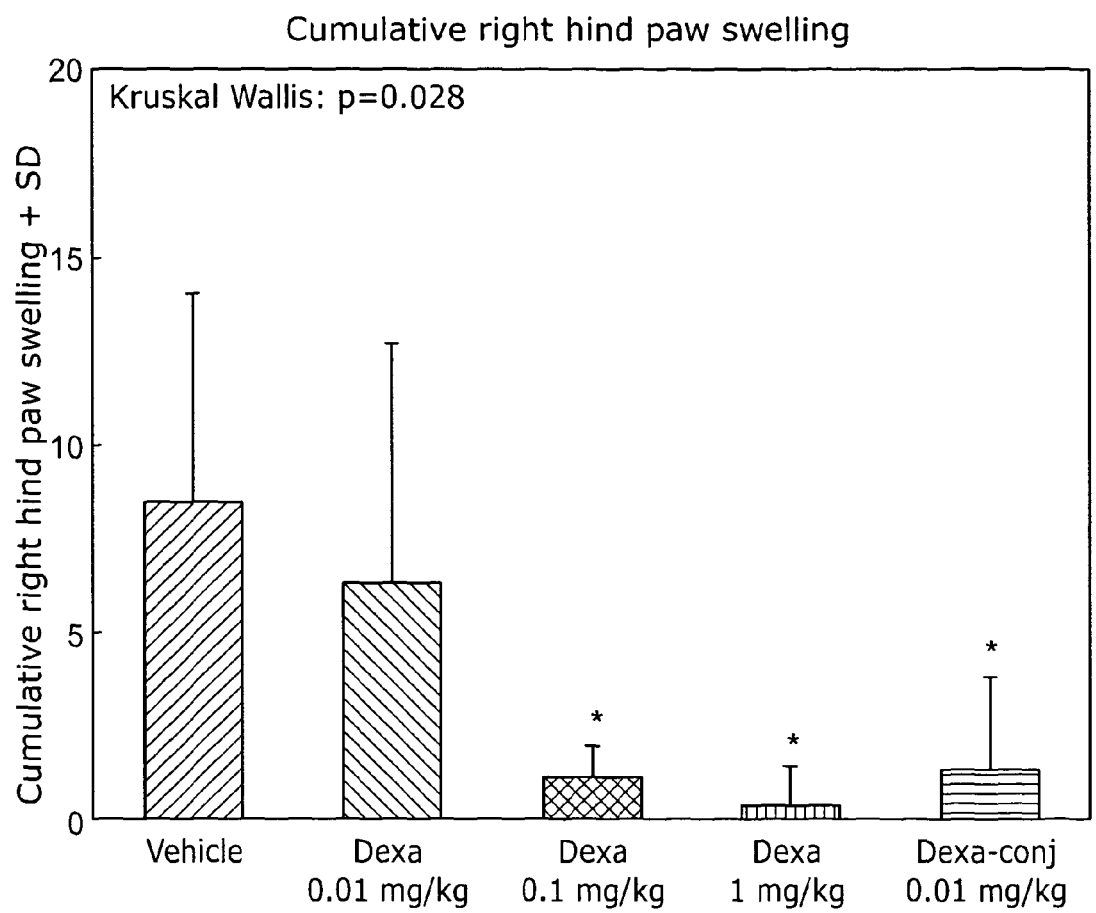

FIG. 55—Effect of treatment on cumulative right hind paw swelling. This figure shows cumulative paw swelling which is defined as the sum of the delta thickness values from day 10 till 21 (delta thickness is paw thickness minus baseline value, which is the mean value of day 0 till 9). Each bar represents group means±SD. * indicates p<0.05 versus vehicle group and # indicates p<0.05 versus 0.01 mg/kg dexamethasone-conjugate. Dexa=dexamethasone, Dexa-conj=dexamethasone-conjugate.

FIG. 56—Effect of treatment on organ weights. Spleen, thymus and liver were collected and weighed at sacrifice. Data were normalized for body weight. Each bar represents group means±SD. * indicates p<0.05 versus vehicle group and # indicates p<0.05 for the dexamethasone groups versus 0.01 mg/kg dexamethasone-conjugate. Dexa=dexamethasone, Dexa-conj=dexamethasone-conjugate.

EXAMPLES

Example 1—Antibodies to SRCR Domain 1 of the CD163 Receptor

Introduction

CD163 is a scavenging receptor consisting of nine extracellular scavenger receptor cysteine-rich (SRCR) type B domains. It mediates the clearance of the haptoglobin-hemoglobin (Hp-Hb) complexes formed when hemoglobin is librated to the circulation during intravascular hemolysis (1;2) and it is also involved in regulation of inflammatory processes (3;4). CD163 is considered to be expressed exclusively on the surface of the monocytic lineage. It is expressed by resident monocytes in the circulation (5;6) and upregulated during maturation to macrophages. It is highly expressed on tissue-resident macrophages (6-10), as well as on alternatively activated macrophages (M2) (11-14), and TIE2+ macrophages (15;16). Furthermore, CD163 has been shown to be expressed by a CD34+ subpopulation of hematopoietic stem/progenitor cells (17) and proposed to be expressed on a subset of myeloid dendritic cells (18;19).

CD163 is cleaved from the cell membrane by a protease-mediated release mechanism in response to toll-like receptor (TLR) activation (20-22), forming soluble CD163 (sCD163) which in serum has been demonstrated to be useful in diagnosis of e.g. sepsis and hemophagocytosis (23-25).

The restricted expression of CD163 limited to the monocytic/macrophage lineage has given rise to increased attention. A large body of evidence has now accumulated demonstrating significant changes in cellular and soluble CD163 levels in inflammatory, malignant, and infectious diseases (11;23;24;26-31). CD163 may be a diagnostic marker in conditions affecting the monocyte/macrophage system and as a therapeutic candidate.

However, whereas the normal concentration range, biological variation, and molecular structure of sCD163 have been described in detail (21;32;33), limited studies exist systematically addressing monocytic CD163 expression. Importantly, using different anticoagulants, antibody clones, and general test conditions, flow cytometric studies continue to exhibit great discrepancy in the level of monocytic CD163 expression, which has been reported to vary from a few to 99% (3;5-7;34-41). Flow cytometric evaluations of monocytic CD163 expression were recently described to vary considerably according to the test conditions (38), and we have previously shown that dendritic cell CD163 expression may show a discrepancy when using different antibody clones (18). It is evident that the applicability of monocytic CD163 expression as a diagnostic tool and therapeutic candidate rests on comparable and reliable measurements in both pathological and physiological conditions.

Materials and Methods

Antibodies and Other Reagents.

The following monoclonal antibodies (mAbs) were used in flow cytometry, immunofluorescence, SPR analysis, and endocytosis experiments with $^{125}$I-labeled anti-CD163: Anti-CD163 (MAC2-158), APC-conjugated anti-CD14 (UCHM1), and R-PE-conjugated Mouse IgG$_1$, k isotype control (MCG1) were obtained from IQ Products, Groningen, The Netherlands. Anti-CD163 (GHI/61) was obtained from BD Biosciences, CA, USA. Anti-CD163 (R-20) was obtained from Trillium Diagnostics, LLC, Scarborough, Me., USA. Anti-CD163 (RM3/1) was obtained from BioLegend, San Diego, Calif., USA. All CD163 mAbs clones were purchased purified and R-PE-conjugated. Goat anti-mouse-conjugated Alexa-Fluor® 488 was obtained from Molecular Probes, Invitrogen, Carlsbad, Calif., USA. Mouse anti Human CD163 Ki-M8 and 5C6-Fat were obtained from Acris Antibodies, Germany, (catalogue numbers BM4112 and BM4041, http://www.acris-antibodies.com/BM4112.htm, http://www.acris-antibodies.com/bm4041.htm). Mouse anti Human CD163 EDHu-1 was obtained from Acris Antibodies, Germany, (catalogue number SM2160P. http://www.acris-antibodies.com/SM2160P.htm). Anti CD163 antibody Mac2-48 was obtained from IQ Products, the Netherlands, catalogue number CD163-48U. http://www.iqproducts.nl/catalog/index.php?pr=783). Mouse anti Human CD163 R20 was obtained from Trillium, Me., USA (catalogue number CD163-20U, http://trilliumdx.com/products/content.php?products id=33). Mouse anti Human CD163 Ber-Mac3 can be obtained from MBL, MA, USA, (catalogue number K-0147.

http://www.mblintl.com/mbli/account/search_results.asp?search=K0147-3).

Blood Samples and Preparation of PBMC.

EDTA, citrate, and heparin stabilized peripheral blood samples were obtained by standard venipuncture from healthy donors in Venoject® vacutainers (Terumo Europe NV, Leuven, Belgium). Peripheral blood mononuclear cells (PBMC) were isolated from leukocyte-rich buffy coats by gradient separation centrifugation using Accuspin System Histopaque®—1077 (Sigma-Aldrich Denmark A/S, Broendby, Denmark). Buffy coats were prepared from units of whole blood (approximately 472 ml) anti-coagulated with CPD-A (Baxter, Munich, Germany) donated by healthy volunteers. Approval for the study was obtained from the regional ethical committee (j.nr. 20040068).

Quantitative Flow Cytometry.

Freshly drawn peripheral whole blood samples or PBMC (approx. $3 \times 10^6$ cells) were stained with isotype-matched control antibody or a relevant antibody for one hour at 4° C. in the dark. When staining whole blood, erythrocytes were lysed for 15 min with 4° C. cold solution of ammonium chloride. When indirect immunofluoresence staining was required, cells were initially incubated with unconjugated primary CD163 antibody for one hour at 4° C., washed three times with D-PBS, pH 7.4, followed by incubation with goat anti-mouse-conjugated Alexa-Fluor® 488 (1:200 dilution; Molecular Probes, Invitrogen, Carlsbad, Calif., USA) for one hour at 4° C. in the dark. The stained cells were washed twice three D-PBS, pH 7.4, re-suspended in 400 µl FACSflow (Becton Dickinson, San Jose, Calif., USA), and kept on ice until analysis. All samples were analyzed using a FACSCalibur flow cytometer and compensated for spectral overlap using FlowJo for Macintosh software version 8.3 (TreeStar, San Carlos, Calif.). For CD163 density quantitation, flow cytometric estimation of antibodies bound/cell (ABCs) was performed using Quantibrite PE beads (Becton Dickinson, San Jose, Calif., USA) as recommended by the manufacturer. After the cells were stained, as detailed, a set of 4 pre-calibrated fluorescently labeled beads was used for standardization before the samples were acquired. The Quantibrite PE beads were run at the same instrument settings as the assay, and the linear regression obtained using the Quantibrite PE beads was used to convert the FL2 linear fluorescence staining of cell population into the number of (CD163) PE molecules bound per cell (ABC).

Enzyme-Linked Immunosorbent Assay (ELISA).

Soluble CD163 was measured using an in-house ELISA assay, as previously described (32).

Preparation, Stimulation and Incubation of Human Monocyte-Derived Macrophages and Stably Transfected Chinese Hamster Ovary (CHO) Cells.

Monocytes were isolated from PBMC by negative selection using magnetic beads from Dynal (Dynabeads® MyPure™ Monocyte Kit 2; Invitrogen A/S, Taastrup, Denmark) according to instructions provided by the manufacturer. Monocyte preparations were more than 95% (CD14$^+$) pure determined by flow cytometry. The isolated cells were washed twice with phosphate-buffered saline. Monocyte-derived macrophages (MDMs) were prepared by cell culture of monocytes (approximately $1 \times 10^7$ cells) for 4 days in 5% $CO_2$ and 37° C. in RPMI 1640 media (RPMI 1640+25 mM HEPES+l-glutamine) (Invitrogen Corporation, Carlsbad, Calif., USA) with 20% FCS containing 100 ng/ml of M-CSF. MDMs were then detached from the flask by incubation with cell dissociation buffer (Invitrogen A/S, Taastrup, Denmark) for 30 minutes at 40□C, then flushed, and scraped. The cells were then cultured for 24 hours in RPMI 1640 media (RPMI 1640+25 mM HEPES+l-glutamine) (Invitrogen Corporation, Carlsbad, Calif., USA) supplemented with 20% FCS containing 100 ng/ml of M-CSF at 37° C. in 95% air and 5% CO in Lab-Tek™ Chamber Slides (Thermo Fisher Scientific, Roskilde, Denmark). 200 nM dexamethasone (Merck KGaA, Darmstadt, Germany) was added during culture to increase CD163 expression. Stably transfected Chinese hamster ovary (CHO) cells expressing the full-length human CD163, as described above, were cultured in serum-free CHO medium (HyQ-CCM, HyClone, Logan, Utah) containing 300 µg/ml Hygromycin B, as previously described (2).

Cells were washed in were washed with 4° C. cold D-PBS, pH 7.4, re-suspended and stained for CD163 expression as described below.

Cellular Binding and Uptake with Fluorescently Labeled CD163 Antibodies

MDMs or CHO cells were washed with 4° C. cold D-PBS, pH 7.4, containing 1% BSA in Lab-Tek™ Chamber Slides (Thermo Fisher Scientific, Roskilde, Denmark). The cells were then incubated with 10 µg/ml different clones of anti-CD163 for one hour at 4° C. and then washed three times with D-PBS, pH 7.4, with 1% BSA. The cells were subsequently either fixated with 4% formaldehyde for one hour at 4° C. or incubated for 30 minutes at 3TC under a humidified atmosphere of 95% air and 5% CO. Cells incubated for 30 minutes were then washed 3 times with D-PBS, pH 7.4, containing 1% BSA and fixated for one hour at 4° C. with 4% formaldehyde. All cells were washed once with D-PBS, pH 7.4, and permeabilised with D-PBS, pH 7.4, containing 0.05% Triton X-100 (Merck) for 15 min at RT. Cells were then incubated with goat anti-mouse-conjugated Alexa-Fluor® 488 (1:200 dilution; Molecular Probes, Invitrogen, Carlsbad, Calif., USA) for one hour at RT washed five times with D-PBS, pH 7.4, containing 0.05% triton X-100. Slides were mounted with Vectashield® mounting medium with 4',6'-diamidino-2-phenylindole (DAPI) to identify cell nucleus (Vector Laboratories, Burlingame, Calif., USA). Fluorescence was visualized using a Zeiss Axiovert 200M microscope (Carl Zeiss GmbH, Jena, Germany) with an ×100 oil-immersion objective. Representative images were acquired using a AxioCam MRm digital camera (Carl Zeiss GmbH, Jena, Germany). Alternatively, immunostained cells were analyzed by confocal immuno-fluorescence microscopy using a Zeiss LSM-510 confocal microscope (Carl Zeiss GmbH, Jena, Germany). Image processing was done using NIH ImageJ software (version 1.38w) and Adobe Photoshop CS4.

Cellular Binding and Uptake of $^{125}$I-Labeled Anti-CD163

Endocytosis of $^{125}$I-labeled anti-CD163 was investigated in CD163 transfected Flp-In Chinese hamster ovary (CHO) cells and mock-transfected Flp-In as described (Madsen, M., Moller, H. J., Nielsen, M. J., Jacobsen, C., Graversen, J. H., van den Berg, T. and Moestrup, S. K. (2004) Molecular characterization of the haptoglobin.hemoglobin receptor CD163. Ligand binding properties of the scavenger receptor cysteine-rich domain region. J. Biol. Chem., 279, 51561-51567.)

Data and Statistical Analysis

All estimates are accompanied by either range values or a 95% confidence interval. Differences between values were analysed for statistical significance with Student's t-test. For comparisons between smaller groups without Gaussian distribution of values, the non-parametric Mann-Whitney rank sum test was used. Differences were considered significant at $p<0.05$. Statistical calculations were carried out using the STATA statistical package version 10 for Windows.

Surface Plasmon Resonance (SPR) Analysis of mAb CD163 Binding

SPR analysis of the binding of mAbs to CD163 was carried out on a Biacore 2000 instrument (Biacore, Uppsala, Sweden). The Biacore sensor chips (type CM5) were activated with a 1:1 mixture of 0.2 M N-ethyl-N'-(3-dimethylaminopropyl) carbodiimide and 0.05 M N-hydroxysuccimide in water. Purified recombinant CD163 were immobilized in 10 mM sodium acetate, pH 4.0, and the remaining binding sites were blocked with 1 M ethanolamine, pH 8.5. The SPR signal generated from immobilized recombinant CD163 proteins corresponded to 40-70 fmol of protein/mm$^2$. Sensorgrams were generated using mAb concentrations ranging from 5-100 nM. The flow cells were regenerated with 1.6 M glycine-HCl, pH 3. The running buffer used for the experiment was either CaHBS 10 mM Hepes, 150 mM NaCl, 3.0 mM CaCl$_2$, 1.0 mM EGTA, and 0.005% Tween 20, pH 7.4. or 10 mM Hepes, 150 mM NaCl, 3.0 mM EDTA, and 0.005% Tween 20, pH 7.4, mAb samples were dissolved in the same buffer as the running buffer used. All binding data were analyzed using the Biamolecular Interaction Analysis evaluation program version 3.1.

Competition of Binding to Mac2-158 Epitope.

To evaluate if there is competition in the binding of a range of mAbs to CD163 we first saturated the CD163-chip with Mac2-158 by injecting 50 μL of 50 μg/ml Mac2-158 and subsequently injecting relevant mAbs in 5 μg/ml. The binding buffer was CaHBS 10 mM Hepes, 150 mM NaCl, 3.0 mM CaCl$_2$, 1.0 mM EGTA, and 0.005% Tween 20, pH 7.4.

Results

Surface CD163 Expression on Human Peripheral Blood Monocytes Determined Using Different Clones of Monoclonal Antibodies.

Freshly drawn EDTA stabilized whole blood was stained with specific mAb defining monocytes as CD14$^+$ cells to investigate monocyte surface CD163 expression using CD163 mAbs clones covering various SRCR domains. The MAC2-158 clone, which binds to SRCR domain 1, recognized a significantly larger fraction of peripheral blood monocytes (84.06% [95% CI: 76.20-91.92%]) (FIG. 1A) as compared with R-20 (75.93% [95% CI: 72.49-79.38%]; p<0.005) (FIG. 1B), GHI/61 (63.03% [95% CI: 54.34-71.73%]; p<0.001) (FIG. 1C), and RM3/1 (0.33% [95% CI: 0.068-0.59]; p<0.0001) (FIG. 1D), which bind to SRCR domain 4, 7, and 9, respectively. The measured density of CD163 receptors per monocyte was significantly higher when using MAC2-158 (17,725 [95% CI: 13,335-22,133]) (FIG. 1A) compared with R-20 (1,650 [95% CI: 1,139-2,163]; p<0.0001) (FIG. 1B), GHI/61 (1,030 [95% CI: 807-1,253]; p<0.0001) (FIG. 1C), and RM3/1 (101 [95% CI: 28-175]; p<0.0001) (FIG. 1D). For comparison, non specific binding was assessed using an isotype-matched non-specific IgG and showed low background staining (94 [95% CI: 76-112]) (not shown). A similar pattern of CD163 expression variation was observed when whole blood was stained using unconjugated primary CD163 antibody clones followed by Alexa Fluor® 488 secondary antibody conjugates (not shown).

Monocytic Surface CD163 Expression on Peripheral Blood Mononuclear Cells Isolated by Density Gradient Centrifugation.

Peripheral blood mononuclear cells were purified to assess the effect of the histopaque gradient isolation on the monocyte surface CD163 expression. Flow cytometric analysis revealed an analogous expression pattern of CD163 expression as observed utilizing freshly drawn EDTA stabilized whole blood. The fraction of CD14$^+$ monocytes stained for CD163 was 81.10% [95% CI: 73.95-88.25%] when using MAC2-158 and 2.50% [95% CI: 0.29-4.71%] when using RM3/1 (2.50% [95% CI: 0.29-4.71%]) However, the fraction of CD14$^+$ monocytes which stained positive for CD163 decreased significantly for the R-20 clone and the GHI/61 clone after density gradient centrifugation. After separation, 54.40% [95% CI: 29.10-79.70%] CD14$^+$ monocytes stained positive for CD163 using R-20 which was significantly lower than in freshly drawn EDTA stabilized whole blood (p<0.05). The fraction of CD163 positive monocytes using GHI/61 diminished considerably and became almost undetectable (1.26% [95% CI: 0.91-1.61%]). The measured density of CD163 receptors per monocyte exhibited a similar pattern: MAC2-158 (11,417 [95% CI: 8,058-14,777]), p<0.01; R-20 (836.7 [95% CI: 654.4-1,019]; p<0.0001), GHI/61 (108.0 [95% CI: 81.71-134.3]; p<0.0001), and RM3/1 (132.3 [95% CI: 66.97-197.7]; p<0.05).

Influence of Different Anticoagulants on Monocytic Surface CD163 Expression.

To investigate the influence of different extracellular calcium concentrations on monocyte surface CD163 expression, CD163 levels were measured in freshly drawn whole blood samples stabilized with three commonly used anticoagulants and using different mAb clones (FIGS. 2, 3, and FIG. 14D). Using the MAC2-158 clone the fraction of CD14$^+$ monocytes stained positive for CD163 was unaffected regardless the extracellular calcium concentration: 87.23% [95% CI: 81.10-93.37%] of CD14$^+$ monocytes stained positive for CD163 when using EDTA as anticoagulant, 83.97% [95% CI: 80.52-87.41%] using citrate, and 84.43% [95% CI: 77.82-91.05%] when using heparin (left panel in FIG. 2; FIG. 3A, and FIG. 14D). The density of receptors per monocyte displayed a similar pattern, showing 17,725 [95% CI: 13,335-22,133] receptors using EDTA as anticoagulant, 17,726 [95% CI: 14,675-20,777] when using citrate, and 18,929 [95% CI: 14,261-23,597] when using heparin (left panel in FIG. 2, FIG. 3B, and FIG. 14D).

CD163 staining with the R-20 clone, 75.93% [95% CI: 72.49-79.38%] of CD14$^+$ monocytes stained positive for CD163 when using EDTA as anticoagulant, 74.73% [95% CI: 70.36-79.11%] when using citrate; however, significantly lower (63.03% [95% CI: 60.38-65.69%]; p<0.005) using heparin (middle left panel in FIG. 2; FIG. 3A, and FIG. 14D). The determined density of CD163 receptors per monocyte was 1,760 [95% CI: 1,600-1,920] in EDTA, 1,988 [95% CI: 1,750-2,226] in citrate, but, unexpectedly higher (3,019 [95% CI: 2,648-3,390]) in heparin stabilized samples (middle left panel in FIG. 2; FIG. 3B, and FIG. 14D).

However, when using the GHI/61 clone the fraction of CD14$^+$ monocytes stained for CD163 was clearly affected by the anticoagulant revealing a significant lower monocytic surface CD163 expression when using heparin as anticoagulant (0.82% [95% CI: 0.55-1.08%]) as compared with blood samples anti-coagulated with EDTA (63.03% [95% CI: 54.34-71.73%]; p<0.0001) and citrate (64.37% [95% CI: 58.17-70.56%]; p<0.0001) (middle right panel in FIG. 2; FIG. 3A, FIG. 14D). This finding was verified by the density of CD163 receptors per monocyte which was 58.33 [95% CI: 24.42-92.24] in heparin, whereas 1,030 [95% CI: 806.9-1,252] (p<0.0001) in EDTA, and 1,152 [95% CI: 962.9-1,342] (p<0.0001) in citrate stabilized samples (middle right panel in FIG. 2; FIG. 3B, and FIG. 14D).

Using RM3/1, the flow cytometric analysis showed that a very little proportion of CD14$^+$ monocytes stained positive for CD163 (0.33% [95% CI: 0.068-0.59%] in EDTA, 12.50% [95% CI: 9.57-15.43%] in citrate, and 3.33% [95% CI: 1.84-4.82%] in heparin [right panel in FIG. 2; and FIG. 3A]) stabilized blood samples. The determined monocyte surface CD163 expression was also extremely low (86.00 [95% CI: 66.28-105.7]) in EDTA, 207.0 [95% CI: 167.0-247.0] in citrate, and 210.3 [95% CI: 163.3-257.4] in heparin when the RM3/1 clone was used regardless the extracellular calcium concentration (right panel in FIG. 2; FIG. 3B, and FIG.14D).

Variation in Detected Surface Expression is not Due to CD163 Shedding

The levels of soluble CD163 (sCD163) were measured in the same freshly drawn whole blood samples stabilized with different anticoagulants. Adjusted for dilution during sample preparation sCD163 levels determined using ELISA were 832.1 µg/l in EDTA stabilized blood samples, 738.3 µg/l in citrate stabilized blood samples, and 897.8 µg/l in heparin stabilized blood samples suggesting that the anticoagulant used (and hence the presence of calcium) did not affect the shedding of sCD163.

Binding to CD163.

Mac2-48, Mac2-158, 5C6-Fat, Ki-M8, EdHu1 and Ber-Mac3 all bound CD163 in both 2 mM free $Ca^{2+}$ and 10 mM EDTA, however, exhibiting somewhat different affinity between the $Ca^{2+}$ and EDTA buffer, but all affinities being in the nanomolar or sub-nanomolar range. The mAb designated GHI/61 did only exhibit very weak binding to CD163 in the calcium containing buffer, whereas it exhibited binding in 10 mM EDTA with an apparent $K_d$ of 29 nM. RM3/1 did not exhibit binding to CD163 in the EDTA buffer, whereas the apparent $K_d$ in 2 mM free $Ca^{2+}$ was 0.6 nM. Typical sensorgrams are shown in FIG. 4, comparing binding in calcium and EDTA.

Endocytosis of $^{125}$I-Labeled CD163 Antibodies in Stable CD163 Transfected Flp-In CHO Cells.

To compare endocytotic ability, the mAb clones were labelled with $^{125}$I and incubated with CD163 expressing Flp-In CHO cells to increasing time points. As shown in FIG. 5A, the time course of cell-associated radioactivity (bound or internalized) reached a plateau after one hour of incubation for most of the antibodies, although the level of cell-associated radioactivity when using $^{125}$I-labelled GHI/61 was at a low level suggesting reduced or no endocytosis. In contrast, when incubating with $^{125}$I-labelled Mac2-48 and Mac2-158 the time course of cell-associated radioactivity did not reach a plateau after two, or even fout, hours of incubation. Using MAC2-158 the percentage of cell-associated radioactivity reached 61.27% [95% CI: 56.56-0.6597%] in stable CD163 transfected Flp-In CHO cells. For comparison, percentage of cell-associated radioactivity reached 1.37% [95% CI: 0.426-2.31%] in non-transfected Flp-In CHO cells using same mAb clone. The percentage of cell-associated radioactivity reached was lower using R-20 (18.97% [95% CI: 18.09-19.84%] vs. 0.97% [95% CI: 0.59-1.35%]), GHI/61 (1.23% [95% CI: 0.854-1.61%] vs. 1.23% [95% CI: 0.72-1.75%]), and RM3/1 (7.77% [95% CI: 4.11-11.43%] vs. 1.47% [95% CI: 0.099-2.84%]). As shown in FIG. 5B, the degree of cell-associated radioactivity detected in non-transfected Flp-In CHO cells was low for all monoclonal antibodies, as expected.

Endocytosis of Fluorescent CD163 Antibodies in Human Monocyte-Derived Macrophages.

Monocyte-derived human macrophages were prepared from peripheral blood monocytes and stimulated with 200 nM dexamethasone to assess binding and uptake of different CD163 mAbs. MAC2-158, R-20, GHI/61, and RM3/1 were able to bind the CD163 receptor on surface of human macrophages which was shown with immunofluorescent staining. However, fluorescence microscopy revealed that staining using MAC2-158 and R-20 exhibited a pronounced cell surface staining as compared with GHI/61 and RM3/1 (upper panels in FIG. 6).

After incubation for 30 min, the immunofluorescent staining showed a distinct punctuate subcellular staining which was characteristic in all investigated clones of CD163 mAbs (lower panels in FIG. 6). However, the intensity of intracellular staining appered most prominent when using MAC2-158 as compared with R20, GHI/61, and RM3/1 (lower panels in FIG. 6), suggesting a more efficient uptake of MAC2-158. A similar pattern of surface staining and cellular uptake was observed in CD163-transfected Flp-In CHO cells by confocal laser scanning microscopic analysis (not shown).

Similar experiments were made on CHO cells expressing CD163 screening a larger panel of mAbs using confocal microscopy (FIGS. 7a and 7b).

Competition with Mac2-158

FIG. 8 shows sensorgrams of binding of different CD163 mAbs to a CD163 sensorchip which has first been saturated with Mac2-158, meaning that virtually all epitopes for Mac2-158 has mAb bound, thus only mAbs binding in competition with Mac2-158 should not be able to bind to the CD163 immobilised on the chip, and induce a further increase in the response units measured, whereas mAb not binding in competition should be able to bind to the immobilised CD163 and thus increase the response units measured. As can be seen from FIG. 8, Mac2-158, Mac2-48, Ber-Mac3 and GHI/61 were not able to bind to a CD163-Fc saturated with Mac2-158 in a 2 mM free calcium buffer. All mAbs but GHI/61 are binding to SRCR domain 1 and GHI/61 is not exhibiting binding in a calcium rich environment. The mAbs EdHU-1, Ki-M8 and RM3/1 all where able to bind to the CD163-Fc regardless of the saturation and are thus not competing for binding to CD163 with Mac2-158. Thus, it appears that all monoclonal antibodies binding to domain 1 bind in competition with Mac2-158.

Discussion

An increasing focus on CD163 for diagnostic purposes led us to examine in detail factors influencing the detection of monocytic CD163 expression in peripheral blood by flow cytometry. Previous studies have reported varying results, from only a few to 99% of monocytes have been proposed to express CD163 (3;5-7;34-41). These studies have used various monoclonal CD163 antibody clones with specificity to different epitopes along the nine extracellular SRCR domains (42).

We have previously demonstrated a higher monocytic and dendritic cell surface CD163 expression using MAC2-158, which recognizes an epitope in SRCR domain-1, than when using GHI/61, which recognizes SRCR domain-7 located in proximity to the cell membrane (18). This led us to hypothesize that the difference in reactivity may be due to steric hindrance when binding close to the cell membrane. We therefore selected four antibodies (MAC2-158, R-20, GHI/61, and RM3/1) on the basis of their diverse epitope-specificity (domain-1, -4, -7, and -9 respectively) (42), and investigated the performance in flow cytometry assessing peripheral blood monocytic cell surface CD163 expression.

Indeed, we observed a SRCR domain dependent binding pattern which may explain the immense inconsistency in monocytic CD163 expression suggested by numerous investigators (3;5-7;34-41). Interestingly, a very small fraction of monocytes was stained when using RM3/1, which is known to recognize an epitope located in recognizes SRCR domain- 9. Conversely, using the MAC2-158 clone, which recognizes SRCR domain-1, we were consistently able to identify a substantial proportion of circulating CD163 expressing monocytes (>80%). This observation was further substantiated by the receptor density investigated by flow cytometry, which showed a similar pattern. It is therefore tempting to speculate that the lower affinity of antibodies, which are raised against SRCR domain, located in proximity to the cell membrane, may partly reflect a steric hindrance which we have previously proposed (18).

Nonetheless, there may be other explanations for the varying reactivity using different clones of CD163 mAbs. This phenomenon may simply suggest a difference in the degree of antibody labeling with fluorescent dye-protein conjugates. In order to maintain an optimal degree of conjugation to give maximum fluorescence intensity, all direct immunofluorescence staining was performed using commercial available primary conjugated anti-CD163. Nevertheless, the fluorescence intensity of a conjugated protein does not vary linearly with the degree of conjugation, but reach a maximum at a relatively low degree of conjugation. The lowest degree of conjugation which gives maximum fluorescence is therefore to be preferred as it will cause least changes in the physical and biological properties of the antibody (43-46). However, when indirect immunofluorescence staining was assessed using unconjugated primary CD163 antibody clones and same fluorescent secondary antibody conjugate, we observed a similar pattern of CD163 cell surface immunostaining by immunofluorescence microscopy and flow cytometry. Another plausible explanation of the decrease in monocytic CD163 expression when using antibodies raised against SRCR domain, located in proximity to the cell membrane, may be fluorescence quenching. In conventional organic fluorochromes, such as FITC and PE, intermolecular interactions and energy transfer between molecules can result in self-quenching of the fluorescence intensity causing loss of absorbed excitation energy and a reduction in fluorescence intensity (47).

In a recent study the authors show, using two different clones of anti-CD163, a significantly higher monocytic CD163 cellular expression in blood samples anti-coagulated with EDTA than when anti-coagulated with heparin (38). To some extent, we observed similar pattern of determined monocytic CD163 expression in EDTA and heparin stabilized blood samples. The difference in proportion of CD14 positive monocytes stained positive for CD163 was most profound when using GHI/61. However, when using MAC2-158 the fraction of CD14 positive monocytes stained positive for CD163 was unaffected of anticoagulant used. CD163 is known to be cleaved from the cell membrane by matrix metallo-proteinases resulting in release of a soluble form of CD163 (20;48). Nonetheless, we excluded that the diversity in CD163 expression using different anticoagulants was due to shedding of CD163 by demonstrating that the levels of soluble CD163 was unaffected in the samples investigated. As heparin stabilized blood samples resembles physiological calcium levels, whereas free calcium is abrogated from EDTA stabilized blood samples, we hypothesized that the variation in CD163 expression may be due to loss of a calcium dependent binding affinity. This was clearly verified in SPR-analysis showing almost complete loss of ligand binding activity in the presence of calcium when using GHI/61. The reverse pattern was observed using RM3/1, which exhibited binding activity when calcium was present in the media. R-20 was slightly affected by calcium, whereas MAC2-158 showed binding activity regardless extracellular levels of calcium which was in accordance to observations when using flow cytometry.

Calcium dependent ligand binding has also been observed for CD163 binding to its only known physiological relevant ligand; Hp-Hb complexes bind to SRCR domain-3 (42). The binding of the SRCR domain containing protein agglutinin to IgA is mediated in a calcium dependent manner by type B SRCR domains (49) and the structure of a type A SRCR domain from MARCO mediating calcium dependent ligand binding, has been determined (50). Three residues of the SRCR of MARCO were found to be of key importance for calcium ligation, Asp447, Asp 448 and Glu511. The calcium binding site of the domain was not interacting with the ligand, but calcium binding was suggested to have an effect of promoting the correct structural conformation to enable ligand binding (50). A sequence alignment of the SRCR domain of MARCO with the SRCR domains of CD163 (not shown) showed that SRCR domain-2, -3, -4, -7, and -9 of CD163 had a conservation of these three residues, whereas one or more of the three residues had a non-conservative substitution in SRCR domain-1, -5, -6, and -8. Though other residues in these four domains could substitute as ligands for divalent cations, the sequence observation is in concord with our observation of only a minor effect of calcium on the binding of a SRCR domain-1 binding mAb (MAC2-158) and a larger effect of calcium on mAb binding to domain-4, -7, and -9. Although the function and possible ligand of specific SRCR domains of CD163 other than SRCR domain-3 is not known, it is tempting to speculate on the role of calcium in these interactions, and that it may not be involved in ligand binding of SRCR domain-1, -5, -6, and -8.

The CD163-mediated internalization of Hb-Hp complexes by macrophages have been proposed to be a possible a mechanism which could be exploited to target-specific drug delivery in CD163 expressing neoplastic cells of monocyte/macrophage lineage (51). Most studies addressing the cellular uptake have either been performed on stably CD163-transfected Flp-In CHO cells (2;4;42) or using fluorescence-conjugated Hb-Hp complexes (4;51). However, CD163-transfected cells do not resemble cells of monocyte/macrophage lineage and future drug-labeling may be more feasible using monoclonal antibodies rather than using Hb-Hp complexes. Therefore, we set out to investigate and evaluate the cellular uptake of different clones of monoclonal CD163 antibodies in monocyte-derived macrophages, which represent functional and immunocompetent CD163 expressing cells.

Surprisingly, the immunofluorescence microscopy analysis revealed that the cellular uptake could be achieved using clones of CD163 mAbs regardless their SRCR domain recognition. However, in accordance with the flow cytometric analysis the proportion of stained cells, degree of fluorescence intensity, and cellular uptake appeared substantially superior using MAC2-158. This was confirmed by CD163 binding and cellular uptake experiments using CD163-transfected Flp-In CHO cells. A similar pattern of surface staining and cellular uptake was observed in CD163-transfected Flp-In CHO cells by confocal laser scanning microscopic analysis suggesting that the epitope recognized by MAC2-158 is more accessible or may likely emerge the correct conformation for antibody binding. This observation was further substantiated by investigating binding and endocytosis of different anti-CD163 clones labeled with $^{125}$I in CD163-transfected Flp-In CHO cells. The time course of cell-associated radioactivity reached a plateau after one hour of incubation using R-20 and GHI/61 which is equivalent to the time course of cell-associated radioactivity when assessing $^{125}$I-labelled Hp-Hb complexes (2). However, when incubating with $^{125}$I-labelled MAC2-158 the time course of cell-associated radioactivity did not reach a plateau within the two hour incubation and exhibited a superior percentage-wise uptake as compared with other clones.

Our findings may be significant since CD163 has been suggested as possible target for drug delivery in acute myeloid leukemia (51). Using flow cytometry, investigators have shown that approximately 5% (range: 0% to 38.5%) of leukemic blast cells of AML type M4 and 23% (range: 1% to 77%) of AML type M5 expressed CD163 (51;52). However, similar to the contradictory data on the cellular distribution of CD163 on monocytes and macrophages, discrepancy in CD163 expression on myelomonocytic neoplastic cells have been report reported. Using a different method and monoclonal antibody clone a recent study demonstrated CD163 immuno-reactivity in 49% of AML cases with monocytic differentiation (53). Taken the presented data to account it is tempting to speculate that a higher proportion of leukemic blasts in both myelomonocytic (M4) and monocytic (M5) subtypes of AML express CD163, suggesting the receptor as a potential candidate for targeted specific drug delivery in acute myeloid leukemia.

In conclusion, we demonstrate that using the MAC2-158 clone, which recognizes SRCR domain-1, we are consistently able to identify a substantial proportion of circulating CD163 expressing monocytes. In addition, we show for the first time the ability of CD163-antibody-mediated cellular uptake in monocyte-derived macrophages which was most efficient when using MAC2-158. Our findings emphasize the clinical applicability of CD163 as a diagnostic tool and therapeutic candidate in diseases affecting the monocyte/macrophage system.

Surprisingly we saw that the cellular uptake and binding of Mac2-158 and Mac2-48 to CD163-expressing cells is considerably higher than for the other tested antibodies (FIG. 5). This is not related to an increased affinity to CD163 of those antibodies compared to the other antibodies as such, since Biacore studies show that though Mac2-158 binds with high affinity to CD163, a number of the other mAbs bind with virtually similar strength, and for instance 5C6-Fat binds even more strongly.

Neither is the increased uptake solely due to binding to domain 1 taking place, since for instance 5C6-Fat is also binding to domain 1, and stronger as judged by Biacore measurements (FIG. 4), yet binding to cell surfaces is weaker than that observed for Mac2-158 (FIGS. 5 and 6). In general, all the mAbs bind with virtually similar strength to CD163 displayed on cell surfaces (FIG. 5), irrespective of which SRCR domain of CD163 binding is taking place to, except for Mac2-48 and Mac2-158 which bind considerably more strongly, and GHI/61 which does not bind in calcium-containing medium. This strongly demonstrates that Mac2-158 binds to an epitope of specific interest, and that Mac2-48 is also binds strongly to cells, and, as can be seen from FIG. 8, binds in competition with Mac2-158.

REFERENCES FOR EXAMPLE 1

1. Law, S. K., Micklem, K. J., Shaw, J. M., Zhang, X. P., Dong, Y., Willis, A. C. and Mason, D. Y. (1993) A new macrophage differentiation antigen which is a member of the scavenger receptor superfamily. Eur. J. Immunol., 23, 2320-2325.
2. Kristiansen, M., Graversen, J. H., Jacobsen, C., Sonne, O., Hoffman, H. J., Law, S. K. and Moestrup, S. K. (2001) Identification of the haemoglobin scavenger receptor. Nature, 409, 198-201.
3. Hogger, P., Dreier, J., Droste, A., Buck, F. and Sorg, C. (1998) Identification of the integral membrane protein RM3/1 on human monocytes as a glucocorticoid-inducible member of the scavenger receptor cysteine-rich family (CD163). J. Immunol., 161, 1883-1890.
4. Nielsen, M. J., Madsen, M., Moller, H. J. and Moestrup, S. K. (2006) The macrophage scavenger receptor CD163: endocytic properties of cytoplasmic tail variants. J. Leukoc. Biol., 79, 837-845.
5. Backe, E., Schwarting, R., Gerdes, J., Ernst, M. and Stein, H. (1991) Ber-MAC3: new monoclonal antibody that defines human monocyte/macrophage differentiation antigen. J. Clin. Pathol., 44, 936-945.
6. Pulford, K., Micklem, K., McCarthy, S., Cordell, J., Jones, M. and Mason, D. Y. (1992) A monocyte/macrophage antigen recognized by the four antibodies GHI/61, Ber-MAC3, Ki-M8 and SM4. Immunology, 75, 588-595.
7. Van den Heuvel, M. M., Tensen, C. P., van As, J. H., Van den Berg, T. K., Fluitsma, D. M., Dijkstra, C. D., Dopp, E. A., Droste, A., Van Gaalen, F. A., Sorg, C. et al., (1999) Regulation of CD 163 on human macrophages: cross-linking of CD163 induces signaling and activation. J. Leukoc. Biol., 66, 858-866.
8. Zwadlo, G., Voegeli, R., Osthoff, K. S, and Sorg, C. (1987) A monoclonal antibody to a novel differentiation antigen on human macrophages associated with the down-regulatory phase of the inflammatory process. Exp. Cell Biol., 55, 295-304.
9. Lau, S. K., Chu, P. G. and Weiss, L. M. (2004) CD163: a specific marker of macrophages in paraffin-embedded tissue samples. Am. J. Clin. Pathol., 122, 794-801.
10. Fabriek, B. O., Van Haastert, E. S., Galea, I., Polfliet, M. M., Dopp, E. D., Van den Heuvel, M. M., Van den Berg, T. K., De Groot, C. J., Van, D., V and Dijkstra, C. D. (2005) CD163-positive perivascular macrophages in the human CNS express molecules for antigen recognition and presentation. Glia, 51, 297-305.
11. Shabo, I., Stal, O., Olsson, H., Dore, S. and Svanvik, J. (2008) Breast cancer expression of CD163, a macrophage scavenger receptor, is related to early distant recurrence and reduced patient survival. Int. J. Cancer, 123, 780-786.
12. Nagorsen, D., Voigt, S., Berg, E., Stein, H., Thiel, E. and Loddenkemper, C. (2007) Tumor-infiltrating macrophages and dendritic cells in human colorectal cancer: relation to local regulatory T cells, systemic T-cell response against tumor-associated antigens and survival. J. Transl. Med., 5, 62.
13. Lee, C. H., Espinosa, I., Vrijaldenhoven, S., Subramanian, S., Montgomery, K. D., Zhu, S., Marinelli, R. J., Peterse, J. L., Poulin, N., Nielsen, T. O. et al. (2008) Prognostic significance of macrophage infiltration in leiomyosarcomas. Clin. Cancer Res., 14, 1423-1430.
14. Ohri, C. M., Shikotra, A., Green, R. H., Waller, D. A. and Bradding, P. (2009) Macrophages within NSCLC tumour islets are predominantly of a cytotoxic M1 phenotype associated with extended survival. Eur. Respir. J., 33, 118-126.
15. De, P. M., Venneri, M. A., Galli, R., Sergi, S. L., Politi, L. S., Sampaolesi, M. and Naldini, L. (2005) Tie2 identifies a hematopoietic lineage of proangiogenic monocytes required for tumor vessel formation and a mesenchymal population of pericyte progenitors. Cancer Cell, 8, 211-226.

16. Venneri, M. A., De, P. M., Ponzoni, M., Pucci, F., Scielzo, C., Zonari, E., Mazzieri, R., Doglioni, C. and Naldini, L. (2007) Identification of proangiogenic TIE2-expressing monocytes (TEMs) in human peripheral blood and cancer. Blood, 109, 5276-5285.

17. Matthews, K. E., Mueller, S. G., Woods, C. and Bell, D. N. (2006) Expression of the hemoglobin-haptoglobin receptor CD163 on hematopoietic progenitors. Stem Cells Dev., 15, 40-48.

18. Maniecki, M. B., Moller, H. J., Moestrup, S. K. and Moller, B. K. (2006) CD163 positive subsets of blood dendritic cells: the scavenging macrophage receptors CD163 and CD91 are coexpressed on human dendritic cells and monocytes. Immunobiology, 211, 407-417.

19. Zaba, L. C., Krueger, J. G. and Lowes, M. A. (2009) Resident and "inflammatory" dendritic cells in human skin. J. Invest Dermatol., 129, 302-308.

20. Droste, A., Sorg, C. and Hogger, P. (1999) Shedding of CD163, a novel regulatory mechanism for a member of the scavenger receptor cysteine-rich family. Biochem. Biophys. Res. Commun., 256, 110-113.

21. Peterslund, N. A., Graversen, J. H. and Moestrup, S. K. (2002) Identification of the hemoglobin scavenger receptor/CD163 as a natural soluble protein in plasma. Blood, 99, 378-380.

22, Weaver, L. K., Hintz-Goldstein, K. A., Pioli, P. A., Wardwell, K., Qureshi, N., Vogel, S. N. and Guyre, P. M. (2006) Pivotal advance: activation of cell surface Toll-like receptors causes shedding of the hemoglobin scavenger receptor CD163. J. Leukoc. Biol., 80, 26-35.

23. Gaini, S., Koldkjaer, O. G., Pedersen, S. S., Pedersen, C., Moestrup, S. K. and Moller, H. J. (2006) Soluble haemoglobin scavenger receptor (sCD163) in patients with suspected community-acquired infections. APMIS, 114, 103-111.

24. Knudsen, T. B., Gustafson, P., Kronborg, G., Kristiansen, T. B., Moestrup, S. K., Nielsen, J. O., Gomes, V., Aaby, P., Lisse, I., Moller, H. J. et al. (2005) Predictive value of soluble haemoglobin scavenger receptor CD163 serum levels for survival in verified tuberculosis patients. Clin. Microbiol. Infect., 11, 730-735.

25. Schaer, D. J., Schleiffenbaum, B., Kurrer, M., Imhof, A., Bachli, E., Fehr, J., Moller, H. J., Moestrup, S. K. and Schaffner, A. (2005) Soluble hemoglobin-haptoglobin scavenger receptor CD163 as a lineage-specific marker in the reactive hemophagocytic syndrome. Eur. J. Haematol., 74, 6-10.

26. Baeten, D., Moller, H. J., Delanghe, J., Veys, E. M., Moestrup, S. K. and De, K. F. (2004) Association of CD163+ macrophages and local production of soluble CD163 with decreased lymphocyte activation in spondylarthropathy synovitis. Arthritis Rheum., 50, 1611-1623.

27. Matsushita, N., Kashiwagi, M., Wait, R., Nagayoshi, R., Nakamura, M., Matsuda, T., Hogger, P., Guyre, P. M., Nagase, H. and Matsuyama, T. (2002) Elevated levels of soluble CD163 in sera and fluids from rheumatoid arthritis patients and inhibition of the shedding of CD163 by TIMP-3. Clin. Exp. Immunol., 130, 156-161.

28. Moller, H. J., Aerts, H., Gronbaek, H., Peterslund, N. A., Hyltoft, P. P., Hornung, N., Rejnmark, L., Jabbarpour, E. and Moestrup, S. K. (2002) Soluble CD163: a marker molecule for monocyte/macrophage activity in disease. Scand. J. Clin. Lab Invest Suppl, 237, 29-33.

29. Moller, H. J., Moestrup, S. K., Weis, N., Wejse, C., Nielsen, H., Pedersen, S. S., Attermann, J., Nexo, E. and Kronborg, G. (2006) Macrophage serum markers in pneumococcal bacteremia: Prediction of survival by soluble CD163. Crit. Care Med., 34, 2561-2566.

30. Knudsen, T. B., Larsen, K., Kristiansen, T. B., Moller, H. J., Tvede, M., Eugen-Olsen, J. and Kronborg, G. (2007) Diagnostic value of soluble CD163 serum levels in patients suspected of meningitis: comparison with CRP and procalcitonin. Scand. J. Infect. Dis., 39, 542-553.

31. Jensen, T. O., Schmidt, H., Moller, H. J., Hoyer, M., Maniecki, M. B. and Steiniche, T. (2009) Macrophage markers in serum and tumor have prognostic impact in AJCC stage I/II melanoma. J. Leukoc. Biol. In press.

32. Moller, H. J., Hald, K. and Moestrup, S. K. (2002) Characterization of an enzyme-linked immunosorbent assay for soluble CD163. Scand. J. Clin. Lab Invest, 62, 293-299.

33. Møller, H., Nielsen, M., Maniecki, M., Madsen, M. and Moestrup, S. (2009) Soluble macrophage-derived CD163: A homogenous ectodomain protein with a dissociable haptoglobin-hemoglobin binding compatible with the CD163-mediated ligand uptake. Immunobiology. In press.

34. Hogger, P., Erpenstein, U., Rohdewald, P. and Sorg, C. (1998) Biochemical characterization of a glucocorticoid-induced membrane protein (RM3/1) in human monocytes and its application as model system for ranking glucocorticoid potency. Pharm. Res., 15, 296-302.

35. Philippidis, P., Mason, J. C., Evans, B. J., Nadra, I., Taylor, K. M., Haskard, D. O. and Landis, R. C. (2004) Hemoglobin scavenger receptor CD163 mediates interleukin-10 release and heme oxygenase-1 synthesis: anti-inflammatory monocyte-macrophage responses in vitro, in resolving skin blisters in vivo, and after cardiopulmonary bypass surgery. Circ. Res., 94, 119-126.

36. Sulahian, T. H., Hogger, P., Wahner, A. E., Wardwell, K., Goulding, N. J., Sorg, C., Droste, A., Stehling, M., Wallace, P. K., Morganelli, P. M. et al. (2000) Human monocytes express CD163, which is upregulated by IL-10 and identical to p155. Cytokine, 12, 1312-1321.

37. Fabriek, B. O., Dijkstra, C. D. and Van den Berg, T. K. (2005) The macrophage scavenger receptor CD163. Immunobiology, 210, 153-160.

38. Moniuszko, M., Kowal, K., Rusak, M., Pietruczuk, M., Dabrowska, M. and Bodzenta-Lukaszyk, A. (2006) Monocyte CD163 and CD36 expression in human whole blood and isolated mononuclear cell samples: influence of different anticoagulants. Clin. Vaccine Immunol., 13, 704-707.

39. Kim, W. K., Alvarez, X., Fisher, J., Bronfin, B., Westmoreland, S., McLaurin, J. and Williams, K. (2006) CD163 identifies perivascular macrophages in normal and viral encephalitic brains and potential precursors to perivascular macrophages in blood. Am. J. Pathol., 168, 822-834.

40. Davis, B. H. and Zarev, P. V. (2005) Human monocyte CD163 expression inversely correlates with soluble CD163 plasma levels. Cytometry B Clin. Cytom., 63, 16-22.

41. Buechler, C., Ritter, M., Orso, E., Langmann, T., Klucken, J. and Schmitz, G. (2000) Regulation of scavenger receptor CD163 expression in human monocytes and macrophages by pro- and antiinflammatory stimuli. J. Leukoc. Biol., 67, 97-103.

42. Madsen, M., Moller, H. J., Nielsen, M. J., Jacobsen, C., Graversen, J. H., van den Berg, T. and Moestrup, S. K. (2004) Molecular characterization of the haptoglobin.hemoglobin receptor CD163. Ligand binding properties of the scavenger receptor cysteine-rich domain region. J. Biol. Chem., 279, 51561-51567.
43. Russell, J., Colpitts, T., Holets-McCormack, S., Spring, T. and Stroupe, S. (2004) Defined protein conjugates as signaling agents in immunoassays. Clin. Chem., 50, 1921-1929.
44. Holmes, K. L., Lantz, L. M. and Russ, W. (2001) Conjugation of fluorochromes to monoclonal antibodies. Curr. Protoc. Cytom., Chapter 4, Unit.
45. Haugland, R. P. (2001) Antibody conjugates for cell biology. Curr. Protoc. Cell Biol., Chapter 16, Unit.
46. Mao, S. Y. (1994) Conjugation of fluorochromes to antibodies. Methods Mol. Biol., 34, 43-47.
47. Chapple, M. R., Johnson, G. D. and Davidson, R. S. (1990) Fluorescence quenching; a practical problem in flow cytometry. J. Microsc., 159, 245-253.
48. Timmermann, M. and Hogger, P. (2005) Oxidative stress and 8-iso-prostaglandin F(2alpha) induce ectodomain shedding of CD163 and release of tumor necrosis factor-alpha from human monocytes. Free Radic. Biol. Med., 39, 98-107.
49. Ligtenberg, A. J., Bikker, F. J., De Blieck-Hogervorst, J. M., Veerman, E. C. and Nieuw Amerongen, A. V. (2004) Binding of salivary agglutinin to IgA. Biochem. J., 383, 159-164.
50. Ojala, J. R., Pikkarainen, T., Tuuttila, A., Sandalova, T. and Tryggvason, K. (2007) Crystal structure of the cysteine-rich domain of scavenger receptor MARCO reveals the presence of a basic and an acidic cluster that both contribute to ligand recognition. J. Biol. Chem., 282, 16654-16666.
51. Bachli, E. B., Schaer, D. J., Walter, R. B., Fehr, J. and Schoedon, G. (2006) Functional expression of the CD163 scavenger receptor on acute myeloid leukemia cells of monocytic lineage. J. Leukoc. Biol., 79, 312-318.
52. Walter, R. B., Bachli, E. B., Schaer, D. J., Ruegg, R. and Schoedon, G. (2003) Expression of the hemoglobin scavenger receptor (CD163/HbSR) as immunophenotypic marker of monocytic lineage in acute myeloid leukemia. Blood, 101, 3755-3756.
53. Garcia, C., Gardner, D. and Reichard, K. K. (2008) CD163: A Specific Immunohistochemical Marker for Acute Myeloid Leukemia With Monocytic Differentiation. Appl. Immunohistochem. Mol. Morphol.

Example 2—CD163-Positive Subsets of Dendritic Cells

Materials and Methods
Materials and Methods are as Described in Example 1.
Quantitative Flow Cytometry
Freshly drawn peripheral whole blood samples (approx. $3 \times 10^6$ cells) were stained with isotype-matched control antibody (Mouse IgG$_1$ PE, k isotype control, MOPC-21, BD Pharmingen™, San Diego, Calif., USA) or a relevant antibody (anti-CD3 FITC, UCHT1, BD Biosciences, San Diego, Calif., USA; anti-CD11c FITC, KB90, DAKO A/S, Glostrup, Denmark; anti-CD14 FITC, RMO52, IOTests®, Beckman and Coulter, Marseille, France; anti-CD16 FITC, 3G8, BD Biosciences, San Diego, Calif., USA; anti-CD19 FITC, SJ25C1, BD Biosciences, San Diego, Calif., USA; anti-CD20 FITC, CAT 13.6E12, Diatec.com A/S, Oslo, Norway; anti-CD56 FITC, NCAM16.2, BD Biosciences, San Diego, Calif., USA; anti-CD91 FITC, A2MR-a2, BD Biosciences, San Diego, Calif.; anti-HLA-DR FITC, EDU-1, Diatec.com A/S, Oslo, Norway; anti-CD163 PE, MAC2-158, IQ Products, Groningen, The Netherlands; anti-CD163 PE, GHI/61, BD Biosciences, CA, USA; anti-ILT3/CD85k PE-Cy5, ZM3.8, IOTests®, Beckman and Coulter, Marseille, France; anti-HLA-DR PerCP, L234, BD Biosciences, San Diego, Calif.; anti-CD4 APC, EDU-2, Diatec.com A/S, Oslo, Norway; anti-CD14 APC, 18D11, Diatec.com A/S, Oslo, Norway) for 15 minutes at room temperature in the dark. Erythrocytes were lysed for 15 minutes with 4° C. cold solution of ammonium chloride for 15 minutes. The stained cells were then washed twice with D-PBS, pH 7.4 and resuspended in 400 µl FACSflow (Becton Dickinson, San Jose, Calif., USA. All samples were analyzed using a BD FACSCalibur™ Flow Cytometer (Becton Dickinson, San Jose, Calif., USA) and compensated for spectral overlap using FlowJo for Macintosh software version 6.3 (TreeStar, San Carlos, Calif.). At least 100,000 events were acquired to ensure an adequate number of cells for analysis. All staining were controlled using non-specific mAbs. In a 2-parameter correlated Dot Plot of forward scatter [FSC] versus side scatter [SSC], a gate was set around the mononuclear cells (MNC) clusters. The gated MNC were re-plotted using two different 4-color staining protocols and cell definition strategies defining dendritic cells as either CD14$^-$ILT3$^+$HLA-DR$^+$ or lineage[CD3,CD14,CD16,CD19,CD20,CD56]$^-$CD4$^+$FILA-DR$^+$. For CD163 density quantitation, flow cytometric estimation of antibodies bound/cell (ABCs) was performed using Quantibrite PE beads (Becton Dickinson, San Jose, Calif., USA) as recommended by the manufacturer. After the cells were stained, as detailed, a set of 4 precalibrated fluorescence labeled beads was used for standardization before the samples were acquired. The Quantibrite PE beads were run at the same instrument settings as the flow cytometric assay, and the linear regression obtained using the Quantibrite PE beads was used to convert the FL2 linear fluorescence staining of the cell population into the number of (CD163) PE molecules bound per cell.

Figure 9D:
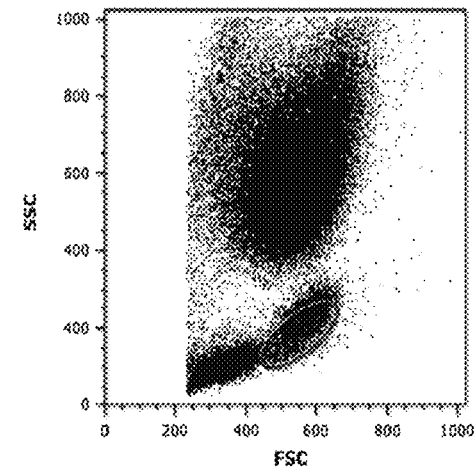

Results
CD163 Positive Subsets of Blood Dendritic Cells: the Scavenging Macrophage Receptors CD163 and CD91 are Co-Expressed on Human Dendritic Cells and Monocytes Using a simple staining strategy, defining dendritic cells as CD14-CD163+, we identified a cell population expressing CD163 but not the monocytic marker CD14. In a plot of forward scatter [FSC] versus CD163 PE, CD163 expressing cells were gated (FIG. 9A). The gated cells were then re-plotted in a plot of CD14 APC versus CD163 PE identifying a small fraction (<1%) of CD14-cells expressing CD163 (FIG. 9B). This novel cell population also highly expressed HLA-DR (FIG. 9C) and the backgating analysis revealed CD14-CD163+ cells as a relatively distinct cell population localized between lymphocytes and monocytes (FIG. 9D).

Defining dendritic cells as either CD14-ILT3+HLA-DRhigh (FIG. 10A-C) or lineage[CD3,CD14,CD16,CD19,CD20,CD56]-CD4+HLA-DR+ (not shown), flow cytometric analysis showed that 10.5% (95% CI: 8.0-12.5) of peripheral blood dendritic cells express CD163 (FIG. 10C). As shown in FIG. 10C, CD163 expressing peripheral blood dendritic cells can be subdivided into two populations; a subset expressing high levels of CD163 (CD163high, Ma 34.6 [95% CI: 30.5-40.7]) and a weaker staining subset (CD163low, MFI: 4.2 [95% CI: 3.7-5.1]). For comparison and consistent with paper I, virtually all CD14+ILT3+HLA-DR+ monocytes (88.0% [95% CI: 85.0-91.0%]) stained positive for CD163 (not shown). Backgating analysis demonstrated Lin-CD4+HLA-DR+CD163+ cells as a distinct cell population belonging to the expected localization of dendritic cells, between lymphocytes and monocytes (FIG.

10D). An isotype-matched non-specific IgG1 served as a negative staining control (MFI: 1.23 [95% CI: 1.14-1.46]) (FIG. 10E).

To exclude unspecific cross-reactivity, the dendritic cell CD163 expression analysis was repeated utilizing the MAC-158 clone of anti-CD163. In accordance to paper I, the MAC2-158 clone binding SRCR domain 1, recognized a significantly higher fraction of peripheral blood dendritic cells (32.3% [95% CI: 19.6-45.1%]) (FIG. 11D) as compared with the GHI/61 clone (10.5% [95% CI: 8.0-12.5%]) (FIG. 11B) binding SRCR domain 7. The MFI, reflecting the amount of CD163 receptors per cell, was also significantly higher for the MAC2-158 antibody clone (107.5 [95% CI: 74.7-140.3]) (FIG. 11C) compared with GHI/61 (22.3 [95% CI: 19.2-25.4]) (FIG. 11A) suggesting that MAC2-158 was able to identify a higher quantity of CD163 receptors per cell.

Figures 12A, 12B, 12C, 12D, 12E:
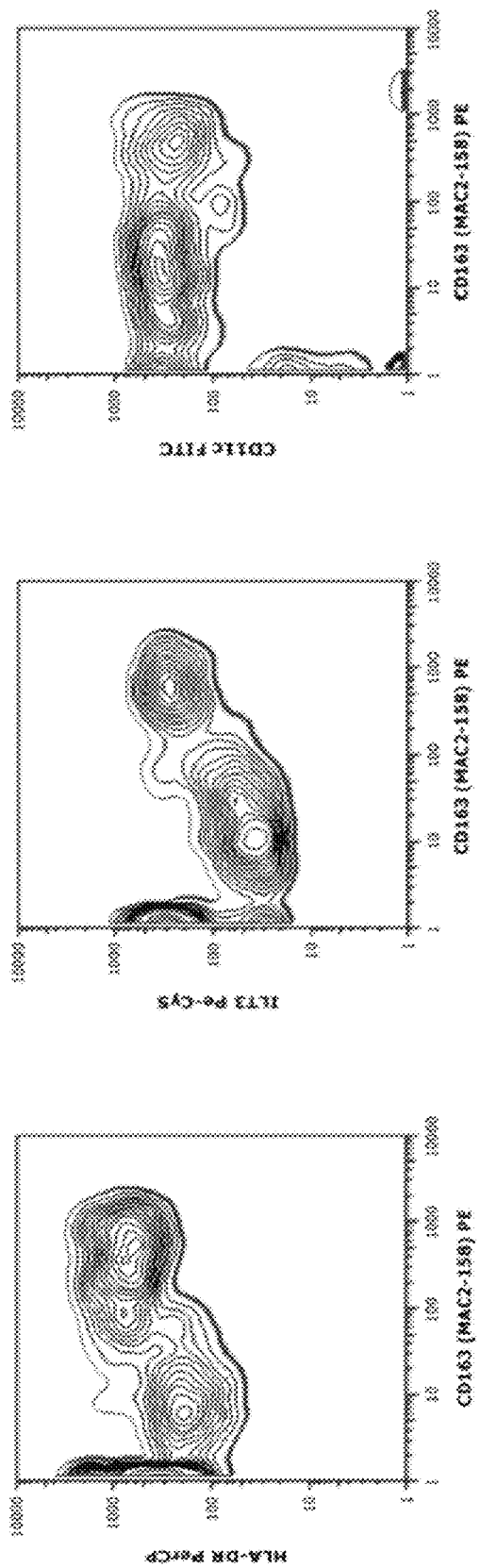

To assess the possible function of the two novel CD163 expressing subsets of peripheral blood cells with dendritic cell characteristics, further phenotyping was performed. The surface antigen assessment revealed that the subset expressing low levels of CD163 also expressed low levels of HLA-DR (FIG. 12A) and ILT3 (FIG. 12B), whereas the subset expressing high levels of CD163 highly expressed HLA-DR (FIG. 12A) and ILT3 (FIG. 12B). Both subsets expressed CD11c indicating relationship to the myeloid lineage (DC1) of dendritic cells (FIG. 12C). The CD163low subset was CD16+, whereas the CD163high subset was CD16− (FIG. 12D). However, both subsets were CD91+ (FIG. 12E), thereby constituting a subfraction of the recently described CD91+CD11c+ dendritic cell subset.

Since evidence has accumulated showing that dendritic cells may be an important contributor to HIV-1 transmission and pathogenesis, we intended to investigate peripheral blood dendritic cell CD163 expression in HIV-1 patients. Generally, the fraction of CD163 expressing dendritic was significantly higher in HIV-1 patients (19.3% [95% CI: 14.7-26.3%]) compared with healthy patients (10.5% [95% CI: 8.0-12.5]) p<0.001 (FIG. 13A).

All investigated HIV-1 infected patients expressed both subsets of CD163+ dendritic cells (CD163low and CD163high), whereas approximately half of the healthy controls only expressed either subset CD163low or CD163high (FIGS. 13B and 14A-C).

Interestingly, the mean amount of CD163 receptors per cell estimated on the CD163high subset was significantly elevated in the HIV-1 patients compared with healthy controls (p<0.001) (FIG. 13C).

Discussion

Since the discovery of CD163 as a novel macrophage restricted marker, the receptor as been extensively investigated in pathophysiological conditions affecting the monocyte/macrophage system.

CD163 may possess potential as a diagnostic marker of monocyte/macrophage activity in inflammatory conditions and as a therapeutic candidate. CD163 expression is tightly regulated by pro- and anti-inflammatory stimuli suggesting an immunoregulatory function of CD163, and CD163 cytoplasmic splice variants respond differently upon pro-inflammatory stimuli. Studies have also demonstrated significant changes in cellular and soluble CD163 conditions, such as inflammatory, malignant, and infectious diseases suggesting affection of the monocyte/macrophage system strongly implicating CD163. We have also shown that tumor-infiltrating macrophages highly express CD163 and that the density of CD163 expressing macrophages in tumor is associated with poor patient survival. In addition, a recent study has shown that TIE2+ macrophages, which are directly involved in angiogenesis, express high levels of CD163. CD163 has also been shown to be expressed on M4/M5 leukemic blast cells and on tumor cells in breast cancer.

The cellular distribution of CD163 on both immune and malignant cells under physiological conditions remain unclear. The varying CD163 surface expression and great discrepancy reported by several investigators has compromised the applicability of CD163 as a diagnostic marker of monocyte/macrophage activity in inflammatory conditions and as a therapeutic candidate.

In this (and the previous) Example, we report the development of a reliable multi-colour flow cytometry-based assay which consistently identifies a substantial proportion of circulating CD163 expressing monocytes (>80%). The CD163 expression has been a topic of debate in the literature for almost two decades. Using different anticoagulants, antibody clones, and general test conditions the level of monocytic CD163 expression has been reported to vary from a few to 99% (Venneri et al., 2007; Backe et al., 1991; Hogger et al. 1998; Philippidis et al. 2004; Sulahian et al., 2000; Van den Heuvel et al., 1999; Fabriek at al. 2005; Moniuszko et al. 2006; Kim et al. 2006; Davis et al. 2005; Buechler at al. 2000). However, we demonstrate a SRCR domain dependent binding pattern when utilizing various monoclonal antibody clones raised against different SRCR domains which may explain the immense inconsistency in monocytic CD163 expression suggested by numerous investigators.

Using the MAC2-158 antibody clone, which recognizes SRCR domain 1, we showed that a significantly higher proportion of circulating monocytes expressed CD163 as compared with R-20 (SRCR domain 4), GHI/61 (SRCR domain 7), and RM3/1 (SRCR domain 9). This observation was further verified by the mean fluorescence intensity, which reflects the amount of CD163 receptors per cell. This phenomenon may simply suggest a significantly difference in antibody binding affinity; however, it seems more likely that this SRCR domain dependent binding pattern probably is partly due to steric hindrance for binding of antibodies, which are raised against SRCR domain, located in proximity to the cell membrane, whereas MAC2-158 recognizes a possible exposed SRCR domain 1.

In a recent study, we have shown, using two different clones of anti-CD163, a significantly higher monocytic CD163 expression in blood samples anti-coagulated with EDTA than when anti-coagulated with heparin (Fabriek et al. 2005). To some extent, we observed similar pattern of CD163 expression in EDTA and heparin stabilized blood samples. The difference in proportion of CD14 positive monocytes stained for CD163 was most profound when using GHI/61. However, when using MAC2-158 the fraction of CD14 positive monocytes stained for CD163 was unaffected regardless anticoagulant used. We excluded that this diversity in CD163 expression using different anticoagulants was due to shedding of CD163, since the levels of soluble CD163 was unaffected in the samples investigated. As heparin stabilized blood samples resembles physiological calcium levels, whereas free calcium is abrogated from EDTA stabilized blood samples we hypothesize that the observed phenomenon may be due to the mechanism underlying the anticoagulant effect of EDTA, which is a calcium chelator, whereas heparin action is independent of calcium. We were not able to demonstrate same calcium dependent binding pattern using other monocyte/macrophage markers, such as CD36, CD91, and CD206. However, previously it has been suggested that some antibodies raised against calcium-binding proteins preferentially recognize specific calcium-induced protein conformational states (206), and that the immunoreactivity of these antibodies depends on the calcium-binding status (Gao et al., 1997).

Some studies have shown that a high density of tumor-infiltrating macrophages is associated with poor prognosis in breast, bladder, and superficial esophageal cancers; however, in others in cancers such as gastrointestinal malignancies it appears that their infiltration correlates with a good prognosis. Most of these studies utilize CD68 as macrophage marker. Unfortunately, CD68 is a general marker which does not discriminate between different subpopulations, either tumor-suppressing or tumor-promoting macrophage populations, and the newly identified Tie2-expressing macrophages. As it is now well established that a variety of macrophage subpopulations exits within the tumor microenvironment of which some exhibit tumor-suppressing and others tumor-promoting capacity the usefulness of a general marker such as CD68 is seriously challenged. Studies suggesting that the correlation of macrophage infiltration with good prognosis may be controversial; thus, the common opinion is that macrophages are attracted to tumor sites and polarized by tumor cells to favor tumor growth and progression. The utility of an unsuitable marker for macrophages with tumor-promoting capacity may explain the observed discrepancy outcome of high density of tumor-infiltrating macrophages.

Extensive immunohistochemical evaluation of CD163 expression has recognized the receptor as a novel marker of cells of monocyte/macrophage lineage in normal and neoplastic conditions using paraffin-embedded tissue samples (Shabo et al., 2008). However, when assessing CD163 immunoreactivity in hematopoietic disorders a study demonstrated that only 1 of 46 cases of acute monoblastic leukemia (AML-M5A) examined was CD163 positive. In addition, the investigators were not able to demonstrate any CD163 immunoreactivity in acute myelomonocytic leukemia (AML-M4) (Shabo et al., 2008). However, using flow cytometry later study showed that approximately 20% of leukemic blast cells of AML types M4 and M5 displays constitutive expression of CD163 (Lau et al., 2004). A recent study demonstrated CD163 immunoreactivity in 49% of AML cases with monocytic differentiation (18). However, these studies are hardly comparable since they utilize different methods and CD163 antibodies recognizing dissimilar SRCR domains.

Based on our observation of SRCR domain dependent binding pattern using different antibody clones in flow cytometry we set out to evaluate immunohistochemical CD163 expression in paraffin-embedded tissue samples.

Optimal immunoreactivity depends on epitope preservation. The composition, pH, type of heating, and amount of retrieval solution have a significant influence on the degree of epitope retrieval and preservation. An overwhelming body of evidence has demonstrated not all epitopes are equally unmasked during the process of epitope retrieval. More importantly from a clinical point of view, this suggests that the CD163 expression may be underestimated on both cells of monocyte/macrophage lineage in normal and neoplastic conditions, especially when performing immunohistochemistry.

The CD163-mediated internalization of Hb-Hp complexes by macrophages may be a possible a mechanism which could be exploited to target-specific drug delivery in CD163 expressing neoplastic cells of monocyte/macrophage lineage. Most studies addressing the cellular uptake have either been performed on stably CD163-transfected Flp-In CHO cells (Bowen et al. 1997) or using fluorescence-conjugated Hb-Hp complexes (Lau et al., 2004). However, CD163-transfected CHO cells do not resemble cells of monocyte/macrophage lineage and future drug-labelling may be more feasible using monoclonal rather than using Hb-Hp complexes. Since CD163 only binds Hb and Hp in complex this suggest that a neo-epitope is presented and therefore it seems reasonable that only antibodies raised against SRCR domain 3, where Hb-Hp complexes are bound (Chakraborty et al., 2004), will be able to facilitate a CD163-mediated endocytosis. Therefore, we initially set out to investigate and evaluate the applicability of CD163 for future targeted therapy, assessing binding and cellular uptake of different clones of monoclonal CD163 antibodies in CD163-transfected FIp-In chinese hamster ovary.

Interestingly, the confocal laser scanning microscopic analysis revealed that the cellular uptake could be achieved using clones of monoclonal CD163 antibodies regardless their SRCR domain recognition. In accordance with the flow cytometric analysis the proportion of stained cells, degree of fluorescence intensity, and cellular uptake appeared substantially superior using MAC2-158. As cells of monocyte/macrophage lineage represent functional and immunocompetent CD163 expressing cells, we then repeated these CD163 binding and cellular uptake experiments utilizing monocyte-derived macrophages. A similar pattern of surface staining and cellular uptake was observed in monocyte-derived macrophages signifying that MAC2-158 may potentially be the CD163 clone giving the most potent response if used for targeted specific drug delivery.

CD163 has been considered to be expressed exclusively on the surface of monocytes and tissue macrophages (Radzun H J. Blood. 1987; Backé E. J Clin Pathol. 1991; Pulford K. Immunology. 1992). CD163 and CD91 are highly expressed during the differentiation of monocytes into the anti-inflammatory macrophage phenotype. CD91 has been shown to be expressed in monocyte-derived dendritic cells, where the receptor serves important functions in T-cell stimulation (Hart, J R J. Immunol. 2004). In addition, evidence has suggested that CD163 may be expressed by a yet unknown tissue component as monocyte CD163 expression and sCD163 levels did not correlate with the monocyte absolute count (Davis. Cytometry Part B Clinical cytometry. 2005; Zarev P V. Lab Hematol. 2004). The dual roles of both CD91 and CD163 in iron metabolism (Hvidberg, V. Blood. 2005; Kristiansen, M. Nature. 2001) and immunomodulation led us to hypothesize that CD163 like CD91 was expressed in dendritic cells in addition to other cells of myelomonocytic origin.

Using a simple staining strategy, defining dendritic cells as CD14-CD163+, we identified a CD163 expressing cell population displaying dendritic cell phenotypic characteristics. This finding is in contrary to previous reports (Ritter. Pathobiology. 1999) and because of the well-known heterogeneity of dendritic cells we utilized two different staining strategies defining dendritic cells as either CD14-ILT3+ HLA-DRhigh or lineage[CD3,CD14,CD19,CD20,CD56]-CD4+HLA-DR+ in order to verify our observation of CD163 expressing dendritic cells.

Flow cytometric analysis revealed two distinct subsets of CD163 expressing dendritic cells, CD163low and CD163high, together constituting approximately 10.5% (95% CI: 8.0-12.5) of peripheral blood dendritic cells. However, in accordance with the previous Example, we demonstrated that using the MAC2-158 clone instead of GHI/61 we were able to identify a significantly higher proportion of CD163 expressing dendritic cells (32.3% [95% CI: 19.6-45.1%]) suggesting that up to almost half of circulating peripheral blood dendritic cells may express the hemoglobin scavenger receptor. An extensive phenotyping characterized both subsets of CD163 expressing dendritic cells as CD91+CD11c+, thus representing a subpopulation of the recently described CD91+CD11c+ myeloid lineage (DC1) of dendritic cells (Hart, J P. J. Immunol. 2004). Since CD91 and CD163 are co-expressed on monocytes, their co-expression on a subfraction of peripheral blood dendritic cells emphasizes the relation between the two receptors. Interestingly, further phenotyping revealed that the subset expressing high levels of CD163 also highly expressed HLA-DR and ILT3 suggesting that this subset possesses both inflammatory and tolerogenic abilities. On the contrary, the subset expressing low levels of CD163, was CD16+ and expressed low levels of HLA-DR and ILT3. This subset has been reported to constitute a significant proportion of myeloid DC (MacDonald K P. Blood. 2002), and micro array analysis has proposed that toll-like receptor 8 (TLR8) is predominant in these cells (Lindstedt M. J Immunol. 2005), suggesting a primary role in ssRNA responses. CD16 (FcγRIII) was originally identified as a NK-cell restricted receptor; however, it is also expressed by monocytes/macrophages, granulocytes, and dendritic cells (Schakel K. Eur J Immunol. 1998). CD16 expressing dendritic cells are shown to exhibit greater phagocytic and oxidative activity than CD16 negative dendritic cells, including produce significant amounts of cytokines (Almeida J. Clin Immunol. 2001), and have a marked capability to activate naïve T-cells (Schakel K. Eur J Immunol. 1998).

Myeloid dendritic cells are potent antigen-presenting cells and play critical roles in host defence. These cells with a partial activation phenotype are known to accumulate in lymphoid tissue during asymptomatic chronic HIV1 infection. Dendritic cells may be an important contributor to HIV-1 transmission and pathogenesis. This led us to investigate peripheral blood dendritic cell CD163 expression in HIV-1 patients.

Surprisingly, CD163 expressing dendritic was significantly higher in HIV-1 patients (19.3% [95% CI: 14.7-26.3%]) compared with healthy individuals (10.5% [95% CI: 8.0-12.5]) p<0.001. These findings are consistent with a recent study showing increased frequency of CD163+CD16+ monocytes in HIV-1-infected patients compared with seronegative individuals. CD163+CD16+ monocytes may therefore be a useful biomarker for HIV-1 infection and a possible target for therapeutic intervention.

In addition, another recent study demonstrate that inflammatory myeloid dermal dendritic cells, which are known to play a significant role in the pathogenesis of psoriasis and accumulate in chronically inflamed tissues, may arise from CD163 expressing peripheral blood dendritic cell precursors (CD11c+HLA-DR+CD16+). The authors speculate that these "pre-inflammatory dendritic cells" may migrate into the skin in response to a chemokine gradient or other stimulus. Hence, it is suggested that these inducing inflammatory dendritic cells may represent novel therapeutic target in psoriasis (Zaba. J Invest Dermatol. 2009).

Direct targeting of dendritic cells via specific surface receptors is a promising method to enhance immunogenicity of vaccines (Gamvrellis. Immunol. Cell Biol. 2004). The restricted expression of CD163 on dendritic cells and other antigen presenting cells emphasize the applicability of CD163 as a diagnostic tool and putative candidate for targeted specific drug delivery. Solid tumors contain not only malignant cells, but also a number of inflammatory, infiltrating cells including macrophages, which are residents in the microenvironment of both primary and secondary tumors (Albini A. Nat Rev Cancer. 2007).

In conclusion, this (and the previous) Example has led to the identification of the unknown tissue component expressing the hemoglobin scavenger receptor CD163 consisting of two distinct subsets of CD163 expressing dendritic cells, CD163low and CD163high, together constituting up to 50% of peripheral blood dendritic cells. One of the identified subsets of CD163 expressing dendritic cells (ILT3highCD163high) potentially possesses inflammatory and tolerogenic characteristics. We show that CD163 expressing dendritic was significantly elevated in HIV-1-infected patients compared with sero-negative individuals further supporting the suggested immunomodulatory role of CD163. Furthermore, we demonstrate that using the MAC2-158 clone, which recognises SRCR domain 1, we are consistently able to identify a substantial proportion of circulating CD163 expressing monocytes (>80%). In addition, we show the ability of CD163-antibody-mediated cellular uptake in both CD163-transfected CHO cells and monocyte-derived macrophages with was most pronounced when using MAC2-158.

Our data propose clinical applicability of CD163 as a diagnostic tool in pathophysiological conditions involving the monocyte/macrophage system which is emphasized by the restricted CD163 expression on monocytes, macrophages, dendritic cells. The CD163 expression on tumor-promoting macrophages and malignant cells depicts the hemoglobin scavenger receptor CD163 as a double-edged sword in malignant disease by suggesting usability of CD163 as a putative candidate for targeted specific drug delivery in hematological malignancies and solid tumors, as well as other diseases involving the monocyte/macrophage system. Our data also implies that the expected adverse effect profile using CD163 as target is potential clinically insignificant compared with comparable treatments currently available.

REFERENCES FOR EXAMPLE 2

1. Albini A, Sporn M B. The tumour microenvironment as a target for chemoprevention. Nat Rev Cancer 2007 February; 7(2):139-47.
2. Almeida J, Bueno C, Alguero M C, Sanchez M L, de S M, Escribano L, et al. Comparative analysis of the morphological, cytochemical, immunophenotypical, and functional characteristics of normal human peripheral blood lineage(−)/CD16(+)/HLA-DR(+)/CD14(−/lo) cells, CD14(+) monocytes, and CD16(−) dendritic cells. Clin Immunol 2001 September; 100(3):325-38.
3. Davis B H, Zarev P V. Human monocyte CD163 expression inversely correlates with soluble CD163 plasma levels. Cytometry B Clin Cytom 2005 January; 63(1):16-22.
4. Zarev P V, Davis B H. Comparative study of monocyte enumeration by flow cytometry: improved detection by combining monocyte-related antibodies with anti-CD163. Lab Hematol. 2004; 10(1):24-31
5. Gamvrellis A, Leong D, Hanley J C, Xiang S D, Mottram P, Plebanski M. Vaccines that facilitate antigen entry into dendritic cells. Immunol Cell Biol 2004 October; 82(5):506-16.
6. Hart J P, Gunn M D, Pizzo S V. A CD91-positive subset of CD11c+ blood dendritic cells: characterization of the APC that functions to enhance adaptive immune responses against CD91-targeted antigens. J Immunol 2004 Jan. 1; 172(1):70-8.
7. Hvidberg V, Maniecki M B, Jacobsen C, Hojrup P, Moller H J, Moestrup S K. Identification of the receptor scavenging hemopexin-heme complexes. Blood 2005 Oct. 1; 106(7):2572-9.
8. Kristiansen M, Graversen J H, Jacobsen C, Sonne O, Hoffman H J, Law S K, et al. Identification of the haemoglobin scavenger receptor. Nature 2001 Jan. 11; 409(6817):198-201.
9. Lindstedt M, Lundberg K, Borrebaeck C A. Gene family clustering identifies functionally associated subsets of human in vivo blood and tonsillar dendritic cells. J Immunol 2005 Oct. 15; 175(8):4839-46.
10. MacDonald K P, Munster D J, Clark G J, Dzionek A, Schmitz J, Hart D N. Characterization of human blood dendritic cell subsets. Blood 2002 Dec. 15; 100(13):4512-20.
11. Radzun H J, Kreipe H, Bodewadt S, Hausmann M L, Barth J, Parwaresch M R. Ki-M8 monoclonal antibody reactive with an intracytoplasmic antigen of monocyte/macrophage lineage. Blood 1987 May; 69(5):1320-7.
12. Backe E, Schwarting R, Gerdes J, Ernst M, Stein H. Ber-MAC3: new monoclonal antibody that defines human monocyte/macrophage differentiation antigen. J Clin Pathol 1991 November; 44(11):936-45.
13. Pulford K, Micklem K, McCarthy S, Cordell J, Jones M, Mason D Y. A monocyte/macrophage antigen recognized by the four antibodies GHI/61, Ber-MAC3, Ki-M8 and SM4. Immunology 1992 April; 75(4):588-95.
14. Ritter M, Buechler C, Langmann T, Schmitz G. Genomic organization and chromosomal localization of the human CD163 (M130) gene: a member of the scavenger receptor cysteine-rich superfamily. Biochem Biophys Res Commun 1999 Jul. 5; 260(2):466-74.
15. Schakel K, Mayer E, Federle C, Schmitz M, Riethmuller G, Rieber E P. A novel dendritic cell population in human blood: one-step immunomagnetic isolation by a specific mAb (M-DC8) and in vitro priming of cytotoxic T lymphocytes. Eur J Immunol 1998 December; 28(12):4084-93.
16. Zaba L C, Krueger J G, Lowes M A. Resident and "inflammatory" dendritic cells in human skin. J Invest Dermatol 2009 February; 129(2):302-8.
17. Shabo I, Stal O, Olsson H, Dore S, Svanvik J. Breast cancer expression of CD163, a macrophage scavenger receptor, is related to early distant recurrence and reduced patient survival. Int J Cancer 2008 Aug. 15; 123(4):780-6.
18. Lau S K, Chu P G, Weiss L M. CD163: a specific marker of macrophages in paraffin-embedded tissue samples. Am J Clin Pathol 2004 November; 122(5):794-801.
19. Venneri M A, De P M, Ponzoni M, Pucci F, Scielzo C, Zonari E, et al. Identification of proangiogenic TIE2-expressing monocytes (TEMs) in human peripheral blood and cancer. Blood 2007 Jun. 15; 109(12):5276-85.
20. Backe E, Schwarting R, Gerdes J, Ernst M, Stein H. Ber-MAC3: new monoclonal antibody that defines human monocyte/macrophage differentiation antigen. J Clin Pathol 1991 November; 44(11):936-45.
21. Hogger P, Dreier J, Droste A, Buck F, Sorg C. Identification of the integral membrane protein RM3/1 on human monocytes as a glucocorticoid-inducible member of the scavenger receptor cysteine-rich family (CD163). J Immunol 1998 Aug. 15; 161(4):1883-90.
22. Philippidis P, Mason J C, Evans B J, Nadra I, Taylor K M, Haskard D O, et al. Hemoglobin scavenger receptor CD163 mediates interleukin-10 release and heme oxygenase-1 synthesis: antiinflammatory monocyte-macrophage responses in vitro, in resolving skin blisters in vivo, and after cardiopulmonary bypass surgery. Circ Res 2004 Jan. 9; 94(1):119-26.
23. Sulahian T H, Hogger P, Wahner A E, Wardwell K, Goulding N J, Sorg C, et al. Human monocytes express CD163, which is upregulated by IL-10 and identical to p155. Cytokine 2000 September; 12(9):1312-21.
24. Van den Heuvel M M, Tensen C P, van As J H, Van den Berg T K, Fluitsma D M, Dijkstra C D, et al. Regulation of CD 163 on human macrophages: cross-linking of CD163 induces signaling and activation. J Leukoc Biol 1999 November; 66(5):858-66.
25. Fabriek B O, Dijkstra C D, Van den Berg T K. The macrophage scavenger receptor CD163. Immunobiology 2005; 210(2-4):153-60.
26. Moniuszko M, Kowal K, Rusak M, Pietruczuk M, Dabrowska M, Bodzenta-Lukaszyk A. Monocyte CD163 and CD36 expression in human whole blood and isolated mononuclear cell samples: influence of different anticoagulants. Clin Vaccine Immunol 2006 June; 13(6):704-7.
27. Kim W K, Alvarez X, Fisher J, Bronfin B, Westmoreland S, McLaurin J, et al. CD163 identifies perivascular macrophages in normal and viral encephalitic brains and potential precursors to perivascular macrophages in blood. Am J Pathol 2006 March; 168(3):822-34.
28. Davis B H, Zarev P V. Human monocyte CD163 expression inversely correlates with soluble CD163 plasma levels. Cytometry B Clin Cytom 2005 January; 63(1):16-22.
29. Buechler C, Ritter M, Orso E, Langmann T, Klucken J, Schmitz G. Regulation of scavenger receptor CD163 expression in human monocytes and macrophages by pro- and antiinflammatory stimuli. J Leukoc Biol 2000 January; 67(1):97-103.
30. Bowen M A, Whitney G S, Neubauer M, Starling G C, Palmer D, Zhang J, et al. Structure and chromosomal location of the human CD6 gene: detection of five human CD6 isoforms. J Immunol 1997 Feb. 1; 158(3):1149-56.
31. Direkze N C, Hodivala-Dilke K, Jeffery R, Hunt T, Poulsom R, Oukrif D, et al. Bone marrow contribution to tumor-associated myofibroblasts and fibroblasts. Cancer Res 2004 Dec. 1; 64(23):8492-5.
32. Chakraborty A, Lazova R, Davies S, Backvall H, Ponten F, Brash D, et al. Donor DNA in a renal cell carcinoma metastasis from a bone marrow transplant recipient. Bone Marrow Transplant 2004 July; 34(2):183-6.
33. Gao et al., Neurone-specific enolase and Sangtex 100 assays during cardiac surgery: Part I—The effects of heparin, protamine and propofol. Perfusion (1997), 12(3), 163-165.

Example 3—Humanisation of CD163 Antibodies

Materials and Methods
Obtaining Hybridoma:
The hybridoma clones (Mac2-158 and Mac2-48) were obtained from Trillium Diagnostics LCC, Maine, USA (http://www.trilliumdx.com/). The cells were thawed and allowed to amplify a few rounds.
Primers:
Primers used for PCR amplification and sequencing of the variable heavy and light chain regions of the hybridoma clones Mac2-158 and Mac2-48 were as described in (1)), but adapting the 5' (GAGG-directional) and 3' (blunt end) sequences for TOPO directional cloning. All primers were obtained from TAG Copenhagen (Copenhagen, Denmark).

List of Primers:

| Leader and constant region primers | | |
|---|---|---|
| VK6 leader | VK6leader | tgaagtcacagacccagg [SEQ ID NO: 32] |
| VKconstant | VKconstant | gcacctccagatgttaactg [SEQ ID NO: 33] |
| VHgconstant | VHgconstant | agggaaataRcccttgaccag (R = a/g) [SEQ ID NO: 34] |
| VH leader2 | VHleader2 | atgagagtgctgattcttttg [SEQ ID NO: 35] |
| Primers for generation of chimeric heavy chain | | |
| VHfor | VHfor | gatgtccagcttcaggag [SEQ ID NO: 36] |
| LeaderbackH | leaderbackH | ctcctgaagctggacatcagacagcacccacctgg [SEQ ID NO: 37] |
| CHfor | CHfor | gcagcgccagcaccaag [SEQ ID NO: 38] |
| VHback | VHback | cttggtgctggcgctgctgactgtgagagcggtgc [SEQ ID NO: 39] |
| Expression vector cloning primers | | |
| Light chain forward | Lfor1 | gccATGGACATGAGAGTGCCTG [SEQ ID NO: 40] |
| Light chain reverse | Lback1 | tcaGCACTCGCCCCTGTTG [SEQ ID NO: 41] |
| Heavy chain forward | Hfor1 | gccATGAAGCACCTGTGGTTC [SEQ ID NO: 42] |
| Heavy chain reverse | Hback1 | tcaCTTGCCCAGGCTCAGGC [SEQ ID NO: 43] |
| Heavy chain SLIM primers | | |
| K43-N43, S50-Y50, Y52-T52 | K-N F | TCACCTACAGCGGCAGC [SEQ ID NO: 44] |
| | K-N FT | TGGAGTGGATGGGCTACA TCACCTACAGCGGCAGC [SEQ ID NO: 45] |
| | K-N RT | tgtagcccatccactcca gcttgttgccggggaac [SEQ ID NO: 46] |
| | K-N R | Gcttgttgccggggaac [SEQ ID NO: 47] |
| S56-I56, Y58-N58 | SY-IN FT | gcggcatcaccaacta caaccccagcctgaag [SEQ ID NO: 48] |
| | SY-IN F | Caaccccagcctgaag [SEQ ID NO: 49] |
| | SY-IN RT | tagttggtgatgccgc tgtaggtgatgtagcc [SEQ ID NO: 50] |
| | SY-IN R | Tgtaggtgatgtagcc [SEQ ID NO: 51] |
| V71-R71 | V-R F | Caagaaccagttcagcctg [SEQ ID NO: 52] |
| | V-R FT | tcagcgaggacaccag caagaaccagttcagc [SEQ ID NO: 53] |
| | V-R RT | ctggtgtcctcgctga tggtcaccctgctctt [SEQ ID NO: 54] |
| | V-R R | Tggtcaccctgctcttcag [SEQ ID NO: 55] |
| Q1-D1 | Q-D F | Gagtctggaccaggacc [SEQ ID NO: 56] |
| | Q-D R | Gacagcacccacctgg [SEQ ID NO: 57] |
| | Q-D FT1 | tgacgtgcagctgcag gagtctggaccaggac [SEQ ID NO: 58] |
| | Q-D RT1 | ctgcagctgcacgtca gacagcacccacctgg [SEQ ID NO: 59] |
| Light chain SLIM primers | | |
| P46L | P-L FT | Ggcaagagccccaagctcctgatctactatgccagc [SEQ ID NO: 60] |
| | P-L F | Ctgatctactatgccagc [SEQ ID NO: 61] |
| | P-L RT | Gagcttggggctcttgccgggcttctgctggaacc [SEQ ID NO: 62] |
| | P-L R | Gggcttctgctggaacc [SEQ ID NO: 63] |

| G89-Q89, T93-S93 | GT-QS FT | Ccagcaggactactccagccctaggaccttcggtg [SEQ ID NO: 64] |
| --- | --- | --- |
| | GT-QS F | Ccctaggaccttcggtg[SEQ ID NO: 65] |
| | GT-QS RT | Ctggagtagtcctgctggcagaagtacacggcgaag [SEQ ID NO: 66] |
| | GT-QS R | Cagaagtacacggcgaag[SEQ ID NO: 67] |

Light chain Quick change primers

| Primers SLQ-NRY | SLQ-NRY for | gatctactatgccagcaaccggtactctggagtgcccagc [SEQ ID NO: 68] |
| --- | --- | --- |
| | SLQ-NRY back | gctgggcactccagagtaccggttgctggcatagtagatc [SEQ ID NO: 69] |

Sequencing primers

| CMV primer | cmv for | Caaatgggcggtaggcgtg [SEQ ID NO: 70] |
| --- | --- | --- |
| TK poly A | TKPA rev | Ccttccgtgtttcagttagc [SEQ ID NO: 71] |
| EMCV IRES | EMCV ires rev | Ccttattccaagcggcttc [SEQ ID NO: 72] |

Sequencing:

Sequencing was performed at Eurofins MWG operon (Ebersberg, Germany) as a Value Read Tube Service. All plasmid preparations and mutations were verified by sequencing.

Extracting Total RNA:

$2 \times 10^6$ cells of each hybridoma cell line were used for extracting total RNA by QIAamp blood RNA kit (QIAGEN Corporation, Copenhagen, Denmark) according to the instructions of the manufacturer. Briefly, the cells were re-suspended in 600 µl buffer RLT (QIAGEN) and homogenized by passing it through a syringe mounted with a 21-G (0.8 mm) needle at least 5 times. 600 µl of 70% ethanol (EtOH) was added and mixed by pipetting. The suspension was applied to the QIAamp spin column and load by multiple centrifugations. The column was washed with 750 µl RW1 (Qiagen) and 750 µl RPE (QIAGEN). The RNA was eluted with 2×50 µl RNase free water (QIAGEN).

Preparation of Buffers for cDNA Synthesis

All buffers for the cDNA synthesis was prepared with Ultra pure or molecular biology grade chemicals and diethyl pyrocarbonat (DEPC)-treated water. DEPC-treated water was prepared by adding DEPC (Sigma-Aldrich, Brøondby, Denmark) to a final concentration of 0.1% and the solution was stirred over night followed by autoclaving. Tris and EDTA stock solutions were made by adding the chemicals to DEPC-treated water followed by autoclaving. Buffers containing LiCl were made by dissolve LiCl in MQ water, add DEPC to 0.1% and stir over night. Subsequently, the solutions were autoclaved and Tris and EDTA solutions where added to appropriate concentrations, pH was adjusted and the solutions were autoclaved again.

cDNA Synthesis:

cDNA was synthesized by Omniscript Reverse Transcriptase (QIAGEN, Copenhagen, Denmark). All buffers were DEPC treated and mixed with molecular biology grade chemicals. Briefly: Secondary structures in the RNA were disrupted by heating to 65° C. for 2 min. 100 µl Dynalbeads Oligo (dT)$_{25}$ (Invitrogen, Taastrup, Denmark) were washed twice in 1 ml binding buffer (20 mM Tris, 1 M LiCl, 2 mM EDTA) and re-suspended in 100 µl binding buffer. The heated purified RNA sample was added to the beads and incubated at room temp. for 3-5 min with rotation for annealing. Subsequently the beads are washed twice in 1 ml buffer B (10 mM Tris, 0.15 M LiCl, 1 mM EDTA) and twice in 1 ml ice-cold DEPC-water. The captured mRNA is reverse transcribed with Omniscript Reverse Transcriptase (Omniscript RT kit, QIAGEN, Copenhagen, Denmark) in a total volume of 80 µl of: 4 units ORT, 8 µl 10× buffer (supplied by Qiagen), 0.5 mM dNTPs, 40 units RNase inhibitor (RiboLock, Fermentas, St. Leon-Rot, Germany), by incubation at 37° C. for 2 h with gentle shaking. Finally the synthesized cDNA was washed twice in 1 ml TE buffer (20 mM Tris, 1 mM EDTA).

PCR Amplification of the Variable Regions of the Light and Heavy Chains:

Primers for amplification of the variable genes were designed according to the degenerate primer sequences of Zhou and co-workers (1). Primer mixes were made with a 100 µM total primer concentration. $V_H$ Forward primer mix was 25 µM in each primer and the $V_H$ Back primer mix was 10 µM in each primer. The $V_L$ Forward mix was 20 µM in each primer concentration and the $V_L$ Back primer mix was 10 µM in each primer concentration.

100 µl PCR reaction was made for amplification of each clone $V_H$ as well as for $V_L$. The reactions contained the following: 10 µl Pfu Buffer with MgSO$_4$; 2 µl 10 mM dNTP mix; 10 µl Forward primer mix (either $V_H$ or $V_L$); 10 µl Back primer mix (either $V_H$ or $V_L$); 67 µl autoclaved water; 1 µl Pfu (2.5 units); and half of the cDNA containing beads from a clone.

The cycling was as follows: Initial denaturation of 3 min at 95° C. and 30 cycles of 50 s at 95° C., 50 s at 55° C., and 3 min at 72° C. The amplified DNA is checked on a 1% agarose gel stained with EtBr and purified by gelextraction kit (Machery-Nagel, AH-Diagnostics, Aarhus, Denmark).

Sequencing:

Each PCR product ($V_H$ or $V_L$) was sequenced as (Value Read Tube premixed with primer) with the Forward primer mix ($V_H$ or $V_L$) or the Back primer mix ($V_H$ or $V_L$). Both were 1 µM in each primer as final concentration. Received sequences were aligned with ClustalW2 (http://www.ebi-.ac.uk/Tools/clustalw2/index.html)(2).

Sequences of $V_H$ inserts in pcDNA3.3 was verified with the primers CMV and TK polyA. Sequences of $V_L$ inserts in pOptiVec was verified with the primers CMV and EMCV IRES.

Secondary PCR Primer Design:

To evaluate if any essential amino acids have been mutated due to primer design a pair of secondary PCR primers were designed. The leader primers (VK6 leader and VH leader2) were based on sequences found in (3) and the gamma and kappa primers (VHgconstant and VKconstant) were adapted after (4). PCR products were amplified by standard PCR with the primer pairs (VK6 leader and VKconstant) and (VH leader2 and VHgconstant). The PCR products were purified and sequenced forward and reverse with the primers used to generate the PCR products.

Sequence Analysis and Donor Framework Design:

The following servers and programs were used for analysis of the variable regions: http://www.bioinf.org.uk/abs/, http://www.ncbi.nlm.nih.gov/igblast/, http://blast.ncbi.nlm.nih.gov/Blast.cgi, http://swissmodel.expasy.org//, and Swiss PDB Viewer.

The humanization was performed as a CDR grafting onto human frameworks. Overall strategy was according to (5). The "best fit complete sequence" for $V_H$ or $V_L$ were used as acceptor frameworks. Complete hypervariable loops were grafted onto the chosen acceptor frameworks. Backmutations are the $V_H$-$V_L$ interface, which were retained to ensure correct orientation of the variable domains (defined as in Morea et al. Table 2) and the mouse residues at key positions important for the canonical structures of the hypervariable loops were retained (according to Morea et al. Table 1).

The acceptor frameworks for the heavy chain was dbj|BAG64279.1| and germline IGHV4-b*01. The acceptor frameworks for the light chain was emb|CAD43020.1| and germline IGKV1D-39*01. The complete sequences for a humanized gamma 4 variant and a humanized Kappa variant were designed after sequences from NCBI BLAST (sp|P01861.1|IGHG4_HUMAN and dbj|BAC01725.1|) and synthesized at GenScript (Piscataway, N.J., USA)).

Generation of Chimeric Heavy Chain

A chimeric heavy chain was generated by splicing by overlap (SOE) extension PCR (6). Three standard PCR reactions where made to generate the templates for the SOE-PCR: (1) Primers Hfor1 and leaderbackH in a PCR reaction on the synthesized gamma4 sequence from GenScript, (2) primers CHfor and Hback1 in a PCR reaction on the synthesized gamma4 sequence from GenScript, and (3) primers VHfor and VHback in a PCR reaction on the beads containing the Mac2-158 cDNA. The PCR products were purified by gel extraction kit (Macherey-Nagel, AH-Diagnostic, Aarhus, Denmark). The SOE-PCR was made as a standard PCR reaction with the primers Hfor1 and Hback1. 2 µl of each of the template PCR products (1-3) was added to the reaction. An approximate 1500 bp band was purified by gel extraction. The purified SOE-PCR product was inserted into the pcDNA3.3 Topo vector from the OptiCHO protein express kit (invitrogen, Taastrup, Denmark) according to manufacturers instructions. The sequence was verified by sequencing with the primers CMV and TK polyA.

Construction of Expression Plasmids:

The synthesized sequences from GenScript were inserted into the expression vectors from the OptiCHO protein express kit (Invitrogen, Taastrup Denmark). The kappa chain was amplified by standard PCR with the Lfor1 and Lback1 primers, and the gamma4 chain was amplified with the Hfor1 and Hback1 primers. The light and heavy chain PCR products were inserted into the pOptiVec (light chain) and pcDNA3.3 (heavy chain) Topo vectors from the OptiCHO protein express kit according to manufacturers instructions.

Site Directed Mutagenesis:

Three mutations were introduced by quick change site directed mutagenesis. In the light chain 53SLQ55 were back-mutated to NRY. The mutagenesis was performed as a standard mutagenesis according to the Stratagene protocol (http://www.stratagene.com/manuals/200518.pdf) with the primers SLQ-NRY for and back. Template was the plasmid pOptiVec-Kappa 8.

SLIM Mutagenesis:

For the remaining mutants the Site-directed Ligation Independent Mutagenesis (SLIM) method was used (7). Primers are listed in the primer table. The templates were for the K-N primers pcDNA3.3-gamma n1 heavy chain, for the SY-IN primers the pcDNA3.3-KN1 plasmid, for the remaining heavy chain mutations the template was pcDNA3.3-KN1IN5. The template for the additional humanization in the light chain was the plasmid pOptiVec-NRY. This was done by two consecutive rounds of SLIM on pOptiVec-NRY with the primer sets P46L (first round) and G89Q, T93S (second round).

Expression of Antibody:

The humanized antibody and a chimeric mouse/human antibody in the IgG4 format were cloned into vectors supplied with OptiCHO protein express kit from invitrogen (pcDNA3.3 and pOptiVec). The expression plasmids were heat shocked into Top10 cells and plated on LB plates containing amp. Colonies were picked to over night cultures and plasmids were prepared from the cultures with the Nucleobond plasmid kit with finalizer (Macherey-Nagel, AH-Diagnostic, Aarhus, Denmark). The sequences of all plasmids were verified by sequencing.

The various mutants and different combinations of antibodies were expressed transient in CHO—S cells as follows:

20 µg of pcDNA3.3 containing a heavy chain was mixed with 20 µg of pOptiVec containing a light chain. The DNA was diluted in OptiCHOPro SFM (8 mM L-glutamine) to a total volume of 0.6 ml. The DNA is gently mixed with 0.6 ml OptiCHOPro SFM containing 40 µl FreeStyle MAX transfection reagent (Invitrogen, Taastrup, Denmark). After 10 min of incubation at room temperature the DNA-FreeStyle MAX mix was added to $1 \times 10^6$ cells/ml in 25 ml. 3 days later the supernatant was harvested by centrifugation and analysed by ELISA.

ELISA Antibody Reactivity Comparison

A nunc maxisorp plate was coated with the following (50 µl/well) over night at 4° C.: 4 µg/ml goat anti-human kappa chain antibody (AbD Serotec, Oxford, UK) and ~4 µg/ml human CD163 (purified as described in 8). Buffer was carbonate buffer, pH 9.0. Each measurement was made in duplicate.

The ELISA steps are as follows
1) The ELISA was washed 3 times in PBS
2) The plate was blocked with PBS containing 3% BSA for 1 h.
3) Optionally, step 1 was repeated
4) After blocking, the primary antibody was added (100 µl per well).

Samples

Undiluted supernatant from transfected cells added to the wells (100 µl/well)

Standards 100 ng/ml human IgG/kappa (Sigma) antibody diluted in PBS containing 1% BSA;

100 ng/ml Mac2-158 diluted in PBS containing 1% BSA;

2 fold dilution series were made on all samples and standards. Dilution in PBS containing 1% BSA.

The samples were incubated on the plate for 1 hour.
5) Step 1 is repeated
6) Addition of secondary antibody (100 µl/well)

For Anti-Kappa/Anti-Gamma ELISA

100 µl/well of goat anti human IgG gamma chain specific HRP 1:6000 in PBS containing 1% BSA.

For CD163 ELISA
100 µl/well of goat anti human IgG (H&L) HRP 1:6000 in PBS containing 1% BSA.
For Mac2-158 goat anti-mouse HRP 1:2000 in PBS containing 1% BSA is added to the wells
7) Step 1 was repeated
8) The ELISA was developed by adding 75 µl of TMB substrate to each well. Incubation was performed for 3 min.
9) The reaction was stopped by adding 30 µl 2 $NH_2SO_4$ to the wells.
10) The plate was read in an ELISA reader at 450 nm.

Background was measured on wells with no coating and wells with no primary antibody.
Results
PCR Amplification of the Variable Genes:
A 1% agarose gel analysis show that the mRNA purifications, cDNA productions, and PCRs for amplification of the variable regions worked (see FIG. 15).
Sequences of PCR Products:
Sequencing of the purified PCR product ($V_H$ and $V_L$) from PCR on the generated cDNA (Mac2-48 and Mac2-158) was done at Eurofins MWG Operon (Ebersberg, Germany). The sequences were aligned.

```
VL48    TDIVMTQTPKFLLVSAGDRVTITCKASQSVSHDVSWFQQKPGQSPKLLIYYTSNRYTGVPDRFTGSGYGT

VL158   -DIVMTQSPKSLLISIGDRVTITCKASQSVSSDVAWFQQKPGQSPKPLIYYASNRYTGVPDRFTGSGYGT

VL48    DFTFTISTVQAEDLAIYFCQQDYSSPRTFGGGTKLEIKRA

VL158   DFTFTISSVQAEDLAVYFCGQDYTSPRTFGGGTKLEIKRA

VH48    DVKLQESGPGLVKPSQSLSLTCTVTGYSITSDYAWNWIRQFPGNKLEWMGFISYSGITSYNPSLKSRISITRD

VH158   DVKLQESGPGLVKPSQSLSLTCTVTGYSITSDYAWNWIRQFPGNKLEWMGYITYSGITNYNPSLKSQISITRD

VH48    TSKNQFFLQLNSVTTEDSATYYCVSGTYYFDYWGQGTTLTVSS

VH158   TSKNQFFLQLNSVTTEDTATYYCVSGTYYFDYWGQGTTLTVSS
```

The secondary PCR products verified the overall sequences of the $V_H$ and $V_L$. The few differences found were:

```
VL158:      N-term  SVVMTQT
VL48:       N-term  SIVMTQT
VH158:      N-term  DVQLQ
VH48:       N-term  DVQLQ
```

The V in position 2 in VL158 might be important for the function of the light chain. Additional the linkers to both the kappa constant and gamma constant domains were found to be normal IgG1 linkers.
Design of Humanized Antibody:
The frameworks chosen as acceptor for the CDR grafting were for the heavy chain: dbjIBAG64279.1 and germline IGHV4-b*01 and for the light chain: embICAD43020.1 and germline IGKV1D-39*01. The light chain as a full length kappa chain with a leader peptide and the heavy chain as a full length gamma 4 with a leader peptide are show as DNA and protein sequences:

```
Light chain
DNA sequence
                                                      [SEQ ID NO: 73]
Atggacatgagagtgcctgctcagctgctgggactgctgctgctgtggctgcctggagctaggtgtgacatc gtgatgacacagtctcccagcagcctgagcgcctctgtgggcgacagggtgaccatcacctgcagggctagc cagagcgtgagcagcgacgtggcctggttccagcagaagcccggcaagagccccaagcccctgatctactat gccagcagcctgcagtctggagtgcccagcaggttcagcggcagcggcagcggaacagacttcaccctgacc atcagcagcctgcaggccgaggacttcgccgtgtacttctgcggccaggactacaccagccctaggaccttc ggtggcggaaccaagctggagatcaagaggaccgtggccgcccccagcgtgttcatcttccctccaagcgac gagcagctgaagagcggcaccgccagcgtggtgtgcctgctgaacaacttctaccccagggaggccaaggtg cagtggaaggtggacaacgccctgcagagcggcaacagccaggagagcgtgaccgagcaggacagcaaggac
```

-continued

```
agcacctacagcctgagcagcaccctgaccctgagcaaggccgactacgagaagcacaaggtgtacgcctgc gaggtgacccaccagggcctgagcagccccgtgaccaagagcttcaacaggggcgagtgc
```

Protein sequence

[SEQ ID NO: 74]

MDMRVPAQLLGLLLLWLPGARCDIVMTQSPSSLSASVGDRVTITCRASQSVSSDVAWFQQKPGKSPKPLIYY

ASSLQSGVPSRFSGSGSGTDFTLTISSLQAEDFAVYFCGQDYTSPRTFGGGTKLEIKRTVAAPSVFIFPPSD

EQLKSGTASVVCLLNNFYPREAKVQWKVDNALQSGNSQESVTEQDSKDSTYSLSSTLTLSKADYEKHKVYAC

EVTHQGLSSPVTKSFNRGEC

Heavy chain
DNA sequence

[SEQ ID NO: 75]

```
atgaagcacctgtggttcttcctgctgctggtggctgccccaggtgggtgctgtctcaggtgcagctgcag gagtctggaccaggactggtgaagccatctgagaccctgagcctgacctgcaccgtgagcggctacagcatc accagcgactacgcctggaactggatcaggcagttccccggcaagaagctggagtggatgggcagcatctac tacagcggcagcacctactacaacccagcctgaagagcagggtgaccatcagcgtggacaccagcaagaac cagttcagcctgaagctgagcagcgtgaccgccgccgacaccgccacctactactgcgtgagcggcacctac tacttcgactactggggccagggcaccaccctgaccgtgagcagcgccagcaccaagggaccaagcgtgttc ccactggctccatgcagcaggagcaccagcgagagcacagccgccctgggatgcctggtgaaggactacttc cctgagcctgtgaccgtgagctggaattctggcgccctgaccagcggagtgcacaccttcccagccgtgctg cagagctctggactgtacagcctgagcagcgtggtgaccgtgccttcttccagcctgggcaccaagacctac acctgcaacgtggaccacaagcccagcaacaccaaggtggacaagagggtggagtctaagtatgacctcca tgcccaagctgtcctgctcctgagttcctgggcggcccaagcgtgttcctgttccctccaaagccaaggac accctgatgatcagcaggacccctgaggtgacctgcgtggtggtggacgtgagccaggaggaccccgaggtg cagttcaactggtacgtggacggcgtggaggtgcacaacgccaagaccaagcccagggaggagcagttcaac agcacctacagggtggtgagcgtgctgaccgtgctgcaccaggactggctgaacggcaaggagtacaagtgc aaggtgagcaacaagggcctgcccagcagcatcgagaagaccatcagcaaggccaagggccagccagggag ccccaggtgtacaccctgcctccaagccaggaggagatgaccaagaaccaggtgagcctgacctgcctggtg aagggcttctaccccagcgacatcgccgtggagtgggagagcaacggccagcccgagaacaactacaagacc accccctccagtgctggacagcgacggcagcttcttcctgtacagcaggctgaccgtggacaagagcaggtgg caggagggcaacgtgttcagctgcagcgtgatgcacgaggccctgcacaaccactacacccagaagagcctg agcctgagcctgggcaag
```

Protein sequence

[SEQ ID NO: 76]

MKHLWFFLLLVAAPRWVLSQVQLQESGPGLVKPSETLSLTCTVSGYSITSDYAWNWIRQFPGKKLEWMGSIY

YSGSTYYNPSLKSRVTISVDTSKNQFSLKLSSVTAADTATYYCVSGTYYFDYWGQGTTLTVSSASTKGPSVF

PLAPCSRSTSESTAALGCLVKDYFPEPVTVSWNSGALTSGVHTFPAVLQSSGLYSLSSVVTVPSSSLGTKTY

TCNVDHKPSNTKVDKRVESKYGPPCPSCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDGSFFLYSRLTVDKSRW

QEGNVFSCSVMHEALHNHYTQKSLSLSLGK

Cloning and Mutagenesis:

The cloning of the sequences obtained from GenScript produced a light chain Kappa 8 (K8) and a heavy chain gamma n1 with correct sequences.

Heavy chain variants: The constructs produces by SLIM reactions where gamma n1 is the template for the first reaction with the primers producing the K43N, S50Y, and Y52T mutations. This generated the pcDNA3.3 plasmids KN1 and KN2. Plasmid KN1 was used as template for the S56I and Y58N mutations. This generated KN11N5 which served as template for the last two single mutations V71R (plasmid VR1) and Q1D (QD2). Subsequent sequencing showed that KN1 had a mis-mutation (N) in position 19, and that the V71R mutation turned out to be a V71E mutation. Clone KN2 had the correct sequence.

Light chain variants: The construct produced by Quick Change Mutagenesis resulted in the light chain plasmid pOptiVec-NRY with correct sequence. Analysis of the plasmids after the two consecutive SLIM mutagenesis reaction (P46L and G89Q, T93S) showed that only two of the mutations where present (P46L and T93S) in the plasmid d3.

mAb ELISA Reactivity

The sequences of the different humanized variant heavy and light chains tested in ELISA are shown in FIG. 16. Three different light chains K8, NRY, and d3 and five different heavy chains chimeric cgamma(6), KN2, KN1IN5, QD2, and VR1 were tested.

The first ELISA comparison was made between two variants of the light chain (K8 and NRY) all paired with the chimeric heavy chain cgamma(6). The result of the ELISA is shown in FIG. 17. cgamma(6)/K8 exhibited the highest expression level and cgamma(6)/NRY the lowest. The exhibited reactivity of the two variants towards CD163 were almost identical. So when including expression level in the comparison of reactivity the light chain NRY is better than the K8 light chain.

FIG. 18 shows a comparison of the humanized heavy chain variants with additional back-mutations all paired with the light chain NRY. The ELISA showed that all combinations more or less displayed similar reactivity towards the antigen CD163. A reactivity which was also comparable with the Mac2-158 reactivity towards CD163.

A few forward mutations were introduced into the light chain NRY to generate a more humanized version of the light chain (d3).

Development of Stable CHO-DG44 Cell Line for KN2/NRY Production and Small Scale Expression The OptiCHO Antibody Express Kit (Invitrogen, Taastrup, Denmark) was used for cloning and expression of the humanized IgG4 antibody designated KN2/NRY. The pcDNA3.3 gamma KN2 and pOptiVEC kappa NRY plasmids (Example 3) were liniearized and transfected into dihydrofolate reductase (DHFR)-negative CHO-DG44 cells (cGMP banked) according to the manufacturer's protocol. Two days post transfection, the CHO DG44 cells were selected for stable transfection of the OptiVEC kappa NRY plasmid in CD OptiCHO Medium supplemented with 8 mM L-glutamine. Every 2-3 days, the cells were centrifuged at 1100 rpm for 10 min, the medium was removed by aspiration and complete CD OptiCHO medium added to a final volume of 25 ml. Following 3 weeks of selection, the cell viability was 100% and the cells were further propagated in complete CD OptiCHO medium with 500 ug/ml Geneticin (G418) to select for CHO-DG44 cells stably transfected with the pOptiVEC kappa NRY and pcDNA3.3 gamma KN2 plasmids. The cells were selected for 2 weeks as described above. When the cell viability reached 100%, the cells were clonally selected in minipools by limiting dilution in 96 well culture plates (10 cells/well). The resulting minipools were analyzed for KN2/NRY expression in a protein-specific ELISA and high producers were propagated before genomic amplification by methotrexate (MTX). Several rounds of MTX selection (50-2000 mM MTX) was performed according to the manufacturer's instructions before the stably transfected and MTX amplified cells were single cell cloned by limiting dilution. Finally, clonally selected cells were analyzed by ELISA and high producing clones were propagated for smale scale production of KN2/NRY. Small scale productions were seeded at $0.5 \times 10^6$ cells/ml in 150-200 ml complete CD OptiCHO medium with 500 ug/ml Geneticin (G418) Medium in Triple layer tissue culture flasks (Nalge-Nunc) for 4 days, medium supernatant was isolated by centrifugation and filtration.

Purification of KN2/NRY

The supernatant from the KN2/NRY expressing CHO cells are added Tris-HCl pH 8.0 buffer to a final concentration of 50 mM, filtered trough a 0.22 μm filter, and loaded on a HiTrap MabSelct SuRe column (Ge Healtcare, Brøondby, Denmark). After loading the column is washed with 10 volumes of PBS pH 7.4 and protein eluted with a 0.1 M Na-Citrate buffer pH 3.2 into fraction tubes filled with ¹⁄₁₀ of the final fraction volume of 1 M Tris-HCl pH 8.0. The protein is buffer gelfiltrated into the final buffer for use. Using Sephadex G-25 (Ge Healtcare, Brøondby, Denmark).

Biacore Affinity Testing of KN2/NRY Binding to CD163

KN2/NRY has been tested for binding to CD163 immobilized on a Biacore chip and compared to the binding of Mac2-158 to the same CD163 chip.

SPR analysis of the binding of mAbs to CD163 was carried out on a Biacore 2000 instrument (Biacore, Uppsala, Sweden). The Biacore sensor chips (type CM5) were activated with a 1:1 mixture of 0.2 M N-ethyl-N'-(3-dimethylaminopropyl)carbodiimide and 0.05 M N-hydroxysuccimide in water. Purified recombinant CD163 were immobilized in 10 mM sodium acetate, pH 4.0, and the remaining binding sites were blocked with 1 M ethanolamine, pH 8.5. The SPR signal generated from immobilized recombinant CD163 proteins corresponded to 40-70 fmol of protein/mm². Sensorgrams were generated using mAb concentrations ranging from 5-100 nM. The flow cells were regenerated with 1.6 M glycine-HCl, pH 3. The running buffer used for the experiment was either CaHBS 10 mM Hepes, 150 mM NaCl, 3.0 mM $CaCl_2$, 1.0 mM EGTA, and 0.005% Tween 20, pH 7.4. or 10 mM Hepes, 150 mM NaCl, 3.0 mM EDTA, and 0.005% Tween 20, pH 7.4, KN2/NRY and Mac-158 samples were dissolved in the same buffer as the running buffer used at a concentration of 5 μg/ml. All binding data were analyzed using the Biamolecular Interaction Analysis evaluation program version 3.1.

The result is shown in FIG. 19, and shows that the affinities of the two monoclonal antibodies for CD163 is virtually identical. Both exhibit sub nM dissociation constants, though exact fitting is difficult due to the high affinity.

REFERENCES FOR EXAMPLE 3

1. Zhou, H., Fisher, R. J. & Papas, T. S. (1994). Optimization of primer sequences for mouse scFv repertoire display library construction. Nucleic Acids Res 22, 888-9.
2. Larkin M. A. et al. (2007). Clustal W and Clustal X version 2.0. Bioinformatics, 23 (21):2947-8.
3. Lefranc, M.-P. et al. (2005), Nucleic Acids Res, 33, D593-D597.
4. Rohatgi, S., et al. (2008). J Immunol Meth, 339, 205-219.
5. Morea, V., et al. (2000). Antibody modeling: implications for engineering and design. Methods 20(3): 267-79.
6. Horton et al. (1989). Engineering hybrid genes without the use of restriction enzymes: gene splicing by overlap extension. Gene 77: 61-8.
7. Chiu et al. (2004). Site-directed, Ligase-Independent Mutagenesis (SLIM): a single-tube methodology approaching 100% efficiency in 4 h. Nucleic Acid Res, 32 (21): e174.

8. Kristiansen M. et al. (2001). Identification of the haemoglobin scavenger receptor. Nature 11:409(6817): 198-201.

Example 4—Single Chain Expression, Refolding, and Function

Materials and Methods
Obtaining the scFv Sequence:

The sequence of the scFv ($V_H$-15 residue linker-$V_L$) was synthesized at GenScript and cloned into pET20b at GenScript via the cloning sites NcoI/XhoI. Linker is chosen as the 15 residue linker described in (1). Protein and DNA sequences are shown below

```
Protein
                                         [SEQ ID NO: 77]
MDQVQLQESGPGLVKPSETLSLTCTVSGYSITSDYAWNWIRQFPGNKLEW

MGYITYSGSTYYNPSLKSRVTISVDTSKNQFSLKLSSVTAADTATYYCVS

GTYYFDYWGQGTTLTVSSGGGGSGGGGSGGGGSDIVMTQSPSSLSASVGD

RVTITCRASQSVSSDVAWFQQKPGKSPKPLIYYASNRYSGVPSRFSGSGS

GTDFTLTISSLQAEDFAVYFCGQDYTSPRTFGGGTKLEIKREQKLISEED

L

DNA
                                         [SEQ ID NO: 78]
CCATGGACCAGGTGCAGCTGCAGGAAAGCGGCCCGGGCCTGGTGAAACCG

AGCGAAACCCTGAGCCTGACCTGCACCGTGAGCGGCTATAGCATTACCAG

CGATTATGCGTGGAACTGGATTCGTCAGTTTCCGGGCAACAAACTGGAAT

GGATGGGCTACATTACTTATAGCGGCAGCACCTATTATAACCCGAGCCTG

AAAAGCCGTGTGACCATTAGCGTGGATACCAGCAAAAACCAGTTTAGCCT

GAAACTGAGCAGCGTGACCGCGGCGGATACCGCGACCTATTATTGCGTGA

GCGGCACCTATTATTTTGATTATTGGGGCCAGGGTACCACCCTGACCGTG

TCTAGCGGTGGGGCGGAAGCGGGGCGGTGGAAGCGGGGCGGTGGATC

TGATATTGTGATGACCCAGAGCCCGAGCAGCCTGAGCGCGAGCGTGGGCG

ATCGTGTGACCATTACCTGCCGTGCGAGCCAGAGCGTGAGCAGCGATGTG

GCGTGGTTTCAGCAGAAACCGGGCAAAAGCCCGAAACCGCTGATTTATTA

TGCGAGCAACCGGTATAGCGGTGTGCCGAGCCGTTTTAGCGGTAGCGGTA

GCGGTACCGATTTTACCCTGACCATTAGCAGCCTGCAGGCGGAAGATTTT

GCGGTGTATTTTTGCGGCCAGGATTATACCAGCCCGCGTACCTTTGGTGG

CGGAACCAAACTGGAAATTAAACGTGAACAGAAACTGATTAGCGAAGAAG

ATCTGCTCGAG
``` scFv Expression and Purification:

The pET20b-scFv plasmid were transformed into BL21 DE3 star cells (Invitrogen, Taastrup, Denmark) by heat shock, and the transformed cells were plated on agar plates with LB media and 0.1 mg/ml ampicilin. A starter culture was made in LB media supplemented with 0.1 mg/ml ampicilin and 1% glucose by transferring one colony from the plate to the media. The starter culture was incubated over night at 30° C. with shaking.

Expression of the scFv in inclusion bodies was done at 37° C. with shaking as follows: 500 ml LB media (supplemented with ampicillin and 0.1% glucose) was inoculated with 1:100 of the starter culture. At $OD_{600}$~0.6 the culture was induced with 2 mM IPTG and the expression was allowed to continue for 4 hours. Subsequently, the bacteria were harvested by centrifugation, solubilized in PBS, sonicated and centrifuged again. The supernatant was aspired and the pellet was washed in PBS and centrifuged again.

The pellet was solubilized in 20 ml 20 mM Tris pH 8, 7 M urea, and bacteria remnants were spun down. The 20 ml supernatant was dialysed over night at 4° C. against 1 liter 20 mM Tris, 3 M urea. The dialysed sample was centrifuged. His tag containing scFv was purified from the supernatant on a 1 ml HisTrap™ HP (GE Healthcare, Brøondby, Denmark) and eluted with 20 mM Tris, 3 M urea, 50 mM EDTA. Eluate was collected in 0.4 ml fractions.

scFv Refolding:

The HisTrap purified protein was refolded as follows: 3 ml protein in 20 mM Tris pH 8, 3 M urea, 50 mM EDTA in a dialysis bag was dialysed against 100 ml buffer B (20 mM Tris pH 8, 3 M urea). A peristaltic pump (0.2 ml/min) loaded 900 ml of buffer C (20 mM Tris pH 8) into buffer B. The dialysis was left for approx. 90 hours.

scFv ELISA:

A nunc Maxisorp ELISA plate (NUNC, Roskilde, Denmark) was coated with 50 µl/well of 2 µg/ml of CD163 (purified as described in (2)) over night at 4° C. The coated plate was washed 3 times in PBS and blocked for 1 hour with 3% BSA in PBS. Fractions from scFv purification were tested by adding 100 µl/well of a 1:10 dilution of each sample in 1% BSA, PBS. The refolded protein sample was added directly to the wells (100 µl/well) and two-fold dilution series was made with dilution in 1% BSA in PBS. After 1 hour incubation at 4° C. the plate was washed 3 times in PBS again. Secondary detection was made with a 1 hour incubation of a HRP conjugated anti-His antibody (Sigma-Aldrich, Brøondby, Denmark) (1:4000 diluted in 1% BSA, PBS). After washing 3 times in PBS the ELISA was developed with 75 µg/well TMB substrate (Invitrogen, Taastrup, Denmark). The reaction was stopped with 40 µl/well of 1 M $H_2SO_4$ and the plate was read in an ELISA reader at 450 nm.

Results

Expression and Purification:

The dialysis of solubilized pellet resulted in heavy precipitation in the dialysis bag. The majority of the His-tagged protein was not precipitated as evaluated by western blot (data not shown). After HisTrap™ purification the fractions were evaluated in ELISA. To mediate protein refolding a sample of each fraction was diluted a 10 fold in 1% BSA which results in an end concentration of 0.3 M urea which should render the protein in a folded state. The diluted samples were analysed for binding to CD163 in ELISA (FIG. 20). ELISA signal was mainly found in the fractions 9-14. Fractions 9-16 were pooled. This gave approx. 3 ml purified protein.

Refolding:

A slow refolding was made by dialysis over 90 hours. The end volume was 4 ml and the concentration of urea was 0.3 M. The dialysis resulted in an insignificant pellet after centrifugation. The supernatant was tested in ELISA.

ELISA with Refolded Protein:

The ELISA of the refolded scFv showed binding to CD163. Signals were detected at dilutions down to a 128 fold (FIG. 21). The undiluted sample (sample in buffer without BSA) did though show a high background binding to BSA. As the sample contained an ensemble of folded protein and misfolded protein, which were not separated, it was not surprising that the presence of misfolded protein resulted in unspecific binding. At a 64 or 128 fold dilution in 1% BSA, PBS the background binding to BSA would be neglectable and it still gave rise to signals of 0.29 or 0.15, respectively, clearly showing binding of refolded scFv to CD163 (FIG. 21).

REFERENCES FOR EXAMPLE 4

1. Todorovska et al. (2001). Design and application of diabodies, triabodies and tetrabodies for cancer targeting. J Immunol Methods 248, 47-66.
2. Kristiansen M. et al. (2001). Identification of the haemoglobin scavenger receptor. Nature 11:409(6817): 198-201.

Example 5—Generation, Production and Testing of a Fab Fragment

Materials and Methods
Primers:

```
Fab P-->stop
                                     [SEQ ID NO: 79]
5'-acaagagggtggagtctaagtatggatagccatgcccaagctg-3'

Fab P-->stop anti
                                     [SEQ ID NO: 80]
5'-cagcttgggcatggctatccatacttagactccaccctcttgt-3'
```

Primers were obtained from TAG Copenhagen (Copenhagen, Denmark).
Sequencing:
Sequencing was performed at Eurofins MWG operon (Ebersberg, Germany) as a Value Read Tube Service. The primer used for sequencing was CMV primer from Eurofins MWG operon.
Quick Change Site Directed Mutagenesis:
A stop codon was introduced by quick change site directed mutagenesis, using the QuickChange kit from Stratagene (USA). The mutagenesis was performed as a standard mutagenesis according to the manufactureres protocol. In the heavy chain P220 was mutated to a stop codon. with the primers Fab P→stop and Fab P→stop anti. Template was the plasmid pcDNA3.3-KN2. Sequence of mutant was verified by sequencing.
Expression of Fab Fragment:
The expression plasmids were heat shocked into Top10 cells and plated on LB plates containing amp. Colonies were picked to over night cultures and plasmids were prepared from the cultures with the Nucleobond plasmid kit with finalizer (Macherey-Nagel, AH-Diagnostic, Aarhus, Denmark). The sequences of all plasmids were verified by sequencing.
The Fab fragment was expressed transient in CHO—S cells as follows:
20 µg of pcDNA3.3-Fab1 was mixed with 20 µg of pOptiVec-NRY. The DNA was diluted in OptiCHOPro SFM (8 mM L-glutamine) to a total volume of 0.6 ml. The DNA is gently mixed with 0.6 ml OptiCHOPro SFM containing 40 µl FreeStyle MAX transfection reagent (Invitrogen, Taastrup, Denmark). After 10 min of incubation at room temperature the DNA-FreeStyle MAX mix was added to 1×10$^6$ cells/ml in 25 ml. 3 days later the supernatant was harvested by centrifugation and analysed by ELISA.
Fab Fragment Activity Measured by ELISA
A nunc maxisorp plate was coated with ~1 µg/ml human CD163 (purified as described by Kristiansen, M. et al. ((2001). Identification of the haemoglobin scavenger receptor. Nature 11:409(6817): 198-201)) was added at 50 µl/well and incubated over night at 4° C. Buffer for coating was carbonate, pH 9.0. Each measurement was made in duplicates.

The primary antibody samples used in ELISA was undiluted supernatant or 30 times concentrated supernatant from transfected cells or antibody standard 100 ng/ml KN2/NRY antibody diluted in PBS containing 1% BSA. The supernatant was concentrated on VIVAspin centrifugal concentrator (10.000 MWCO) (Sigma-Aldrich, Brøondby, Denmark).

The ELISA steps were as follows: ELISA plates were washed 3 times in PBS and blocked with PBS containing 3% BSA for 1 h. After blocking the primary antibody samples were added to the wells (100 µl/well). 2 fold dilution series were made on all samples and standards (dilutions in PBS containing 1% BSA). The samples were incubated on the plates for 1 h. Subsequently, the plates were washed 3 times in PBS and secondary antibody goat anti human kappa chain HRP (AbD Serotec, Oxford, UK) 1:4000 in PBS containing 1% BSA (100 µl/well) was added to the wells. After 1 hour incubation the wells were washed 3 times in PBS and the ELISA was developed by adding 75 µl of TMB substrate to each well. The reaction was stopped after 10 min by adding 40 µl 1 M $H_2SO_4$ to the wells. The plates were read in an ELISA reader at 450 nm.

Background was measured on both wells with no coating and wells with no primary antibody.
Results
Site Directed Mutagenesis
The DNA sequence of the purified plasmid after mutagenesis and the corresponding protein sequence is shown below:

```
DNA
                                     [SEQ ID NO: 81]
caggtgcagctgcaggagtctggaccaggactggtgaagccatctgagac cctgagcctgacctgcaccgtgagcggctacagcatcaccagcgactacg cctggaactggatcaggcagttccccggcaacaagctggagtggatgggc tacatcacctacagcggcagcacctactacaacccagcctgaagagcag ggtgaccatcagcgtggacaccagcaagaaccagttcagcctgaagctga gcagcgtgaccgccgccgacaccgccacctactactgcgtgagcggcacc tactacttcgactactggggccagggcacccctgaccgtgagcagcgc cagcaccaagggaccaagcgtgttcccactggctccatgcagcaggagca ccagcgagagcacagccgccctgggatgcctggtgaaggactacttccct gagcctgtgaccgtgagctggaattctggcgccctgaccagcggagtgca caccttcccagccgtgctgcagagctctggactgtacagcctgagcagcg tggtgaccgtgccttcttccagcctgggcaccaagacctacacctgcaac gtggaccacaagcccagcaacaccaaggtggacaagagggtggagtctaa gtatggatag Protein
                                     [SEQ ID NO: 82]
QVQLQESGPGLVKPSETLSLTCTVSGYSITSDYAWNWIRQFPGNKLEWMG

YITYSGSTYYNPSLKSRVTISVDTSKNQFSLKLSSVTAADTATYYCVSGT

YYFDYWGQGTTLIVSSASTKGPSVFPLAPCSRSTSESTAALGCLVKDYFP

EPVTVSWNSGALTSGVHTFPAVLQSSGLYSLSSVVTVPSSSLGTKTYTCN

VDHKPSNTKVDKRVESKYG(stop)
```

Figure 23:
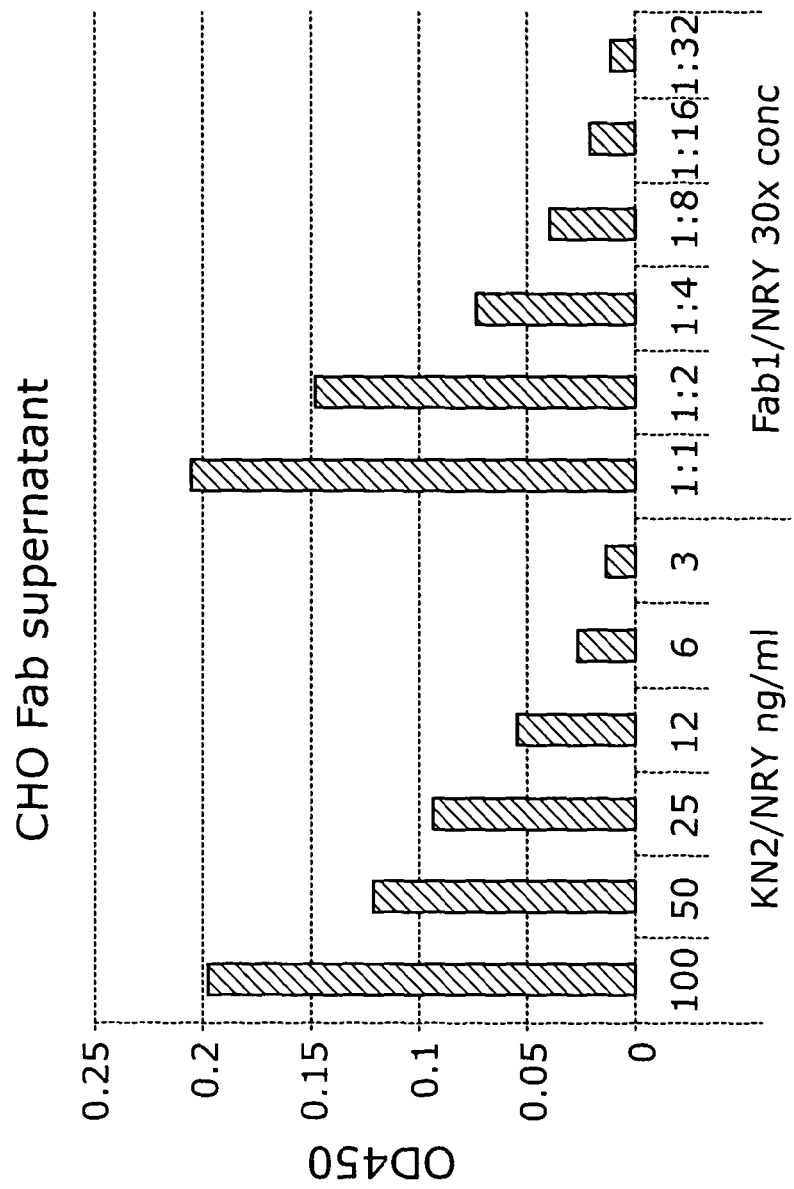

ELISA Testing of Fab:

The undiluted and the non-concentrated supernatant gave rise to a measurable but very small signal in ELISA (FIG. 22). The 30× concentrated supernatant gave rise to a larger ELISA signal. The intensity of the signal and dilution series was comparable to the standard dilution series (100 ng/ml), clealrly showing binding of Fab fragment to CD163 (FIG. 23).

Example 6: Generation and Characterization of a Rat Anti Murine CD163 Monoclonal Antibody The hybridoma clone rat anti-mouse E10B10 (IgG2a) was generated by GenScript (Piscataway, N.J., USA). As follows:

The mouse CD163 domain 1-3 was used as immunogen and 3 rats were immunized. All rats showedimmune response and the rat with highest response was used for cell fusion and hybridoma production using standard techniques. Total 18 hybridoma cell lines derived from 9 parental clones were produced and screened Murine CD163 domain 1-3 was produced as follows
1. Subcloning Target DNA sequence of mouse CD163 domain 1-3 was optimized and synthesized with C-terminal his tag, and subcloned into mammalian expression vector for transient transfection and production.
2. Evaluation of Mouse CD163 Domain 1-3 Expression and Purification 1 L of 293 cell culture were harvested and processed by one-step purification procedure using HiTrap Chelating column. The target protein was primarily eluted in the fraction of 250 mM Imidazole. Eluted material was analyzed by SDS-PAGE for the protein of interest, see FIG. 24. We obtained about 6.0 mg of protein after affinity purification.
Screening of Clones The clones were screened by testing binding of supernatants to murine CD163 in solubilized murine spleen loaded on a SDS-PAGE and western blotted, using standard techniques. The clone displaying highest signal upon binding to non-reduced CD163 was chosen, the clone is named E10B10.

The hybridoma cells were thawed and allowed to amplify a few rounds. Genscript obtained the hybridoma using standard techniques after immunization of two rats with recombinant murine CD163.
Primers:

Primers used for primary PCR amplification and sequencing of the variable light chain region of the hybridoma clone were as described in (1), but adapting the 5' (GAGG-directional) and 3' (blunt end) sequences for TOPO directional cloning. PCR amplification of the heavy chain variable region was done with the primers:

```
                                        [SEQ ID NO: 83]
3b    5'-AGGT(C/G)(A/C)AACTGCAG(C/G)AGTC(A/T)GG-3'

[SEQ ID NO: 84]
4     5'-CCAGGGGCCAGTGGATAGACAAGCTTGGGTGTCGTTTT-3'
``` as described in (2).

All primers were obtained from TAG Copenhagen (Copenhagen, Denmark).
Sequencing:

Sequencing was performed at Eurofins MWG operon (Ebersberg, Germany) as a Value Read Tube Service.

Extracting Total RNA:

$2 \times 10^6$ cells of the hybridoma cell line were used for extracting total RNA by QIAamp blood RNA kit (QIAGEN, Copenhagen, Denmark) according to the instructions of the manufacturer. Briefly, the cells were re-suspended in 600 µl buffer RLT and homogenized by passing it through a syringe mounted with a 21-G (0.8 mm) needle at least 5 times. 600 µl of 70% ethanol was added and mixed by pipetting. The suspension was applied to the QIAamp spin column and load by multiple centrifugations. The column was washed with 750 µl RW1 and 750 µl RPE. The RNA was eluted with 2×50 µl RNase free water.
Preparation of Buffers for cDNA Synthesis All buffers for the cDNA synthesis was prepared with Ultra pure or mol. bio. grade chemicals and DEPC-treated water. DEPC-treated water was prepared by adding DEPC (Sigma-Aldrich, Brøondby, Denmark) to 0.1% and the solution was stirred over night followed by autoclaving. Tris and EDTA stock solutions were made by adding the chemicals to DEPC-treated water followed by autoclaving. Buffers containing LiCl were made by dissolve LiCl in MQ water, add DEPC to 0.1% and stir over night. Subsequently, the solutions were autoclaved and Tris and EDTA solutions where added to appropriate concentrations, pH was adjusted and the solutions were autoclaved again.
cDNA Synthesis:

cDNA was synthesized by Omniscript Reverse Transcriptase (QIAGEN, Copenhagen Denmark). All buffers were DEPC treated and mixed with molecular biology grade chemicals. Briefly: Secondary structures in the RNA were disrupted by heating to 65° C. for 2 min. 100 µl Dynalbeads Oligo (dT)$_{25}$ (Invitrogen, Taastrup, Denmark) were washed twice in 1 ml binding buffer (20 mM Tris, 1 M LiCl, 2 mM EDTA) and re-suspended in 100 µl binding buffer. The heated purified RNA sample was added to the beads and incubated at room temp. for 3-5 min with rotation for annealing. Subsequently the beads were washed twice in 1 ml buffer B (10 mM Tris, 0.15 M LiCl, 1 mM EDTA) and twice in 1 ml ice-cold DEPC-water. The captured mRNA was reverse transcribed with Omniscript Reverse Transcriptase (Omniscript RT kit, QIAGEN, Copenhagen, Denmark) in a total volume of 80 µl of: 4 units ORT, 8 µl 10× buffer, 0.5 mM dNTPs, 40 units RNase inhibitor (RiboLock, Fermentas, St. Leon-Rot, Germany), by incubation at 37° C. for 2 h with gentle shaking. Finally the synthesized cDNA was washed twice in 1 ml TE buffer (20 mM Tris, 1 mM EDTA).
PCR Amplification of the Variable Regions of the Light and Heavy Chains:

Primers for amplification of the light chain variable gene were designed according to the degenerate primer sequences of Zhou and co-workers (1). Primer mixes were made with a 100 µM total primer concentration. The $V_L$ Forward mix was 20 µM in each primer concentration and the $V_L$ Back primer mix was 10 µM in each primer concentration. Primers (3b and 4) for amplification of the heavy chain variable gene were designed according DUbel et al. (2)

100 µl PCR reaction was made for amplification of $V_H$ as well as for $V_L$. The reactions contained the following: 10 µl Pfu Buffer with MgSO$_4$; 2 µl 10 mM dNTP mix; 5 µl Forward primer mix ($V_L$) or 5 pMol primer 3b ($V_H$); 5 µl Back primer mix ($V_L$) or 5 pMol primer 4 ($V_H$); 77 µl autoclaved water; 1 µl Pfu (2.5 units); and half of the cDNA containing beads from the E10B10 clone.

The cycling was as follows: Initial denaturation of 3 min at 95° C. and 30 cycles of 50 s at 95° C., 50 s at 55 (54 for $V_H$) ° C., and 3 min at 72° C. The amplified DNA is checked on a 1% agarose gel stained with EtBr and purified by gelextraction kit (Machery-Nagel, AH-Diagnostics, Aarhus, Denmark).

Sequencing:

Each purified PCR product ($V_H$ or $V_L$) was sequenced as (Value Read Tube premixed with primer) with the Forward and Back primer mix ($V_L$) or the primers 3 and 4($V_H$). All were 1 µM in each primer as final concentration.

Results

PCR Amplification of Variable Genes

1% agarose gel analysis's showed that the mRNA purifications, cDNA productions, and PCRs for amplification of the variable regions worked (see FIGS. 25 and 26).

Sequences

The products from the PCR amplification of the variable regions were purified by gel extraction and send for sequencing. Both the VH and the VL were successfully sequenced. The obtained DNA and corresponding protein sequences are shown below:

DNA
VH

[SEQ ID NO: 85]
caggtcaaactgcaggagtctggtggaggattggtgcagcctaaggagtc tttgaaaatctcatgtgcagcctctggattcaccttcagtactgctgcca tgtactgggtccgccaggctccaggaaagggtctggattgggttgctcgc ataagaactaaacctgataattatgcaacatattaccctgcttcagtgaa aggcagattcaccatctccagagatgattcaaagggcatggtctacctac aaatggataacttaaagactgaggacacagccatttattactgtacagca gcttattactatgatggccgctttgattactggggccaaggagtcatggt cacagtcgcctcagctgaaacgacacccaagcttgtctatccactggccc ctggaaaacactcg

VL

[SEQ ID NO: 86]
gacattgtgatgacccagactccatcctcccaggctgtgtcagcaggga gagggtcactatgaggtgcaagtccagtcagagtcttttatacagtgaaa acaaaaagaactacttggcctggtaccaacagaaaccagggcagtctcct aaactgttgatttcctgggcatccactagggaatctggggtccctgatcg cttcataggcagtggatctgggacagatttcactctgaccatcagcagtg tgcaggcagaagacctggctgtttattactgtgaccagtattatgatcct ccattcacgttcggctcagggacgaagttggaaataaaacgggctgatgc tgcaccaactgtatcc Protein
VH

[SEQ ID NO: 87]
QVKLQESGGGLVQPKESLKISCAASGFTFSTAAMYWVRQAPGKGLDWVAR

IRTKPDNYATYYPASVKGRFTISRDDSKGMVYLQMDNLKTEDTAIYYCTA

AYYYDGRFDYWGQGVMVTVASAETTPKLVYPLAPGKHS

VL

[SEQ ID NO: 88]
DIVMTQTPSSQAVSAGERVTMRCKSSQSLLYSENKKNYLAWYQQKPGQSP

KLLISWASTRESGVPDRFIGSGSGTDFTLTISSVQAEDLAVYYCDQYYDP

PFTFGSGTKLEIKRADAAPTVS

Production of 3E10B10

The rat hybridoma 3E10B10 (Genscript, New Jersey, USA) producing anti-mouse CD163 (domain 1-3) were adapted to serum Hybridoma-SFM serum free medium (GIBCO, Invitrogen, Denmark, Taastrup, Denmark) and antibody production was verified in a sandwich ELISA assay. Smale scale productions were seeded at $0.2 \times 10^6$ cells/ml in 15-200 ml Hybridoma-SFM medium in Triple layer tissue culture flasks (Nalge-Nunc, Roskilde, Denmark) for 5-6 days.

Purification of E10B10

The supernatant from the E10B10 expressing hybridoma cells are added Tris-HCl pH 8.0 buffer to a final concentration of 50 mM, filtered trough a 0.22 µm filter, and loaded on a Protein G-resin column (Genscript, New Jersey, USA). After loading the column is washed with 10 volumes of PBS pH 7.4 and protein eluted with a 0.1 M Na-Citrate buffer pH 3.2 into fraction tubes filled with ⅒ of the final fraction volume of 1 M Tris-HCl pH 8.0. The protein is buffer gelfiltrated into the final buffer for use. Using Sephadex G-25 (Ge Healtcare, Brøondby, Denmark)

REFERENCES FOR EXAMPLE 6

1. Zhou, H., Fisher, R. J. & Papas, T. S. (1994). Optimization of primer sequences for mouse scFv repertoire display library construction. *Nucleic Acids Res* 22, 888-9.
2. Dübel et al. (1994). Isolation of IgG antibody Fv-DNA from various mouse and rat hybridoma cell lines using the polymerase chain reaction with a simple set of primers. *J Immunol Methods:*175; 89-95

Example 7—Mac2-158 and KN2/NRY Epitope Mapping

Materials and Methods

Primers:

Primers used for SLIM mutagenesis of human CD163 to map the epitope of Mac2-158 and KN2/NRY. Primers were obtained from TAG Copenhagen (Copenhagen, Denmark).

List of Primers:

VKVQEE-->LKIHEK
LKI FT

[SEQ ID NO: 89]
attgaaaatccacgagaagtggggaacggtgtgtaataatg

LKI F

[SEQ ID NO: 90]
gtggggaacggtgtgtaataatg

LKI RT

[SEQ ID NO: 91]
ttctcgtggattttcaattccactctcccgctacac

LKI R

[SEQ ID NO: 92]
tccactctcccgctacac

R60D
R60D FT

[SEQ ID NO: 93]
gttctggagacatttggatggatcatgtttcttgtcgtg

R60D F

[SEQ ID NO: 94]
tggatcatgtttcttgtcgtg

```
R60D RT
                                            [SEQ ID NO: 95]
tccaaatgtctccagaacctgcactggaattagcccatc R60D R
                                            [SEQ ID NO: 96]
ctgcactggaattagcccatc
```

Sequencing:

Sequencing was performed at Eurofins MWG operon (Ebersberg, Germany) as a Value Read Tube Service. The primer used for sequencing was CMV primer from Eurofins MWG operon. The plasmids were considered sequenced when at least domain 1 was correctly sequenced.

SLIM Mutagenesis:

For the mutant generation the Site-directed Ligation Independent Mutagenesis (SLIM) method was used (1). Primers are listed in the primer table. The template for the generation of the two first mutants was a pcDNA5-FRT-humanCD163 plasmid harboring the full length human CD163 cDNA. The primers LKI FT, RT, F, and R were used to generate the mutant plasmid pcDNA5-FRT-humanCD163 (VKVQEE→LKIHEK). The primers R60D FT, RT, F, and R were used to generate the mutant plasmid pcDNA5-FRT-humanCD163 (R60D). Generation of a double mutant was done by performing a SLIM reaction on pcDNA5-FRT-humanCD163 (VKVQEE→LKIHEK) with the primers R60D FT, RT, F, and R.

Expression of Human CD163 and Mutants:

The expression plasmids were heat shocked into DH5a cells and plated on LB plates containing amp. Colonies were picked to over night cultures and plasmids were prepared from the cultures with the Nucleobond plasmid kit with finalizer (Macherey-Nagel, AH-Diagnostic, Aarhus, Denmark). The sequences of all plasmids were verified by sequencing.

The human CD163 wt and the three mutants were expressed transient in HEK 293 cells as follows:

8 µg of the DNA was diluted in OptiCHOPro SFM (8 mM L-glutamine) to a total volume of 0.15 ml. The DNA was gently mixed with 0.15 ml OptiCHOPro SFM containing 8 µl FreeStyle MAX transfection reagent (Invitrogen, Taastrup, Denmark). After 10 min of incubation at room temperature the DNA-FreeStyle MAX mix was added to $1\times10^6$ cells/ml in 5 ml. 3 days later the cells were harvested by centrifugation.

HRP Conjugation of KN2/NRY

HRP (P6782, Sigma-Aldrich, Brøndby, Denmark) was conjugated to MabSelect Sure purified KN2/NRY by periodate oxidation essentially as described in (2). Separation of unconjugated HRP from conjugate KN2/NRY-HRP was done by ultrafiltration on VIVAspin centrifugal concentrator (100.000 MWCO) (Sigma-Aldrich, Brøndby, Denmark). The buffer was exchanged 1000 times to PBS containing 10 mM glycine and finally BSA was added to 10 mg/ml and the conjugate was stored at 4° C. ELISA determined working dilution to 1:100-1:2000.

Western Blotting of Human CD163 and Knock Out Mutants.

Each cell pellet was added 1 ml lysis buffer (10 mM Tris pH 8, 140 mM NaCl, 15 mM $MgSO_4$ 1% Triton X-100) and incubated for 15 min at 4 □C with rotation. After centrifugation for 30 min at 6000 rpm the supernatants were sterile filtered.

90 µl of each of the supernatants were added 30 µl of 4×LDS sample buffer. 3×20 µl samples of each supernatant and 8 µl SeeBlue plus2 prestained marker were loaded on NuPage 4-12% Bis-Tris-Gels (Invitrogen, Taastrup, Denmark) and the SDS-PAGEs were run with MOPS running buffer according to instructions of the manufacturer (200 V constant for 50 min). Blotting to PVDF membranes (Invitrogen, Taastrup, Denmark) was done on an iBLOT device according to instructions of the manufacturer. After blotting the membranes were washed briefly in 1×PBS 0.1% Tween and blocked for 30 min in 1×PBS 2% Tween at room temperature with shaking. After blocking the membranes were washed 3×5 min in 1×PBS 0.1% Tween and incubated 1 hour with: (1) 10 ml 1 µg/ml polyclonal rabbit anti-human CD163; (2) 10 ml 1 µg/ml Mac2-158; (3) 10 ml 1:500 KN2/NRY-HRP all diluted in 1×PBS 0.1% Tween. The membranes were washed with 3×5 min 1×PBS 0.1% Tween again and incubated with: (1) 10 ml Goat anti-rabbit-HRP 1:1000 (AbD Serotec, Oxford, UK); or (2) 10 ml Goat anti-mouse-HRP 1:1000 (Dako, Glostrup, Denmark) for 1 hour. The membranes were washed 3×5 min in 1×PBS 0.1% Tween and were developed with Novex HRP chromogenic substrate by briefly washing the membranes in MilliQ water and adding 10 ml substrate to each blot. The precipitation of the chromogen was stopped by washing twice in MilliQ water.

Results

Site Directed Mutagenesis

The DNA sequences of the purified plasmids after mutagenesis and the corresponding protein sequences are shown below:

```
DNA
VKVQEE-->LKIHEK mutant
                                            [SEQ ID NO: 97]
Atgagcaaactcagaatggtgctacttgaagactctggatctgctgacttcagaagacat tttgtcaacctgagtcccttcaccattactgtggtcttacttctcagtgcctgttttgtc accagttctcttggaggaacagacaaggagctgaggctagtggatggtgaaaacaagtgt agcgggagagtggaattgaaaatccacgagaagtggggaacggtgtgtaataatggctgg agcatggaagcggtctctgtgatttgtaaccagctgggatgtccaactgctatcaaagcc cctggatgggctaattccagtgcaggttctggacgcatttggatggatcatgtttcttgt cgtgggaatgagtcagctctttgggattgcaaacatgatggatggggaaagcatagtaac tgtactcaccaacaagatgctggagtgacctgctcagatggatccaatttggaaatgagg ctgacgcgtggagggaatatgtgttctggaagaatagagatcaaattccaaggacggtgg
```

-continued ggaacagtgtgtgatgataacttcaacatagatcatgcatctgtcatttgtagacaactt gaatgtggaagtgctgtcagtttctctggttcatctaattttggagaaggctctggacca atctggtttgatgatcttatatgcaacggaaatgagtcagctctctggaactgcaaacat caaggatggggaaagcataactgtgatcatgctgaggatgctggagtgatttgctcaaag ggagcagatctgagcctgagactggtagatggagtcactgaatgttca R60D
[SEQ ID NO: 98]
Atgagcaaactcagaatggtgctacttgaagactctggatctgctgacttcagaagacat tttgtcaacctgagtcccttcaccattactgtggtcttacttctcagtgcctgttttgtc accagttctcttggaggaacagacaaggagctgaggctagtggatggtgaaaacaagtgt agcgggagagtggaagtgaaagtccaggaggagtggggaacggtgtgtaataatggctgg agcatggaagcggtctctgtgatttgtaaccagctgggatgtccaactgctatcaaagcc cctggatgggctaattccagtgcaggttctggagacatttggatggatcatgtttcttgt cgtgggaatgagtcagctcttgggattgcaaacatgatggatggggaaagcatagtaac tgtactcaccaacaagatgctggagtgacctgctcagatggatccaatttggaaatgagg ctgacgcgtggagggaatatgtgttctggaagaatagagatcaaattccaaggacggtgg ggaacagtgtgtgatgataacttcaacatagatcatgcatctgtcatttgtagacaactt gaatgtggaagtgctgtcagtttctctggttcatctaattttggagaaggctctggacca atc Double mutant
[SEQ ID NO: 99]
Atgagcaaactcagaatggtgctacttgaagactctggatctgctgacttcagaagacat tttgtcaacctgagtcccttcaccattactgtggtcttacttctcagtgcctgttttgtc accagttctcttggaggaacagacaaggagctgaggctagtggatggtgaaaacaagtgt agcgggagagtggaattgaaaatccacgagaagtggggaacggtgtgtaataatggctgg agcatggaagcggtctctgtgatttgtaaccagctgggatgtccaactgctatcaaagcc cctggatgggctaattccagtgcaggttctggagacatttggatggatcatgtttcttgt cgtgggaatgagtcagctcttgggattgcaaacatgatggatggggaaagcatagtaac tgtactcaccaacaagatgctggagtgacctgctcagatggatccaatttggaaatgagg ctgacgcgtggagggaatatgtgttctggaagaatagagatcaaattccaaggacggtgg ggaacagtgtgtgatgataacttcaacatagatcatgcatctgtcatttgtagacaactt gaatgtggaagtgctgtcagtttctct Protein
VKVQEE-->LKIHEK mutant
[SEQ ID NO: 100]
MSKLRMVLLEDSGSADFRRHFVNLSPFTITVVLLLSACFVTSSLGGTDKELRLVDGENKCSGRVE

LKIHEKWGTVCNNGWSMEAVSVICNQLGCPTAIKAPGWANSSAGSGRIWMDHVSCRGNESAL

WDCKHDGWGKHSNCTHQQDAGVTCSDGSNLEMRLTRGGNMCSGRIEIKFQGRWGTVCDDNF

NIDHASVICRQLECGSAVSFSGSSNFGEGSGPIWFDDLICNGNESALWNCKHQGWGKHNCDHA

EDAGVICSKGADLSLRLVDGVTECS

R60D

[SEQ ID NO: 101]

MSKLRMVLLEDSGSADFRRHFVNLSPFTITVVLLLSACFVTSSLGGTDKELRLVDGENKCSGRVE

VKVQEEWGTVCNNGWSMEAVSVICNQLGCPTAIKAPGWANSSAGSGDIWMDHVSCRGNESAL

WDCKHDGWGKHSNCTHQQDAGVTCSDGSNLEMRLTRGGNMCSGRIEIKFQGRWGTVCDDNF

NIDHASVICRQLECGSAVSFSGSSNFGEGSGPI

Double mutant

[SEQ ID NO: 102]

MSKLRMVLLEDSGSADFRRHFVNLSPFTITVVLLLSACFVTSSLGGTDKELRLVDGENKCSGRVE

LKIHEKWGTVCNNGWSMEAVSVICNQLGCPTAIKAPGWANSSAGSGDIWMDHVSCRGNESAL

WDCKHDGWGKHSNCTHQQDAGVTCSDGSNLEMRLTRGGNMCSGRIEIKFQGRWGTVCDDNF

NIDHASVICRQLECGSAVSFS

Western Blotting of Mutants:

Three western blots were made. The SDS-PAGE had in all blots the following loaded: SeeBlue plus2 prestained marker (lane 1); human CD163 wt (lane 2); human CD163 R60D (lane 3); human CD163 VKVQEE→LKIHEK (lane 4); human CD163 double mutant (lane 5); and negative transfection control (lane 6). Western blotting with polyclonal rabbit anti-CD163 was used to estimate the protein expression level. This western blot (FIG. 27 A) showed that the mutant R60D was not expressed to the same extend as was the wild type human CD163, the VKVQEE→LKIHEK mutant, or the double mutant (which were al expressed to the same extent), but still at a detectable level. FIG. 27 B shows the testing of Mac2-158 on the different mutants. Mac2-158 bound to the human CD163 wt and the R60D mutant. Binding to the R60D mutant was very weak. No binding was detected to any of the LKIHEK containing mutants. The humanized antibody KN2/NRY-HRP conjugated showed only binding to the human CD163 wt (FIG. 27 C). Binding to the R60D mutant could for this antibody not be detected.

This showed that we could knock-out binding of Mac2-158 and KN2/NRY with the same mutants, identifying at least part of the binding epitope for these mAbs.

Knock in Mac2-158 and KN2/NRY Epitope.

Materials and Methods

Plasmids:

A midiprep of pEF4N5/His vector (Invitrogen, Taastrup, Denmark) containing mouse CD163 domain 1-5 was used for expression of mouse CD163 domain 1-5N5/His. A mutant (LKIHDK→VKVQEE, Y60R) in domain 1 of mouse CD163 1-5 was ordered as midiprep at GenScript (Piscataway, N.J., USA). Sequences DNA and protein of mutants are show below (mutant only domain 1).

HRP Conjugation of KN2/NRY

HRP (P6782, Sigma-Aldrich, Brøondby, Denmark) was conjugated to MabSelect Sure purified KN2/NRY by periodate oxidation essentially as described in (2). Separation of unconjugated HRP from conjugate KN2/NRY-HRP was done by ultrafiltration on VIVAspin centrifugal concentrator (100.000 MWCO) (Sigma-Aldrich, Brøondby, Denmark). The buffer was exchanged 1000 times to PBS containing 10 mM glycine and finally BSA was added to 10 mg/ml and the conjugate was stored at 4° C. ELISA determined working dilution to 1:100-1:2000 (data not shown).

DNA
mouse CD163 1-5 wt

[SEQ ID NO: 103]

atgggtggacacagaatggttcttcttggaggtgctggatctcctggttgtaaaaggttt gtccatctaggtttctttgttgtggctgtgagctcacttctcagtgcctctgctgtcact aacgctcctggagaaatgaagaaggaactgagactggcgggtggtgaaaacaactgtagt gggagagtggaacttaagatccatgacaagtggggcacagtgtgcagtaacggctggagc atgaatgaagtgtccgtggtttgccagcagctgggatgcccaacttctattaaagcccctt ggatgggctaactccagcgccggctctggatatatctggatggacaaagtttcttgtaca gggaatgagtcagctctttgggactgcaaacatgatgggtggggaaagcataactgtacc catgaaaaagatgctggagtgacctgctcagatggatctaatttggagatgagactggtg aacagtgcgggccaccgatgcttaggaagagtagaaataaagttccagggaaagtggggg acggtgtgtgacgacaacttcagcaaagatcacgcttctgtgatttgtaaacagcttgga tgtggaagtgccattagtttctctggctcagctaaattgggagctggttctggaccaatc tggctcgatgacctggcatgcaatggaaatgagtcagctctctgggactgcaaacaccgg ggatggggcaagcataactgtgaccatgctgaggatgtcggtgtgatttgcttagaggga -continued

```
gcagatctgagcctgagactagtggatggagtgtccagatgttcaggaagattggaagtg agattccaaggagaatgggggaccgtgtgtgatgataactgggatctccgggatgcttct gtggtgtgcaagcaactgggatgtccaactgccatcagtgccattggtcgagttaatgcc agtgagggatctggacagatttggcttgacaacatttcatgcgaaggacatgaggcaact ctttggagtgtaaacaccaagagtggggaaagcattactgtcatcatagagaagacgct ggcgtgacatgttctgatggagcagatctggaacttagacttgtaggtggaggcagtcgc tgtgctggcattgtggaggtggagattcagaagctgactgggaagatgtgtagccgaggc tggacactggcagatgcggatgtggtttgcagacagcttggatgtggatctgcgcttcaa acccaggctaagatctactctaaaactggggcaacaaatacgtggctctttcctggatct tgtaatggaaatgaaactactttttggcaatgcaaaaactggcagtggggcggccttcc tgtgataatttcgaagaagccaaagttacctgctcaggccacagggaacccagactggtt ggaggagaaatcccatgctctggtcgtgtggaagtgaaacacggagacgtgtgggctcc gtctgtgattttgacttgtctctggaagctgccagtgtggtgtgcagggaattacaatgt ggaacagtcgtctctatcctaggggagcacattttggagaaggaagtggacagatctgg ggtgaagaattccagtgtagtggggatgagtcccatctttcactatgctcagtggcgccc ccgctagacagaacttgtacccacagcagggatgtcagcgtagtctgctcaaatctagag ggcccgcggttcgaaggtaagcctatccctaaccctctcctcggtctcgattctacgcgt accggtcatcatcaccatcaccattga
```

Mouse CD163 1-5 LKIHDK-->VKVQEE, Y60R mutant

[SEQ ID NO: 104]

```
Atgggtggacacagaatggttcttcttggaggtgctggatctcctggttgtaaaaggttt gtccatctaggtttctttgttgtggctgtgagctcacttctcagtgcctctgctgtcact aacgctcctggagaaatgaagaaggaactgagactggcgggtggtgaaaacaactgtagt gggagagtggaagtgaaggtgcaggaggagtggggcacagtgtgcagtaacggctggagc atgaatgaagtgtccgtggtttgccagcagctgggatgcccaacttctattaaagcccct ggatgggctaactccagcgccggctctggacggatctggatggacaaagtttcttgtaca gggaatgagtcagctctttgggactgcaaacatgatgggtggggaaagcataactgtacc catgaaaaagatgctggagtgacctgctcagatggatctaatttggagatgagactggtg aacagtgcgggccaccgatgcttaggaagagtagaaataaagttccagggaaagtggggg acggtgtgtgacgacaacttcagcaaagatcacgcttctgtgatttgtaaacagcttgga tgtggaagtgccattagtttctctggctcagctaaattgggagctggttctggaccaatc tggctcgatgac
```

Protein
Mouse CD163 1-5 wt

[SEQ ID NO: 105]

MGGHRMVLLGGAGSPGCKRFVHLGFFVVAVSSLLSASAVTNAPGEMKKELRLAGGENNCS

GRVELKIHDKWGTVCSNGWSMNEVSVVCQQLGCPTSIKALGWANSSAGSGYIWMDKVSCT

GNESALWDCKHDGWGKHNCTHEKDAGVTCSDGSNLEMRLVNSAGHRCLGRVEIKFQGKWG

TVCDDNFSKDHASVICKQLGCGSAISFSGSAKLGAGSGPIWLDDLACNGNESALWDCKHR

GWGKHNCDHAEDVGVICLEGADLSLRLVDGVSRCSGRLEVRFQGEWGTVCDDNWDLRDAS

VVCKQLGCPTAISAIGRVNASEGSGQIWLDNISCEGHEATLWECKHQEWGKHYCHHREDA

GVTCSDGADLELRLVGGGSRCAGIVEVEIQKLTGKMCSRGWTLADADVVCRQLGCGSALQ

TQAKIYSKTGATNTWLFPGSCNGNETTFWQCKNWQWGGLSCDNFEEAKVTCSGHREPRLV

```
GGEIPCSGRVEVKHGDVWGSVCDFDLSLEAASVVCRELQCGTVVSILGGAHFGEGSGQIW

GEEFQCSGDESHLSLCSVAPPLDRTCTHSRDVSVVCSNLEGPRFEGKPIPNPLLGLDSTR

TGHHHHHH

Mouse CD163 1-5 LKIHDK-->2VKVQEE, Y60R mutant
                                                [SEQ ID NO: 106]
MGGHRMVLLGGAGSPGCKRFVHLGFFVVAVSSLLSASAVTNAPGEMKKELRLAGGENNCS

GRVEVKVQEEWGTVCSNGWSMNEVSVVCQQLGCPTSIKALGWANSSAGSGRIWMDKVSCT

GNESALWDCKHDGWGKHNCTHEKDAGVTCSDGSNLEMRLVNSAGHRCLGRVEIKFQGKWG

TVCDDNFSKDHASVICKQLGCGSAISFSGSAKLGAGSGPIWLDD
```

Expression of Mouse CD163 1-5 and Mutant:

The mouse CD163 1-5 and the mouse CD163 domain 1 mutant were expressed transient in Lenti-X 293T cells as follows: 1.5 µg of the DNA was diluted in OptiCHOPro SFM (8 mM L-glutamine) to a total volume of 50 µl. The DNA was gently mixed with 50 µl of OptiCHOPro SFM containing 1.5 µl Freestyle MAX transfection reagent (Invitrogen, Taastrup, Denmark). After 10 min of incubation at room temperature the complexes were added to $1\times10^6$ cells in 1 ml. Three days later, the cell supernatants were harvested by centrifugation.

Western Blotting of Mouse CD163 and Knock in Mutant.

Ni-NTA His-bind resin (Merck-Chemicals, Darmstadt, Germany) was washed in 50 mM Tris pH 8 buffer, and cell culture supernatants were added 60 µl of Ni-NTA His-bind resin slurry. After 1 hour shaking at 4° C. the supernatants were aspired and each of the purifications were eluted with 90 µl 50 mM Tris pH 8, 25 mM EDTA buffer.

90 µl of each of the eluates were added 30 µl of 4×LDS sample buffer. 20 µl samples of each supernatant and 8 µl SeeBlue plus2 prestained marker were loaded on NuPage 4-12% Bis-Tris-Gels (Invitrogen, Taastrup, Denmark) and the SDS-PAGEs were run with MOPS running buffer according to instructions of the manufacturer (200 V constant for 50 min). Blotting to PVDF membranes (Invitrogen, Taastrup, Denmark) was done on an iBLOT device according to instructions of the manufacturer. After blotting the membranes were washed briefly in 1×PBS 0.1% Tween and blocked for 30 min in 1×PBS 2% Tween at room temperature with shaking. After blocking the membranes were washed 3×5 min in 1×PBS 0.1% Tween and incubated 1 hour with: (1) 1:5000 Anti-V5 (Invitrogen, Taastrup, Denmark); or (2) 1 µg/ml Mac2-158. The membranes were washed with 3×5 min 1×PBS 0.1% Tween again and incubated with: Goat anti-mouse-HRP 1:2000 (Dako, Glostrup, Denmark) for 1 hour. The membranes were washed 3×5 min in 1×PBS 0.1% Tween and developed with Novex HRP chromogenic substrate (Invitrogen, Taastrup, Denmark) by briefly washing the membranes in MilliQ water and adding 10 ml substrate to each blot. The precipitation of the chromogen was stopped by washing twice in MilliQ water.

Results

Sequences of the Mouse CD163 Domain 1-5 wt and Mutants:

```
DNA
mouse CD163 1-5 wt
                                                [SEQ ID NO: 107]
atgggtggacacagaatggttcttcttggaggtgctggatctcctggttgtaaaaggttt gtccatctaggtttctttgttgtggctgtgagctcacttctcagtgcctctgctgtcact aacgctcctggagaaatgaagaaggaactgagactggcgggtggtgaaaacaactgtagt gggagagtggaacttaagatccatgacaagtggggcacagtgtgcagtaacggctggagc atgaatgaagtgtccgtggtttgccagcagctgggatgcccaacttctattaaagcccctt ggatgggctaactccagcgccggctctggatatatctggatggacaaagtttcttgtaca gggaatgagtcagctctttgggactgcaaacatgatgggtggggaaagcataactgtacc catgaaaaagatgctggagtgacctgctcagatggatctaatttggagatgagactggtg aacagtgcgggccaccgatgcttaggaagagtagaaataaagttccagggaaagtggggg acggtgtgtgacgacaacttcagcaaagatcacgcttctgtgatttgtaaacagcttgga tgtggaagtgccattagtttctctggctcagccaaattgggagctggttctggaccaatc tggctcgatgacctggcatgcaatggaaatgagtcagctctctgggactgcaaacaccgg ggatggggcaagcataactgtgaccatgctgaggatgtcggtgtgatttgcttagaggga gcagatctgagcctgagactagtggatggagtgtccagatgttcaggaagattggaagtg agattccaaggagaatgggggaccgtgtgtgatgataactgggatctccgggatgcttct gtggtgcgcaagcaactgggatgtccaactgccatcagtgccattggtcgagttaatgcc
```

-continued

```
agtgagggatctggacagattcggcttgacaacatctcatgcgaaggacatgaggcaact ctttggagtgtaaacaccaagagtggggsaagcattactgtcatcatagagaagacgct ggcgcgacatgttctgatggagcagatctcgaacteagacttgtaggtggaggcagtcgc tgtgctggcattgcggaggtggagattcacaagctgactgggaagatgtgtagccgaggc tggacactggcagatgcggatgtggtttgcagacagcttggatgtggacctgcgcttcaa acccaggctaagatctactctaaaactggcgcaacaaatacgcggctccttcccggacct tgtaatggaaatgaaactacttttggcaatgcaaaaactggcagtggggcggcctttcc tgtgataatttcgaagaagccaaagttacctgctcaggccacagggaacccagactggtt ggaggagaaatcccacgctctggtcgtgtcgaagtgaaacacggagacgtgtgggctcc gtctgtgattttgacttgtctctggaagctgccagtgtggtgtgcagggaattacaatgt ggaacagtcgtctctatcctagggggagcscatcttggagaaggaagtggacagatctgg ggtgaagaattccagcgtagtggggatgacccccatctttcactatgctcagtggcgccc ccgctagacagaacttgtacccacagcagggatgtcagcgtagtctgctcaaatctagag ggcccgcggttcgaaggtaagcctatccctaaccctctcctcggtctcgattctacgcgt accggtcatcatcaccatcaccattga
```

Mouse CD163 1-5 LKIHDK-->VKVQEE, Y60D mutant
[SEQ ID NO: 108]

```
Atgggtggacacagaatggttcttcttgcsggtgctggatctcctggttgtaaaaggttt gtccatctaggtttctttgttgtggctgtcagctcacttctcagtgcctctgctgtcact aacgctcctggagaaatgaagaaggaactcagactggcgggtggtgaaaacaactgtagc gggagagtggaagtgaaggtgcaggaggactggggcacagtgtgcagtaacggctggagc atgaatgaagtgtccgtggcttgccagcacctgggatgcccaacttctattaaagccctt ggatgggctaactccagcgccggctctggacggatctggatggacaaagtttcttgtaca gggaatgagtcagctctttgggactgcaaacatgatgggtggggaaagcataactgtacc catgaaaaagatgctggagtgacccgctcagacggatctaatttggagatgagactggtg aacagtgcgggccaccgatgcttaggaagagtagaaataaagttccagggaaagtggggg acggtgtgtgacgacaacttcagcaaagatcacgcttctgtgatttgtaaacagcttgga tgtggaagtgccattagtttctctggctcagctaaattgggagctggttctggaccaatc tggctcgatgac
```

Protein
Mouse CD163 1-5 wt
[SEQ ID NO: 109]

MGGHRMVLLGGAGSPGCKRFVHLGFFVVAVSSLLSASAVTNAPGEMKKELRLAGGENNCS
GRVELKIHDKWGTVCSNGWSMNEVSVVCQQLGCPTSIKALGWANSSAGSGYIWMDKVSCT
GNESALWDCKHDGWGKHNCTHEKDAGVTCSDGSNLEMRLVNSAGHRCLGRVEIKFQGKWG
TVCDDNFSKDHASVICKQLGCGSAISFSGSAKLGAGSGPIWLDDLACNGNESALWDCKHR
GWGKHNCDHAEDVGVICLEGADLSLRLVDGVSRCSGRLEVRFQGEWGTVCDDNWDLRDAS
VVCKQLGCPTAISAIGRVNASEGSGQIWLDNISCEGHEATLWECKHQEWGKHYCHHREDA
GVTCSDGADLELRLVGGGSRCAGIVEVEIQKLTGKMCSRGWTLADADVVCRQLGCGSALQ
TQAKIYSKTGATNTWLFPGSCNGNETTFWQCKNWQWGGLSCDNFEEAKVTCSGHREPRLV
GGEIPCSGRVEVKHGDVWGSVCDFDLSLEAASVVCRELQCGTVVSILGGAHFGEGSGQIW
GEEFQCSGDESHLSLCSVAPPLDRTCTHSRDVSVVCSNLEGPRFEGKPIPNPLLGLDSTR
TGHHHHHH

```
Mouse CD163 1-5 LKIHDK-->VKVQEE, Y60R mutant
                                           [SEQ ID NO: 110]
MGGHRMVLLGGAGSPGCKRFVHLGFFVVAVSSLLSASAVTNAPGEMKKELRLAGGENNCS

GRVEVKVQEEWGTVCSNGWSMNEVSVVCQQLGCPTSIKALGWANSSAGSGRIWMDKVSCT

GNESALWDCKHDGWGKHNCTHEKDAGVTCSDGSNLEMRLVNSAGHRCLGRVEIKFQGKWG

TVCDDNFSKDHASVICKQLGCGSAISFSGSAKLGAGSGPIWLDD
```

Western Blotting of Mutants:

SDS-PAGE gels had the following loaded: (1) Mouse CD163 1-5 LKIHDK→VKVQEE, Y60R mutant, (2) mouse CD163 1-5 wt, (3) negative transfection control, (4) SeeBlue plus2 pre-stained marker, (5) positive blotting control (mouse CD163 (D) or human CD163 (E)) (FIG. 27). The V5 antibody was used to confirm and estimate protein expression. This showed that both the wt mouse CD163 1-5 and the mutant were expressed at reasonable level. The blot incubated with Mac2-158 showed that Mac2-158 did not bind to the wt mouse CD163 1-5 but that Mac2-158 did bind to the mutant mouse CD163 1-5 LKIHDK→VKVQEE, Y60R. A similar but faint band could be seen in the blots developed using Kn22NRY-HRP (not shown). Thus we can insert the hypotized KN2/NRY and Mac2-158 epitope onto a murine CD163 framework, showing that it is indeed, at least part of, the epitope.

REFERENCES FOR EXAMPLE 7

1. Chiu et al. (2004). Site-directed Ligase Independent Mutagenesis (SLIM): a single-tube methodology approaching 100% efficiency in 4 h. *Nucleic Acids Res* 32(21): e174.
2. Boorsma and Streefkerk (1979). Periodate or glutaraldehyde for preparing peroxidase conjugates. *J Immunol. Methods* 30: 245-55.

Example 8—Preparation of Corticosteroid Conjugated Antibodies

Origin of Antibodies and Haptoglobin to be Conjugated

Anti-human CD163 murine mAbs Mac2-48 and Mac 2-158, from IQ-products, the Netherlands. The humanized CD163 antibody KN2/NRY described in example 3. Anti-rat CD163 ED2, purchased from AbD-Serotec, the Netherlands, product number MCA342R and described by Dijkstra et al. (Immunology (1985), 54:589-99) E10B10 a rat anti-mouse CD163 antibody described in example 6. Haptoglobin of phenotype 1-1 (Hp) was purchaced from Sigma-Aldrich (St. Louis, Mo., USA, product number H9762).

Details concerning dexamethasone-MVCP and dexamethasone-NHS, and their preparation, are given in the accompanying Examples (such as Example 10).

Determination of Free and Protein-Conjugated Corticosteroids by HPLC

Material and Methods

This method is used to measure the amount of free corticosteroids (Dexamethasone, Dexamethasone-phosphate, Dexamethasone-acetate, Prednisolone, Methyl-Prednisolone or Fluocinolone-Acetonide) and corticosteroid-hemisuccinate (Dexamethasone-hemisuccinate, Prednisolone-hemisuccinate, Methylprednisolone-hemisuccinate or Fluocinolone-Acetonide-hemisuccinate) in aqueous samples as well as the amount of total corticosteroids in protein-corticosteroid-conjugates.

Sample Preparation for Free Corticosteroids and Corticosteroid-Hemisuccinate

HPLC at pH 5

About 100 μl of sample or diluted sample are filtered through 0.45 μm RC membrane syringe filters (Phenomenex, Danmark) directly into HPLC vials.

HPLC at pH 2

Spin filters (30 kD cut off, 500 μl volume, Millipore, Danmark) are rinsed by spinning twice with 500 μl water for 10 minutes each. Water is discarded, 50 μl of sample or diluted sample are filtered through and filter is rinsed with 50 μl of the respective sample buffer. Volume of filtrate is determined and filtrate transferred to HPLC vials.

Total Corticosteroid in Protein-Corticosteroid-Conjugates

20 μl samples of protein-corticosteroid-conjugates are hydrolyzed by incubation with 50 μl 0.1 M sodium hydroxide for 15 minutes at room temperature. The pH is adjusted afterwards with 50 μl 0.1 M hydrochloric acid. Samples are filtered through 0.45 μm syringe filters (Phenomenex, Danmark) into HPLC vials.

Total Corticosteroid in Corticosteroid Loaded Liposomes

20 μl samples of corticosteroid loaded liposome are diluted with a 10% ethanole solution and loaded into HPLC vials and injected directly on the column. The 40% acetonitrile in the running buffer disintegrates the liposomes, as verified by light scatter measurements (not shown).

HPLC Analysis of Samples 1 to 50 μl samples are run over an C18 column (Hyperclone C18, 3 μm, 150×460, Phenomenex, Danmark) in an Shimadzu 10 A HPLC System (Shimadzu, Japan) and eluted isocratically with either 40% acetonitril (HPLC-grade, Scharlau, Germany) in 50 mM potassium-acetate buffer, pH 5.0 or 40% acetonitril, 0.005% Trifluoracetic Acid (Sigma-Aldrich, Danmark) (pH 2) at 0.5 ml/min. Peaks are detected by absorption measurement at 240 nm by a Shimadzu SPD 10A VP detector. Run time per injection is between 15 and 30 minutes, depending on retention time of the corticosteroid analyzed. Column heater is set to 30° C. and autosampler/vial holder to 4° C.

All solvents are filtered through 0.45 μm RC-membrane filters (Whatman, RC 55) and degassed under vacuum.

Calibration of HPLC for Corticosteroids and Corticosteroid-Hemisuccinate

A 2 ug/ml solution of corticosteroid, respectively corticosteroid-hemisuccinate, in 10% EtOH (Dexamethasone for HPLC; Dexamethasone-21-phosphate disodium salt 98%, Dexamethasone-21-acetate 99%, Prednisolone 99%, Prednisolone 21-hemisuccinate sodium salt, Fluocinolone acetonide 98%, 6α-Methylprednisolone 21-hemisuccinate sodium salt, all Sigma-Aldrich, Danmark; is used in triplicate at different injection volumes to obtain a linear calibration curve.

Amount of corticosteroid or corticosteroid-hemisuccinate in sample injected is calculated by integration of peak area and calculating the amount according to the respective calibration curve by LC Solution software (Shimadzu, Japan).

Estimation of Residual MVCP-Dexamethasone

To estimate amount of residual MVCP-dexamethasone in the conjugates, MVCP-dexamethasone (10 mg/ml in DMSO) is diluted 25 times in 50 mM borate buffer and mixture run over HPLC as described above. Area of all peaks in conjugate samples corresponding to peaks in MVCP-dexamethasone chromatogram (3 peaks) is summarized and amount of MVCP-dexamethasone estimated according to dexamethasone-calibration curve.

FIG. 28 shows a typical chromatogram from a determination of free dexamethasone/dexamethasone-hemisuccinate and total dexamethasone in a conjugate sample (ED2-dexamethasone). Samples between 0.02 mg/l and 3 mg/l corticosteroid or corticosteroid-hemisuccinate can reliably be analyzed by this HPLC method. Mean standard deviation in concentration of samples injected three times from the same vial is 3.6%, (max. 17.3%, min. 0%, median 1.5%, n=56*3 runs). Mean standard deviation in concentration of total dexamethasone in two independent determinations (two times alcalic hydrolysis) of one sample is 3.4% (max. 8.1%, min. 0%, median 2.9%, n=46*2 runs).

The described method for the determination of free and protein-conjugated corticosteroids by HPLC works well for a range of corticosteroids and corticosteroid-hemisuccinate tested. It is fast, sensitive and highly reproducible.

Synthesis of Antibody-Corticosteroid-Conjugates

1. Synthesis by Aminocoupling to Corticosteroid-NHS

Materials and Methods

Corticosteroid-NHS preparations (Dexamethasone-NHS, Prednisolone-NHS, Fluocinolone-Acetonide-NHS, all freeze-dried) were stored at −20° C. and a 1 mg/ml solution in DMSO prepared freshly for each conjugation reaction.

Antibody and protein solutions were used in a final concentration of 1 mg/ml in 50 mM borate buffer, pH 8.3.

Typically, 50 µl of the 1 mg/ml Corticosteroid-NHS solution in DMSO per mg protein were added slowly to the protein/antibody solution while gently stirring the solution on a laboratory mixer. This gives a final ratio of conjugated corticosteroid to protein (M/M, with ED2 as antibody) of 4-5, but ratio can be adjusted by in-/decreasing volume of Corticosteroid-NHS solution per mg antibody.

Reaction mix was then incubated for 15 minutes at 25° C. on a thermomixer (Thermomixer comfort, Eppendorf Ag) while gently agitating.

To stop the conjugation reaction 100 µl 5 mM Glycin in 50 mM borate buffer pH 8.3 were added per ml reaction mix and incubated at 25° C. for further 30 minutes with gentle agitation. Reaction mixture were then diafiltered in spin filters (Amicon-Ultra, 30K, Millipore Corp.) into storage buffer, typically PBS (Gibco, Invitrogen)+2.5% EtOH or 10 mM Citrat buffer, 144 mM NaCl, 2.5% EtOH, pH 6.0 or 25 mM Citrat buffer, 125 mM NaCl, 2.5% EtOH, pH 5.0. Conjugates were sterile filtered and analyzed for protein concentration and amount of free and total (free+bound) corticosteroid. They were diluted to desired concentration in respective buffer and stored either at 4° C. or in liquid nitrogen.

FIG. 28D shows typical conjugation parameters of different NHS-conjugates. In all different kinds of conjugates percentage of free corticosteroid-HS after coupling is very low (under 3%), which indicates a good conjugation efficiency.

Aminocoupling of antibodies to Corticosteroid-NHS has been tested for the antibodies ED2, E10B10, Mac2-158 and KN2NRY and to the natural CD163 protein ligand haptoglobin and with the corticosteroids. Dexamethasone, Prednisolone and Fluocinolone-acetonide. Our data show, that it is an efficient and, with regard to ratio, reproducible method for conjugation of corticosteroids to antibodies. The degree of reactivity seems to depend as well on the type of corticosteroid used as on antibody characteristics. Conjugates are stored frozen.

2. Synthesis by Reduction of Protein Disulfide-Bonds and Conjugation with MVCP-Corticosteroid Materials and Methods MVCP-dexamethasone preparations (freeze-dried) were dissolved in DMSO at 10 mg/ml and stored at −20° C. Antibody solutions were obtained either from purification of cell culture supernatants prepared in house (3E10B10, KN2NRY) or from AbD Serotec (ED2) and were used in a final concentration of 1 mg/ml in 50 mM borate buffer, pH 8.3.

Reduction of Antibody

Typically, 70 µl of a 100 mM DTT (Fluka, >99%) solution were added per mg of protein and mixture was incubated for 30 minutes at 25° C. with gentle agitation on a thermomixer (Thermomixer comfort, Eppendorf AG). This leads to complete reduction of interchain disulphide bridges of the antibody. To achieve lower conjugation ratios, incomplete reduction can be achieved by lowering the amount of DTT added.

To remove DTT, reaction mix was run over a gel filtration column (Sephadex G 25, GE Heathcare), which was previously sanitized by running with 0.5 M NaOH+ 0.5 M NaCl for one hour and afterwards equilibrated in PBS+5 mM EDTA. Protein was eluted with PBS+5 mM EDTA to preserve reduced Cysteins and protein-containing fractions were pooled. Protein concentration in pool was determined by $OD_{280}$ measurement (Nanodrop ND-1000, Nanodrop Technologies).

Conjugation of Antibody to MVCP-Dexamethasone

MVCP-dexa is added in a 150 fold molar excess. In practice, 40 µl of the 10 mg/ml MVCP-dexamethasone solution in DMSO per mg of antibody were slowly added to antibody solution while gently stirring on a laboratory mixer. Reaction mix was incubated for 1 hour at 25 1 C with gentle agitation on a thermomixer. Reaction mixture was then diafiltered in spin filters (Amicon-Ultra, 30K, Millipore Corp.) into storage buffer, typically PBS (10×PBS; Gibco, Invitrogen)+2.5% EtOH. Conjugates were sterile filtered and analyzed for protein concentration and amount of free and total (free+bound) dexamethasone. They were diluted to desired concentration in respective buffer and stored either at 4° C. or in liquid nitrogen.

Results

FIG. 28E shows typical conjugation parameters of different MVCP-conjugations. A ratio of about 8-12 is generally achieved. Coupling of corticosteroids to reduced antibodies via Cysteine-linker has been tested with MVCP-dexamethasone and the antibodies ED2, 3E10B10 and KN2NRY. Our results show, that this method of conjugation works reproducible with different antibodies.

Affinity Testing of Conjugated KN2/NRY

NHS-dexamethasone and MVCP-dexamethasone conjugated KN2/NRY has been tested for binding to CD163 immobilized on a Biacore chip. The binding experiment was conducted as for example 1. The result is shown in FIGS. 29B and E, and shows that only a minimal reduction in affinity was induced by the conjugations, regardless of the method used.

Formation of Stealth-Liposomes

Methylprednisolone hemisuccinate (MPS-HS, Sigma) was loaded into liposomes using the remote loading method described by Avnir et. al (Avnir et al. Amphipathic weak acid glucocorticoid prodrugs remote-loaded into sterically stabilized nanoliposomes evaluated in arthritic rats and in a Beagle dog: a novel approach to treating autoimmune arthritis. Arthritis Rheum (2008) vol. 58 (1) pp. 119-29) and briefly explained here. Liposomes were prepared using the ethanol-injection method from a mixture of HSPC, mPEG2000-PE and Cholesterol (molar ratio of 55:40:5) (all Avanti polar lipids, Alabaster, Ala., USA). Lipids were dissolved in 100 µl EtOH at ~65□C for 15 min and hydrated in 900 ul of aqueous buffer to from MLV's. Liposomes were sized by extrusion 25 times through a 100 nm filter and dialysed twice against 150 mM NaCl (0.9% NaCl) with second dialysis being over might at 4□C to generate a transmembrane calcium gradient. For loading of liposomes with methylprednisolone-hemisuccinate, methyl-rednisolone hemisuccinate (preparred as described in example 10) is incubated with liposomes for 15 min at 60° C. (molar drug:lipid ratio 1:20). Finaly MPS-loaded liposomes were cooled to 4° C. and dialysed against 150 mM NaCl to remove excess drug. Liposome size was estimated using a Wyatt minidawn light scatter (Wyatt Technologies, Santa Barbara, Calif., USA).

Attachment of Protein to pNP-PEG2000-PE.

For attachment of protein or antibody to liposomes antibodies was initially modified by pNP-PEG2000-PE (NGPE). NGPE was synthesized an described by Torchilin et. al. (Torchilin et al. p-Nitrophenylcarbonyl-PEG-PE-liposomes: fast and simple attachment of specific ligands, including monoclonal antibodies, to distal ends of PEG chains via p-nitrophenylcarbonyl groups. (Biochim Biophys Acta (2001) vol. 1511 (2) pp. 397-411)). NGPE were dried by argon from chloroform and then solubilzed in 50 µl of CBS pH 5.0 (5 mM NaCltrate, 140 mM NaCl)+5 mg/ml Octyl glucoside. Protein was added to solubilized NGPE (1:40 molar ratio) and pH was adjusted to 8.5 using PBS pH 8.5 and 0.1 M NaOH, the mixture was incubated over night at 4□C. Modified antibody or protein was then added to preformed liposomes incubated over night at 4□C and finaly purified by dialysis in a spectrum dialysis tube (MWCO 250 kDa)(SpectrumLaboratories, California, USA) overnight against 150 mM NaCl at 4□C. Protein concentration was measured using the PIERCE BCA protein micro assay (Fisher denmark, Slangerup, Denmark), and lipid concentration was measured using the Stewart Assay (Stewart, J. C. M. (1980). *Anal Biochem,* 104:10). The amount of methylprednisolone in the prepared liposomes was determined using the HPLC method described above.

Example 9: In Vitro and In Vivo Experiments Using Corticosteroid Conjugates Targeted to CD163

Materials and Methods
Isolation and Cultivation of Human Mono Nuclear Cells (MNC)

Outdated buffy coats were obtained from the blood bank at Skejby University Hospital. MNC were isolated with Accuspin System Histopaque®—1077 (Sigma-Aldrich Denmark A/S, Broendby, Denmark) according to the manufacturer's instructions and cultured in RMPI 1640, 10% fetal calf serum (FCS), penicillin/streptomycin (pen/strep) in Tissue culture flasks at 37° C. and 5% $CO_2$. MNC were detached from the flasks by flushing.

Dexamethasone Treatment of Mono Nuclear Cells (MNC)

The cultured MNCs were incubated with the indicated dexamethasone constructs and concentrations by addition of the reagents to the media and incubation for specified time at 37° C. and CD163 mRNA level was measured.

Gaining cDNA and Real-Time, Quantitative PCR Analysis of CD163 mRNA

Total cellular RNA was extracted from MNC and macrophages after RLT buffer fixation with QUIAamp RNA blood Minin (Qiagen, Albertslund, Denmark) according to the manufacturer's protocol and stored at −80° C. until further use.

Reverse transcription was performed by adding 1 µl of the extracted mRNA to a reaction mixture consisting of 2 µl 10×PCR buffer II (Applied Biosystems, Naerum, Denmark) supplemented with 6.3 mM $MgCl_2$, 0.3 mM of each of the four deoxyribonucleoside triphosphates (dATP, dTTP, dGTP, dCTP), 2.5 mM 16mer oligo dT nucleotide, 20 U RNase inhibitor, and 50 U MULV reverse transcriptase in a total volume of 20 µl (All reagents from Applied Biosystems, Naerum, Denmark). The cDNA synthesis was carried out in a GeneAmp® PCR System 9700 Thermal Cycler (Applied Biosystems, Naerum, Denmark) at 42° C. for 30 min followed by 99° C. for 5 min. The resulting cDNA provided template for the real-time qPCR assay. The synthesized cDNA was stored at −20° C.

Two µl of cDNA were used as template for real-time qPCR in a reaction mixture containing 10 pmol of each primer being either (CD163 WT; forward primer 5'-ACA TAG ATC ATG CAT CTG TCA TTT G-3'; reverse primer 5'-CAT TCT CCT TGG AAT CTC ACT TCT A-3'; MWG Biotech AG, Edersberg, Germany) ore (TNF-alpha; forward primer 5'-TGG GGT GGA GCT GAG AGA-3' reverse primer 5'-GCA ATG ATC CCA AAG TAG ACC T-3'), 1.0 µl LightCycler® FastStart DNA Master$^{PLUS}$ SYBR Green I (Roche Diagnostics, Hvidovre, Denmark), containing FastStart Taq DNA Polymerase, reaction buffer, deoxyribonucleoside triphosphates (dATP, dUTP, dGTP, dCTP), SYBR Green I dye, and 10 mM of $MgCl_2$. The volume was adjusted to 10 µl with nuclease-free $H_2O$. The real-time hot-start qPCR was performed in a LightCycler® System (Roche Diagnostics, Hvidovre, Denmark) with an initial denaturation step of 95° C. for 15 min, then 50 cycles with a 95° C. denaturation for 10 s. followed by 65° C. annealing for 10 s and 72° C. extension for 5 s. Amplification specificity was checked by melting curve analysis.

Monocyte Isolation and Macrophage In Vitro Maturation

Monocytes were obtained from MNC after isolation using Dynal Monocyte Negative Isolation Kit (Invitrogen) according to the manufacturer's instructions. Monocytes were collected by negative selection in a magnetic field. The effluent was collected as a negative fraction representing highly enriched monocytes.

Maturing the Monocytes to Macrophages:

Monocytes were resuspended in RMPI 1640 medium (Sigma-Aldrich, Brondby, Denmark) containing 20% fetal calf serum (FCS) supplemented with 100 ng/ml M-CSF (GenScript Corporation, New Jersey, USA) and pencillin/streptomycin (pen/strep) for 7 days. The first 3 days in Tissue Culture Flasks at 37° C. and 5% $CO_2$. The monocytes were then detached from the flask by flushing and scraping. The monocytes were divided into smaller portions and further grown for four days. $0.9 > 10^5$ cells per well were grown in 96 well tissue culture plates for TNF CBA use.

Activating Macrophages into Proinflammatory Subtype:

Subsequently, the macrophages were activated in RMPI 1640 containing 5% FCS, 1 ug/ml lipopolysaccharide (LPS)

(Sigma-Aldrich, Brøondby, Denmark) and 20 ng/ml INF-gamma (Genscript Corporation, New Jersey, USA) for 18 hours making them pro-inflammatory.

Dexamethasone Treatment of Cultivated Pro-Inflammatory Macrophages

The pro-inflammatory macrophages were stimulated with RMPI160, 5% FCS, 1 ug/ml LPS and 20 ng/ml INF-gamma containing either dexamethasone, Ab-dexamethasone or no drug.

Cytometry Bead Array (BD) Determination of Soluble TNF Concentration

To detect the change in soluble TNF-alpha concentration we used the Cytometry Bead Array Kit (BD Biosciences, New Jersey, USA). The media from the in vitro stimulated macrophages (described earlier) grown in 96 well tissue culture plates were analyzed according to the manufacturer's protocol.

Flow Cytometry

The cell suspensions were washed in PBS pH 7.4 (0.1% $NaN_3$) and the cell density adjusted to $3-5 \times 10^6$/ml. The cells were incubated at $0.3-0.5 \times 10^6$/ml with primary mAb (0.1-0.5 µg) in 100 µl PBS pH 7.4 (0.1% NaN3 and 2% FBS) for one hour at 4° C. Subsequently, the cells were washed in PBS (0.1% NaN3) and incubated with secondary Ab (anti-mouse IgG-FITC or anti-human IgG-FITC (both AbD-Serotec Dusseldorf, Germany)) for 30 min at 4° C. The stained cells were washed twice in PBS pH 7.4 (0.1% $NaN_3$ and 2 FBS) by centrifugation at 1200 rpm for 5 min, 4° C. before analysis on a FACSCalibur (BD Biosciences, New Jersey, USA). The data were further analyzed using the FlowJo7 software package (Tri Star, Origon, USA).

The Human, Rat and Mouse In Vitro LPS Models

Rat or mouse peritoneal or spleen cell suspensions were prepared from female Lewis rats (Harlan) or BalB/cA mice (Taconic). Human mononuclear cells were isolated from buffycoats (Skejby University Hospital) as described above. The purified cells were suspended in RPMI medium supplemented with 10% FCS and 2 mM L-glutamine and cultured ($2 \times 10^5$ per well) overnight in 96-well flat bottomed plates (125 µl per well) at 37° C. and 5% $CO_2$. Glucocorticoid conjugates (Example 8), free glucocorticoids or PBS were serial diluted in supplemented RPMI medium and added (100 µl) to the overnight cell cultures at final concentrations ranging from $1-10^{-7}$ µg glucocorticoid/ml. After incubation for a specific time ranging from 30 min-24 hours, 150 µl supernatant was carefully aspirated and 150 µl supplemented RPMI medium added to the wells before further incubation overnight. Each incubation condition was tested in duplicates or triplicates. After 16-20 hours, the cells were challenged with lipopolysaccaride (LPS) (250 ng/ml) for 4 hours before supernatant was aspirated from each well and frozen at −20° C. The supernatants were analyzed for the presence of TNFα using the human, rat or mouse CytoSet Antibody Pairs (Invitrogen, Taastrup, Denmark) in a sandwich ELISA according to the manufacturer's instructions.

The Rat and Mouse In Vivo LPS Models

Female Lewis rats (9-11 weeks) or female Balb/cA mice (8-9 weeks) were injected intravenously with either free glucocorticoid, glucocorticoid-conjugates or vehicle (PBS pH 7.4 2.5% ethanol). After 18-20 hours, lipopolysaccaride (LPS) (0.9 mg/kg) was injected intravenously. Blood samples were collected at the following time points: before glucocorticoid injection, 2 hours post LPS injection, and again after 24 hours. Serum samples were analyzed for TNFα using the rat or mouse CytoSet Antibody Pairs (Invitrogen, Taastrup, Denmark) in a sandwich ELISA according to the manufacturer's instructions the. Two days post LPS challenge, the animals were sacrificed and thymus and spleen were dissected and weighed.

Induction of Collagen Antibody Induced Arthritis (CAIA) and Treatment Schedule.

Female Balb/cA mice (7-8 weeks) were injected intravenously with 1 mg of a cocktail of 5 monoclonal antibodies (Chondrex) at day zero. Three days later, the mice were injected intravenously with 35 µg LPS from *E. Coli* 0111:B4 to induce higher severity and a longer period of active inflammatory arthritis. On the first day of disease onset at day four, the mice were divided into treatment groups. Treatment with methyl-prednisolone, liposome-methyl-prednisolone, liposome-methyl-prednisolone coated with 3E10B10 or vehicle (PBS pH 7.4 2.5% ethanol). were initiated on day four and repeated every second-third day with a total of 4 treatments over 10 days. Changes in ankle size and body weight were monitored during the treatment process. Clinical severity of CAIA was determined by swelling of individual joints and the number of affected joints in the front and rear paws. Each paw was scored from 1 to 4, so the maximum clinical score, including all four paws was 16. On day 14, all animals were sacrificed and spleen and liver were dissected and weighed.

Results

Mac2-158-Dexamethasone Conjugates

FIG. 30A shows the effect on human mononuclear cells isolated from buffy coats (outdated plasma) of haptoglobin coupled with dexamethasone and afterwards complexed with hemoglobin to induce CD163 expression. The effect measured is the induction of CD163 mRNA synthesis by dexamethasone. The number after Hp-dexa refers to different batches of Hp-dexa.

FIG. 30B shows the results of a time study showing the effect of 10 nM dexamethasone on CD163 expression in human mononuclear cells isolated from buffy coats (outdated plasma).

To enable the measurement of changes in TNF synthesis of the cell in the assay, the isolated monocytes were matured into pro-inflammatory macrophages, which produce TNF. Furthermore, dexamethasone was conjugated to a CD163 mAb (Mac2-158). The macrophages were then incubated with increasing concentrations of dexamethasone, either conjugated to Mac2-158 or as free dexamethasone. For cells not treated with dexamethasone conjugate the TNF concentration measured was 112 pg/ml (FIG. 31A).

The concentration of 10 nM dexamethasone was then used in a time study on the same pro-inflammatory macrophage cell type (FIG. 31B). As can be seen, the conjugated dexamethasone is as efficient as free dexamethasone whether the conjugation is to a monoclonal Ab or Hp. Mac2-158 without dexamethasone was also tested on macrophages with no effect different from buffer (results not shown).

KN2/NRY-Dexamethasone Conjugates

Binding of the humanized KN2/NRY antibody to human monocytes was initially analyzed by flow cytometric analysis of mononuclear cells isolated from buffycoat. FIG. 32 demonstrates specific binding of KN2/NRY to CD14 positive monocytes. Approximately, 70% of the peripheral monocytes showed co-binding of KN2/NRY and Mac2-158 suggesting specific binding to CD163.

The effect of conjugation of KN2/NRY to dexamethasone using the activated NHS ester method was analyzed in a flow cytometric binding analysis of CD163-expressing CHO cells (FIG. 33) and revealed that dexamethasone conjugation had no or very little effect on binding to CD163 displayed on CHO cells.

The ability of the KN2/NRY-conjugates to inhibit LPS mediated TNFα stimulation of human mononuclear cells was analyzed in vitro and FIG. 34 demonstrates similar effect of free dexamethasone and KN2/NRY-dexamethasone conjugates in suppression of LPS mediated TNFα stimulation.

Overall the human cell data corresponds with our results from rat macrophages, indicating that conjugate drugs will be equally effective in both organisms. However, access to matured spleen derived human macrophages are obviously very difficult and experiments on macrophages have thus only been conducted on rat and mice macrophages.

ED2-Dexamethasone Conjugates

Binding of the rat CD163 specific antibody ED2 to rat macrophages was demonstrated by flow cytometric analysis of peritoneal macrophages and revealed that approximately 42% of the peritoneal macrophages were CD163 positive (FIG. 35). The effect of dexmathasone conjugation to ED2 was analyzed in a similar binding assay using CHO cells expressing rat CD163 (FIG. 36) and it was shown that binding of non-conjugated ED2 was comparable to CD163 binding of the ED2-dexamethasone conjugate.

Lipopolysaccaride (LPS) Mediated TNFα Stimulation of Rat Macrophages In Vitro

The ED2-NHS-dexamethasone conjugate was analyzed for the ability to inhibit TNFα stimulation of rat macrophages in vitro, ED2-NHS-dexamethasone conjugates and free dexamethasone (1 µg/ml) prevented LPS mediated stimulation of rat macrophages, whereas ED2 alone had no effect on TNFα secretion. The concentration of TNFα was approximately 10 fold higher in cell supernatants from macrophages stimulated for 20 hours without dexamethasone or ED2-dexamethasone conjugate (ED2 or PBS) (FIG. 37). The dose effects of dexamethasone and ED2-dexamethasone were comparable using the incubation conditions described above and similar titration curves were observed (data not shown). In a timestudy, the dose effect of dexamethasone and ED2-NHS-dexamethasone was compared over a time period from 15 minutes to 24 hours (FIG. 38 and data not shown) and revealed that after 15 minutes of incubation, the level of TNFα suppression of the ED2-NHS-dexamethasone conjugate (1e-4 to 1e-5 µg/ml dexamethasone) was 2 fold higher compared to free dexamethasone. Thus, the rat in vitro model was considered as a valuable method to evaluate the effect of ED2-dexamethasone conjugates before proceeding to animal studies and clearly showed the effect of increased efficacy of conjugates. It is not to be expected that extensive incubation time should yield different results for free and conjugated dexamethasone, since the free dexamethasone will eventually end up in the cells.

The Rat In Vivo LPS Model

The LPS model was established in Lewis rats to obtain an in vivo model for further characterization of macrophage targeting of dexamethasone, using ED2-dexamethasone.conjugates. Free dexamethasone, dexamethasone conjugate or vehicle was injected intravenously 20 hours before injection of LPS (FIG. 39). Two hours after LPS administration, the level of TNFα was 2 fold lower in rats injected with dexamethasone compared to vehicle (FIG. 39A). The level of TNFα was comparable in rats injected with conjugate and free dexamethasone, at a total dexamethasone concentration 100 fold lower for the conjugate. After 24 hours the TNFα level had returned to normal levels for all groups (data not shown). Thus dexamethasone conjugate formulated as ED2-dexamethasone was significantly more efficient than free dexamethasone in lowering the TNFα level. The avoidance of the systemic side-effects of dexamethasone by administrating it as a ED-2-dexamethasone conjugate was also indicated by spleen and thymus weight, which was significantly lower in rats injected with dexamethasone than for rats injected with ED2-dexamethasone (FIGS. 39B and C), indicating that leukocytes has been directed towards apoptosis by free dexamethasone, but not by the conjugated form.

Figure 40A:
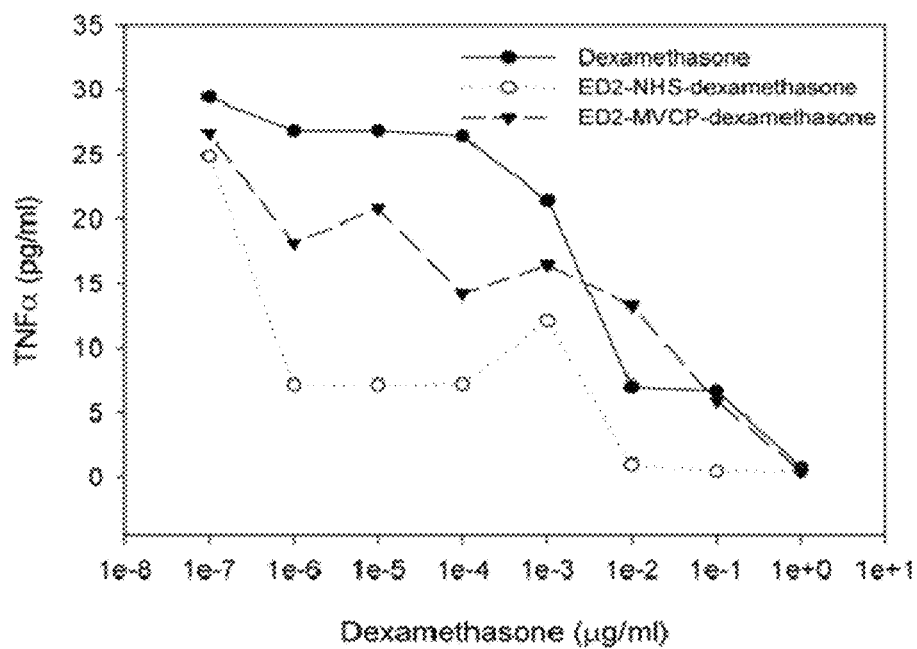
Figure 40B:
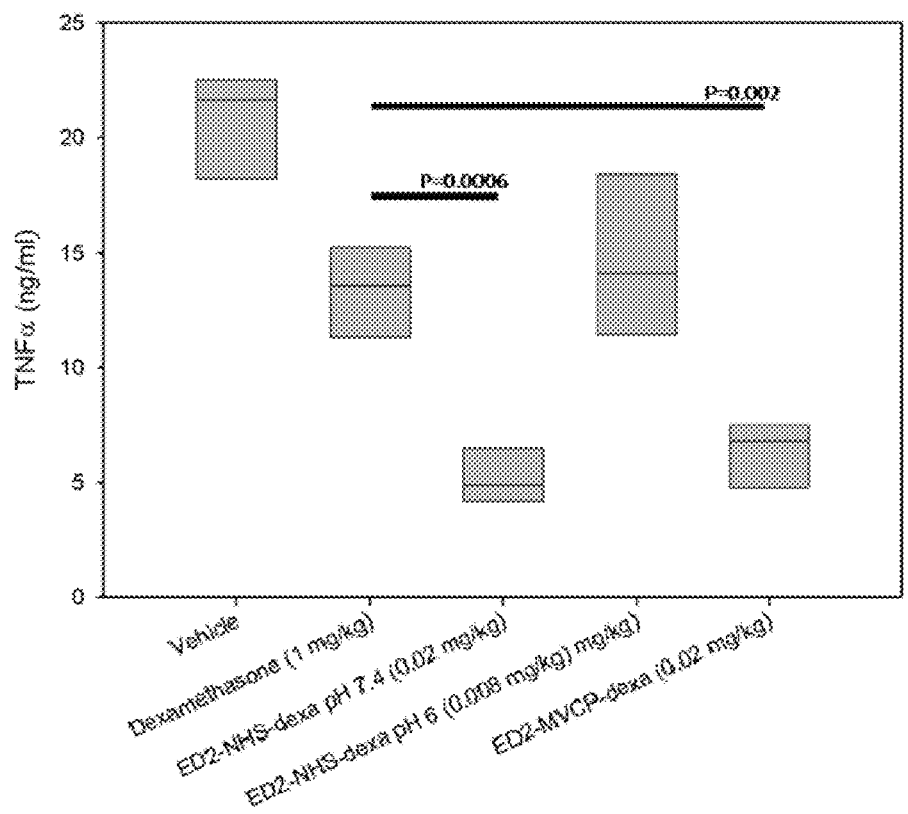
Figure 40C:
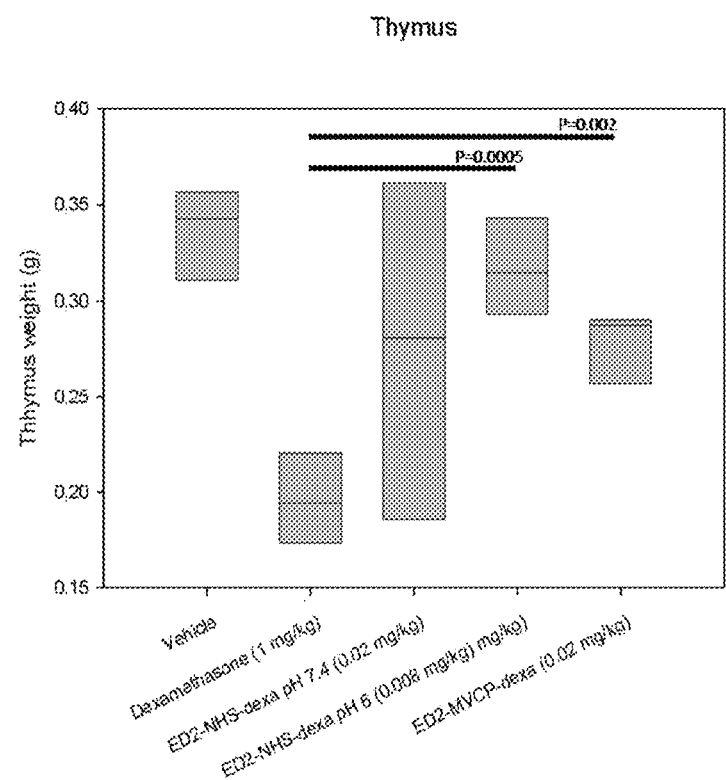
Figure 40D:
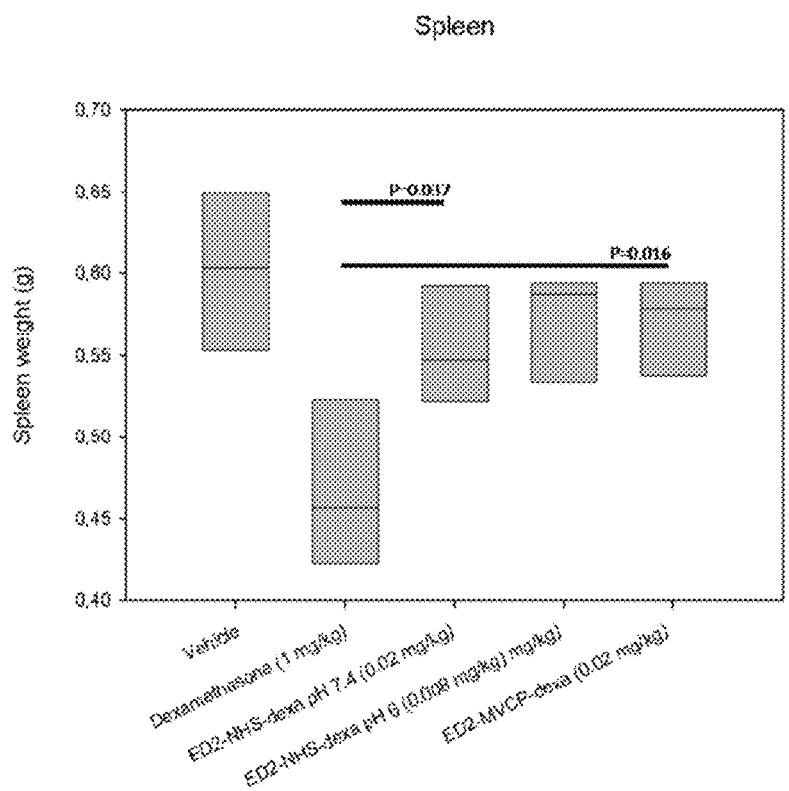

Having established the rat LPS model, different formulations of ED2-dexamethasone conjugates were analyzed using both the in vitro and in vivo LPS models. FIG. 40 shows the effect of the ED2-NHS-demethasone and ED2-MVCP-dexamethasone conjugates. In vitro (FIG. 40A), the suppressive effect of ED2-MVCP-dexamethasone was 3 fold higher compared to free dexamethasone and the effect of ED2-NHS-dexamethasone was about 2 fold higher at dexamethasone concentrations ranging from 1e-3 to 1e-6 µg/ml. Overall, the titration curves suggest a 100-1000 fold higher dexamethasone potency of the ED2 conjugates compared to free dexametasone. When injected into rats, the suppressive effect of both formulations was significantly higher compared to free dexamethasone. Two hours post LPS admiinistration, the TNFα level was 2 fold lower in rats injected with dexamethasone conjugate formulations compared to free dexamethasone at a total dexamethasone dose 50 times higher than conjugate (FIG. 40B). Again, systemic effect in the form of reduced weight of organs (presumably due to induction of apoptosis of lymphocytes of free dexamethasone) was not observed since there was no significant difference between organ weight for vehicle and conjugate groups, whereas the free dexamethasone group was significantly different from free dexamethasone using the conjugated dexamethasone preparations (FIGS. 40C and D). Thus efficacy is increased more than 50 fold and adverse effects avoided.

In sum, these results show selective targeting of the ED2-dexamethasone conjugate to CD163 expressing macrophages. Furthermore, the suppressive effect of the conjugates demonstrated in vivo indicate up to at least a 100 fold higher potency of the conjugates compared to free dexamethasone.

ED2-Prednislone and ED2-Fluocinolone Conjugations.

The effect of targeting of other glucocorticoids to macrophages was analyzed using ED2-prednisolone and ED2-fluocinolone-acetoniode conjugates. FIG. 41 shows the suppressive effect of free fluocinolone, free prednislone, ED2-NHS-fluocinolone-acetonide and ED2-NHS-prednisolone in vitro (A) and in vivo (B). The suppressive in vitro effect of fluocinolone-acetoniode was significantly higher compared to prednisolone. and the dose effect ED2 conjugated prednisolone and fluocinolone-acetoniode was comparable to free prednisolone and fluocinoloneacetonoide, respectively. The TNFα level was 5 times lower in rats injected intravenously with free prednislone and fluocinolone and challenged with LPS compared to vehicle. Injected intravenously into rats both ED2 glucocorticoid conjugates prevented LPS mediated TNFα stimulation at least 10 times more efficiently compared to free glucocorticoids.

In sum, targeting of macrophages using ED2-glucocorticoid formulations was demonstrated to be significantly more efficient than free glucocortiods in suppressing LPS mediated TNFα stimulation of macrophages in vivo. Repeated experiments suggest that the ED2-dexamethasone formulations are up to 100 times more potent than free dexamethasone. The non-significant impact on thymas and other organ weights of conjugated glucocortioid as compared to free glucocorticoid clearly demonstrates that adverse systemic effects are avoided upon macrophage targeted delivery of glucocorticoids.

3E10B10-Dexamethasone Conjugations

The CD163 specific mouse antibody, 3E10B10, was conjugated to dexamethasone and the conjugates were analyzed in pilot experiments.

The Mouse In Vitro and In Vivo LPS Models

The suppressive effect of the 3E10B10-NHS-dexamethasone conjugate on LPS mediated TNFα production in splenocytes is shown in FIG. 42). The dose effect was comparable to free dexamethasone or eventually slightly higher. The ED2-NHS-dexamthasone, ED2-MVCP-dexamethasone conjugates, free dexamethasone or vehicle were injected intravenously into mice and serum TNFα levels were analyzed 2 hours post LPS challenge. The TNFα level was 2 fold lower in rats injected with dexamethasone compared to vehicle (FIG. 42). The suppressive effect of 3E10B10-NHS-dexamethasone was low or absent whereas the effect of 3E10B10-MVCP-dexamethasone was comparable to free dexamethasone at a total dexamethasone dose 50 times higher than conjugate. The difference between E10B10-NHS-dexamethasone and E10B10-MVCP-dexamethasone is due to the fact, that modification of the amino groups of E10B10 greatly diminished the binding to murine macrophages in FACS and isolated murine CD163 immobilized on a Biacore chip (results not shown).

3E10B10-Liposome Conjugations

The CAIA Model

The collagen antibody induced arthritis (CAIA) animal model was established to analyze the treatment effect of 3E10B10-glucocorticoid formulations on development of arthritis in mice. CAIA was induced by injecting Balb/cA mice with 1 mg of anti-collagen antibodies, followed by 35 µg LPS 3 days later. Treatment with intravenous injections of methyl-prednisolone, liposome-methyl-prednisolone, liposome-prednisolone-3E10B10 or vehicle was initiated at day 4. At this timepoint, at least one animal in each treatment group showed clinical signs of arthritis. At day 7, disease incidence was 97%. The disease severity (mean clinical score as well as cumulative score) was significantly lower in CAIA mice treated with methyl-prednisolone and liposome-methyl-prednisolone-3E10B10 compared to vehicle-treated CAIA mice (FIG. 43). Furthermore, the clinical score as well as the cumulative score was comparable in mice treated with liposome-methylprednisolone-3E10B10 compared to free prednisolone at a total prednisolone dose 50 times higher than conjugate. Arthritis in CAIA mice treated with liposome-methyl-prednisolone without coated 3E10B10 was not significantly different from arthritis in the vehicle group. Thus, when administrated systemically in the mouse CAIA model, selective targeting of 3E10B10 coated liposomes to macrophages seems to require a lower prednisolone treatment dose compared to free prednisolone and liposome-prednisolone.

Conclusion

Data obtained from the in vitro LPS model, the in vivo LPS model as well as the CAIA model suggest that targeting of macrophages using conjugate-glucocorticid formulations results in drug conjugates with a significantly higher glucorticoid potency compared to free glucorticoid. In several experiments, the rat in vivo LPS model indicate up to a 100 fold higher suppression effect of ED2-dexamethasone compared to free dexametasone. Other ED2-glucocorticoid conjugates were also demonstrated to have an suppressive effect higher than free glucocortiod in the rat in vivo LPS model. In the CAIA model, liposome-methyl-prednisolone coated with the mouse antibody 3E10B10 was shown to have a significant treatment effect on development of arthritis. This study also indicate selective targeting of 3E10B10 coated liposomes to macrophages as well as lower dose requirements compared to free glucocortiod. Furthermore, all the studies using conjugated glucocorticoids demonstrated that the adverse systemic effects, otherwise seen upon using free glucocorticoids at a dose having a pharmacologic effect, are avoided in terms of reduced weight of organs.

Example 10—Synthesis of Activated Glucocorticoid for Protein Conjugation

Preparation of Dexamethasone-MVCP

Dexamethasone.-MVCP also called Mal-Val-Cit-PABC-dexamethasone, for conjugation to free SH groups of proteins were prepared as described in the following. All numbers refer to FIG. 44.

Fmoc-Cit-PABA (2)

HOBt (2.19 g, 16.21 mmol) and EDC (1.26 g, 8.12 mmol) were added to a stirred suspension of 4-aminobenzylalcohol (1, 1.00 g, 8.12 mmol) and Fmoc-Cit-OH (3.23 g, 8.13 mmol) in 150 ml dry DCM at rt. The mixture quickly became clear followed by formation of a white precipitate. After 2 hours, TLC analysis showed only small amounts of remaining 4-aminobenzylalcohol. The reaction mixture was filtered and the residue was washed multiple times with DCM. The filtrate was dissolved in EtOH/DCM (9:1) and filtered. The solvents was removed in vacuo giving 2 (3.51 g, 86%) as a yellow solid sufficient pure to be used in the following reaction without further purification.

Boc-Val-Cit-PABA (3)

Fmoc-Cit-PABA (2, 2.00 g, 3.98 mmol) was dissolved in 10 ml DMF containing 20% piperidine. The mixture was stirred for 30 min at rt and the solvent was removed in vacuo. The remaining solid was dissolved in 5 ml dry DMF. Boc-Val-OH (865 mg, 3.98 mmol) was dissolved in 10 ml dry DCM and cooled to 4° C. in an ice bath. HOBt (1.08 g, 7.99 mmol) and EDC (618 mg, 3.98 mmol) were added and the mixture was stirred at 4° C. for 20 min. The solution of deprotected Cit-PABA in DMF was added, the ice bath was removed and the reaction was stirred overnight at rt. The solvent was removed and without further workup the product was purified by flash chromatography (DCM-MeOH; 18:2→17:3). This gave 3 (782 mg, 41%) as a slightly yellow solid.

Boc-Val-Cit-PABC-Dexamethasone (5)

Boc-Val-Cit-PABA (200 mg, 0.417 mmol) was dissolved in 5 ml DMF-DCM (3:7), dexamethasone 21-(p-nitrocarbonate) (prepared following the procedure of Ponpipom, M. M.; Bugianesi, R. L.; Robbins, J. C.; Doebber, T. W.; Shen, T. Y., J. Med. Chem., 1981, 24:1388-1395) (4, 698 mg, 1.25 mmol), pyridine (67 µl, 0.828 mmol) and DMAP (255 mg, 2.09 mmol) were added and the mixture was stirred overnight at room temperature (rt). The solvent was removed in vacuo and the product was purified by flash chromatography (DCM-MeOH; 19:1→23:2). This gave 5 (116 mg, 31%) as a white solid.

Mal-Val-Cit-PABC-Dexamethasone (6)

Boc-Val-Cit-PABA-dexamethasone (6, 116 mg, 0.129 mmol) was stirred in 5 ml DCM containing 20% TFA. After TLC analysis showed full conversion of the starting material (10-30 min) the solvent was removed in vacuo. The resulting free amine was dissolved in 5 ml dry DCM/DMF (1:1) followed by addition of 6-maleimidoproprionic acid (prepared following the procedure of Figueiredo, R. M. de; Oczipka, P.; Froehlich, R.; Christmann, M. *Synthesis,* 2008, 8:1316-1318) (33 mg, 0.195 mmol), TEA (125 μl, 0.900 mmol) and EDC (40 mg, 0.258 mmol). After stirring at rt for 6 hours, the solvent was removed in vacuo and the product purified by flash chromatography (DCM-MeOH; 19:1→9:1). The obtained white solid was washed three times with DCM (5-10 ml), giving the desired product 6 (34 mg, 28%) as a white solid.

Preparation of Glucocorticoid-NHS

Glucocorticoid-NHS for conjugation to primary amino groups of proteins were generally prepared as described in the following for dexamethasone-NHS, also called dexamethasone-hs-NHS. All numbers refer to FIG. 45.

The example shown is for dexamethasone, but other glucocorticoids can also be used. Using the same method methylprednisolone, prednisolone and fluocinolone acetonoid hemisuccinate were also prepared.

Dexamethasone-hs (7)

Dexamethasone (1.00 g, 2.55 mmol) and succinic anhydride (1.27 g, 12.69 mmol) was stirred overnight at it in 15 ml pyridine. The solution was poured into a mixture of 50 g ice and 20 ml conc. hydrochloric acid, filtered and the obtained precipitate was washed twice with 20 ml ice cold HCl (4 M). The precipitate was dissolved in THF and transferred to a round bottom flask and evaporated three times with toluene. This gave 7 (1.25 g, 97%) as a white solid.

Dexamethasone-hs-NHS (8)

Dexamethasone-hs (7, 500 mg, 0.988 mol) was dissolved in 20 ml dry THF. N-hydroxysuccinimide (171 mg, 1.48 mmol) and EDC (200 mg, 1.29 mg) was added and the reaction was stirred overnight at rt. The solvent was removed in vacuo and the product was purified by flash chromatography (pentane-EtOAc; 1:1) giving 8 (376 mg, 63%) as a white solid.

Abbreviations

Boc tert-butyloxycarbonyl;
Cit Citruline
DCM Dichloromethane
DMF Dimethylformaide
EDC N-ethyl-N'-(3-dimethylaminopropyl)carbodiimide
Fmoc Fluorenylmethyloxycarbonyl
HOBt 1-Hydroxybenzotriazole
hs Hemisuccinate
MC 6-maleimidocaproic acid
NHS N-hydroxysuccinimide
PAPA para-Aminobenzylalcohol
PABC para-Aminobenzylcarbonate
TEA Triethylamine
TFA Triluoroacetic acid
THF Tetrahydrofuran
Val Valine

Example 11—Further Experiments Using Dexamethasone Conjugates

Introduction
Summary

The rat collagen-induced arthritis (CIA) model was performed successfully in this study as judged by the 100% disease incidence in the vehicle group in conjunction with increasing total clinical score over time, reaching a value of 6.3 a.u. at the end of the study. Dexamethasone suppressed clinical signs of arthritis in a dose-dependent manner, showing significance at the 0.1 and 1 mg/kg dose level. Administration of 0.01 mg/kg dexamethasone resulted in a lower total clinical score and reduced paw swelling compared to vehicle. Administration of conjugated dexamethasone resulted in a significant reduction of the total clinical score and paw swelling, indicating that the conjugated form is more effective than the non-conjugated form. At the 0.01 mg/kg dose level, no effect of dexamethasone or dexamethasone-conjugate on thymus weight was observed, while higher dosages of dexamethasone reduced thymus weight. In summary, this pilot study showed that at a dose level of 0.01 mg/kg suppression of clinical symptoms in the rat CIA model by dexamethasone treatment is minimal and that the dexamethasone-conjugate is significantly more effective in suppressing clinical signs of arthritis at the same dose level.

Aim

This study was designed to determine the effect of escalating doses of intravenously administered dexamethasone on the development of experimental arthritis. The aim of the study was to determine a dexamethasone dose with minimal or no suppressive effect on arthritis to be able to show superiority of a dexamethasone conjugate at the same dose level in the main study. In this study, a group treated with dexamethasone-conjugate was included to obtain an indication of the efficacy of this conjugate compared to dexamethasone in suppressing arthritis.

For this purpose the model of collagen-induced arthritis (CIA) in the Lewis rat was used. Lewis rats are highly susceptible for the induction of arthritis by intradermal injection of bovine type II collagen. The main pathological features of CIA include infiltration of the joints with inflammatory cells, cartilage degradation, erosion of bone tissue and fibrosis. These pathological features result in clinical signs including less loading of the paws and thickening of the paws.

Study Design

The effect of dexamethasone on arthritis development in the rat CIA model was tested at three dosages (0.01, 0.1 and 1 mg/kg). Dexamethasone was administered intravenously on day 10 (day of disease onset), 13, 16 and 19. Dexamethasone conjugate produced as described in Example 5 was tested at 0.01 mg/kg using the same treatment regimen as for dexamethasone. Treatment with vehicle (PBS/2.5% EtOH) served as negative control. Rats were sacrificed 21 days after immunization.

| Study groups | | | |
|---|---|---|---|
| [1] Vehicle | | n = 4 | day 10, 13, 16, 19 |
| [2] Dexamethasone | 0.01 mg/kg | n = 4 | day 10, 13, 16, 19 |
| [3] Dexamethasone | 0.1 mg/kg | n = 4 | day 10, 13, 16, 19 |
| [4] Dexamethasone | 1 mg/kg | n = 4 | day 10, 13, 16, 19 |
| [5] Dexamethasone-conjugate | 0.01 mg/kg | n = 4 | day 10, 13, 16, 19 |

Outcome Parameters
  Individual body weight (6× per week)
  Clinical arthritis score (6× per week)
  Hind paw swelling (5× per week)
  Disease incidence
  Day of disease incidence
  Spleen, thymus and liver weights at sacrifice
Sample Storage
  Serum collection before immunization (day −4)
  Serum collection at sacrifice
  Storage of hind paws for histological analysis Materials and Methods
Reagents
  Incomplete Freunds Adjuvant, Chondrex, lot no. 080292
  Bovine type II collagen, Chondrex, lot no. 080280
Test Compounds
  Dexamethasone, Sigma, lot no. 078H1176
  Phosphate buffered saline (PBS), Braun, lot no. 8344A162
  Ethanol, Merck, lot no. K37694210732
  Dexamethasone-conjugate, supplied by Cytoguide ApS as ready-to-use solution of 0.01 mg/ml PBS/2.5% EtOH. Vials (containing 1.25 ml of compound solution) were stored at −20° C. until use.
  Manufacture of the dexamethasone-conjugate is described in the accompanying Examples.
  Dexamethasone and dexamethasone-conjugate were dissolved in PBS/2.5% EtOH for i.v. administration. Dexamethasone was freshly prepared once a week. Rats were dosed at 1 ml/kg using the following scheme:
126-175 gram body weight: 150 µl dosing volume
176-225 gram body weight: 200 µl dosing volume
225-275 gram body weight: 250 µl dosing volume
Animals
  Female Lewis rats were purchased from Charles River laboratories at an age of 7 weeks and a body weight range of maximal 10%. Animals were housed under clean conventional conditions at 21±3° C., relative humidity of 55±15% and a light/dark cycle of 12 hours. Rats had free access to rodent chow-diet (SSNIFF, Bio-Services, The Netherlands). Before start of the experiment rats were handled for a 2-weeks period. Rats were housed in pairs. Individual animals were identified by marking on their tails.
Induction of Arthritis
  Collagen arthritis was induced in 9 weeks old female Lewis rats using a two-step immunization protocol. On day 0, all mice were immunized by intradermal injection of 1 mg/ml bovine type II collagen emulsified in Incomplete Freund's adjuvant at several sites at the back. Arthritis development was accelerated by an intradermal boost in the back and tail-base with 100 Sg bovine type II collagen in IFA on day 7. In order to perform immunization and intradermal boost, rats were anesthetized by inhalation of 3-4% isoflurane in a mixture of oxygen and N2O.
Read-Out Parameters
Body Weights
  Body weight of each individual rat was measured 6 times per week (once during weekends).
Disease Incidence
  Disease incidence is defined as the percentage of mice within one group that have a clinical arthritis score above 0.
Clinical Arthritis Score
  Rats were evaluated 6 times per week (once during weekends) for arthritis severity using a macroscopic scoring system of 0-4 for each paw as detailed below:
0=no signs of arthritis
0.5=unloading of the paw and/or light redness of ankle joint
1=redness and mild swelling of the ankle joint
2=redness and swelling of paw
3=severe redness and swelling of entire paw including digits
4=maximally swollen paw, often involvement of multiple joints and extending towards knee joint.
  The total clinical score of an individual rat is defined as the sum of the clinical scores of all four paws for each day. At the end of the study, the cumulative arthritis score is calculated for each rat. This cumulative arthritis score is defined as the sum of the total clinical scores obtained from day 0 till day 21.
Day of Disease Onset
  The day of disease is defined as the first day of three consecutive days on which a total arthritis score of more than 0 was observed.
Hind Paw Swelling
  The swelling of the hind paws was measured during weekdays with a laser scan micrometer (Mitutoyo, LSM-503S/6200). At the end of the study, the cumulative paw swelling was calculated for each rat as follows: a baseline value was determined by averaging the paw thickness values of day 0-9 when no signs of arthritis were visible. Next, increase in paw thickness was calculated by subtracting the baseline value from the paw thickness values obtained on day 10-21 (delta value). Cumulative paw swelling is defined as the sum of the delta paw thickness values from day 10 till 21.
Organ Weights
  Spleen, thymus and liver were isolated and weighed at sacrifice. Weights were normalized for body weight.
Sample Storage
  Serum was collected before immunization (day −4) by tail vein puncture (±100 µl) and at sacrifice by heart punction (±500 µl) and stored at −80° C. Hind paws were collected at sacrifice and fixed in 4% formalin to enable future histological analysis.
Deviations from the Protocol
  Baseline serum samples were collected at day −4 instead of day 0 as mentioned in the study protocol. At day 0 serum collection would be performed when the rats were under anaesthesia for immunisation. However, anaesthetics might interfere with parameters to be determined in the serum and therefore it was decided to collect baseline serum samples at day −4.
  Rat #4 of the 0.01 mg/kg dexamethasone-conjugate group received only 180 µl of compound instead of 200 µl on the first day of treatment (day 10).
Production of Dexamethasone Coupled mAbs
  Anti-human CD163 murine mAbs Mac2-48 and Mac 2-158 were conjugated as described (Melgert), we found that exchanging the solvent for the activated dexamethasone upon addition to haptoglobin from DMSO to ethanol significantly increased the affinity for CD163, as judged by Biacore. Different ratios between mAb and activated dexamethasone was tested, and the optimal final ratio for a conserved CD163 affinity and avoidance of aggregation was 3-5 dexamethasones per mAb.
Dose Study of Dexamethasone in the Rat Collagen-Induced Arthritis Model (TNO)
  Collagen-induced arthrtitis (CIA) was induced in female Lewis rats (9 weeks of age) by intradermal injection of approximately 1 mg bovine type II collagen (Chondrex) emulsified in Incomplete Freund's adjuvant (IFA). The rats were immunized at several sites at the back under isoflurane anaesthesia (day 0) and boosted intradermal at the back and tail-base with 100 µg bovine type II collagen in IFA at day 7. The rats were scored 6 times per weeks for clinical signs of arthritis. Clinical severity of CIA was determined by swelling of individual joints and the number of affected joints in the front and rear paws. Each paw was scored from 1 to 4, so the maximum clinical score, including all four paws was 16.
  A total of 20 rats were divided into five treatment groups (4 rats each). Three groups were injected intravenously with dexamethasone (1.0, 0.1 or 0.01 mg/kg), one group with ED2-dexamethasone (0.01 mg/kg) and one group with vehicle. Treatment of CIA was initiated at disease onset (the day the first animal showed signs arthritis) and repeated every third day with a total of 4 treatments. Changes in ankle size and body weight were monitored during the treatment process. On day 21, all animals were sacrificed and joint tissue, spleen, liver and thymus were dissected.

Results

Preamble

Data Presentation

The presentation of outcome parameters is organized as follows:

The clinical data are presented as line graphs for the time-dependent outcome parameters in two separate panels. In the left panel, data of the vehicle and the dexamethasone groups are presented. In the right panel, data of the vehicle group and the 0.01 mg/kg dexamethasone and dexamethasone-conjugate groups are presented. Changes in body weight, disease incidence, total clinical arthritis score and paw thickness are shown in FIGS. 47, 49, 50, 52 and 54. Group means are depicted.

Non time-dependent outcome parameters are shown as bar graphs. The cumulative arthritis score, day of disease onset, cumulative paw swelling and organ weight are presented in FIGS. 48, 51, 53, 55 and 56. Group data are presented as mean±standard deviation (SD).

Statistical Analysis

All statistical analyses were performed using the statistical software program SPSS 14.0 for Windows (SPSS Inc. Chicago, USA). During the weekends the body weights and the arthritis score were determined once. For these missing data points the mean of the day before and the day of the respective time point was used.

Basic statistical analyses were performed as follows:

The significance of differences between the treatment groups in the non-time dependent outcome parameters were tested using Kruskall Wallis H followed by Mann-Whitney U post hoc testing to evaluate significance of difference between each treatment group and the control (vehicle) group.

Interpretation of p-values:

p≤0.05 indicates statistically significant differences p>0.05 is considered not significant Characterization of the Test Model: Vehicle-Treated Rats In an adequate CIA model, the vehicle-treated group must show an increase in total clinical score over time together with a high disease incidence (i.e. the vehicle-treated rats must have developed arthritis). The current study fulfils these criteria as shown by the following observations:

After an initial increase of body weight due to the growth of the animals, there was a moderate decrease in body weight from day 10 onwards, which is expected for rats developing arthritis (FIG. 47). First clinical signs of arthritis were observed on day 10, which is in line with historical data. Mean day of disease onset was 10.3±0.5 days (mean±SD, FIG. 48)

Within one day after the first rats showed clinical features of arthritis, all rats in the vehicle group developed arthritis. Disease incidence remained 100% throughout the study in this group (FIG. 49).

The total clinical score steadily increased up to a value of 6.3 a.u. at the end of the study (day 21, FIG. 50). Theoretically, a maximal score of 16 a.u. per rat can be reached, but front paws are hardly affected within the timeframe of this CIA model. The mean cumulative arthritis score reached a value of 51.6±14.9 a.u. (mean±SD, FIG. 51).

The development of arthritis was reflected by swelling of the hind paws. Swelling of the hind paws started around day 10, reaching a maximum on day 15 (FIGS. 52 and 54).

Mean values of spleen, thymus and liver weights were 2.31±0.13, 2.28±0.40, 43.62±2.60 mg/g body weight, respectively in the vehicle group.

Effect of Treatment with Escalating Doses of Dexamethasone

Intravenous administration of dexamethasone with a frequency of once every three days dose-dependently suppressed clinical signs of arthritis in this study. This is based on the following observations:

As for the vehicle group, first clinical signs of arthritis were also observed on day 10, since a therapeutic treatment regimen was used. However, definite disease onset as defined by three consecutive days of arthritis is significantly delayed in the 0.1 and 1 mg/kg dexamethasone groups (13.8±1.0 days; p=0.017 and 18.3±2.1 days; p=0.017, respectively, FIG. 48).

Disease incidence of 100% was reached in the 0.01 and 0.1 mg/kg groups, however, at a later stage in the study than the vehicle group. The 1 mg/kg dexamethasone group never reached 100% disease incidence (FIG. 49).

Severity of arthritis as judged by the total clinical score was suppressed in all dexamethasone groups throughout the study (FIG. 50). Cumulative arthritis scores were 39%, 69% and 91% reduced with respect to the vehicle group. Significant differences in cumulative arthritis score were observed for the 0.1 and 1 mg/kg groups (p=0.021 for both groups, FIG. 51).

Thickness of the hind paws in the dexamethasone groups was reduced throughout the study (FIGS. 52 and 54) and significant differences in hind paw swelling were observed for the 0.1 and 1 mg/kg groups (p=0.021 and 0.021 for the left paw, respectively and p=0.043 and 0.043 for the right paw, respectively, FIGS. 53 and 55).

Additional Observations:

Body weight of the rats decreased gradually after initiation of the dexamethasone treatment (FIG. 47), irrespectively of arthritis development. This effect of dexamethasone treatment is always observed in rat arthritis studies and is due to the corticosteroid treatment rather than the development of arthritis. A relationship between body weight loss and increasing dexamethasone dose is evident from FIG. 47.

No significant differences were observed for spleen and liver weights in the dexamethasone groups compared to the vehicle group (FIG. 56). Thymus weight, on the other hand, was significantly decreased in the 0.1 and 1 mg/kg groups (p=0.043 and p=0.021, respectively).

Effect of Treatment with 0.01 mg/kg Dexamethasone-Conjugate

Intravenous administration of 0.01 mg/kg dexamethasone-conjugate with a frequency of once every three days was more effective in suppressing clinical signs of arthritis than dexamethasone at the same dose level. This is based on the following observations:

First clinical signs of arthritis were observed on day 10, which is comparable to the vehicle group since a therapeutic treatment regimen was used. However, definite disease onset as defined by three consecutive days of arthritis is significantly delayed in the dexamethasone-conjugate group (13.8±3.0 days; p=0.025, FIG. 48). This delay was similar to the 0.1 mg/kg dexamethasone group.

Disease incidence of 100% was reached, but at a much later stage (day 18) in the study than the vehicle group (FIG. 49). In comparison, the 0.01 mg/kg dexamethasone group reached 100% incidence already at day 14.

Total clinical score in the 0.01 mg/kg dexamethasone-conjugate group was reduced to a large extent. As a result, the cumulative arthritis score was significantly decreased as compared to the vehicle group (p=0.021). Suppression of arthritis severity by dexamethasone-conjugate was superior to dexamethasone at the same dose level (p=0.021, FIGS. 50 and 51). The effect of 0.01 mg/kg dexamethasone conjugate on cumulative score was in between the effect of the 0.1 and 1 mg/kg dexamethasone group (FIG. 51).

Thickness of the hind paws in the 0.01 mg/kg dexamethasone-conjugate group was reduced throughout the study (FIGS. 52 and 54). Hind paw swelling was significantly decreased with respect to the vehicle group (p=0.021 (left) and p=0.043 (right), FIGS. 53 and 55). No significant differences were observed between the dexamethasone-conjugate group and the different dexamethasone dose groups.

Additional Observations:

Body weight of the 0.01 mg/kg dexamethasone-conjugate group remained more or less the same after initiation of the treatment, which is different from the 0.01 mg/kg dexamethasone group which still showed a certain degree of body weight loss (FIG. 47).

No significant differences were observed for spleen, thymus and liver weights in the dexamethasone-conjugate group compared to the vehicle group or compared to the 0.01 mg/kg dexamethasone group (FIG. 56).

Treatment with intravenous injections of dexamethasone or ED2-dexamethasone was initiated at day 10. At this timepoint, at least one animal in each treatment group showed clinical signs of arthritis. Further disease onset was delayed in rats treated with dexamethasone and ED2-dexamethasone compared to the control group injected with vehicle (FIGS. 48 and 49).

The disease severity (total clinical arthritis score as well as cumulative arthritis score) was correlated to free dexamethasone dose (FIGS. 50 and 51). Interestingly, the suppressive effect of 0.01 mg/kg ED2-dexamethasone was higher than the effect of 0.01 mg/kg free dexamethasone (p=0.004) and not statically different from the effect of higher doses of free dexamethasone.

In sum, these data show that significantly lower doses of ED2-dexamethasone compared to free dexamethasone delay and prevent severe arthritis in the rat CIA mode.

At day 21, the mean body weight of rats in the ED2-dexamethasone treatment group was higher compared to vehicle and dexamethasone treatment groups (data not shown). Thymus weight in the ED2-dexamethasone group was similar to thymus weight in the control group (FIG. 56), whereas thymus weight was significantly lower in rats treated with free dexamethasone doses (0.1 mg/kg) showing clinical effect s comparable to ED2-dexamethasone (p=0.005).

Thus, when administered systemically in the rat CIA model, selective targeting of ED2-dexamethasone to macrophages requires a lower dexamethasone treatment dose and also seems to reduce adverse side effects observed with free dexamethasone, including suppression of thymus as well as growth retardation.

Discussion

In the current rat collagen-induced arthritis study, all vehicle-treated rats developed arthritis, indicating a successful induction of arthritis. Escalating doses of dexamethasone were intravenously administered every three days starting at disease onset to determine a minimal effective dose for future comparison with dexamethasone conjugate, which is expected to be superior due to the macrophage-targeting aspects of this compound. At a dose level of 0.01 mg/kg dexamethasone, suppression of clinical signs of arthritis (clinical score and paw swelling) was observed. At higher dose levels, dexamethasone reduced disease severity to a larger extent and the total clinical score showed a dose-dependent relationship between the dexamethasone dose and suppression of arthritis. In addition, one group was incorporated in this study that was treated with dexamethasone-conjugate at a dose level of 0.01 mg/kg. Increased efficacy of this compound compared to non-conjugated dexamethasone was demonstrated. Cumulative arthritis score was suppressed by 83% versus 39% of dexamethasone at the same dose level. Also, reduced paw swelling was observed, but this effect was not significant. Overall, the same effect on arthritis development can be obtained with 10-100 times lower concentrations of dexamethasone-conjugate. No significant effect on thymus weight was observed in the 0.01 mg/kg dexamethasone-conjugate group, which was also observed for the same dose level of dexamethasone. Increased concentrations of dexamethasone resulted in decreased weight of the thymus, indicating that at the same efficacy level there is less effect on thymus weight of the conjugate.

In summary, dexamethasone concentrations were determined at which sub-maximal suppression of clinical signs of arthritis is observed. In addition, this study yielded valuable information on the performance of dexamethasone-conjugate, which was significantly more effective in suppressing arthritis compared to dexamethasone at the same dose level.

Example 12: Exemplary Pharmaceutical Formulations

Whilst it is possible for an agent of the invention to be administered alone, it is preferable to present it as a medicament or pharmaceutical formulation, together with one or more acceptable carriers. The carrier(s) must be "acceptable" in the sense of being compatible with the agent of the invention and not deleterious to the recipients thereof. Typically, the carriers will be water or saline which will be sterile and pyrogen-free.

The following examples illustrate medicaments and pharmaceutical compositions according to the invention in which the active ingredient is an agent of the invention.

Preferably, the agent of the invention is provided in an amount from 5 mg to 1400 mg (for example, from 7 mg to 1400 mg, or 5 mg to 1000 mg), preferably 5 mg to 200 mg. It will be appreciated that the following exemplary medicaments and pharmaceutical compositions may be prepared containing an amount of the agent from 5 mg to 1400 mg or from 7 mg to 1400 mg, or 5 mg to 1000 mg and preferably 5 mg to 200 mg.

For example, the agent may be present in a $10^{th}$ or $100^{th}$ or $200^{th}$ or $500^{th}$ of the amount shown in the following exemplary medicaments and pharmaceutical compositions with the amounts of the remaining ingredients changed accordingly.

Thus, for example, the tablets or capsules of the medicaments and pharmaceutical compositions of the invention may contain active agent for administration singly or two or more at a time, as appropriate.

Example A: Tablet

| Active ingredient | 1 mg |
|---|---|
| Lactose | 200 mg |
| Starch | 50 mg |
| Polyvinylpyrrolidone | 5 mg |
| Magnesium stearate | 4 mg |

Tablets are prepared from the foregoing ingredients by wet granulation followed by compression.

Example B: Ophthalmic Solution

| Active ingredient | 1 mg |
|---|---|
| Sodium chloride, analytical grade | 0.9 g |
| Thiomersal | 0.001 g |
| Purified water to | 100 ml |
| pH adjusted to | 7.5 |

Example C: Tablet Formulations

The following formulations A and B are prepared by wet granulation of the ingredients with a solution of povidone, followed by addition of magnesium stearate and compression.

Formulation A

| | mg/tablet | mg/tablet |
|---|---|---|
| (a) Active ingredient | 1 | 1 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
| | 251 | 51 |

Formulation B

| | mg/tablet | mg/tablet |
|---|---|---|
| (a) Active ingredient | 1 | 1 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
| | 251 | 51 |

Formulation C

| | mg/tablet |
|---|---|
| Active ingredient | 1 |
| Lactose | 200 |
| Starch | 50 |
| Povidone | 5 |
| Magnesium stearate | 4 |
| | 260 |

The following formulations, D and E, are prepared by direct compression of the admixed ingredients. The lactose used in formulation E is of the direction compression type.

Formulation D

| | mg/capsule |
|---|---|
| Active Ingredient | 1 |
| Pregelatinised Starch NF15 | 150 |
| | 151 |

Formulation E

| | mg/capsule |
|---|---|
| Active Ingredient | 1 |
| Lactose | 150 |
| Avicel ® | 100 |
| | 251 |

Formulation F (Controlled Release Formulation)

The formulation is prepared by wet granulation of the ingredients (below) with a solution of povidone followed by the addition of magnesium stearate and compression.

| | mg/tablet |
|---|---|
| (a) Active Ingredient | 1 |
| (b) Hydroxypropylmethylcellulose (Methocel K4M Premium) ® | 112 |
| (c) Lactose B.P. | 53 |
| (d) Povidone B.P.C. | 28 |
| (e) Magnesium Stearate | 7 |
| | 201 |

Drug release takes place over a period of about 6-8 hours and was complete after 12 hours.

Example D: Capsule Formulations

Formulation A

A capsule formulation is prepared by admixing the ingredients of Formulation D in Example C above and filling into a two-part hard gelatin capsule. Formulation B (infra) is prepared in a similar manner.

Formulation B

| | mg/capsule |
|---|---|
| (a) Active ingredient | 1 |
| (b) Lactose B.P. | 143 |

Formulation B

| | mg/capsule |
|---|---|
| (c) Sodium Starch Glycolate | 25 |
| (d) Magnesium Stearate | 2 |
| | 171 |

Formulation C

| | mg/capsule |
|---|---|
| (a) Active ingredient | 1 |
| (b) Macrogol 4000 BP | 350 |
| | 351 |

Capsules are prepared by melting the Macrogol 4000 BP, dispersing the active ingredient in the melt and filling the melt into a two-part hard gelatin capsule.

Formulation D

| | mg/capsule |
|---|---|
| Active ingredient | 1 |
| Lecithin | 100 |
| *Arachis* Oil | 100 |
| | 201 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

| | mg/capsule |
|---|---|
| (a) Active ingredient | 1 |
| (b) Microcrystalline Cellulose | 125 |
| (c) Lactose BP | 125 |
| (d) Ethyl Cellulose | 13 |
| | 264 |

Example E: Injectable Formulation

| | |
|---|---|
| Active ingredient | 1 mg |
| Sterile, pyrogen free phosphate buffer (pH 7.0) | to 10 ml |

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F: Intramuscular Infection

| | |
|---|---|
| Active ingredient | 1 mg |
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G: Syrup Suspension

| | |
|---|---|
| Active ingredient | 1 mg |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H: Suppository

| | mg/suppository |
|---|---|
| Active ingredient (63 μm)* | 1 |
| Hard Fat, BP (Witepsol H15 - Dynamit Nobel) | 1770 |
| | 1771 |

*The active ingredient is used as a powder wherein at least 90% of the particles are of 63 μm diameter or less.

One fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I: Pessaries

| | mg/pessary |
|---|---|
| Active ingredient | 1 |
| Anhydrate Dextrose | 380 |
| Potato Starch | 363 |
| Magnesium Stearate | 7 |
| | 751 |

The above ingredients are mixed directly and pessaries prepared by direct compression of the resulting mixture.

The invention claimed is:

1. An agent comprising a binding moiety with binding specificity for SRCR domain 1 of the CD163 receptor, wherein the agent comprises a cytotoxic moiety and/or a drug to be delivered to a cell having a CD163 receptor localized on its surface, wherein the agent is internalized into the cell when bound to the CD163 receptor,
   - wherein said cytotoxic moiety and/or a drug is selected from the group consisting of an alkylating agent, an antimetabolite, an antimitotic, a topoisomerase inhibitor, a toxin, an immunosuppressive drug, an immunostimulatory drug, and a protein having biological activity having efficacy in the treatment of a condition or disorder affecting macrophage.

2. An agent according to claim 1 wherein the binding moiety with specificity for SRCR domain 1 of the CD163 receptor is selected from the group consisting of:
   - (a) an antibody or an antigen-binding fragment thereof, or a variant, fusion or derivative of said antibody or an antigen-binding fragment, or a fusion of a said variant or derivative thereof, which retains the binding specificity for SRCR domain 1 of the CD163 receptor;
   - (b) antibody mimics (for example, based on non-antibody scaffolds);
   - (c) RNA aptamers;
   - (d) small molecules; and
   - (e) CovX-bodies.

3. An agent according to claim 1 wherein the CD163 receptor is a human CD163 receptor.

4. An agent according to claim 1 wherein the binding moiety is capable of binding to the consensus sequence:

SEQ ID NO: 26

$K-X_1-VKVQEE-X_2-R$ wherein:

$X_1$ represents $Xaa_{5-8}$ (wherein Xaa represents any amino acid(s)); and;

$X_2$ is absent or represents $Xaa_{38-42}$ (wherein Xaa represents any amino acid(s)).

5. An agent according to claim 1 wherein the binding moiety is capable of binding to the sequence:

SEQ ID NO: 27
KCSGRVEVKVQEEWGTVCNNGWSMEAVSVICNQLGCPTAIKAPGWANSSAGSGR.

6. An agent according to claim 1 wherein the CD163 receptor is localised on the surface of a cell.

7. An agent according to claim 6 wherein the cell is a malignant cell, immune modulatory cell, inflamed cell or infected cell expressing the CD163 receptor.

8. An agent according to claim 6 wherein the cell is a monocyte and/or monocyte-derived cell.

9. An agent according to claim 1 wherein the binding moiety exhibits greater binding affinity for SRCR domain 1 of the CD163 receptor in the presence of calcium than in the absence of calcium.

10. An agent according to claim 2 wherein the binding moiety comprises an antibody or an antigen-binding fragment thereof, or a variant, fusion or derivative of said antibody or an antigen-binding fragment, or a fusion of a said variant or derivative thereof, which retains the binding specificity for SRCR domain 1 of the CD163 receptor.

11. An agent comprising a binding moiety with binding specificity for SRCR domain 1 of the CD163 receptor, wherein the agent is internalized into the cell when bound to the CD163 receptor, wherein the agent comprises a cytotoxic moiety and/or a drug to be delivered to a cell having a CD163 receptor localized on its surface, wherein the binding moiety comprises an antibody or an antigen-binding fragment thereof, or a variant, fusion or derivative of said antibody or an antigen-binding fragment, or a fusion of a said variant or derivative thereof, which retains the binding specificity for SRCR domain 1 of the CD163 receptor, wherein the antibody, antigen-binding fragment, variant, fusion or derivative thereof comprises:
 a heavy-chain variable ($V_H$) region comprising SEQ ID NO: 20 and a light-chain variable ($V_L$) region comprising SEQ ID NO: 21; or
 a heavy-chain variable ($V_H$) region comprising SEQ ID NO: 22 and a light-chain variable ($V_L$) region comprising SEQ ID NO: 23.

12. An agent according to claim 1 wherein said cytotoxic moiety and/or a drug is a immunosuppressive drug, an immunostimulatory drug, or a protein having biological activity having efficacy in the treatment of a condition or disorder affecting macrophage.

13. A pharmaceutical composition comprising an effective amount of an agent as defined in claim 1 and a pharmaceutically-acceptable diluent, carrier or excipient.

14. A kit comprising an agent as defined in claim 1.

15. An agent according to claim 1, wherein said cytotoxic moiety and/or a drug is selected from the group consisting of an alkylating agent, an antimetabolite, an antimitotic, a topoisomerase inhibitor, and a toxin.

16. An agent according to claim 15, wherein said cytotoxic moiety and/or a drug is an alkylating agent.

17. An agent according to claim 16, wherein said alkylating agent is cisplatin or carboplatin.

18. An agent according to claim 15, wherein said cytotoxic moiety and/or a drug is an antimetabolite.

19. An agent according to claim 18, wherein said antimetabolite is azathioprine or methotrexate.

20. An agent according to claim 15, wherein said cytotoxic moiety and/or a drug is an antimitotic.

21. An agent according to claim 20, wherein said antimitotic is vincristine.

22. An agent according to claim 15, wherein said cytotoxic moiety and/or a drug is a topoisomerase inhibitor.

23. An agent according to claim 22, wherein said topoisomerase inhibitor is doxorubicin or etoposide.

24. An agent according to claim 15, wherein said cytotoxic moiety and/or a drug is a toxin.

25. An agent according to claim 24, wherein said toxin is calicheamicin.

26. An agent according to claim 12, wherein said cytotoxic moiety and/or a drug is an immunosuppressive drug.

27. An agent according to claim 26, wherein said immunosuppressive drug is an anti-inflammatory drug, a glucocorticoid, methotrexate, cyclophosphamide, 6-mercaptopurin, cyclosporine, tacrolimus, mycophenolate mofetil, sirulimus, everolimus, an siRNA molecule inhibiting synthesis of proinflammatory cytokines, a non-steroidal anti-inflammatory drug (NSAIDs), a steroid, and a disease-modifying anti-rheumatic drug.

28. An agent according to claim 26, wherein said immunosuppressive drug is a glucocorticoid.

29. An agent according to claim 12, wherein said cytotoxic moiety and/or a drug is an immunostimulatory drug.

30. An agent according to claim 29, wherein said immunostimulatory drug is an siRNA molecule.

31. An agent according to claim 12, wherein said cytotoxic moiety and/or a drug is a protein having biological activity having efficacy in the treatment of a condition or disorder affecting macrophage.

32. An agent according to claim 31, wherein said protein having biological activity having efficacy in the treatment of a condition or disorder affecting macrophage is glucocerebrosidase.

* * * * *

SEQUENCE LISTING

<160> NUMBER OF SEQ ID NOS: 137

<210> SEQ ID NO 1
<211> LENGTH: 100
<212> TYPE: PRT
<213> ORGANISM: Homo sapiens

<400> SEQUENCE: 1

Leu Val Asp Gly Glu Asn Lys Cys Ser Gly Arg Val Glu Val Lys Val
1               5                   10                  15

Gln Glu Glu Trp Gly Thr Val Cys Asn Asn Gly Trp Ser Met Glu Ala
            20                  25                  30

Val Ser Val Ile Cys Asn Gln Leu Gly Cys Pro Thr Ala Ile Lys Ala
        35                  40                  45

Pro Gly Trp Ala Asn Ser Ser Ala Gly Ser Gly Arg Ile Trp Met Asp
    50                  55                  60

His Val Ser Cys Arg Gly Asn Glu Ser Ala Leu Trp Asp Cys Lys His
65                  70                  75                  80

Asp Gly Trp Gly Lys His Ser Asn Cys Thr His Gln Gln Asp Ala Gly
                85                  90                  95

Val Thr Cys Ser
            100

<210> SEQ ID NO 2
<211> LENGTH: 100
<212> TYPE: PRT
<213> ORGANISM: Macaca mulatta

<400> SEQUENCE: 2

Leu Val Asp Gly Glu Asn Lys Cys Ser Gly Arg Val Glu Val Lys Val
1               5                   10                  15

Gln Glu Glu Trp Gly Thr Val Cys Asn Asn Gly Trp Ser Met Glu Ala
            20                  25                  30

Val Ser Val Ile Cys Asn Gln Leu Gly Cys Pro Thr Ala Ile Lys Ala
        35                  40                  45

Thr Gly Trp Ala Asn Ser Ser Ala Gly Ser Gly Arg Ile Trp Met Asp
    50                  55                  60

His Val Ser Cys Arg Gly Asn Glu Ser Ala Leu Trp Asp Cys Lys His
65                  70                  75                  80

Asp Gly Trp Gly Lys His Ser Asn Cys Thr His Gln Gln Asp Ala Gly
                85                  90                  95

Val Thr Cys Ser
            100

<210> SEQ ID NO 3
<211> LENGTH: 100
<212> TYPE: PRT
<213> ORGANISM: Pan troglodytes

<400> SEQUENCE: 3

Leu Val Asp Gly Glu Asn Lys Cys Ser Gly Arg Val Glu Val Lys Val
1               5                   10                  15

Gln Glu Glu Trp Gly Thr Val Cys Asn Asn Gly Trp Ser Met Glu Ala
            20                  25                  30

Val Ser Val Ile Cys Asn Gln Leu Gly Cys Pro Thr Ala Ile Lys Ala
        35                  40                  45

Thr Gly Trp Ala Asn Ser Ser Ala Gly Ser Gly Arg Ile Trp Met Asp
    50                  55                  60

```
His Val Ser Cys Arg Gly Asn Glu Ser Ala Leu Trp Asp Cys Lys His
 65                  70                  75                  80

Asp Gly Trp Gly Lys His Ser Asn Cys Thr His Gln Gln Asp Ala Gly
                 85                  90                  95

Val Thr Cys Ser
            100

<210> SEQ ID NO 4
<211> LENGTH: 99
<212> TYPE: PRT
<213> ORGANISM: Sus scrofa

<400> SEQUENCE: 4

Leu Thr Gly Gly Glu Asn Lys Cys Ser Gly Arg Val Glu Val Lys Val
  1               5                  10                  15

Gln Glu Glu Trp Gly Thr Val Cys Asn Asn Gly Trp Asp Met Asp Val
                 20                  25                  30

Val Ser Val Val Cys Arg Gln Leu Gly Cys Pro Thr Ala Ile Lys Ala
             35                  40                  45

Thr Gly Trp Ala Asn Phe Ser Ala Gly Ser Gly Arg Ile Trp Met Asp
 50                  55                  60

His Val Ser Cys Arg Gly Asn Glu Ser Ala Leu Trp Asp Cys Lys His
 65                  70                  75                  80

Asp Gly Trp Gly Lys His Asn Cys Thr His Gln Gln Asp Ala Gly Val
                 85                  90                  95

Thr Cys Ser

<210> SEQ ID NO 5
<211> LENGTH: 99
<212> TYPE: PRT
<213> ORGANISM: Canis lupus familiaris

<400> SEQUENCE: 5

Leu Thr Asp Gly Glu Asp Asn Cys Ser Gly Arg Val Glu Val Lys Val
  1               5                  10                  15

Gln Glu Glu Trp Gly Thr Val Cys Asn Asn Gly Trp Gly Met Asp Glu
                 20                  25                  30

Val Ser Val Ile Cys Arg Gln Leu Gly Cys Pro Thr Ala Ile Lys Ala
             35                  40                  45

Ala Gly Trp Ala Asn Ser Arg Ala Gly Ser Gly Arg Ile Trp Met Asp
 50                  55                  60

His Val Ser Cys Arg Gly Asn Glu Ser Ala Leu Trp Asp Cys Lys His
 65                  70                  75                  80

Asp Gly Trp Gly Lys His Asn Cys Ser His Gln Gln Asp Ala Gly Val
                 85                  90                  95

Thr Cys Ser

<210> SEQ ID NO 6
<211> LENGTH: 99
<212> TYPE: PRT
<213> ORGANISM: Rattus norvegicus

<400> SEQUENCE: 6

Leu Ala Gly Gly Glu Asn Asn Cys Ser Gly Arg Val Glu Leu Lys Ile
  1               5                  10                  15

His Glu Lys Trp Gly Thr Val Cys Gly Asn Gly Trp Ser Met Asn Glu
                 20                  25                  30
```

```
Val Ser Val Cys Gln Gln Leu Gly Cys Pro Thr Leu Ile Lys Ala
        35                  40                  45

Pro Gly Trp Ala Asn Ala Ser Ala Gly Ser Gly Asp Ile Trp Met Asp
 50                  55                  60

Lys Val Ser Cys Thr Gly Asn Glu Ser Ala Leu Trp Asp Cys Lys His
 65                  70                  75                  80

Glu Gly Trp Gly Lys His Asn Cys Thr His Glu Gln Asp Ala Gly Val
                 85                  90                  95

Thr Cys Ala

<210> SEQ ID NO 7
<211> LENGTH: 98
<212> TYPE: PRT
<213> ORGANISM: Mus musculus

<400> SEQUENCE: 7

Leu Ala Gly Gly Glu Asn Asn Cys Ser Gly Arg Val Glu Leu Lys Ile
 1               5                   10                  15

His Lys Trp Gly Thr Val Cys Ser Asn Gly Trp Ser Met Asn Glu Val
             20                  25                  30

Ser Val Val Cys Gln Gln Leu Gly Cys Pro Thr Ser Ile Lys Ala Leu
        35                  40                  45

Gly Trp Ala Asn Ser Ser Ala Gly Ser Gly Tyr Ile Trp Met Asp Lys
 50                  55                  60

Val Ser Cys Thr Gly Asn Glu Ser Ala Leu Trp Asp Cys Lys His Asp
 65                  70                  75                  80

Gly Trp Gly Lys His Asn Cys Thr His Glu Lys Asp Ala Gly Val Thr
                 85                  90                  95

Cys Ser

<210> SEQ ID NO 8
<211> LENGTH: 99
<212> TYPE: PRT
<213> ORGANISM: Bos primigenius taurus

<400> SEQUENCE: 8

Leu Val Ala Gly Gln Thr Lys Cys Ser Gly Arg Val Glu Val Lys Val
 1               5                   10                  15

Gln Glu Glu Trp Gly Thr Val Cys Asn Thr Gly Trp Asp Leu Ala Ala
             20                  25                  30

Val Ser Val Val Cys Lys Gln Leu Gly Cys Pro Ser Val Ile Lys Ala
        35                  40                  45

Thr Gly Trp Thr Asn Ser Ser Ala Gly Thr Gly Arg Ile Trp Met Asp
 50                  55                  60

His Val Ser Cys Arg Gly Asn Glu Ser Ala Leu Trp Asp Cys Lys His
 65                  70                  75                  80

Glu Gly Trp Gly Lys His Asn Cys Thr His Gln Gln Asp Val Gly Val
                 85                  90                  95

Thr Cys Ser

<210> SEQ ID NO 9
<211> LENGTH: 97
<212> TYPE: PRT
<213> ORGANISM: Artificial Sequence
<220> FEATURE:
<223> OTHER INFORMATION: Human framework region sequence IGHV4-b01
```

<400> SEQUENCE: 9

Val Gln Leu Gln Glu Ser Gly Pro Gly Leu Val Lys Pro Ser Glu Thr
1               5                   10                  15

Leu Ser Leu Thr Cys Ala Val Ser Gly Tyr Ser Ile Ser Ser Gly Tyr
            20                  25                  30

Tyr Trp Gly Trp Ile Arg Gln Pro Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 10
<211> LENGTH: 95
<212> TYPE: PRT
<213> ORGANISM: Artificial Sequence
<220> FEATURE:
<223> OTHER INFORMATION: Human framework region sequence IGKV1D-39*01

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 11
<211> LENGTH: 8
<212> TYPE: PRT
<213> ORGANISM: Artificial Sequence
<220> FEATURE:
<223> OTHER INFORMATION: Mac2-48 and Mac2-158 VH CDR sequence

<400> SEQUENCE: 11

Gly Tyr Ser Ile Thr Ser Asp Tyr
1               5

<210> SEQ ID NO 12
<211> LENGTH: 3
<212> TYPE: PRT
<213> ORGANISM: Artificial Sequence
<220> FEATURE:
<223> OTHER INFORMATION: Mac2-48 and Mac2-158 VH CDR sequence

<400> SEQUENCE: 12

Tyr Ser Gly
1

<210> SEQ ID NO 13
<211> LENGTH: 12

```
<212> TYPE: PRT
<213> ORGANISM: Artificial Sequence
<220> FEATURE:
<223> OTHER INFORMATION: Mac2-48 and Mac2-158 VH CDR sequence

<400> SEQUENCE: 13

Cys Val Ser Gly Thr Tyr Tyr Phe Asp Tyr Trp Gly
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Mac2-158 VL CDR sequence

<400> SEQUENCE: 14

Ala Ser Gln Ser Val Ser Ser Asp Val
1               5

<210> SEQ ID NO 15
<211> LENGTH: 3
<212> TYPE: PRT
<213> ORGANISM: Artificial Sequence
<220> FEATURE:
<223> OTHER INFORMATION: Mac2-158 VL CDR sequence

<400> SEQUENCE: 15

Tyr Ala Ser
1

<210> SEQ ID NO 16
<211> LENGTH: 8
<212> TYPE: PRT
<213> ORGANISM: Artificial Sequence
<220> FEATURE:
<223> OTHER INFORMATION: Mac2-158 VL CDR sequence

<400> SEQUENCE: 16

Gln Asp Tyr Thr Ser Pro Arg Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Mac2-48 VL CDR sequence

<400> SEQUENCE: 17

Ala Ser Gln Ser Val Ser His Asp Val
1               5

<210> SEQ ID NO 18
<211> LENGTH: 3
<212> TYPE: PRT
<213> ORGANISM: Artificial Sequence
<220> FEATURE:
<223> OTHER INFORMATION: Mac2-48 VL CDR sequence

<400> SEQUENCE: 18

Tyr Thr Ser
1

<210> SEQ ID NO 19
<211> LENGTH: 8
<212> TYPE: PRT
```

```
<213> ORGANISM: Artificial Sequence
<220> FEATURE:
<223> OTHER INFORMATION: Mac2-48 VL CDR sequence

<400> SEQUENCE: 19

Gln Asp Tyr Ser Ser Pro Arg Thr
1               5

<210> SEQ ID NO 20
<211> LENGTH: 116
<212> TYPE: PRT
<213> ORGANISM: Artificial Sequence
<220> FEATURE:
<223> OTHER INFORMATION: Mac2-158 VH sequence

<400> SEQUENCE: 20

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Thr Tyr Ser Gly Ile Thr Asn Tyr Asn Pro Ser Leu
    50                  55                  60

Lys Ser Gln Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Val Ser Gly Thr Tyr Tyr Phe Asp Tyr Trp Gly Gln Gly Thr Thr Leu
            100                 105                 110

Thr Val Ser Ser
        115

<210> SEQ ID NO 21
<211> LENGTH: 109
<212> TYPE: PRT
<213> ORGANISM: Artificial Sequence
<220> FEATURE:
<223> OTHER INFORMATION: Mac2-158 VL sequence

<400> SEQUENCE: 21

Ser Val Val Met Thr Gln Thr Pro Lys Ser Leu Leu Ile Ser Ile Gly
1               5                   10                  15

Asp Arg Val Thr Ile Thr Cys Lys Ala Ser Gln Ser Val Ser Ser Asp
                20                  25                  30

Val Ala Trp Phe Gln Gln Lys Pro Gly Gln Ser Pro Lys Pro Leu Ile
            35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Ser Val Gln Ala
65                  70                  75                  80

Glu Asp Leu Ala Val Tyr Phe Cys Gly Gln Asp Tyr Thr Ser Pro Arg
                85                  90                  95

Thr Phe Gly Gly Gly Thr Lys Leu Glu Ile Lys Arg Ala
            100                 105

<210> SEQ ID NO 22
<211> LENGTH: 116
<212> TYPE: PRT
<213> ORGANISM: Artificial Sequence
```

<220> FEATURE:
<223> OTHER INFORMATION: Mac2-48 VH sequence

<400> SEQUENCE: 22

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Phe Ile Ser Tyr Ser Gly Ile Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ser Ala Thr Tyr Tyr Cys
                85                  90                  95

Val Ser Gly Thr Tyr Tyr Phe Asp Tyr Trp Gly Gln Gly Thr Thr Leu
            100                 105                 110

Thr Val Ser Ser
            115

<210> SEQ ID NO 23
<211> LENGTH: 109
<212> TYPE: PRT
<213> ORGANISM: Artificial Sequence
<220> FEATURE:
<223> OTHER INFORMATION: Mac2-48 VL sequence

<400> SEQUENCE: 23

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser His Asp
            20                  25                  30

Val Ser Trp Phe Gln Gln Lys Pro Gly Gln Ser Pro Lys Leu Leu Ile
        35                  40                  45

Tyr Tyr Thr Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Ile Tyr Phe Cys Gln Gln Asp Tyr Ser Ser Pro Arg
                85                  90                  95

Thr Phe Gly Gly Gly Thr Lys Leu Glu Ile Lys Arg Ala
            100                 105

<210> SEQ ID NO 24
<211> LENGTH: 116
<212> TYPE: PRT
<213> ORGANISM: Artificial Sequence
<220> FEATURE:
<223> OTHER INFORMATION: Humanised VH sequence

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

```
Met Gly Tyr Ile Thr Tyr Ser Gly Ser Thr Tyr Tyr Asn Pro Ser Leu
    50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Thr Tyr Tyr Cys
                 85                  90                  95

Val Ser Gly Thr Tyr Tyr Phe Asp Tyr Trp Gly Gln Gly Thr Thr Leu
            100                 105                 110

Thr Val Ser Ser
        115

<210> SEQ ID NO 25
<211> LENGTH: 108
<212> TYPE: PRT
<213> ORGANISM: Artificial Sequence
<220> FEATURE:
<223> OTHER INFORMATION: Humanised VL sequence

<400> SEQUENCE: 25

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Asp
                20                  25                  30

Val Ala Trp Phe Gln Gln Lys Pro Gly Lys Ser Pro Lys Pro Leu Ile
            35                  40                  45

Tyr Tyr Ala Ser Asn Arg Tyr Ser Gly Val Pro Ser Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Phe Ala Val Tyr Phe Cys Gly Gln Asp Tyr Thr Ser Pro Arg
                 85                  90                  95

Thr Phe Gly Gly Gly Thr Lys Leu Glu Ile Lys Arg
            100                 105

<210> SEQ ID NO 26
<211> LENGTH: 58
<212> TYPE: PRT
<213> ORGANISM: Artificial Sequence
<220> FEATURE:
<223> OTHER INFORMATION: Target consensus sequence for binding moiety
<220> FEATURE:
<221> NAME/KEY: SITE
<222> LOCATION: (2)...(9)
<223> OTHER INFORMATION: Xaa at locations 2 through 9 represent any
      amino acid.  At locations 7 through 9, one, two, or three
      Xaa may be absent
<220> FEATURE:
<221> NAME/KEY: SITE
<222> LOCATION: (16)...(57)
<223> OTHER INFORMATION: Xaa at locations 16 through 57 represent any
      amino acid.  At locations 54 through 57, one, two, three,
      or four Xaa may be absent

<400> SEQUENCE: 26

Lys Xaa Xaa Xaa Xaa Xaa Xaa Xaa Val Lys Val Gln Glu Glu Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Arg
         50                  55
```

<210> SEQ ID NO 27
<211> LENGTH: 54
<212> TYPE: PRT
<213> ORGANISM: Artificial Sequence
<220> FEATURE:
<223> OTHER INFORMATION: Target sequence for binding moiety

<400> SEQUENCE: 27

```
Lys Cys Ser Gly Arg Val Glu Val Lys Val Gln Glu Glu Trp Gly Thr
1               5                   10                  15

Val Cys Asn Asn Gly Trp Ser Met Glu Ala Val Ser Val Ile Cys Asn
            20                  25                  30

Gln Leu Gly Cys Pro Thr Ala Ile Lys Ala Pro Gly Trp Ala Asn Ser
        35                  40                  45

Ser Ala Gly Ser Gly Arg
    50
```

<210> SEQ ID NO 28
<211> LENGTH: 1156
<212> TYPE: PRT
<213> ORGANISM: Homo sapiens

<400> SEQUENCE: 28

```
Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Thr Asp
        35                  40                  45

Lys Glu Leu Arg Leu Val Asp Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255
```

Ile Cys Ser Lys Gly Ala Asp Leu Ser Leu Arg Leu Val Asp Gly Val
              260                 265                 270

Thr Glu Cys Ser Gly Arg Leu Glu Val Arg Phe Gln Gly Glu Trp Gly
              275                 280                 285

Thr Ile Cys Asp Asp Gly Trp Asp Ser Tyr Asp Ala Ala Val Ala Cys
              290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
                    325                 330                 335

Gly His Glu Pro Ala Val Trp Gln Cys Lys His His Glu Trp Gly Lys
              340                 345                 350

His Tyr Cys Asn His Asn Glu Asp Ala Gly Val Thr Cys Ser Asp Gly
              355                 360                 365

Ser Asp Leu Glu Leu Arg Leu Arg Gly Gly Ser Arg Cys Ala Gly
              370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                    405                 410                 415

Gly Ser Ala Leu Lys Thr Ser Tyr Gln Val Tyr Ser Lys Ile Gln Ala
              420                 425                 430

Thr Asn Thr Trp Leu Phe Leu Ser Ser Cys Asn Gly Asn Glu Thr Ser
              435                 440                 445

Leu Trp Asp Cys Lys Asn Trp Gln Trp Gly Gly Leu Thr Cys Asp His
450                 455                 460

Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Glu Val Lys His Gly
                    485                 490                 495

Asp Thr Trp Gly Ser Ile Cys Asp Ser Asp Phe Ser Leu Glu Ala Ala
              500                 505                 510

Ser Val Leu Cys Arg Glu Leu Gln Cys Gly Thr Val Val Ser Ile Leu
              515                 520                 525

Gly Gly Ala His Phe Gly Glu Gly Asn Gly Gln Ile Trp Ala Glu Glu
              530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                    565                 570                 575

Cys Ser Arg Tyr Thr Glu Ile Arg Leu Val Asn Gly Lys Thr Pro Cys
              580                 585                 590

Glu Gly Arg Val Glu Leu Lys Thr Leu Gly Ala Trp Gly Ser Leu Cys
              595                 600                 605

Asn Ser His Trp Asp Ile Glu Asp Ala His Val Leu Cys Gln Gln Leu
              610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                    645                 650                 655

Gln His Met Gly Asp Cys Pro Val Thr Ala Leu Gly Ala Ser Leu Cys
              660                 665                 670

Pro Ser Glu Gln Val Ala Ser Val Ile Cys Ser Gly Asn Gln Ser Gln

```
                    675                 680                 685
Thr Leu Ser Ser Cys Asn Ser Ser Leu Gly Pro Thr Arg Pro Thr
    690                 695                 700
Ile Pro Glu Glu Ser Ala Val Ala Cys Ile Glu Ser Gly Gln Leu Arg
705                 710                 715                 720
Leu Val Asn Gly Gly Arg Cys Ala Gly Arg Val Glu Ile Tyr His
                725                 730                 735
Glu Gly Ser Trp Gly Thr Ile Cys Asp Asp Ser Trp Asp Leu Ser Asp
                740                 745                 750
Ala His Val Val Cys Arg Gln Leu Gly Cys Gly Glu Ala Ile Asn Ala
            755                 760                 765
Thr Gly Ser Ala His Phe Gly Glu Gly Thr Gly Pro Ile Trp Leu Asp
770                 775                 780
Glu Met Lys Cys Asn Gly Lys Glu Ser Arg Ile Trp Gln Cys His Ser
785                 790                 795                 800
His Gly Trp Gly Gln Gln Asn Cys Arg His Lys Glu Asp Ala Gly Val
                805                 810                 815
Ile Cys Ser Glu Phe Met Ser Leu Arg Leu Thr Ser Glu Ala Ser Arg
                820                 825                 830
Glu Ala Cys Ala Gly Arg Leu Glu Val Phe Tyr Asn Gly Ala Trp Gly
            835                 840                 845
Thr Val Gly Lys Ser Ser Met Ser Glu Thr Thr Val Gly Val Val Cys
850                 855                 860
Arg Gln Leu Gly Cys Ala Asp Lys Gly Lys Ile Asn Pro Ala Ser Leu
865                 870                 875                 880
Asp Lys Ala Met Ser Ile Pro Met Trp Val Asp Asn Val Gln Cys Pro
                885                 890                 895
Lys Gly Pro Asp Thr Leu Trp Gln Cys Pro Ser Ser Pro Trp Glu Lys
                900                 905                 910
Arg Leu Ala Ser Pro Ser Glu Glu Thr Trp Ile Thr Cys Asp Asn Lys
            915                 920                 925
Ile Arg Leu Gln Glu Gly Pro Thr Ser Cys Ser Gly Arg Val Glu Ile
        930                 935                 940
Trp His Gly Gly Ser Trp Gly Thr Val Cys Asp Asp Ser Trp Asp Leu
945                 950                 955                 960
Asp Asp Ala Gln Val Val Cys Gln Gln Leu Gly Cys Gly Pro Ala Leu
                965                 970                 975
Lys Ala Phe Lys Glu Ala Glu Phe Gly Gln Gly Thr Gly Pro Ile Trp
                980                 985                 990
Leu Asn Glu Val Lys Cys Lys Gly Asn Glu Ser Ser Leu Trp Asp Cys
            995                 1000                1005
Pro Ala Arg Arg Trp Gly His Ser Glu Cys Gly His Lys Glu Asp Ala
        1010                1015                1020
Ala Val Asn Cys Thr Asp Ile Ser Val Gln Lys Thr Pro Gln Lys Ala
1025                1030                1035                1040
Thr Thr Gly Arg Ser Ser Arg Gln Ser Ser Phe Ile Ala Val Gly Ile
                1045                1050                1055
Leu Gly Val Val Leu Leu Ala Ile Phe Val Ala Leu Phe Phe Leu Thr
            1060                1065                1070
Lys Lys Arg Arg Gln Arg Gln Arg Leu Ala Val Ser Ser Arg Gly Glu
        1075                1080                1085
Asn Leu Val His Gln Ile Gln Tyr Arg Glu Met Asn Ser Cys Leu Asn
        1090                1095                1100
```

-continued

```
Ala Asp Asp Leu Asp Leu Met Asn Ser Ser Glu Asn Ser His Glu Ser
1105                1110                1115                1120

Ala Asp Phe Ser Ala Ala Glu Leu Ile Ser Val Ser Lys Phe Leu Pro
                1125                1130                1135

Ile Ser Gly Met Glu Lys Glu Ala Ile Leu Ser His Thr Glu Lys Glu
            1140                1145                1150

Asn Gly Asn Leu
        1155

<210> SEQ ID NO 29
<211> LENGTH: 1122
<212> TYPE: PRT
<213> ORGANISM: Homo sapiens

<400> SEQUENCE: 29

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Gly Thr Asp
            35                  40                  45

Lys Glu Leu Arg Leu Val Asp Gly Glu Asn Lys Cys Ser Gly Arg Val
50                  55                  60

Glu Val Lys Val Gln Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
    130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser Tyr Asp Ala Ala Val Ala Cys
    290                 295                 300

Lys Gln Leu Gly Cys Pro Thr Ala Val Thr Ala Ile Gly Arg Val Asn
```

```
              305                 310                 315                 320
         Ala Ser Lys Gly Phe Gly His Ile Trp Leu Asp Ser Val Ser Cys Gln
                         325                 330                 335
         Gly His Glu Pro Ala Val Trp Gln Cys Lys His His Glu Trp Gly Lys
                         340                 345                 350
         His Tyr Cys Asn His Asn Glu Asp Ala Gly Val Thr Cys Ser Asp Gly
                         355                 360                 365
         Ser Asp Leu Glu Leu Arg Leu Arg Gly Gly Ser Arg Cys Ala Gly
                 370                 375                 380
         Thr Val Glu Val Glu Ile Gln Arg Leu Leu Gly Lys Val Cys Asp Arg
         385                 390                 395                 400
         Gly Trp Gly Leu Lys Glu Ala Asp Val Val Cys Arg Gln Leu Gly Cys
                         405                 410                 415
         Gly Ser Ala Leu Lys Thr Ser Tyr Gln Val Tyr Ser Lys Ile Gln Ala
                         420                 425                 430
         Thr Asn Thr Trp Leu Phe Leu Ser Ser Cys Asn Gly Asn Glu Thr Ser
                         435                 440                 445
         Leu Trp Asp Cys Lys Asn Trp Gln Trp Gly Gly Leu Thr Cys Asp His
                 450                 455                 460
         Tyr Glu Glu Ala Lys Ile Thr Cys Ser Ala His Arg Glu Pro Arg Leu
         465                 470                 475                 480
         Val Gly Gly Asp Ile Pro Cys Ser Gly Arg Val Glu Val Lys His Gly
                         485                 490                 495
         Asp Thr Trp Gly Ser Ile Cys Asp Ser Asp Phe Ser Leu Glu Ala Ala
                         500                 505                 510
         Ser Val Leu Cys Arg Glu Leu Gln Cys Gly Thr Val Val Ser Ile Leu
                         515                 520                 525
         Gly Gly Ala His Phe Gly Glu Gly Asn Gly Gln Ile Trp Ala Glu Glu
                         530                 535                 540
         Phe Gln Cys Glu Gly His Glu Ser His Leu Ser Leu Cys Pro Val Ala
         545                 550                 555                 560
         Pro Arg Pro Glu Gly Thr Cys Ser His Ser Arg Asp Val Gly Val Val
                         565                 570                 575
         Cys Ser Arg Tyr Thr Glu Ile Arg Leu Val Asn Gly Lys Thr Pro Cys
                         580                 585                 590
         Glu Gly Arg Val Glu Leu Lys Thr Leu Gly Ala Trp Gly Ser Leu Cys
                         595                 600                 605
         Asn Ser His Trp Asp Ile Glu Asp Ala His Val Leu Cys Gln Gln Leu
                         610                 615                 620
         Lys Cys Gly Val Ala Leu Ser Thr Pro Gly Gly Ala Arg Phe Gly Lys
         625                 630                 635                 640
         Gly Asn Gly Gln Ile Trp Arg His Met Phe His Cys Thr Gly Thr Glu
                         645                 650                 655
         Gln His Met Gly Asp Cys Pro Val Thr Ala Leu Gly Ala Ser Leu Cys
                         660                 665                 670
         Pro Ser Glu Gln Val Ala Ser Val Ile Cys Ser Gly Asn Gln Ser Gln
                         675                 680                 685
         Thr Leu Ser Ser Cys Asn Ser Ser Ser Leu Gly Pro Thr Arg Pro Thr
                         690                 695                 700
         Ile Pro Glu Glu Ser Ala Val Ala Cys Ile Glu Ser Gly Gln Leu Arg
         705                 710                 715                 720
         Leu Val Asn Gly Gly Gly Arg Cys Ala Gly Arg Val Glu Ile Tyr His
                         725                 730                 735
```

Glu Gly Ser Trp Gly Thr Ile Cys Asp Asp Ser Trp Asp Leu Ser Asp
                740                 745                 750

Ala His Val Val Cys Arg Gln Leu Gly Cys Gly Glu Ala Ile Asn Ala
                755                 760                 765

Thr Gly Ser Ala His Phe Gly Glu Gly Thr Gly Pro Ile Trp Leu Asp
                770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
                820                 825                 830

Glu Ala Cys Ala Gly Arg Leu Glu Val Phe Tyr Asn Gly Ala Trp Gly
                835                 840                 845

Thr Val Gly Lys Ser Ser Met Ser Glu Thr Thr Val Gly Val Val Cys
                850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
                900                 905                 910

Arg Leu Ala Ser Pro Ser Glu Glu Thr Trp Ile Thr Cys Asp Asn Lys
                915                 920                 925

Ile Arg Leu Gln Glu Gly Pro Thr Ser Cys Ser Gly Arg Val Glu Ile
                930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
                980                 985                 990

Leu Asn Glu Val Lys Cys Lys Gly Asn Glu Ser Ser Leu Trp Asp Cys
                995                 1000                1005

Pro Ala Arg Arg Trp Gly His Ser Glu Cys Gly His Lys Glu Asp Ala
1010                1015                1020

Ala Val Asn Cys Thr Asp Ile Ser Val Gln Lys Thr Pro Gln Lys Ala
1025                1030                1035                1040

Thr Thr Gly Arg Ser Ser Arg Gln Ser Ser Phe Ile Ala Val Gly Ile
                1045                1050                1055

Leu Gly Val Val Leu Leu Ala Ile Phe Val Ala Leu Phe Phe Leu Thr
                1060                1065                1070

Lys Lys Arg Arg Gln Arg Gln Arg Leu Ala Val Ser Ser Arg Gly Glu
                1075                1080                1085

Asn Leu Val His Gln Ile Gln Tyr Arg Glu Met Asn Ser Cys Leu Asn
                1090                1095                1100

Ala Asp Asp Leu Asp Leu Met Asn Ser Ser Gly Gly His Ser Glu Pro
1105                1110                1115                1120

His Asx

<210> SEQ ID NO 30
<211> LENGTH: 1161
<212> TYPE: PRT

<213> ORGANISM: Homo sapiens

<400> SEQUENCE: 30

```
Met Ser Lys Leu Arg Met Val Leu Leu Glu Asp Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
    50                  55                  60

Glu Val Lys Val Gln Glu Glu Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser Tyr Asp Ala Ala Val Ala Cys
290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Ser Arg Cys Ala Gly
370                 375                 380

Thr Val Glu Val Glu Ile Gln Arg Leu Leu Gly Lys Val Cys Asp Arg
385                 390                 395                 400
```

```
Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Thr Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
    450                 455                 460

Tyr Glu Glu Ala Lys Ile Thr Cys Ser Ala His Arg Glu Pro Arg Leu
465                 470                 475                 480

Val Gly Asp Ile Pro Cys Ser Gly Arg Val Glu Val Lys His Gly
                485                 490                 495

Asp Thr Trp Gly Ser Ile Cys Asp Ser Asp Phe Ser Leu Glu Ala Ala
            500                 505                 510

Ser Val Leu Cys Arg Glu Leu Gln Cys Gly Thr Val Val Ser Ile Leu
        515                 520                 525

Gly Gly Ala His Phe Gly Glu Gly Asn Gly Gln Ile Trp Ala Glu Glu
    530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Arg Tyr Thr Glu Ile Arg Leu Val Asn Gly Lys Thr Pro Cys
            580                 585                 590

Glu Gly Arg Val Glu Leu Lys Thr Leu Gly Ala Trp Gly Ser Leu Cys
        595                 600                 605

Asn Ser His Trp Asp Ile Glu Asp Ala His Val Leu Cys Gln Gln Leu
    610                 615                 620

Lys Cys Gly Val Ala Leu Ser Thr Pro Gly Gly Ala Arg Phe Gly Lys
625                 630                 635                 640

Gly Asn Gly Gln Ile Trp Arg His Met Phe His Cys Thr Gly Thr Glu
                645                 650                 655

Gln His Met Gly Asp Cys Pro Val Thr Ala Leu Gly Ala Ser Leu Cys
            660                 665                 670

Pro Ser Glu Gln Val Ala Ser Val Ile Cys Ser Gly Asn Gln Ser Gln
        675                 680                 685

Thr Leu Ser Ser Cys Asn Ser Ser Ser Leu Gly Pro Thr Arg Pro Thr
    690                 695                 700

Ile Pro Glu Glu Ser Ala Val Ala Cys Ile Glu Ser Gly Gln Leu Arg
705                 710                 715                 720

Leu Val Asn Gly Gly Gly Arg Cys Ala Gly Arg Val Glu Ile Tyr His
                725                 730                 735

Glu Gly Ser Trp Gly Thr Ile Cys Asp Asp Ser Trp Asp Leu Ser Asp
            740                 745                 750

Ala His Val Val Cys Arg Gln Leu Gly Cys Gly Glu Ala Ile Asn Ala
        755                 760                 765

Thr Gly Ser Ala His Phe Gly Glu Gly Thr Gly Pro Ile Trp Leu Asp
    770                 775                 780

Glu Met Lys Cys Asn Gly Lys Glu Ser Arg Ile Trp Gln Cys His Ser
785                 790                 795                 800

His Gly Trp Gly Gln Gln Asn Cys Arg His Lys Glu Asp Ala Gly Val
                805                 810                 815

Ile Cys Ser Glu Phe Met Ser Leu Arg Leu Thr Ser Glu Ala Ser Arg
```

```
                820                 825                 830
Glu Ala Cys Ala Gly Arg Leu Glu Val Phe Tyr Asn Gly Ala Trp Gly
            835                 840                 845

Thr Val Gly Lys Ser Ser Met Ser Glu Thr Thr Val Gly Val Val Cys
        850                 855                 860

Arg Gln Leu Gly Cys Ala Asp Lys Gly Lys Ile Asn Pro Ala Ser Leu
865                 870                 875                 880

Asp Lys Ala Met Ser Ile Pro Met Trp Val Asp Asn Val Gln Cys Pro
                885                 890                 895

Lys Gly Pro Asp Thr Leu Trp Gln Cys Pro Ser Ser Pro Trp Glu Lys
            900                 905                 910

Arg Leu Ala Ser Pro Ser Glu Glu Thr Trp Ile Thr Cys Asp Asn Lys
        915                 920                 925

Ile Arg Leu Gln Glu Gly Pro Thr Ser Cys Ser Gly Arg Val Glu Ile
            930                 935                 940

Trp His Gly Gly Ser Trp Gly Thr Val Cys Asp Asp Ser Trp Asp Leu
945                 950                 955                 960

Asp Asp Ala Gln Val Val Cys Gln Gln Leu Gly Cys Gly Pro Ala Leu
                965                 970                 975

Lys Ala Phe Lys Glu Ala Glu Phe Gly Gln Gly Thr Gly Pro Ile Trp
            980                 985                 990

Leu Asn Glu Val Lys Cys Lys Gly Asn Glu Ser Ser Leu Trp Asp Cys
        995                 1000                1005

Pro Ala Arg Arg Trp Gly His Ser Glu Cys Gly His Lys Glu Asp Ala
    1010                1015                1020

Ala Val Asn Cys Thr Asp Ile Ser Val Gln Lys Thr Pro Gln Lys Ala
1025                1030                1035                1040

Thr Thr Gly Arg Ser Ser Arg Gln Ser Ser Phe Ile Ala Val Gly Ile
            1045                1050                1055

Leu Gly Val Val Leu Leu Ala Ile Phe Val Ala Leu Phe Phe Leu Thr
        1060                1065                1070

Lys Lys Arg Arg Gln Arg Gln Arg Leu Ala Val Ser Ser Arg Gly Glu
            1075                1080                1085

Asn Leu Val His Gln Ile Gln Tyr Arg Glu Met Asn Ser Cys Leu Asn
    1090                1095                1100

Ala Asp Asp Leu Asp Leu Met Asn Ser Ser Gly Leu Trp Val Leu Gly
1105                1110                1115                1120

Gly Ser Ile Ala Gln Gly Phe Arg Ser Val Ala Ala Val Glu Ala Gln
            1125                1130                1135

Thr Phe Tyr Phe Asp Lys Gln Leu Lys Lys Ser Lys Asn Val Ile Gly
        1140                1145                1150

Ser Leu Asp Ala Tyr Asn Gly Gln Glu
        1155                1160

<210> SEQ ID NO 31
<211> LENGTH: 1154
<212> TYPE: PRT
<213> ORGANISM: Homo sapiens

<400> SEQUENCE: 31

Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30
```

```
Leu Leu Leu Ser Ala Cys Phe Val Thr Ser Ser Leu Gly Gly Thr Asp
             35                  40                  45

Lys Glu Leu Arg Leu Val Asp Gly Glu Asn Lys Cys Ser Gly Arg Val
 50                  55                  60

Glu Val Lys Val Gln Glu Glu Trp Gly Thr Val Cys Asn Asn Gly Trp
 65                  70                  75                  80

Ser Met Glu Ala Val Ser Val Ile Cys Asn Gln Leu Gly Cys Pro Thr
                 85                  90                  95

Ala Ile Lys Ala Pro Gly Trp Ala Asn Ser Ser Ala Gly Ser Gly Arg
                100                 105                 110

Ile Trp Met Asp His Val Ser Cys Arg Gly Asn Glu Ser Ala Leu Trp
            115                 120                 125

Asp Cys Lys His Asp Gly Trp Gly Lys His Ser Asn Cys Thr His Gln
        130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
    210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser Gly Arg Leu Glu Val Arg Phe Gln Gly Glu Trp Gly
        275                 280                 285

Thr Ile Cys Asp Asp Gly Trp Asp Ser Tyr Asp Ala Ala Val Ala Cys
    290                 295                 300

Lys Gln Leu Gly Cys Pro Thr Ala Val Thr Ala Ile Gly Arg Val Asn
305                 310                 315                 320

Ala Ser Lys Gly Phe Gly His Ile Trp Leu Asp Ser Val Ser Cys Gln
                325                 330                 335

Gly His Glu Pro Ala Val Trp Gln Cys Lys His His Glu Trp Gly Lys
            340                 345                 350

His Tyr Cys Asn His Asn Glu Asp Ala Gly Val Thr Cys Ser Asp Gly
        355                 360                 365

Ser Asp Leu Glu Leu Arg Leu Arg Gly Gly Ser Arg Cys Ala Gly
    370                 375                 380

Thr Val Glu Val Glu Ile Gln Arg Leu Leu Gly Lys Val Cys Asp Arg
385                 390                 395                 400

Gly Trp Gly Leu Lys Glu Ala Asp Val Val Cys Arg Gln Leu Gly Cys
                405                 410                 415

Gly Ser Ala Leu Lys Thr Ser Tyr Gln Val Tyr Ser Lys Ile Gln Ala
            420                 425                 430

Thr Asn Thr Trp Leu Phe Leu Ser Ser Cys Asn Gly Asn Glu Thr Ser
        435                 440                 445

Leu Trp Asp Cys Lys Asn Trp Gln Trp Gly Gly Leu Thr Cys Asp His
```

```
              450         455         460
Tyr Glu Glu Ala Lys Ile Thr Cys Ser Ala His Arg Glu Pro Arg Leu
465                 470                 475                 480

Val Gly Gly Asp Ile Pro Cys Ser Gly Arg Val Val Lys His Gly
                485                 490                 495

Asp Thr Trp Gly Ser Ile Cys Asp Ser Asp Phe Ser Leu Glu Ala Ala
                500                 505                 510

Ser Val Leu Cys Arg Glu Leu Gln Cys Gly Thr Val Val Ser Ile Leu
                515                 520                 525

Gly Gly Ala His Phe Gly Glu Gly Asn Gly Gln Ile Trp Ala Glu Glu
                530                 535                 540

Phe Gln Cys Glu Gly His Glu Ser His Leu Ser Leu Cys Pro Val Ala
545                 550                 555                 560

Pro Arg Pro Glu Gly Thr Cys Ser His Ser Arg Asp Val Gly Val Val
                565                 570                 575

Cys Ser Ser Lys Thr Gln Lys Thr Ser Leu Ile Gly Ser Tyr Thr Val
                580                 585                 590

Lys Gly Thr Gly Leu Gly Ser His Ser Cys Leu Phe Leu Lys Pro Cys
                595                 600                 605

Leu Leu Pro Gly Tyr Thr Glu Ile Arg Leu Val Asn Gly Lys Thr Pro
                610                 615                 620

Cys Glu Gly Arg Val Glu Leu Lys Thr Leu Gly Ala Trp Gly Ser Leu
625                 630                 635                 640

Cys Asn Ser His Trp Asp Ile Glu Asp Ala His Val Leu Cys Gln Gln
                645                 650                 655

Leu Lys Cys Gly Val Ala Leu Ser Thr Pro Gly Gly Ala Arg Phe Gly
                660                 665                 670

Lys Gly Asn Gly Gln Ile Trp Arg His Met Phe His Cys Thr Gly Thr
                675                 680                 685

Glu Gln His Met Gly Asp Cys Pro Val Thr Ala Leu Gly Ala Ser Leu
                690                 695                 700

Cys Pro Ser Glu Gln Val Ala Ser Val Ile Cys Ser Gly Asn Gln Ser
705                 710                 715                 720

Gln Thr Leu Ser Ser Cys Asn Ser Ser Ser Leu Gly Pro Thr Arg Pro
                725                 730                 735

Thr Ile Pro Glu Glu Ser Ala Val Ala Cys Ile Glu Ser Gly Gln Leu
                740                 745                 750

Arg Leu Val Asn Gly Gly Gly Arg Cys Ala Gly Arg Val Glu Ile Tyr
                755                 760                 765

His Glu Gly Ser Trp Gly Thr Ile Cys Asp Asp Ser Trp Asp Leu Ser
                770                 775                 780

Asp Ala His Val Val Cys Arg Gln Leu Gly Cys Gly Glu Ala Ile Asn
785                 790                 795                 800

Ala Thr Gly Ser Ala His Phe Gly Glu Gly Thr Gly Pro Ile Trp Leu
                805                 810                 815

Asp Glu Met Lys Cys Asn Gly Lys Glu Ser Arg Ile Trp Gln Cys His
                820                 825                 830

Ser His Gly Trp Gly Gln Gln Asn Cys Arg His Lys Glu Asp Ala Gly
                835                 840                 845

Val Ile Cys Ser Glu Phe Met Ser Leu Arg Leu Thr Ser Glu Ala Ser
                850                 855                 860

Arg Glu Ala Cys Ala Gly Arg Leu Glu Val Phe Tyr Asn Gly Ala Trp
865                 870                 875                 880
```

```
Gly Thr Val Gly Lys Ser Ser Met Ser Glu Thr Val Gly Val Val
            885                 890                 895
Cys Arg Gln Leu Gly Cys Ala Asp Lys Gly Lys Ile Asn Pro Ala Ser
        900                 905                 910
Leu Asp Lys Ala Met Ser Ile Pro Met Trp Val Asp Asn Val Gln Cys
    915                 920                 925
Pro Lys Gly Pro Asp Thr Leu Trp Gln Cys Pro Ser Ser Pro Trp Glu
930                 935                 940
Lys Arg Leu Ala Ser Pro Ser Glu Glu Thr Trp Ile Thr Cys Asp Asn
945                 950                 955                 960
Lys Ile Arg Leu Gln Glu Gly Pro Thr Ser Cys Ser Gly Arg Val Glu
                965                 970                 975
Ile Trp His Gly Gly Ser Trp Gly Thr Val Cys Asp Asp Ser Trp Asp
            980                 985                 990
Leu Asp Asp Ala Gln Val Val Cys Gln Gln Leu Gly Cys Gly Pro Ala
        995                 1000                1005
Leu Lys Ala Phe Lys Glu Ala Glu Phe Gly Gln Gly Thr Gly Pro Ile
    1010                1015                1020
Trp Leu Asn Glu Val Lys Cys Lys Gly Asn Glu Ser Ser Leu Trp Asp
1025                1030                1035                1040
Cys Pro Ala Arg Arg Trp Gly His Ser Glu Cys Gly His Lys Glu Asp
                1045                1050                1055
Ala Ala Val Asn Cys Thr Asp Ile Ser Val Gln Lys Thr Pro Gln Lys
            1060                1065                1070
Ala Thr Thr Gly Arg Ser Ser Arg Gln Ser Ser Phe Ile Ala Val Gly
        1075                1080                1085
Ile Leu Gly Val Val Leu Leu Ala Ile Phe Val Ala Leu Phe Phe Leu
    1090                1095                1100
Thr Lys Lys Arg Arg Gln Arg Gln Arg Leu Ala Val Ser Ser Arg Gly
1105                1110                1115                1120
Glu Asn Leu Val His Gln Ile Gln Tyr Arg Glu Met Asn Ser Cys Leu
                1125                1130                1135
Asn Ala Asp Asp Leu Asp Leu Met Asn Ser Ser Gly Gly His Ser Glu
            1140                1145                1150
Pro His

<210> SEQ ID NO 32
<211> LENGTH: 18
<212> TYPE: DNA
<213> ORGANISM: Artificial Sequence
<220> FEATURE:
<223> OTHER INFORMATION: VK6 leader primer

<400> SEQUENCE: 32
tgaagtcaca gacccagg                                                 18

<210> SEQ ID NO 33
<211> LENGTH: 20
<212> TYPE: DNA
<213> ORGANISM: Artificial Sequence
<220> FEATURE:
<223> OTHER INFORMATION: VK constant primer

<400> SEQUENCE: 33
gcacctccag atgttaactg                                               20
```

```
<210> SEQ ID NO 34
<211> LENGTH: 21
<212> TYPE: DNA
<213> ORGANISM: Artificial Sequence
<220> FEATURE:
<223> OTHER INFORMATION: VHg constant primer

<400> SEQUENCE: 34
agggaaatar cccttgacca g                                           21

<210> SEQ ID NO 35
<211> LENGTH: 21
<212> TYPE: DNA
<213> ORGANISM: Artificial Sequence
<220> FEATURE:
<223> OTHER INFORMATION: VH leader 2 primer

<400> SEQUENCE: 35
atgagagtgc tgattctttt g                                           21

<210> SEQ ID NO 36
<211> LENGTH: 18
<212> TYPE: DNA
<213> ORGANISM: Artificial Sequence
<220> FEATURE:
<223> OTHER INFORMATION: VHfor primer

<400> SEQUENCE: 36
gatgtccagc ttcaggag                                               18

<210> SEQ ID NO 37
<211> LENGTH: 35
<212> TYPE: DNA
<213> ORGANISM: Artificial Sequence
<220> FEATURE:
<223> OTHER INFORMATION: LeaderbackH primer

<400> SEQUENCE: 37
ctcctgaagc tggacatcag acagcaccca cctgg                            35

<210> SEQ ID NO 38
<211> LENGTH: 17
<212> TYPE: DNA
<213> ORGANISM: Artificial Sequence
<220> FEATURE:
<223> OTHER INFORMATION: CHfor primer

<400> SEQUENCE: 38
gcagcgccag caccaag                                                17

<210> SEQ ID NO 39
<211> LENGTH: 35
<212> TYPE: DNA
<213> ORGANISM: Artificial Sequence
<220> FEATURE:
<223> OTHER INFORMATION: VHback primer

<400> SEQUENCE: 39
cttggtgctg gcgctgctga ctgtgagagc ggtgc                            35

<210> SEQ ID NO 40
<211> LENGTH: 22
<212> TYPE: DNA
<213> ORGANISM: Artificial Sequence
<220> FEATURE:
<223> OTHER INFORMATION: Lfor1 primer
```

<400> SEQUENCE: 40
gccatggaca tgagagtgcc tg                                              22

<210> SEQ ID NO 41
<211> LENGTH: 19
<212> TYPE: DNA
<213> ORGANISM: Artificial Sequence
<220> FEATURE:
<223> OTHER INFORMATION: Lback1 primer

<400> SEQUENCE: 41
tcagcactcg ccctgttg                                                   19

<210> SEQ ID NO 42
<211> LENGTH: 21
<212> TYPE: DNA
<213> ORGANISM: Artificial Sequence
<220> FEATURE:
<223> OTHER INFORMATION: Hfor1 primer

<400> SEQUENCE: 42
gccatgaagc acctgtggtt c                                               21

<210> SEQ ID NO 43
<211> LENGTH: 20
<212> TYPE: DNA
<213> ORGANISM: Artificial Sequence
<220> FEATURE:
<223> OTHER INFORMATION: Hback1 primer

<400> SEQUENCE: 43
tcacttgccc aggctcaggc                                                 20

<210> SEQ ID NO 44
<211> LENGTH: 17
<212> TYPE: DNA
<213> ORGANISM: Artificial Sequence
<220> FEATURE:
<223> OTHER INFORMATION: K-N F primer

<400> SEQUENCE: 44
tcacctacag cggcagc                                                    17

<210> SEQ ID NO 45
<211> LENGTH: 35
<212> TYPE: DNA
<213> ORGANISM: Artificial Sequence
<220> FEATURE:
<223> OTHER INFORMATION: K-N FT pimer

<400> SEQUENCE: 45
tggagtggat gggctacatc acctacagcg gcagc                                35

<210> SEQ ID NO 46
<211> LENGTH: 35
<212> TYPE: DNA
<213> ORGANISM: Artificial Sequence
<220> FEATURE:
<223> OTHER INFORMATION: K-N RT primer

<400> SEQUENCE: 46
tgtagcccat ccactccagc ttgttgccgg ggaac                                35

<210> SEQ ID NO 47
<211> LENGTH: 17

```
<212> TYPE: DNA
<213> ORGANISM: Artificial Sequence
<220> FEATURE:
<223> OTHER INFORMATION: K-N R primer

<400> SEQUENCE: 47
gcttgttgcc ggggaac                                                   17

<210> SEQ ID NO 48
<211> LENGTH: 32
<212> TYPE: DNA
<213> ORGANISM: Artificial Sequence
<220> FEATURE:
<223> OTHER INFORMATION: SY-IN FT primer

<400> SEQUENCE: 48
gcggcatcac caactacaac cccagcctga ag                                  32

<210> SEQ ID NO 49
<211> LENGTH: 16
<212> TYPE: DNA
<213> ORGANISM: Artificial Sequence
<220> FEATURE:
<223> OTHER INFORMATION: SY-IN F primer

<400> SEQUENCE: 49
caaccccagc ctgaag                                                    16

<210> SEQ ID NO 50
<211> LENGTH: 32
<212> TYPE: DNA
<213> ORGANISM: Artificial Sequence
<220> FEATURE:
<223> OTHER INFORMATION: SY-IN RT primer

<400> SEQUENCE: 50
tagttggtga tgccgctgta ggtgatgtag cc                                  32

<210> SEQ ID NO 51
<211> LENGTH: 16
<212> TYPE: DNA
<213> ORGANISM: Artificial Sequence
<220> FEATURE:
<223> OTHER INFORMATION: SY-IN R primer

<400> SEQUENCE: 51
tgtaggtgat gtagcc                                                    16

<210> SEQ ID NO 52
<211> LENGTH: 19
<212> TYPE: DNA
<213> ORGANISM: Artificial Sequence
<220> FEATURE:
<223> OTHER INFORMATION: V-R F primer

<400> SEQUENCE: 52
caagaaccag ttcagcctg                                                 19

<210> SEQ ID NO 53
<211> LENGTH: 32
<212> TYPE: DNA
<213> ORGANISM: Artificial Sequence
<220> FEATURE:
<223> OTHER INFORMATION: V-R FT primer

<400> SEQUENCE: 53
```
tcagcgagga caccagcaag aaccagttca gc          32

<210> SEQ ID NO 54
<211> LENGTH: 32
<212> TYPE: DNA
<213> ORGANISM: Artificial Sequence
<220> FEATURE:
<223> OTHER INFORMATION: V-R RT primer

<400> SEQUENCE: 54
ctggtgtcct cgctgatggt caccctgctc tt          32

<210> SEQ ID NO 55
<211> LENGTH: 19
<212> TYPE: DNA
<213> ORGANISM: Artificial Sequence
<220> FEATURE:
<223> OTHER INFORMATION: V-R R primer

<400> SEQUENCE: 55
tggtcaccct gctcttcag                         19

<210> SEQ ID NO 56
<211> LENGTH: 17
<212> TYPE: DNA
<213> ORGANISM: Artificial Sequence
<220> FEATURE:
<223> OTHER INFORMATION: Q-D F primer

<400> SEQUENCE: 56
gagtctggac caggacc                           17

<210> SEQ ID NO 57
<211> LENGTH: 16
<212> TYPE: DNA
<213> ORGANISM: Artificial Sequence
<220> FEATURE:
<223> OTHER INFORMATION: Q-D R primer

<400> SEQUENCE: 57
gacagcaccc acctgg                            16

<210> SEQ ID NO 58
<211> LENGTH: 32
<212> TYPE: DNA
<213> ORGANISM: Artificial Sequence
<220> FEATURE:
<223> OTHER INFORMATION: Q-D FT1 primer

<400> SEQUENCE: 58
tgacgtgcag ctgcaggagt ctggaccagg ac          32

<210> SEQ ID NO 59
<211> LENGTH: 32
<212> TYPE: DNA
<213> ORGANISM: Artificial Sequence
<220> FEATURE:
<223> OTHER INFORMATION: Q-D RT1 primer

<400> SEQUENCE: 59
ctgcagctgc acgtcagaca gcacccacct gg          32

<210> SEQ ID NO 60
<211> LENGTH: 36
<212> TYPE: DNA
<213> ORGANISM: Artificial Sequence

```
<220> FEATURE:
<223> OTHER INFORMATION: P-L FT primer

<400> SEQUENCE: 60
ggcaagagcc ccaagctcct gatctactat gccagc                              36

<210> SEQ ID NO 61
<211> LENGTH: 18
<212> TYPE: DNA
<213> ORGANISM: Artificial Sequence
<220> FEATURE:
<223> OTHER INFORMATION: P-L F primer

<400> SEQUENCE: 61
ctgatctact atgccagc                                                  18

<210> SEQ ID NO 62
<211> LENGTH: 35
<212> TYPE: DNA
<213> ORGANISM: Artificial Sequence
<220> FEATURE:
<223> OTHER INFORMATION: P-L RT primer

<400> SEQUENCE: 62
gagcttgggg ctcttgccgg gcttctgctg gaacc                               35

<210> SEQ ID NO 63
<211> LENGTH: 17
<212> TYPE: DNA
<213> ORGANISM: Artificial Sequence
<220> FEATURE:
<223> OTHER INFORMATION: P-L R primer

<400> SEQUENCE: 63
gggcttctgc tggaacc                                                   17

<210> SEQ ID NO 64
<211> LENGTH: 35
<212> TYPE: DNA
<213> ORGANISM: Artificial Sequence
<220> FEATURE:
<223> OTHER INFORMATION: GT-QS FT primer

<400> SEQUENCE: 64
ccagcaggac tactccagcc ctaggacctt cggtg                               35

<210> SEQ ID NO 65
<211> LENGTH: 17
<212> TYPE: DNA
<213> ORGANISM: Artificial Sequence
<220> FEATURE:
<223> OTHER INFORMATION: GT-QS F primer

<400> SEQUENCE: 65
ccctaggacc ttcggtg                                                   17

<210> SEQ ID NO 66
<211> LENGTH: 36
<212> TYPE: DNA
<213> ORGANISM: Artificial Sequence
<220> FEATURE:
<223> OTHER INFORMATION: GT-QS RT primer

<400> SEQUENCE: 66
ctggagtagt cctgctggca gaagtacacg gcgaag                              36
```

<210> SEQ ID NO 67
<211> LENGTH: 18
<212> TYPE: DNA
<213> ORGANISM: Artificial Sequence
<220> FEATURE:
<223> OTHER INFORMATION: GT-QS R primer

<400> SEQUENCE: 67
cagaagtaca cggcgaag                                                 18

<210> SEQ ID NO 68
<211> LENGTH: 40
<212> TYPE: DNA
<213> ORGANISM: Artificial Sequence
<220> FEATURE:
<223> OTHER INFORMATION: SLQ-NRY for primer

<400> SEQUENCE: 68
gatctactat gccagcaacc ggtactctgg agtgcccagc                         40

<210> SEQ ID NO 69
<211> LENGTH: 40
<212> TYPE: DNA
<213> ORGANISM: Artificial Sequence
<220> FEATURE:
<223> OTHER INFORMATION: SLQ-NRY back primer

<400> SEQUENCE: 69
gctgggcact ccagagtacc ggttgctggc atagtagatc                         40

<210> SEQ ID NO 70
<211> LENGTH: 19
<212> TYPE: DNA
<213> ORGANISM: Artificial Sequence
<220> FEATURE:
<223> OTHER INFORMATION: CMV for primer

<400> SEQUENCE: 70
caaatgggcg gtaggcgtg                                                19

<210> SEQ ID NO 71
<211> LENGTH: 20
<212> TYPE: DNA
<213> ORGANISM: Artificial Sequence
<220> FEATURE:
<223> OTHER INFORMATION: TKPA rev primer

<400> SEQUENCE: 71
ccttccgtgt ttcagttagc                                               20

<210> SEQ ID NO 72
<211> LENGTH: 19
<212> TYPE: DNA
<213> ORGANISM: Artificial Sequence
<220> FEATURE:
<223> OTHER INFORMATION: EMCV ires rev primer

<400> SEQUENCE: 72
ccttattcca agcggcttc                                                19

<210> SEQ ID NO 73
<211> LENGTH: 708
<212> TYPE: DNA
<213> ORGANISM: Artificial Sequence
<220> FEATURE:
<223> OTHER INFORMATION: Humanized antibody light chain

<400> SEQUENCE: 73

```
atggacatga gagtgcctgc tcagctgctg ggactgctgc tgctgtggct gcctggagct      60
aggtgtgaca tcgtgatgac acagtctccc agcagcctga gcgcctctgt gggcgacagg     120
gtgaccatca cctgcagggc tagccagagc gtgagcagcg acgtggcctg gttccagcag     180
aagcccggca agagccccaa gcccctgatc tactatgcca gcagcctgca gtctggagtg     240
cccagcaggt tcagcggcag cggcagcgga acagacttca ccctgaccat cagcagcctg     300
caggccgagg acttcgccgt gtacttctgc ggccaggact acaccagccc taggaccttc     360
ggtggcggaa ccaagctgga gatcaagagg accgtggccg cccccagcgt gttcatcttc     420
cctccaagcg acgagcagct gaagagcggc accgccagcg tggtgtgcct gctgaacaac     480
ttctacccca gggaggccaa ggtgcagtgg aaggtggaca cgccctgca gagcggcaac      540
agccaggaga gcgtgaccga gcaggacagc aaggacagca cctacagcct gagcagcacc     600
ctgaccctga gcaaggccga ctacgagaag cacaaggtgt acgcctgcga ggtgacccac     660
cagggcctga gcagccccgt gaccaagagc ttcaacaggg gcgagtgc                  708
```

<210> SEQ ID NO 74
<211> LENGTH: 236
<212> TYPE: PRT
<213> ORGANISM: Artificial Sequence
<220> FEATURE:
<223> OTHER INFORMATION: Humanized antibody light chain

<400> SEQUENCE: 74

```
Met Asp Met Arg Val Pro Ala Gln Leu Leu Gly Leu Leu Leu Leu Trp
1               5                   10                  15
Leu Pro Gly Ala Arg Cys Asp Ile Val Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Ser Val Ser Ser Asp Val Ala Trp Phe Gln Gln Lys Pro Gly Lys
    50                  55                  60
Ser Pro Lys Pro Leu Ile Tyr Tyr Ala Ser Ser Leu Gln Ser Gly Val
65                  70                  75                  80
Pro Ser Arg Phe Ser Gly Ser Gly Ser Gly Thr Asp Phe Thr Leu Thr
                85                  90                  95
Ile Ser Ser Leu Gln Ala Glu Asp Phe Ala Val Tyr Phe Cys Gly Gln
            100                 105                 110
Asp Tyr Thr Ser Pro Arg Thr Phe Gly Gly Gly Thr Lys Leu Glu Ile
        115                 120                 125
Lys Arg Thr Val Ala Ala Pro Ser Val Phe Ile Phe Pro Pro Ser Asp
    130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
```

```
<210> SEQ ID NO 75
<211> LENGTH: 1386
<212> TYPE: DNA
<213> ORGANISM: Artificial Sequence
<220> FEATURE:
<223> OTHER INFORMATION: Humanized antibody heavy chain

<400> SEQUENCE: 75
```

| | | | | | |
|---|---|---|---|---|---|
| atgaagcacc | tgtggttctt | cctgctgctg | gtggctgccc | ccaggtgggt | gctgtctcag | 60 |
| gtgcagctgc | aggagtctgg | accaggactg | gtgaagccat | ctgagaccct | gagcctgacc | 120 |
| tgcaccgtga | gcggctacag | catcaccagc | gactacgcct | ggaactggat | caggcagttc | 180 |
| cccggcaaga | gctggagtg | gatgggcagc | atctactaca | gcggcagcac | ctactacaac | 240 |
| cccagcctga | agagcagggt | gaccatcagc | gtggacacca | gcaagaacca | gttcagcctg | 300 |
| aagctgagca | gcgtgaccgc | cgccgacacc | gccacctact | actgcgtgag | cggcacctac | 360 |
| tacttcgact | actggggcca | gggcaccacc | ctgaccgtga | gcagcgccag | caccaaggga | 420 |
| ccaagcgtgt | tcccactggc | tccatgcagc | aggagcacca | gcgagagcac | agccgccctg | 480 |
| ggatgcctgg | tgaaggacta | cttccctgag | cctgtgaccg | tgagctggaa | ttctggcgcc | 540 |
| ctgaccagcg | gagtgcacac | cttcccagcc | gtgctgcaga | gctctggact | gtacagcctg | 600 |
| agcagcgtgg | tgaccgtgcc | cttcttccagc | ctgggcacca | agacctacac | ctgcaacgtg | 660 |
| gaccacaagc | ccagcaacac | caaggtggac | aagagggtgg | agtctaagta | tggacctcca | 720 |
| tgcccaagct | gtcctgctcc | tgagttcctg | ggcggcccaa | gcgtgttcct | gttccctcca | 780 |
| aagccaaagg | acaccctgat | gatcagcagg | acccctgagg | tgacctgcgt | ggtggtggac | 840 |
| gtgagccagg | aggaccccga | ggtgcagttc | aactggtacg | tggacggcgt | ggaggtgcac | 900 |
| aacgccaaga | ccaagcccag | ggaggagcag | ttcaacagca | cctacagggt | ggtgagcgtg | 960 |
| ctgaccgtgc | tgcaccagga | ctggctgaac | ggcaaggagt | acaagtgcaa | ggtgagcaac | 1020 |
| aagggcctgc | cagcagcat | cgagaagacc | atcagcaagg | ccaagggcca | gccaagggag | 1080 |
| ccccaggtgt | acaccctgcc | tccaagccag | gaggagatga | ccaagaacca | ggtgagcctg | 1140 |
| acctgcctgg | tgaagggctt | ctaccccagc | gacatcgccg | tggagtggga | gagcaacggc | 1200 |
| cagcccgaga | acaactacaa | gaccaccct | ccagtgctgg | acagcgacgg | cagcttcttc | 1260 |
| ctgtacagca | ggctgaccgt | ggacaagagc | aggtggcagg | agggcaacgt | gttcagctgc | 1320 |
| agcgtgatgc | acgaggccct | gcacaaccac | tacacccaga | agagcctgag | cctgagcctg | 1380 |
| ggcaag | | | | | | 1386 |

```
<210> SEQ ID NO 76
<211> LENGTH: 462
<212> TYPE: PRT
<213> ORGANISM: Artificial Sequence
<220> FEATURE:
<223> OTHER INFORMATION: Humanized antibody heavy chain

<400> SEQUENCE: 76
```

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Tyr Ser Ile
        35                  40                  45

Thr Ser Asp Tyr Ala Trp Asn Trp Ile Arg Gln Phe Pro Gly Lys Lys
    50                  55                  60

Leu Glu Trp Met Gly Ser Ile Tyr Tyr Ser Gly Ser Thr Tyr Tyr Asn
65                  70                  75                  80

Pro Ser Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Thr
            100                 105                 110

Tyr Tyr Cys Val Ser Gly Thr Tyr Tyr Phe Asp Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Ser Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460

<210> SEQ ID NO 77
<211> LENGTH: 251
<212> TYPE: PRT
<213> ORGANISM: Artificial Sequence
<220> FEATURE:
<223> OTHER INFORMATION: scFv sequence

<400> SEQUENCE: 77

```
Met Asp Gln Val Gln Leu Gln Glu Ser Gly Pro Gly Leu Val Lys Pro
1               5                   10                  15

Ser Glu Thr Leu Ser Leu Thr Cys Thr Val Ser Gly Tyr Ser Ile Thr
            20                  25                  30

Ser Asp Tyr Ala Trp Asn Trp Ile Arg Gln Phe Pro Gly Asn Lys Leu
        35                  40                  45

Glu Trp Met Gly Tyr Ile Thr Tyr Ser Gly Ser Thr Tyr Tyr Asn Pro
    50                  55                  60

Ser Leu Lys Ser Arg Val Thr Ile Ser Val Asp Thr Ser Lys Asn Gln
65                  70                  75                  80

Phe Ser Leu Lys Leu Ser Ser Val Thr Ala Ala Asp Thr Ala Thr Tyr
                85                  90                  95

Tyr Cys Val Ser Gly Thr Tyr Tyr Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Val Ser Ser Asp Val Ala Trp Phe Gln Gln Lys Pro Gly Lys Ser
                165                 170                 175

Pro Lys Pro Leu Ile Tyr Tyr Ala Ser Asn Arg Tyr Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Ala Glu Asp Phe Ala Val Tyr Phe Cys Gly Gln Asp
    210                 215                 220

Tyr Thr Ser Pro Arg Thr Phe Gly Gly Gly Thr Lys Leu Glu Ile Lys
225                 230                 235                 240

Arg Glu Gln Lys Leu Ile Ser Glu Glu Asp Leu
                245                 250
```

<210> SEQ ID NO 78
<211> LENGTH: 761
<212> TYPE: DNA
<213> ORGANISM: Artificial Sequence
<220> FEATURE:
<223> OTHER INFORMATION: scFv sequence

<400> SEQUENCE: 78

```
ccatggacca ggtgcagctg caggaaagcg gcccgggcct ggtgaaaccg agcgaaaccc    60
tgagcctgac ctgcaccgtg agcggctata gcattaccag cgattatgcg tggaactgga   120
ttcgtcagtt tccgggcaac aaactggaat ggatgggcta cattacttat agcggcagca   180
cctattataa cccgagcctg aaaagccgtg tgaccattag cgtggatacc agcaaaaacc   240
agtttagcct gaaactgagc agcgtgaccg cggcggatac cgcgacctat tattgcgtga   300
gcggcaccta ttattttgat tattgggggcc aggtaccac cctgaccgtg tctagcggtg   360
```

```
ggggcggaag cggggggcggt ggaagcgggg gcggtggatc tgatattgtg atgacccaga    420
gcccgagcag cctgagcgcg agcgtgggcg atcgtgtgac cattacctgc cgtgcgagcc    480
agagcgtgag cagcgatgtg gcgtggtttc agcagaaacc gggcaaaagc ccgaaaccgc    540
tgatttatta tgcgagcaac cggtatagcg gtgtgccgag ccgttttagc ggtagcggta    600
gcggtaccga ttttaccctg accattagca gcctgcaggc ggaagatttt gcggtgtatt    660
tttgcggcca ggattatacc agcccgcgta cctttggtgg cggaaccaaa ctggaaatta    720
aacgtgaaca gaaactgatt agcgaagaag atctgctcga g                         761
```

<210> SEQ ID NO 79
<211> LENGTH: 43
<212> TYPE: DNA
<213> ORGANISM: Artificial Sequence
<220> FEATURE:
<223> OTHER INFORMATION: Fab P stop primer

<400> SEQUENCE: 79

```
acaagagggt ggagtctaag tatggatagc catgcccaag ctg                        43
```

<210> SEQ ID NO 80
<211> LENGTH: 43
<212> TYPE: DNA
<213> ORGANISM: Artificial Sequence
<220> FEATURE:
<223> OTHER INFORMATION: Fab P stop anti primer

<400> SEQUENCE: 80

```
cagcttgggc atggctatcc atacttagac tccaccctct tgt                        43
```

<210> SEQ ID NO 81
<211> LENGTH: 660
<212> TYPE: DNA
<213> ORGANISM: Artificial Sequence
<220> FEATURE:
<223> OTHER INFORMATION: Purified plasmid sequence after mutagenesis

<400> SEQUENCE: 81

```
caggtgcagc tgcaggagtc tggaccagga ctggtgaagc catctgagac cctgagcctg     60
acctgcaccg tgagcggcta cagcatcacc agcgactacg cctggaactg gatcaggcag    120
ttccccggca acaagctgga gtggatgggc tacatcacct acagcggcag cacctactac    180
aaccccagcc tgaagagcag ggtgaccatc agcgtggaca ccagcaagaa ccagttcagc    240
ctgaagctga gcagcgtgac cgccgccgac accgccacct actactgcgt gagcggcacc    300
tactacttcg actactgggg ccagggcacc accctgaccg tgagcagcgc cagcaccaag    360
ggaccaagcg tgttcccact ggctccatgc agcaggagca ccagcgagag cacagccgcc    420
ctgggatgcc tggtgaagga ctacttccct gagcctgtga ccgtgagctg gaattctggc    480
gccctgacca gcggagtgca caccttccca gccgtgctgc agagctctgg actgtacagc    540
ctgagcagcg tggtgaccgt gccttcttcc agcctgggca ccaagaccta cacctgcaac    600
gtggaccaca agcccagcaa caccaaggtg gacaagaggg tggagtctaa gtatggatag    660
```

<210> SEQ ID NO 82
<211> LENGTH: 219
<212> TYPE: PRT
<213> ORGANISM: Artificial Sequence
<220> FEATURE:
<223> OTHER INFORMATION: Purified plasmid corresponding protein sequence
      after mutagenesis

<400> SEQUENCE: 82

```
Gln Val Gln Leu Gln Glu Ser Gly Pro Gly Leu Val Lys Pro Ser Glu
 1               5                  10                  15
Thr Leu Ser Leu Thr Cys Thr Val Ser Gly Tyr Ser Ile Thr Ser Asp
            20                  25                  30
Tyr Ala Trp Asn Trp Ile Arg Gln Phe Pro Gly Asn Lys Leu Glu Trp
        35                  40                  45
Met Gly Tyr Ile Thr Tyr Ser Gly Ser Thr Tyr Tyr Asn Pro Ser Leu
    50                  55                  60
Lys Ser Arg Val Thr Ile Ser Val Asp Thr Ser Lys Asn Gln Phe Ser
 65                  70                  75                  80
Leu Lys Leu Ser Ser Val Thr Ala Ala Asp Thr Ala Thr Tyr Tyr Cys
                85                  90                  95
Val Ser Gly Thr Tyr Tyr Phe Asp Tyr Trp Gly Gln Gly Thr Thr Leu
            100                 105                 110
Thr Val Ser Ser Ala Ser Thr Lys Gly Pro Ser Val Phe Pro Leu Ala
        115                 120                 125
Pro Cys Ser Arg Ser Thr Ser Glu Ser Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
        195                 200                 205
Lys Val Asp Lys Arg Val Glu Ser Lys Tyr Gly
    210                 215
```

<210> SEQ ID NO 83
<211> LENGTH: 22
<212> TYPE: DNA
<213> ORGANISM: Artificial Sequence
<220> FEATURE:
<223> OTHER INFORMATION: 3b primer

<400> SEQUENCE: 83
aggtsmaact gcagsagtcw gg        22

<210> SEQ ID NO 84
<211> LENGTH: 38
<212> TYPE: DNA
<213> ORGANISM: Artificial Sequence
<220> FEATURE:
<223> OTHER INFORMATION: 4 primer

<400> SEQUENCE: 84
ccagggccca gtggatagac aagcttgggt gtcgtttt        38

<210> SEQ ID NO 85
<211> LENGTH: 414
<212> TYPE: DNA
<213> ORGANISM: Artificial Sequence
<220> FEATURE:
<223> OTHER INFORMATION: sequenced VH region

<400> SEQUENCE: 85

```
caggtcaaac tgcaggagtc tggtggagga ttggtgcagc ctaaggagtc tttgaaaatc    60
tcatgtgcag cctctggatt caccttcagt actgctgcca tgtactgggt ccgccaggct   120
ccaggaaagg gtctggattg ggttgctcgc ataagaacta aacctgataa ttatgcaaca   180
tattaccctg cttcagtgaa aggcagattc accatctcca gagatgattc aaagggcatg   240
gtctacctac aaatggataa cttaaagact gaggacacag ccatttatta ctgtacagca   300
gcttattact atgatggccg ctttgattac tggggccaag gagtcatggt cacagtcgcc   360
tcagctgaaa cgacacccaa gcttgtctat ccactggccc ctggaaaaca ctcg         414
```

<210> SEQ ID NO 86
<211> LENGTH: 366
<212> TYPE: DNA
<213> ORGANISM: Artificial Sequence
<220> FEATURE:
<223> OTHER INFORMATION: sequenced VL region

<400> SEQUENCE: 86

```
gacattgtga tgacccagac tccatcctcc caggctgtgt cagcagggga gagggtcact    60
atgaggtgca agtccagtca gagtctttta tacagtgaaa acaaaaagaa ctacttggcc   120
tggtaccaac agaaaccagg gcagtctcct aaactgttga tttcctgggc atccactagg   180
gaatctgggg tccctgatcg cttcataggc agtggatctg ggacagattt cactctgacc   240
atcagcagtg tgcaggcaga agacctggct gtttattact gtgaccagta ttatgatcct   300
ccattcacgt tcggctcagg gacgaagttg gaaataaaac gggctgatgc tgcaccaact   360
gtatcc                                                             366
```

<210> SEQ ID NO 87
<211> LENGTH: 138
<212> TYPE: PRT
<213> ORGANISM: Artificial Sequence
<220> FEATURE:
<223> OTHER INFORMATION: sequenced VH region

<400> SEQUENCE: 87

Gln Val Lys Leu Gln Glu Ser Gly Gly Gly Leu Val Gln Pro Lys Glu
1               5                   10                  15

Ser Leu Lys Ile Ser Cys Ala Ala Ser Gly Phe Thr Phe Ser Thr Ala
            20                  25                  30

Ala Met Tyr Trp Val Arg Gln Ala Pro Gly Lys Gly Leu Asp Trp Val
        35                  40                  45

Ala Arg Ile Arg Thr Lys Pro Asp Asn Tyr Ala Thr Tyr Tyr Pro Ala
    50                  55                  60

Ser Val Lys Gly Arg Phe Thr Ile Ser Arg Asp Asp Ser Lys Gly Met
65                  70                  75                  80

Val Tyr Leu Gln Met Asp Asn Leu Lys Thr Glu Asp Thr Ala Ile Tyr
                85                  90                  95

Tyr Cys Thr Ala Ala Tyr Tyr Tyr Asp Gly Arg Phe Asp Tyr Trp Gly
            100                 105                 110

Gln Gly Val Met Val Thr Val Ala Ser Ala Glu Thr Thr Pro Lys Leu
        115                 120                 125

Val Tyr Pro Leu Ala Pro Gly Lys His Ser
    130                 135

<210> SEQ ID NO 88
<211> LENGTH: 122
<212> TYPE: PRT

<213> ORGANISM: Artificial Sequence
<220> FEATURE:
<223> OTHER INFORMATION: sequenced VL region

<400> SEQUENCE: 88

```
Asp Ile Val Met Thr Gln Thr Pro Ser Ser Gln Ala Val Ser Ala Gly
1               5                   10                  15
Glu Arg Val Thr Met Arg Cys Lys Ser Ser Gln Ser Leu Leu Tyr Ser
            20                  25                  30
Glu Asn Lys Asn Tyr Leu Ala Trp Tyr Gln Gln Lys Pro Gly Gln
        35                  40                  45
Ser Pro Lys Leu Leu Ile Ser Trp Ala Ser Thr Arg Glu Ser Gly Val
    50                  55                  60
Pro Asp Arg Phe Ile Gly Ser Gly Ser Gly Thr Asp Phe Thr Leu Thr
65                  70                  75                  80
Ile Ser Ser Val Gln Ala Glu Asp Leu Ala Val Tyr Tyr Cys Asp Gln
                85                  90                  95
Tyr Tyr Asp Pro Pro Phe Thr Phe Gly Ser Gly Thr Lys Leu Glu Ile
            100                 105                 110
Lys Arg Ala Asp Ala Ala Pro Thr Val Ser
        115                 120
```

<210> SEQ ID NO 89
<211> LENGTH: 41
<212> TYPE: DNA
<213> ORGANISM: Artificial Sequence
<220> FEATURE:
<223> OTHER INFORMATION: LKI FT primer

<400> SEQUENCE: 89
attgaaaatc cacgagaagt ggggaacggt gtgtaataat g          41

<210> SEQ ID NO 90
<211> LENGTH: 23
<212> TYPE: DNA
<213> ORGANISM: Artificial Sequence
<220> FEATURE:
<223> OTHER INFORMATION: LKI F primer

<400> SEQUENCE: 90
gtggggaacg gtgtgtaata atg          23

<210> SEQ ID NO 91
<211> LENGTH: 36
<212> TYPE: DNA
<213> ORGANISM: Artificial Sequence
<220> FEATURE:
<223> OTHER INFORMATION: LKI RT primer

<400> SEQUENCE: 91
ttctcgtgga ttttcaattc cactctcccg ctacac          36

<210> SEQ ID NO 92
<211> LENGTH: 18
<212> TYPE: DNA
<213> ORGANISM: Artificial Sequence
<220> FEATURE:
<223> OTHER INFORMATION: LKI R primer

<400> SEQUENCE: 92
tccactctcc cgctacac          18

```
<210> SEQ ID NO 93
<211> LENGTH: 39
<212> TYPE: DNA
<213> ORGANISM: Artificial Sequence
<220> FEATURE:
<223> OTHER INFORMATION: R60D FT primer

<400> SEQUENCE: 93
gttctggaga catttggatg gatcatgttt cttgtcgtg                     39

<210> SEQ ID NO 94
<211> LENGTH: 21
<212> TYPE: DNA
<213> ORGANISM: Artificial Sequence
<220> FEATURE:
<223> OTHER INFORMATION: R60D F primer

<400> SEQUENCE: 94
tggatcatgt ttcttgtcgt g                                        21

<210> SEQ ID NO 95
<211> LENGTH: 39
<212> TYPE: DNA
<213> ORGANISM: Artificial Sequence
<220> FEATURE:
<223> OTHER INFORMATION: R60D RT primer

<400> SEQUENCE: 95
tccaaatgtc tccagaacct gcactggaat tagcccatc                     39

<210> SEQ ID NO 96
<211> LENGTH: 21
<212> TYPE: DNA
<213> ORGANISM: Artificial Sequence
<220> FEATURE:
<223> OTHER INFORMATION: R60D R primer

<400> SEQUENCE: 96
ctgcactgga attagcccat c                                        21

<210> SEQ ID NO 97
<211> LENGTH: 828
<212> TYPE: DNA
<213> ORGANISM: Artificial Sequence
<220> FEATURE:
<223> OTHER INFORMATION: VKVQEE-LKIHEK mutant

<400> SEQUENCE: 97
atgagcaaac tcagaatggt gctacttgaa gactctggat ctgctgactt cagaagacat    60
tttgtcaacc tgagtccctt caccattact gtggtcttac ttctcagtgc ctgttttgtc   120
accagttctc ttggaggaac agacaaggag ctgaggctag tggatggtga aaacaagtgt   180
agcgggagag tggaattgaa atccacgag aagtgggaa cggtgtgtaa taatggctgg    240
agcatggaag cggtctctgt gatttgtaac cagctggat gtccaactgc tatcaaagcc   300
cctggatggg ctaattccag tgcaggttct ggacgcattt ggatggatca tgtttcttgt   360
cgtgggaatg agtcagctct ttgggattgc aaacatgatg gatggggaaa gcatagtaac   420
tgtactcacc aacaagatgc tggagtgacc tgctcagatg gatccaattt ggaaatgagg   480
ctgacgcgtg gagggaatat gttgctgga gaatagaga tcaaattcca aggacggtgg   540
ggaacagtgt gtgatgataa cttcaacata gatcatgcat ctgtcatttg tagacaactt   600
gaatgtggaa gtgctgtcag tttctctggt tcatctaatt ttgagaagg ctctggacca   660
```

```
atctggtttg atgatcttat atgcaacgga aatgagtcag ctctctggaa ctgcaaacat    720
caaggatggg gaaagcataa ctgtgatcat gctgaggatg ctggagtgat ttgctcaaag    780
ggagcagatc tgagcctgag actggtagat ggagtcactg aatgttca                 828
```

<210> SEQ ID NO 98
<211> LENGTH: 663
<212> TYPE: DNA
<213> ORGANISM: Artificial Sequence
<220> FEATURE:
<223> OTHER INFORMATION: R60D mutant

<400> SEQUENCE: 98

```
atgagcaaac tcagaatggt gctacttgaa gactctggat ctgctgactt cagaagacat     60
tttgtcaacc tgagtccctt caccattact gtggtcttac ttctcagtgc ctgttttgtc    120
accagttctc ttggaggaac agacaaggag ctgaggctag tggatggtga aaacaagtgt    180
agcgggagag tggaagtgaa agtccaggag gagtggggaa cggtgtgtaa taatggctgg    240
agcatggaag cggtctctgt gatttgtaac cagctggat gtccaactgc tatcaaagcc    300
cctggatggg ctaattccag tgcaggttct ggagacattt ggatggatca tgtttcttgt    360
cgtgggaatg agtcagctct ttgggattgc aaacatgatg gatggggaaa gcatagtaac    420
tgtactcacc aacaagatgc tggagtgacc tgctcagatg gatccaattt ggaaatgagg    480
ctgacgcgtg gagggaatat gtgttctgga agaatagaga tcaaattcca aggacggtgg    540
ggaacagtgt gtgatgataa cttcaacata gatcatgcat ctgtcatttg tagacaactt    600
gaatgtggaa gtgctgtcag tttctctggt tcatctaatt ttggagaagg ctctggacca    660
atc                                                                  663
```

<210> SEQ ID NO 99
<211> LENGTH: 627
<212> TYPE: DNA
<213> ORGANISM: Artificial Sequence
<220> FEATURE:
<223> OTHER INFORMATION: Double mutant

<400> SEQUENCE: 99

```
atgagcaaac tcagaatggt gctacttgaa gactctggat ctgctgactt cagaagacat     60
tttgtcaacc tgagtccctt caccattact gtggtcttac ttctcagtgc ctgttttgtc    120
accagttctc ttggaggaac agacaaggag ctgaggctag tggatggtga aaacaagtgt    180
agcgggagag tggaattgaa atccacgag aagtggggaa cggtgtgtaa taatggctgg    240
agcatggaag cggtctctgt gatttgtaac cagctgggat gtccaactgc tatcaaagcc    300
cctggatggg ctaattccag tgcaggttct ggagacattt ggatggatca tgtttcttgt    360
cgtgggaatg agtcagctct ttgggattgc aaacatgatg gatggggaaa gcatagtaac    420
tgtactcacc aacaagatgc tggagtgacc tgctcagatg gatccaattt ggaaatgagg    480
ctgacgcgtg gagggaatat gtgttctgga agaatagaga tcaaattcca aggacggtgg    540
ggaacagtgt gtgatgataa cttcaacata gatcatgcat ctgtcatttg tagacaactt    600
gaatgtggaa gtgctgtcag tttctct                                        627
```

<210> SEQ ID NO 100
<211> LENGTH: 276
<212> TYPE: PRT
<213> ORGANISM: Artificial Sequence
<220> FEATURE:
<223> OTHER INFORMATION: VKVQEE-LKIHEK mutant

<400> SEQUENCE: 100

```
Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
50                  55                  60

Glu Leu Lys Ile His Glu Lys Trp Gly Thr Val Cys Asn Asn Gly Trp
65                  70                  75                  80

Ser Met Glu Ala Val Ser Val Ile Cys Asn Gln Leu Gly Cys Pro Thr
                85                  90                  95

Ala Ile Lys Ala Pro Gly Trp Ala Asn Ser Ser Ala Gly Ser Gly Arg
            100                 105                 110

Ile Trp Met Asp His Val Ser Cys Arg Gly Asn Glu Ser Ala Leu Trp
        115                 120                 125

Asp Cys Lys His Asp Gly Trp Gly Lys His Ser Asn Cys Thr His Gln
130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
        195                 200                 205

Ser Gly Ser Ser Asn Phe Gly Glu Gly Ser Gly Pro Ile Trp Phe Asp
210                 215                 220

Asp Leu Ile Cys Asn Gly Asn Glu Ser Ala Leu Trp Asn Cys Lys His
225                 230                 235                 240

Gln Gly Trp Gly Lys His Asn Cys Asp His Ala Glu Asp Ala Gly Val
                245                 250                 255

Ile Cys Ser Lys Gly Ala Asp Leu Ser Leu Arg Leu Val Asp Gly Val
            260                 265                 270

Thr Glu Cys Ser
        275
```

<210> SEQ ID NO 101
<211> LENGTH: 221
<212> TYPE: PRT
<213> ORGANISM: Artificial Sequence
<220> FEATURE:
<223> OTHER INFORMATION: R60D mutant

<400> SEQUENCE: 101

```
Met Ser Lys Leu Arg Met Val Leu Leu Glu Asp Ser Gly Ser Ala Asp
1               5                   10                  15

Phe Arg Arg His Phe Val Asn Leu Ser Pro Phe Thr Ile Thr Val Val
            20                  25                  30

Leu Leu Leu Ser Ala Cys Phe Val Thr Ser Ser Leu Gly Gly Thr Asp
        35                  40                  45

Lys Glu Leu Arg Leu Val Asp Gly Glu Asn Lys Cys Ser Gly Arg Val
50                  55                  60
```

```
Glu Val Lys Val Gln Glu Trp Gly Thr Val Cys Asn Asn Gly Trp
 65                  70                  75                  80

Ser Met Glu Ala Val Ser Val Ile Cys Asn Gln Leu Gly Cys Pro Thr
                 85                  90                  95

Ala Ile Lys Ala Pro Gly Trp Ala Asn Ser Ser Ala Gly Ser Gly Asp
            100                 105                 110

Ile Trp Met Asp His Val Ser Cys Arg Gly Asn Glu Ser Ala Leu Trp
            115                 120                 125

Asp Cys Lys His Asp Gly Trp Gly Lys His Ser Asn Cys Thr His Gln
130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
            195                 200                 205

Ser Gly Ser Ser Asn Phe Gly Glu Gly Ser Gly Pro Ile
            210                 215                 220

<210> SEQ ID NO 102
<211> LENGTH: 209
<212> TYPE: PRT
<213> ORGANISM: Artificial Sequence
<220> FEATURE:
<223> OTHER INFORMATION: Double mutant

<400> SEQUENCE: 102

Met Ser Lys Leu Arg Met Val Leu Leu Glu Asp Ser Gly Ser Ala Asp
 1               5                  10                  15

Phe Arg Arg His Phe Val Asn Leu Ser Pro Phe Thr Ile Thr Val Val
                20                  25                  30

Leu Leu Leu Ser Ala Cys Phe Val Thr Ser Ser Leu Gly Gly Thr Asp
            35                  40                  45

Lys Glu Leu Arg Leu Val Asp Gly Glu Asn Lys Cys Ser Gly Arg Val
 50                  55                  60

Glu Leu Lys Ile His Glu Lys Trp Gly Thr Val Cys Asn Asn Gly Trp
 65                  70                  75                  80

Ser Met Glu Ala Val Ser Val Ile Cys Asn Gln Leu Gly Cys Pro Thr
                 85                  90                  95

Ala Ile Lys Ala Pro Gly Trp Ala Asn Ser Ser Ala Gly Ser Gly Asp
            100                 105                 110

Ile Trp Met Asp His Val Ser Cys Arg Gly Asn Glu Ser Ala Leu Trp
            115                 120                 125

Asp Cys Lys His Asp Gly Trp Gly Lys His Ser Asn Cys Thr His Gln
130                 135                 140

Gln Asp Ala Gly Val Thr Cys Ser Asp Gly Ser Asn Leu Glu Met Arg
145                 150                 155                 160

Leu Thr Arg Gly Gly Asn Met Cys Ser Gly Arg Ile Glu Ile Lys Phe
                165                 170                 175

Gln Gly Arg Trp Gly Thr Val Cys Asp Asp Asn Phe Asn Ile Asp His
            180                 185                 190

Ala Ser Val Ile Cys Arg Gln Leu Glu Cys Gly Ser Ala Val Ser Phe
            195                 200                 205
```

Ser

<210> SEQ ID NO 103
<211> LENGTH: 1827
<212> TYPE: DNA
<213> ORGANISM: Mus musculus

<400> SEQUENCE: 103

| | | | | | |
|---|---|---|---|---|---|
| atgggtggac | acagaatggt | tcttcttgga | ggtgctggat | ctcctggttg | taaaaggttt | 60 |
| gtccatctag | gtttctttgt | tgtggctgtg | agctcacttc | tcagtgcctc | tgctgtcact | 120 |
| aacgctcctg | gagaaatgaa | gaaggaactg | agactggcgg | gtggtgaaaa | caactgtagt | 180 |
| gggagagtgg | aacttaagat | ccatgacaag | tggggcacag | tgtgcagtaa | cggctggagc | 240 |
| atgaatgaag | tgtccgtggt | ttgccagcag | ctgggatgcc | caacttctat | taaagcccttt | 300 |
| ggatgggcta | actccagcgc | cggctctgga | tatatctgga | tggacaaagt | ttcttgtaca | 360 |
| gggaatgagt | cagctctttg | ggactgcaaa | catgatgggt | ggggaaagca | taactgtacc | 420 |
| catgaaaaag | atgctggagt | gacctgctca | gatggatcta | atttggagat | gagactggtg | 480 |
| aacagtgcgg | gccaccgatg | cttaggaaga | gtagaaataa | agttccaggg | aaagtggggg | 540 |
| acggtgtgtg | acgacaactt | cagcaaagat | cacgcttctg | tgatttgtaa | acagcttgga | 600 |
| tgtggaagtg | ccattagttt | ctctggctca | gctaaattgg | gagctggttc | tggaccaatc | 660 |
| tggctcgatg | acctggcatg | caatggaaat | gagtcagctc | tctgggactg | caaacaccgg | 720 |
| ggatggggca | agcataactg | tgaccatgct | gaggatgtcg | gtgtgatttg | cttagaggga | 780 |
| gcagatctga | gcctgagact | agtggatgga | gtgtccagat | gttcaggaag | attggaagtg | 840 |
| agattccaag | gagaatgggg | gaccgtgtgt | gatgataact | gggatctccg | ggatgcttct | 900 |
| gtggtgtgca | gcaactggg | atgtccaact | gccatcagtg | ccattggtcg | agttaatgcc | 960 |
| agtgagggat | ctggacagat | ttggcttgac | aacatttcat | gcgaaggaca | tgaggcaact | 1020 |
| ctttgggagt | gtaaacacca | agagtgggga | aagcattact | gtcatcatag | agaagacgct | 1080 |
| ggcgtgacat | gttctgatgg | agcagatctg | gaacttagac | ttgtaggtgg | aggcagtcgc | 1140 |
| tgtgctggca | ttgtggaggt | ggagattcag | aagctgactg | gaagatgtg | tagccgaggc | 1200 |
| tggacactgg | cagatgcgga | tgtggtttgc | agacagcttg | gatgtggatc | tgcgcttcaa | 1260 |
| acccaggcta | agatctactc | taaaactggg | gcaacaaata | cgtggctctt | tcctggatct | 1320 |
| tgtaatggaa | atgaaactac | tttttggcaa | tgcaaaaact | ggcagtgggg | cggccttttcc | 1380 |
| tgtgataatt | tcgaagaagc | caaagttacc | tgctcaggcc | acagggaacc | cagactggtt | 1440 |
| ggaggagaaa | tcccatgctc | tggtcgtgtg | gaagtgaaac | acggagacgt | gtggggctcc | 1500 |
| gtctgtgatt | ttgacttgtc | tctggaagct | gccagtgtgg | tgtgcaggga | attacaatgt | 1560 |
| ggaacagtcg | tctctatcct | agggggagca | cattttggag | aaggaagtgg | acagatctgg | 1620 |
| ggtgaagaat | tccagtgtag | tgggggatgag | tcccatctttt | cactatgctc | agtggcgccc | 1680 |
| ccgctagaca | gaacttgtac | ccacagcagg | gatgtcagcg | tagtctgctc | aaatctagag | 1740 |
| ggcccgcggt | tcgaaggtaa | gcctatccct | aaccctctcc | tcggtctcga | ttctacgcgt | 1800 |
| accggtcatc | atcaccatca | ccattga | | | | 1827 |

<210> SEQ ID NO 104
<211> LENGTH: 672
<212> TYPE: DNA
<213> ORGANISM: Artificial Sequence
<220> FEATURE:
<223> OTHER INFORMATION: Mouse CD163 LKIHDK-VKVQEE Y60R mutant

<400> SEQUENCE: 104

```
atgggtggac acagaatggt tcttcttgga ggtgctggat ctcctggttg taaaaggttt    60
gtccatctag gtttctttgt tgtggctgtg agctcacttc tcagtgcctc tgctgtcact   120
aacgctcctg gagaaatgaa gaaggaactg agactggcgg tggtgaaaa caactgtagt    180
gggagagtgg aagtgaaggt gcaggaggag tggggcacag tgtgcagtaa cggctggagc   240
atgaatgaag tgtccgtggt ttgccagcag ctgggatgcc caacttctat taaagccctt   300
ggatgggcta actccagcgc cggctctgga cggatctgga tggacaaagt ttcttgtaca   360
gggaatgagt cagctctttg ggactgcaaa catgatgggt ggggaaagca taactgtacc   420
catgaaaaag atgctggagt gacctgctca gatggatcta atttggagat gagactggtg   480
aacagtgcgg ccaccgatg cttaggaaga gtagaaataa agttccaggg aaagtggggg    540
acggtgtgtg acgacaactt cagcaaagat cacgcttctg tgatttgtaa acagcttgga   600
tgtggaagtg ccattagttt ctctggctca gctaaattgg gagctggttc tggaccaatc   660
tggctcgatg ac                                                      672
```

<210> SEQ ID NO 105
<211> LENGTH: 608
<212> TYPE: PRT
<213> ORGANISM: Mus musculus

<400> SEQUENCE: 105

```
Met Gly Gly His Arg Met Val Leu Leu Gly Gly Ala Gly Ser Pro Gly
1               5                   10                  15
Cys Lys Arg Phe Val His Leu Gly Phe Phe Val Ala Val Ser Ser
            20                  25                  30
Leu Leu Ser Ala Ser Ala Val Thr Asn Ala Pro Gly Glu Met Lys Lys
        35                  40                  45
Glu Leu Arg Leu Ala Gly Gly Glu Asn Asn Cys Ser Gly Arg Val Glu
    50                  55                  60
Leu Lys Ile His Asp Lys Trp Gly Thr Val Cys Ser Asn Gly Trp Ser
65                  70                  75                  80
Met Asn Glu Val Ser Val Val Cys Gln Gln Leu Gly Cys Pro Thr Ser
                85                  90                  95
Ile Lys Ala Leu Gly Trp Ala Asn Ser Ser Ala Gly Ser Gly Tyr Ile
            100                 105                 110
Trp Met Asp Lys Val Ser Cys Thr Gly Asn Glu Ser Ala Leu Trp Asp
        115                 120                 125
Cys Lys His Asp Gly Trp Gly Lys His Asn Cys Thr His Glu Lys Asp
    130                 135                 140
Ala Gly Val Thr Cys Ser Asp Gly Ser Asn Leu Glu Met Arg Leu Val
145                 150                 155                 160
Asn Ser Ala Gly His Arg Cys Leu Gly Arg Val Glu Ile Lys Phe Gln
                165                 170                 175
Gly Lys Trp Gly Thr Val Cys Asp Asp Asn Phe Ser Lys Asp His Ala
            180                 185                 190
Ser Val Ile Cys Lys Gln Leu Gly Cys Gly Ser Ala Ile Ser Phe Ser
        195                 200                 205
Gly Ser Ala Lys Leu Gly Ala Gly Ser Gly Pro Ile Trp Leu Asp Asp
    210                 215                 220
Leu Ala Cys Asn Gly Asn Glu Ser Ala Leu Trp Asp Cys Lys His Arg
225                 230                 235                 240
```

Gly Trp Gly Lys His Asn Cys Asp His Ala Glu Asp Val Gly Val Ile
                245                 250                 255

Cys Leu Glu Gly Ala Asp Leu Ser Leu Arg Leu Val Asp Gly Val Ser
                260                 265                 270

Arg Cys Ser Gly Arg Leu Glu Val Arg Phe Gln Gly Glu Trp Gly Thr
                275                 280                 285

Val Cys Asp Asp Asn Trp Asp Leu Arg Asp Ala Ser Val Val Cys Lys
            290                 295                 300

Gln Leu Gly Cys Pro Thr Ala Ile Ser Ala Ile Gly Arg Val Asn Ala
305                 310                 315                 320

Ser Glu Gly Ser Gly Gln Ile Trp Leu Asp Asn Ile Ser Cys Glu Gly
                325                 330                 335

His Glu Ala Thr Leu Trp Glu Cys Lys His Gln Glu Trp Gly Lys His
                340                 345                 350

Tyr Cys His His Arg Glu Asp Ala Gly Val Thr Cys Ser Asp Gly Ala
                355                 360                 365

Asp Leu Glu Leu Arg Leu Val Gly Gly Ser Arg Cys Ala Gly Ile
            370                 375                 380

Val Glu Val Glu Ile Gln Lys Leu Thr Gly Lys Met Cys Ser Arg Gly
385                 390                 395                 400

Trp Thr Leu Ala Asp Ala Asp Val Val Cys Arg Gln Leu Gly Cys Gly
                405                 410                 415

Ser Ala Leu Gln Thr Gln Ala Lys Ile Tyr Ser Lys Thr Gly Ala Thr
                420                 425                 430

Asn Thr Trp Leu Phe Pro Gly Ser Cys Asn Gly Asn Glu Thr Thr Phe
                435                 440                 445

Trp Gln Cys Lys Asn Trp Gln Trp Gly Gly Leu Ser Cys Asp Asn Phe
            450                 455                 460

Glu Glu Ala Lys Val Thr Cys Ser Gly His Arg Glu Pro Arg Leu Val
465                 470                 475                 480

Gly Gly Glu Ile Pro Cys Ser Gly Arg Val Glu Val Lys His Gly Asp
                485                 490                 495

Val Trp Gly Ser Val Cys Asp Phe Asp Leu Ser Leu Glu Ala Ala Ser
                500                 505                 510

Val Val Cys Arg Glu Leu Gln Cys Gly Thr Val Val Ser Ile Leu Gly
            515                 520                 525

Gly Ala His Phe Gly Glu Gly Ser Gly Gln Ile Trp Gly Glu Glu Phe
530                 535                 540

Gln Cys Ser Gly Asp Glu Ser His Leu Ser Leu Cys Ser Val Ala Pro
545                 550                 555                 560

Pro Leu Asp Arg Thr Cys Thr His Ser Arg Asp Val Ser Val Val Cys
                565                 570                 575

Ser Asn Leu Glu Gly Pro Arg Phe Glu Gly Lys Pro Ile Pro Asn Pro
            580                 585                 590

Leu Leu Gly Leu Asp Ser Thr Arg Thr Gly His His His His His
            595                 600                 605

<210> SEQ ID NO 106
<211> LENGTH: 224
<212> TYPE: PRT
<213> ORGANISM: Artificial Sequence
<220> FEATURE:
<223> OTHER INFORMATION: Mouse CD163 LKIHDK-VKVQEE Y60R mutant

<400> SEQUENCE: 106

```
Met Gly Gly His Arg Met Val Leu Leu Gly Gly Ala Gly Ser Pro Gly
1               5                   10                  15
Cys Lys Arg Phe Val His Leu Gly Phe Phe Val Ala Val Ser Ser
            20                  25                  30
Leu Leu Ser Ala Ser Ala Val Thr Asn Ala Pro Gly Glu Met Lys Lys
        35                  40                  45
Glu Leu Arg Leu Ala Gly Gly Glu Asn Asn Cys Ser Gly Arg Val Glu
    50                  55                  60
Val Lys Val Gln Glu Glu Trp Gly Thr Val Cys Ser Asn Gly Trp Ser
65                  70                  75                  80
Met Asn Glu Val Ser Val Val Cys Gln Gln Leu Gly Cys Pro Thr Ser
                85                  90                  95
Ile Lys Ala Leu Gly Trp Ala Asn Ser Ser Ala Gly Ser Gly Arg Ile
            100                 105                 110
Trp Met Asp Lys Val Ser Cys Thr Gly Asn Glu Ser Ala Leu Trp Asp
        115                 120                 125
Cys Lys His Asp Gly Trp Gly Lys His Asn Cys Thr His Glu Lys Asp
    130                 135                 140
Ala Gly Val Thr Cys Ser Asp Gly Ser Asn Leu Glu Met Arg Leu Val
145                 150                 155                 160
Asn Ser Ala Gly His Arg Cys Leu Gly Arg Val Glu Ile Lys Phe Gln
                165                 170                 175
Gly Lys Trp Gly Thr Val Cys Asp Asp Asn Phe Ser Lys Asp His Ala
            180                 185                 190
Ser Val Ile Cys Lys Gln Leu Gly Cys Gly Ser Ala Ile Ser Phe Ser
        195                 200                 205
Gly Ser Ala Lys Leu Gly Ala Gly Ser Gly Pro Ile Trp Leu Asp Asp
    210                 215                 220

<210> SEQ ID NO 107
<211> LENGTH: 1827
<212> TYPE: DNA
<213> ORGANISM: Mus musculus

<400> SEQUENCE: 107
atgggtggac acagaatggt tcttcttgga ggtgctggat ctcctggttg taaaaggttt    60
gtccatctag gtttctttgt tgtggctgtg agctcacttc tcagtgcctc tgctgtcact   120
aacgctcctg gagaaatgaa gaaggaactg agactggcgg gtggtgaaaa caactgtagt   180
gggagagtgg aacttaagat ccatgacaag tggggcacag tgtgcagtaa cggctggagc   240
atgaatgaag tgtccgtggt ttgccagcag ctgggatgcc caacttctat taaagccctt   300
ggatgggcta actccagcgc cggctctgga tatatctgga tggacaaagt ttcttgtaca   360
gggaatgagt cagctctttg ggactgcaaa catgatgggt ggggaaagca taactgtacc   420
catgaaaaag atgctggagt gacctgctca gatggatcta atttggagat gagactggtg   480
aacagtgcgg gccaccgatg cttaggaaga gtagaaataa agttccaggg aaagtggggg   540
acggtgtgtg acgacaactt cagcaaagat cacgcttctg tgatttgtaa acagcttgga   600
tgtggaagtg ccattagttt ctctggctca gctaaattgg gagctggttc tggaccaatc   660
tggctcgatg acctggcatg caatggaaat gagtcagctc tctgggactg caaacaccgg   720
ggatggggca agcataactg tgaccatgct gaggatgtcg gtgtgatttg cttagaggga   780
gcagatctga gcctgagact agtggatgga gtgtccagat gttcaggaag attggaagtg   840
```

```
agattccaag gagaatgggg gaccgtgtgt gatgataact gggatctccg ggatgcttct    900
gtggtgtgca agcaactggg atgtccaact gccatcagtg ccattggtcg agttaatgcc    960
agtgagggat ctggacagat ttggcttgac aacatttcat gcgaaggaca tgaggcaact   1020
ctttgggagt gtaaacacca agagtgggga aagcattact gtcatcatag agaagacgct   1080
ggcgtgacat gttctgatgg agcagatctg gaacttagac ttgtaggtgg aggcagtcgc   1140
tgtgctggca ttgtggaggt ggagattcag aagctgactg gaagatgtgt agccgaggc    1200 tggacactgg cagatgcgga tgtggtttgc agacagcttg gatgtggatc tgcgcttcaa   1260
acccaggcta agatctactc taaaactggg gcaacaaata cgtggctctt tcctggatct   1320
tgtaatggaa atgaaactac tttttggcaa tgcaaaaact ggcagtgggg cggccttcc    1380 tgtgataatt tcgaagaagc caaagttacc tgctcaggcc acagggaacc cagactggtt   1440
ggaggagaaa tcccatgctc tggtcgtgtg gaagtgaaac acggagacgt gtggggctcc   1500
gtctgtgatt ttgacttgtc tctggaagct gccagtgtgg tgtgcaggga attacaatgt   1560
ggaacagtcg tctctatcct aggggagca cattttggag aaggaagtgg acagatctgg    1620
ggtgaagaat tccagtgtag tggggatgag tcccatcttt cactatgctc agtggcgccc   1680
ccgctagaca gaacttgtac ccacagcagg gatgtcagcg tagtctgctc aaatctagag   1740
ggcccgcggt tcgaaggtaa gcctatccct aaccctctcc tcggtctcga ttctacgcgt   1800
accggtcatc atcaccatca ccattga                                       1827

<210> SEQ ID NO 108
<211> LENGTH: 672
<212> TYPE: DNA
<213> ORGANISM: Artificial Sequence
<220> FEATURE:
<223> OTHER INFORMATION: Mouse CD163 LKIHDK-VKVQEE Y60D mutant

<400> SEQUENCE: 108
atgggtggac acagaatggt tcttcttgga ggtgctggat ctcctggttg taaaaggtttt    60 gtccatctag gtttctttgt tgtggctgtg agctcacttc tcagtgcctc tgctgtcact   120
aacgctcctg gagaaatgaa gaaggaactg agactggcgg tggtgaaaaa caactgtagt   180
gggagagtgg aagtgaaggt gcaggaggag tggggcacag tgtgcagtaa cggctggagc   240
atgaatgaag tgtccgtggt ttgccagcag ctgggatgcc caacttctat taaagcccttt   300 ggatgggcta actccagcgc cggctctgga cggatctgga tggacaaagt tcttgtaca    360 gggaatgagt cagctctttg ggactgcaaa catgatgggg ggggaaagca taactgtacc   420
catgaaaaag atgctggagt gacctgctca gatggatcta atttggagat gagactggtg   480
aacagtgcgg gccaccgatg cttaggaaga gtagaaataa agttccaggg aaagtggggg   540
acggtgtgtg acgacaactt cagcaaagat cacgcttctg tgatttgtaa acagcttgga   600
tgtggaagtg ccattagttt ctctggctca gctaaattgg gagctggttc tggaccaatc   660
tggctcgatg ac                                                        672

<210> SEQ ID NO 109
<211> LENGTH: 608
<212> TYPE: PRT
<213> ORGANISM: Mus musculus

<400> SEQUENCE: 109

Met Gly Gly His Arg Met Val Leu Leu Gly Gly Ala Gly Ser Pro Gly
1               5                   10                  15
```

-continued

```
Cys Lys Arg Phe Val His Leu Gly Phe Val Val Ala Val Ser Ser
             20                  25                  30

Leu Leu Ser Ala Ser Ala Val Thr Asn Ala Pro Gly Glu Met Lys Lys
         35                  40                  45

Glu Leu Arg Leu Ala Gly Gly Glu Asn Asn Cys Ser Gly Arg Val Glu
     50                  55                  60

Leu Lys Ile His Asp Lys Trp Gly Thr Val Cys Ser Asn Gly Trp Ser
 65                  70                  75                  80

Met Asn Glu Val Ser Val Cys Gln Gln Leu Gly Cys Pro Thr Ser
                 85                  90                  95

Ile Lys Ala Leu Gly Trp Ala Asn Ser Ser Ala Gly Ser Gly Tyr Ile
                100                 105                 110

Trp Met Asp Lys Val Ser Cys Thr Gly Asn Glu Ser Ala Leu Trp Asp
             115                 120                 125

Cys Lys His Asp Gly Trp Gly Lys His Asn Cys Thr His Glu Lys Asp
         130                 135                 140

Ala Gly Val Thr Cys Ser Asp Gly Ser Asn Leu Glu Met Arg Leu Val
145                 150                 155                 160

Asn Ser Ala Gly His Arg Cys Leu Gly Arg Val Glu Ile Lys Phe Gln
                165                 170                 175

Gly Lys Trp Gly Thr Val Cys Asp Asp Asn Phe Ser Lys Asp His Ala
            180                 185                 190

Ser Val Ile Cys Lys Gln Leu Gly Cys Gly Ser Ala Ile Ser Phe Ser
        195                 200                 205

Gly Ser Ala Lys Leu Gly Ala Gly Ser Gly Pro Ile Trp Leu Asp Asp
210                 215                 220

Leu Ala Cys Asn Gly Asn Glu Ser Ala Leu Trp Asp Cys Lys His Arg
225                 230                 235                 240

Gly Trp Gly Lys His Asn Cys Asp His Ala Glu Asp Val Gly Val Ile
                245                 250                 255

Cys Leu Glu Gly Ala Asp Leu Ser Leu Arg Leu Val Asp Gly Val Ser
            260                 265                 270

Arg Cys Ser Gly Arg Leu Glu Val Arg Phe Gln Gly Glu Trp Gly Thr
        275                 280                 285

Val Cys Asp Asp Asn Trp Asp Leu Arg Asp Ala Ser Val Val Cys Lys
290                 295                 300

Gln Leu Gly Cys Pro Thr Ala Ile Ser Ala Ile Gly Arg Val Asn Ala
305                 310                 315                 320

Ser Glu Gly Ser Gly Gln Ile Trp Leu Asp Asn Ile Ser Cys Glu Gly
                325                 330                 335

His Glu Ala Thr Leu Trp Glu Cys Lys His Gln Glu Trp Gly Lys His
            340                 345                 350

Tyr Cys His His Arg Glu Asp Ala Gly Val Thr Cys Ser Asp Gly Ala
        355                 360                 365

Asp Leu Glu Leu Arg Leu Val Gly Gly Ser Arg Cys Ala Gly Ile
    370                 375                 380

Val Glu Val Glu Ile Gln Lys Leu Thr Gly Lys Met Cys Ser Arg Gly
385                 390                 395                 400

Trp Thr Leu Ala Asp Ala Asp Val Val Cys Arg Gln Leu Gly Cys Gly
                405                 410                 415

Ser Ala Leu Gln Thr Gln Ala Lys Ile Tyr Ser Lys Thr Gly Ala Thr
            420                 425                 430

Asn Thr Trp Leu Phe Pro Gly Ser Cys Asn Gly Asn Glu Thr Thr Phe
```

-continued

```
                435                 440                 445
Trp Gln Cys Lys Asn Trp Gln Trp Gly Gly Leu Ser Cys Asp Asn Phe
450                 455                 460

Glu Glu Ala Lys Val Thr Cys Ser Gly His Arg Glu Pro Arg Leu Val
465                 470                 475                 480

Gly Gly Glu Ile Pro Cys Ser Gly Arg Val Glu Val Lys His Gly Asp
                485                 490                 495

Val Trp Gly Ser Val Cys Asp Phe Asp Leu Ser Leu Glu Ala Ala Ser
                500                 505                 510

Val Val Cys Arg Glu Leu Gln Cys Gly Thr Val Val Ser Ile Leu Gly
                515                 520                 525

Gly Ala His Phe Gly Glu Gly Ser Gly Gln Ile Trp Gly Glu Glu Phe
                530                 535                 540

Gln Cys Ser Gly Asp Glu Ser His Leu Ser Leu Cys Ser Val Ala Pro
545                 550                 555                 560

Pro Leu Asp Arg Thr Cys Thr His Ser Arg Asp Val Ser Val Val Cys
                565                 570                 575

Ser Asn Leu Glu Gly Pro Arg Phe Glu Gly Lys Pro Ile Pro Asn Pro
                580                 585                 590

Leu Leu Gly Leu Asp Ser Thr Arg Thr Gly His His His His His His
                595                 600                 605
```

<210> SEQ ID NO 110
<211> LENGTH: 224
<212> TYPE: PRT
<213> ORGANISM: Artificial Sequence
<220> FEATURE:
<223> OTHER INFORMATION: Mouse CD163 LKIHDK-VKVQEE Y60R mutant

<400> SEQUENCE: 110

```
Met Gly Gly His Arg Met Val Leu Leu Gly Gly Ala Gly Ser Pro Gly
1               5                   10                  15

Cys Lys Arg Phe Val His Leu Gly Phe Val Val Ala Val Ser Ser
                20                  25                  30

Leu Leu Ser Ala Ser Ala Val Thr Asn Ala Pro Gly Glu Met Lys Lys
                35                  40                  45

Glu Leu Arg Leu Ala Gly Gly Glu Asn Asn Cys Ser Gly Arg Val Glu
50                  55                  60

Val Lys Val Gln Glu Glu Trp Gly Thr Val Cys Ser Asn Gly Trp Ser
65                  70                  75                  80

Met Asn Glu Val Ser Val Val Cys Gln Gln Leu Gly Cys Pro Thr Ser
                85                  90                  95

Ile Lys Ala Leu Gly Trp Ala Asn Ser Ser Ala Gly Ser Gly Arg Ile
                100                 105                 110

Trp Met Asp Lys Val Ser Cys Thr Gly Asn Glu Ser Ala Leu Trp Asp
                115                 120                 125

Cys Lys His Asp Gly Trp Gly Lys His Asn Cys Thr His Glu Lys Asp
                130                 135                 140

Ala Gly Val Thr Cys Ser Asp Gly Ser Asn Leu Glu Met Arg Leu Val
145                 150                 155                 160

Asn Ser Ala Gly His Arg Cys Leu Gly Arg Val Glu Ile Lys Phe Gln
                165                 170                 175

Gly Lys Trp Gly Thr Val Cys Asp Asp Asn Phe Ser Lys Asp His Ala
                180                 185                 190

Ser Val Ile Cys Lys Gln Leu Gly Cys Gly Ser Ala Ile Ser Phe Ser
```

```
                195                 200                 205
Gly Ser Ala Lys Leu Gly Ala Gly Ser Gly Pro Ile Trp Leu Asp Asp
        210                 215                 220

<210> SEQ ID NO 111
<211> LENGTH: 25
<212> TYPE: DNA
<213> ORGANISM: Artificial Sequence
<220> FEATURE:
<223> OTHER INFORMATION: CD163 WT forward primer

<400> SEQUENCE: 111
acatagatca tgcatctgtc atttg                                           25

<210> SEQ ID NO 112
<211> LENGTH: 25
<212> TYPE: DNA
<213> ORGANISM: Artificial Sequence
<220> FEATURE:
<223> OTHER INFORMATION: CD163 WT reverse primer

<400> SEQUENCE: 112
cattctcctt ggaatctcac ttcta                                           25

<210> SEQ ID NO 113
<211> LENGTH: 18
<212> TYPE: DNA
<213> ORGANISM: Artificial Sequence
<220> FEATURE:
<223> OTHER INFORMATION: TNF-alpha forward primer

<400> SEQUENCE: 113
tggggtggag ctgagaga                                                   18

<210> SEQ ID NO 114
<211> LENGTH: 22
<212> TYPE: DNA
<213> ORGANISM: Artificial Sequence
<220> FEATURE:
<223> OTHER INFORMATION: TNF-alpha reverse primer

<400> SEQUENCE: 114
gcaatgatcc caaagtagac ct                                              22

<210> SEQ ID NO 115
<211> LENGTH: 110
<212> TYPE: PRT
<213> ORGANISM: Artificial Sequence
<220> FEATURE:
<223> OTHER INFORMATION: VL48 PCR product

<400> SEQUENCE: 115

Thr Asp Ile Val Met Thr Gln Thr Pro Lys Phe Leu Leu Val Ser Ala
1               5                   10                  15

Gly Asp Arg Val Thr Ile Thr Cys Lys Ala Ser Gln Ser Val Ser His
            20                  25                  30

Asp Val Ser Trp Phe Gln Gln Lys Pro Gly Gln Ser Pro Lys Leu Leu
        35                  40                  45

Ile Tyr Tyr Thr Ser Asn Arg Tyr Thr Gly Val Pro Asp Arg Phe Thr
    50                  55                  60

Gly Ser Gly Tyr Gly Thr Asp Phe Thr Phe Thr Ile Ser Thr Val Gln
65                  70                  75                  80

Ala Glu Asp Leu Ala Ile Tyr Phe Cys Gln Gln Asp Tyr Ser Ser Pro
```

```
                    85                  90                  95

Arg Thr Phe Gly Gly Gly Thr Lys Leu Glu Ile Lys Arg Ala
            100                 105                 110

<210> SEQ ID NO 116
<211> LENGTH: 109
<212> TYPE: PRT
<213> ORGANISM: Artificial Sequence
<220> FEATURE:
<223> OTHER INFORMATION: VL158 PCR product

<400> SEQUENCE: 116

Asp Ile Val Met Thr Gln Ser Pro Lys Ser Leu Leu Ile Ser Ile Gly
1               5                   10                  15

Asp Arg Val Thr Ile Thr Cys Lys Ala Ser Gln Ser Val Ser Ser Asp
            20                  25                  30

Val Ala Trp Phe Gln Gln Lys Pro Gly Gln Ser Pro Lys Pro Leu Ile
        35                  40                  45

Tyr Tyr Ala Ser Asn Arg Tyr Thr Gly Val Pro Asp Arg Phe Thr Gly
50                  55                  60

Ser Gly Tyr Gly Thr Asp Phe Thr Phe Thr Ile Ser Ser Val Gln Ala
65                  70                  75                  80

Glu Asp Leu Ala Val Tyr Phe Cys Gln Gln Asp Tyr Thr Ser Pro Arg
                85                  90                  95

Thr Phe Gly Gly Gly Thr Lys Leu Glu Ile Lys Arg Ala
            100                 105

<210> SEQ ID NO 117
<211> LENGTH: 116
<212> TYPE: PRT
<213> ORGANISM: Artificial Sequence
<220> FEATURE:
<223> OTHER INFORMATION: VH48 PCR product

<400> SEQUENCE: 117

Asp Val Lys Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Phe Ile Ser Tyr Ser Gly Ile Thr Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Ser Ala Thr Tyr Tyr Cys
                85                  90                  95

Val Ser Gly Thr Tyr Tyr Phe Asp Tyr Trp Gly Gln Gly Thr Thr Leu
            100                 105                 110

Thr Val Ser Ser
        115

<210> SEQ ID NO 118
<211> LENGTH: 116
<212> TYPE: PRT
<213> ORGANISM: Artificial Sequence
<220> FEATURE:
<223> OTHER INFORMATION: VH158 PCR product

<400> SEQUENCE: 118
```

```
Asp Val Lys Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ile Thr Asn Tyr Asn Pro Ser Leu
    50                  55                  60

Lys Ser Gln Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Val Ser Gly Thr Tyr Tyr Phe Asp Tyr Trp Gly Gln Gly Thr Thr Leu
            100                 105                 110

Thr Val Ser Ser
        115
```

<210> SEQ ID NO 119
<211> LENGTH: 115
<212> TYPE: PRT
<213> ORGANISM: Artificial Sequence
<220> FEATURE:
<223> OTHER INFORMATION: VH Template dbj BAG64279.1

<400> SEQUENCE: 119

```
Val Gln Leu Gln Glu Ser Gly Pro Gly Leu Val Lys Pro Ser Glu Thr
1               5                   10                  15

Leu Ser Leu Thr Cys Ala Val Ser Gly Tyr Ser Ile Thr Ser Gly Tyr
            20                  25                  30

Tyr Trp Gly Trp Ile Arg Gln Pro Pro Gly Lys Gly Leu Glu Trp Ile
        35                  40                  45

Gly Ser Ile Tyr His Ser Gly Ser Thr Tyr Tyr Asn Pro Ser Leu Lys
    50                  55                  60

Ser Arg Val Thr Leu Ser Val Asp Thr Ser Lys Asn Gln Phe Ser Leu
65                  70                  75                  80

Lys Met Ser Ser Val Thr Ala Ala Asp Thr Ala Val Tyr Tyr Cys Ala
                85                  90                  95

Arg Glu Arg Asn Tyr Met Asp Val Trp Gly Glu Gly Thr Thr Val Thr
            100                 105                 110

Val Ser Ser
        115
```

<210> SEQ ID NO 120
<211> LENGTH: 97
<212> TYPE: PRT
<213> ORGANISM: Artificial Sequence
<220> FEATURE:
<223> OTHER INFORMATION: VH Germline IGHV4-b*01

<400> SEQUENCE: 120

```
Val Gln Leu Gln Glu Ser Gly Pro Gly Leu Val Lys Pro Ser Glu Thr
1               5                   10                  15

Leu Ser Leu Thr Cys Ala Val Ser Gly Tyr Ser Ile Ser Ser Gly Tyr
            20                  25                  30

Tyr Trp Gly Trp Ile Arg Gln Pro Pro Gly Lys Gly Leu Glu Trp Ile
        35                  40                  45

Gly Ser Ile Tyr His Ser Gly Ser Thr Tyr Tyr Asn Pro Ser Leu Lys
```

```
                    50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                    85                  90                  95

Arg
```

```
<210> SEQ ID NO 121
<211> LENGTH: 116
<212> TYPE: PRT
<213> ORGANISM: Artificial Sequence
<220> FEATURE:
<223> OTHER INFORMATION: VH KN2

<400> SEQUENCE: 121

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Ile Thr Ser Asp
                    20                  25                  30

Tyr Ala Trp Asn Trp Ile Arg Gln Phe Pro Gly Asn Lys Leu Glu Trp
                35                  40                  45

Met Gly Tyr Ile Thr Tyr Ser Gly Ser Thr Tyr Tyr Asn Pro Ser Leu
         50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Thr Tyr Tyr Cys
                    85                  90                  95

Val Ser Gly Thr Tyr Tyr Phe Asp Tyr Trp Gly Gln Gly Thr Thr Leu
                    100                 105                 110

Thr Val Ser Ser
         115
```

```
<210> SEQ ID NO 122
<211> LENGTH: 116
<212> TYPE: PRT
<213> ORGANISM: Artificial Sequence
<220> FEATURE:
<223> OTHER INFORMATION: VH KN1IN5

<400> SEQUENCE: 122

Gln Val Gln Leu Gln Glu Ser Gly Pro Gly Leu Val Lys Pro Ser Glu
 1               5                  10                  15

Thr Leu Asn Leu Thr Cys Thr Val Ser Gly Tyr Ser Ile Thr Ser Asp
                    20                  25                  30

Tyr Ala Trp Asn Trp Ile Arg Gln Phe Pro Gly Asn Lys Leu Glu Trp
                35                  40                  45

Met Gly Tyr Ile Thr Tyr Ser Gly Ile Thr Asn Tyr Asn Pro Ser Leu
         50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Thr Tyr Tyr Cys
                    85                  90                  95

Val Ser Gly Thr Tyr Tyr Phe Asp Tyr Trp Gly Gln Gly Thr Thr Leu
                    100                 105                 110

Thr Val Ser Ser
         115
```

```
<210> SEQ ID NO 123
<211> LENGTH: 116
<212> TYPE: PRT
<213> ORGANISM: Artificial Sequence
<220> FEATURE:
<223> OTHER INFORMATION: VH KN1IN5 VR1

<400> SEQUENCE: 123

Gln Val Gln Leu Gln Glu Ser Gly Pro Gly Leu Val Lys Pro Ser Glu
1               5                   10                  15

Thr Leu Asn Leu Thr Cys Thr Val Ser Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ile Thr Asn Tyr Asn Pro Ser Leu
    50                  55                  60

Lys Ser Arg Val Thr Ile Ser Glu Asp Thr Ser Lys Asn Gln Phe Ser
65                  70                  75                  80

Leu Lys Leu Ser Ser Val Thr Ala Ala Asp Thr Ala Thr Tyr Tyr Cys
                85                  90                  95

Val Ser Gly Thr Tyr Tyr Phe Asp Tyr Trp Gly Gln Gly Thr Thr Leu
            100                 105                 110

Thr Val Ser Ser
        115

<210> SEQ ID NO 124
<211> LENGTH: 116
<212> TYPE: PRT
<213> ORGANISM: Artificial Sequence
<220> FEATURE:
<223> OTHER INFORMATION: VH KN1IN5 QD2

<400> SEQUENCE: 124

Asp Val Gln Leu Gln Glu Ser Gly Pro Gly Leu Val Lys Pro Ser Glu
1               5                   10                  15

Thr Leu Asn Leu Thr Cys Thr Val Ser Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Ile Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Thr Tyr Tyr Cys
                85                  90                  95

Val Ser Gly Thr Tyr Tyr Phe Asp Tyr Trp Gly Gln Gly Thr Thr Leu
            100                 105                 110

Thr Val Ser Ser
        115

<210> SEQ ID NO 125
<211> LENGTH: 109
<212> TYPE: PRT
<213> ORGANISM: Artificial Sequence
<220> FEATURE:
<223> OTHER INFORMATION: VL Template emb CAD43020.1

<400> SEQUENCE: 125

Asp Ile Val Met Thr Gln Ser Pro Ser Ser Leu Ser Ala Ser Val Gly
1               5                   10                  15
```

-continued

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gly Gly Thr Lys Val Glu Ile Lys Arg Ala
                100                 105

<210> SEQ ID NO 126
<211> LENGTH: 95
<212> TYPE: PRT
<213> ORGANISM: Artificial Sequence
<220> FEATURE:
<223> OTHER INFORMATION: VL Germline IGKV1D-39*01

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 127
<211> LENGTH: 109
<212> TYPE: PRT
<213> ORGANISM: Artificial Sequence
<220> FEATURE:
<223> OTHER INFORMATION: VL NRY

<400> SEQUENCE: 127

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Asp
            20                  25                  30

Val Ala Trp Phe Gln Gln Lys Pro Gly Lys Ser Pro Lys Pro Leu Ile
        35                  40                  45

Tyr Tyr Ala Ser Asn Arg Tyr Ser Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Val Tyr Phe Cys Gly Gln Asp Tyr Thr Ser Pro Arg
                85                  90                  95

Thr Phe Gly Gly Gly Thr Lys Leu Glu Ile Lys Arg Ala
                100                 105

-continued

<210> SEQ ID NO 128
<211> LENGTH: 109
<212> TYPE: PRT
<213> ORGANISM: Artificial Sequence
<220> FEATURE:
<223> OTHER INFORMATION: VL NRY d3

<400> SEQUENCE: 128

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Asp
            20                  25                  30

Val Ala Trp Phe Gln Gln Lys Pro Gly Lys Ser Pro Lys Leu Leu Ile
        35                  40                  45

Tyr Tyr Ala Ser Asn Arg Tyr Ser Gly Val Pro Ser Arg Phe Ser Gly
    50                  55                  60

Ser Gly Ser Gly Thr Asp Phe Thr Leu Thr Ile Ser Ser Leu Gln Ala
65                  70                  75                  80

Glu Asp Phe Ala Val Tyr Phe Cys Gly Gln Asp Tyr Ser Ser Pro Arg
                85                  90                  95

Thr Phe Gly Gly Gly Thr Lys Leu Glu Ile Lys Arg Ala
            100                 105
```

<210> SEQ ID NO 129
<211> LENGTH: 102
<212> TYPE: PRT
<213> ORGANISM: Homo sapiens

<400> SEQUENCE: 129

```
Leu Arg Leu Val Asp Gly Glu Asn Lys Cys Ser Gly Arg Val Glu Val
1               5                   10                  15

Lys Val Gln Glu Glu Trp Gly Thr Val Cys Asn Asn Gly Trp Ser Met
            20                  25                  30

Glu Ala Val Ser Val Ile Cys Asn Gln Leu Gly Cys Pro Thr Ala Ile
        35                  40                  45

Lys Ala Pro Gly Trp Ala Asn Ser Ser Ala Gly Ser Gly Arg Ile Trp
    50                  55                  60

Met Asp His Val Ser Cys Arg Gly Asn Glu Ser Ala Leu Trp Asp Cys
65                  70                  75                  80

Lys His Asp Gly Trp Gly Lys His Ser Asn Cys Thr His Gln Gln Asp
                85                  90                  95

Ala Gly Val Thr Cys Ser
            100
```

<210> SEQ ID NO 130
<211> LENGTH: 101
<212> TYPE: PRT
<213> ORGANISM: Homo sapiens

<400> SEQUENCE: 130

```
Met Arg Leu Thr Arg Gly Gly Asn Met Cys Ser Gly Arg Ile Glu Ile
1               5                   10                  15

Lys Phe Gln Gly Arg Trp Gly Thr Val Cys Asp Asp Asn Phe Asn Ile
            20                  25                  30

Asp His Ala Ser Val Ile Cys Arg Gln Leu Glu Cys Gly Ser Ala Val
        35                  40                  45

Ser Phe Ser Gly Ser Ser Asn Phe Gly Glu Gly Ser Gly Pro Ile Trp
    50                  55                  60
```

Phe Asp Asp Leu Ile Cys Asn Gly Asn Glu Ser Ala Leu Trp Asn Cys
65                  70                  75                  80

Lys His Gln Gly Trp Gly Lys His Asn Cys Asp His Ala Glu Asp Ala
                85                  90                  95

Gly Val Ile Cys Ser
            100

<210> SEQ ID NO 131
<211> LENGTH: 101
<212> TYPE: PRT
<213> ORGANISM: Homo sapiens

<400> SEQUENCE: 131

Leu Arg Leu Val Asp Gly Val Thr Glu Cys Ser Gly Arg Leu Glu Val
1               5                   10                  15

Arg Phe Gln Gly Glu Trp Gly Thr Ile Cys Asp Asp Gly Trp Asp Ser
                20                  25                  30

Tyr Asp Ala Ala Val Ala Cys Lys Gln Leu Gly Cys Pro Thr Ala Val
            35                  40                  45

Thr Ala Ile Gly Arg Val Asn Ala Ser Lys Gly Phe Gly His Ile Trp
        50                  55                  60

Leu Asp Ser Val Ser Cys Gln Gly His Glu Pro Ala Val Trp Gln Cys
65                  70                  75                  80

Lys His His Glu Trp Gly Lys His Tyr Cys Asn His Asn Glu Asp Ala
                85                  90                  95

Gly Val Thr Cys Ser
            100

<210> SEQ ID NO 132
<211> LENGTH: 101
<212> TYPE: PRT
<213> ORGANISM: Homo sapiens

<400> SEQUENCE: 132

Leu Arg Leu Arg Gly Gly Gly Ser Arg Cys Ala Gly Thr Val Glu Val
1               5                   10                  15

Glu Ile Gln Arg Leu Leu Gly Lys Val Cys Asp Arg Gly Trp Gly Leu
                20                  25                  30

Lys Glu Ala Asp Val Val Cys Arg Gln Leu Gly Cys Gly Ser Ala Leu
            35                  40                  45

Lys Thr Ser Tyr Gln Val Tyr Ser Lys Ile Gln Ala Thr Asn Thr Trp
        50                  55                  60

Leu Phe Leu Ser Ser Cys Asn Gly Asn Glu Thr Ser Leu Trp Asp Cys
65                  70                  75                  80

Lys Asn Trp Gln Trp Gly Gly Leu Thr Cys Asp His Tyr Glu Glu Ala
                85                  90                  95

Lys Ile Thr Cys Ser
            100

<210> SEQ ID NO 133
<211> LENGTH: 100
<212> TYPE: PRT
<213> ORGANISM: Homo sapiens

<400> SEQUENCE: 133

Arg Leu Val Gly Gly Asp Ile Pro Cys Ser Gly Arg Val Glu Val Lys
1               5                   10                  15

His Gly Asp Thr Trp Gly Ser Ile Cys Asp Ser Asp Phe Ser Leu Glu

```
                20                  25                  30

Ala Ala Ser Val Leu Cys Arg Glu Leu Gln Cys Gly Thr Val Val Ser
            35                  40                  45

Ile Leu Gly Gly Ala His Phe Gly Glu Gly Asn Gly Gln Ile Trp Ala
        50                  55                  60

Glu Glu Phe Gln Cys Glu Gly His Glu Ser His Leu Ser Leu Cys Pro
65                  70                  75                  80

Val Ala Pro Arg Pro Glu Gly Thr Cys Ser His Ser Arg Asp Val Gly
                85                  90                  95

Val Val Cys Ser
            100

<210> SEQ ID NO 134
<211> LENGTH: 101
<212> TYPE: PRT
<213> ORGANISM: Homo sapiens

<400> SEQUENCE: 134

Ile Arg Leu Val Asn Gly Lys Thr Pro Cys Glu Gly Arg Val Glu Leu
1               5                   10                  15

Lys Thr Leu Gly Ala Trp Gly Ser Leu Cys Asn Ser His Trp Asp Ile
            20                  25                  30

Glu Asp Ala His Val Leu Cys Gln Gln Leu Lys Cys Gly Val Ala Leu
        35                  40                  45

Ser Thr Pro Gly Gly Ala Arg Phe Gly Lys Gly Asn Gly Gln Ile Trp
    50                  55                  60

Arg His Met Phe His Cys Thr Gly Thr Glu Gln His Met Gly Asp Cys
65                  70                  75                  80

Pro Val Thr Ala Leu Gly Ala Ser Leu Cys Pro Ser Glu Gln Val Ala
                85                  90                  95

Ser Val Ile Cys Ser
            100

<210> SEQ ID NO 135
<211> LENGTH: 101
<212> TYPE: PRT
<213> ORGANISM: Homo sapiens

<400> SEQUENCE: 135

Leu Arg Leu Val Asn Gly Gly Arg Cys Ala Gly Arg Val Glu Ile
1               5                   10                  15

Tyr His Glu Gly Ser Trp Gly Thr Ile Cys Asp Asp Ser Trp Asp Leu
            20                  25                  30

Ser Asp Ala His Val Val Cys Arg Gln Leu Gly Cys Gly Glu Ala Ile
        35                  40                  45

Asn Ala Thr Gly Ser Ala His Phe Gly Glu Gly Thr Gly Pro Ile Trp
    50                  55                  60

Leu Asp Glu Met Lys Cys Asn Gly Lys Glu Ser Arg Ile Trp Gln Cys
65                  70                  75                  80

His Ser His Gly Trp Gly Gln Gln Asn Cys Arg His Lys Glu Asp Ala
                85                  90                  95

Gly Val Ile Cys Ser
            100

<210> SEQ ID NO 136
<211> LENGTH: 102
<212> TYPE: PRT
```

```
<213> ORGANISM: Homo sapiens

<400> SEQUENCE: 136

Leu Arg Leu Thr Ser Glu Ala Ser Arg Glu Ala Cys Ala Gly Arg Leu
1               5                   10                  15

Glu Val Phe Tyr Asn Gly Ala Trp Gly Thr Val Gly Lys Ser Ser Met
            20                  25                  30

Ser Glu Thr Thr Val Gly Val Val Cys Arg Gln Leu Gly Cys Ala Asp
                35                  40                  45

Lys Gly Lys Ile Asn Pro Ala Ser Leu Asp Lys Ala Met Ser Ile Pro
    50                  55                  60

Met Trp Val Asp Asn Val Gln Cys Pro Lys Gly Pro Asp Thr Leu Trp
65                  70                  75                  80

Gln Cys Pro Ser Ser Pro Trp Glu Lys Arg Leu Ala Ser Pro Ser Glu
                85                  90                  95

Glu Thr Trp Ile Thr Cys
            100

<210> SEQ ID NO 137
<211> LENGTH: 101
<212> TYPE: PRT
<213> ORGANISM: Homo sapiens

<400> SEQUENCE: 137

Ile Arg Leu Gln Glu Gly Pro Thr Ser Cys Ser Gly Arg Val Glu Ile
1               5                   10                  15

Trp His Gly Gly Ser Trp Gly Thr Val Cys Asp Asp Ser Trp Asp Leu
            20                  25                  30

Asp Asp Ala Gln Val Val Cys Gln Gln Leu Gly Cys Gly Pro Ala Leu
                35                  40                  45

Lys Ala Phe Lys Glu Ala Glu Phe Gly Gln Gly Thr Gly Pro Ile Trp
    50                  55                  60

Leu Asn Glu Val Lys Cys Lys Gly Asn Glu Ser Ser Leu Trp Asp Cys
65                  70                  75                  80

Pro Ala Arg Arg Trp Gly His Ser Glu Cys Gly His Lys Glu Asp Ala
                85                  90                  95

Ala Val Asn Cys Thr
            100
```